US010925543B2

(12) United States Patent
Rogers et al.

(10) Patent No.: US 10,925,543 B2
(45) Date of Patent: Feb. 23, 2021

(54) BIORESORBABLE SILICON ELECTRONICS FOR TRANSIENT IMPLANTS

(71) Applicant: The Board of Trustees of the University of Illinois, Urbana, IL (US)

(72) Inventors: John A. Rogers, Champaign, IL (US); Ki Jun Yu, Urbana, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 869 days.

(21) Appl. No.: 15/349,525

(22) Filed: Nov. 11, 2016

(65) Prior Publication Data

US 2017/0128015 A1 May 11, 2017

Related U.S. Application Data

(60) Provisional application No. 62/254,118, filed on Nov. 11, 2015.

(51) Int. Cl.
*A61B 5/0478* (2006.01)
*A61B 5/04* (2006.01)
(Continued)

(52) U.S. Cl.
CPC .............. *A61B 5/6868* (2013.01); *A61B 5/24* (2021.01); *A61B 5/291* (2021.01); *A61L 31/022* (2013.01);
(Continued)

(58) Field of Classification Search
CPC . A61B 5/6868; A61B 5/04001; A61B 5/0478; A61B 2562/046; A61L 31/022; A61L 31/028; A61L 31/148; A61N 1/0529
(Continued)

(56) References Cited

U.S. PATENT DOCUMENTS 3,949,410 A 4/1976 Bassous
4,058,418 A 11/1977 Lindmayer
(Continued)

FOREIGN PATENT DOCUMENTS

CN 1222758 7/1999
CN 1454045 11/2003
(Continued)

OTHER PUBLICATIONS

Lu, Qiang. "Molybdenum Metal Gate MOS Technology for Post-SiO2 Gate Dielectrics ." Molybdenum Metal Gate MOS Technology for Post-SiO/Sub 2/ Gate Dielectrics—IEEE Conference Publication, IEEE, 2000, ieeexplore.ieee.org/stamp/stamp.jsp?tp=&arnumber=904401&tag=1. (Year: 2000).*
(Continued)

*Primary Examiner* — Linda C Dvorak
*Assistant Examiner* — Christine A Dedoulis
(74) *Attorney, Agent, or Firm* — Leydig, Voit & Mayer, Ltd.

(57) ABSTRACT

Provided are implantable and bioresorbable medical devices comprising a bioresorbable substrate and an electronic circuit supported by the bioresorbable substrate. The electronic circuit comprises a membrane of silicon having a thickness less than or equal to 5 μm and an array of dissolvable electrodes, wherein the dissolvable electrodes are formed from the membrane of silicon. The electronic circuit is configured to conformally contact a biological tissue and electrically interface with biological tissue during use. The silicon may be highly doped to provide the requisite characteristics for electrically interfacing with biological tissue, and may be further used to form other components of the electronic circuit, including back-plane transistors electrically connected to the electrode array.

43 Claims, 36 Drawing Sheets

(51) Int. Cl.
  *A61N 1/05* (2006.01)
  *A61B 5/00* (2006.01)
  *A61L 31/14* (2006.01)
  *A61L 31/02* (2006.01)
  *A61B 5/24* (2021.01)
  *A61B 5/291* (2021.01)

(52) U.S. Cl.
  CPC ........... *A61L 31/028* (2013.01); *A61L 31/148* (2013.01); *A61N 1/0529* (2013.01); *A61B 2562/046* (2013.01)

(58) Field of Classification Search
  USPC ......... 600/372–373, 377–378, 393, 544–545
  See application file for complete search history.

(56) References Cited

U.S. PATENT DOCUMENTS

| | | | |
|---|---|---|---|
| 4,392,451 A | 7/1983 | Mickelsen et al. | |
| 4,471,003 A | 9/1984 | Cann | |
| 4,487,162 A | 12/1984 | Cann | |
| 4,663,828 A | 5/1987 | Hanak | |
| 4,761,335 A | 8/1988 | Aurichio et al. | |
| 4,766,670 A | 8/1988 | Gazdik et al. | |
| 4,784,720 A | 11/1988 | Douglas | |
| 4,855,017 A | 8/1989 | Douglas | |
| 5,041,973 A | 8/1991 | Lebron et al. | |
| 5,118,400 A | 6/1992 | Wollam | |
| 5,178,957 A | 1/1993 | Kolpe et al. | |
| 5,204,144 A | 4/1993 | Cann et al. | |
| 5,313,094 A | 5/1994 | Beyer et al. | |
| 5,339,180 A | 8/1994 | Katoh | |
| 5,376,820 A | 12/1994 | Crafts et al. | |
| 5,403,700 A | 4/1995 | Heller et al. | |
| 5,427,096 A | 6/1995 | Bogusiewicz et al. | |
| 5,434,751 A | 7/1995 | Cole, Jr. et al. | |
| 5,455,178 A | 10/1995 | Fattnger | |
| 5,469,845 A | 11/1995 | Delonzor et al. | |
| 5,501,893 A | 3/1996 | Laermer et al. | |
| 5,512,218 A | 4/1996 | Gresser et al. | |
| 5,525,815 A | 6/1996 | Einset | |
| 5,545,291 A | 8/1996 | Smith et al. | |
| 5,625,471 A | 4/1997 | Smith | |
| 5,648,148 A | 7/1997 | Simpson | |
| 5,653,742 A | 8/1997 | Parker et al. | |
| 5,687,737 A | 11/1997 | Branham et al. | |
| 5,691,245 A | 11/1997 | Bakhit | |
| 5,753,529 A | 5/1998 | Chang et al. | |
| 5,757,081 A | 5/1998 | Chang et al. | |
| 5,767,578 A | 6/1998 | Chang et al. | |
| 5,772,905 A | 6/1998 | Chou | |
| 5,783,856 A | 7/1998 | Smith et al. | |
| 5,790,151 A | 8/1998 | Mills | |
| 5,817,242 A | 10/1998 | Biebuyck et al. | |
| 5,824,186 A | 10/1998 | Smith et al. | |
| 5,904,545 A | 5/1999 | Smith et al. | |
| 5,907,189 A | 5/1999 | Mertol | |
| 5,915,180 A | 6/1999 | Hara et al. | |
| 5,917,534 A | 6/1999 | Rajeswaran | |
| 5,928,001 A | 7/1999 | Gilette et al. | |
| 5,954,715 A | 9/1999 | Harrington et al. | |
| 5,955,781 A | 9/1999 | Joshi et al. | |
| 5,976,683 A | 11/1999 | Liehrr et al. | |
| 5,998,291 A | 12/1999 | Bakhit et al. | |
| 6,024,702 A | 2/2000 | Iverson | |
| 6,057,212 A | 5/2000 | Chan et al. | |
| 6,080,608 A | 6/2000 | Nowak | |
| 6,091,979 A | 7/2000 | Madsen | |
| 6,097,984 A | 8/2000 | Douglas | |
| 6,134,045 A | 10/2000 | Jiang et al. | |
| 6,165,391 A | 12/2000 | Vedamuttu | |
| 6,171,730 B1 | 1/2001 | Kuroda et al. | |
| 6,225,149 B1 | 5/2001 | Gan et al. | |
| 6,236,883 B1 | 5/2001 | Ciaccio et al. | |
| 6,265,326 B1 | 7/2001 | Ueno | |
| 6,274,508 B1 | 8/2001 | Jacobsen et al. | |
| 6,276,775 B1 | 8/2001 | Schulte | |
| 6,277,712 B1 | 8/2001 | Kang et al. | |
| 6,281,038 B1 | 8/2001 | Jacobsen et al. | |
| 6,284,418 B1 | 9/2001 | Trantolo | |
| 6,291,896 B1 | 9/2001 | Smith | |
| 6,316,278 B1 | 11/2001 | Jacobsen et al. | |
| 6,316,283 B1 | 11/2001 | Saurer | |
| 6,317,175 B1 | 11/2001 | Salerno et al. | |
| 6,322,895 B1 | 11/2001 | Canham | |
| 6,334,960 B1 | 1/2002 | Wilson et al. | |
| 6,380,729 B1 | 4/2002 | Smith | |
| 6,403,397 B1 | 6/2002 | Katz | |
| 6,413,790 B1 | 6/2002 | Duthaler et al. | |
| 6,417,025 B1 | 7/2002 | Gengel | |
| 6,420,266 B1 | 7/2002 | Smith et al. | |
| 6,433,401 B1 | 8/2002 | Clark et al. | |
| 6,451,191 B1 | 9/2002 | Bentsen et al. | |
| 6,459,418 B1 | 10/2002 | Comiskey et al. | |
| 6,468,638 B2 | 10/2002 | Jacobsen et al. | |
| 6,479,395 B1 | 11/2002 | Smith et al. | |
| 6,517,995 B1 | 2/2003 | Jacobson et al. | |
| 6,555,408 B1 | 4/2003 | Jacobsen et al. | |
| 6,527,964 B1 | 5/2003 | Smith et al. | |
| 6,559,905 B1 | 5/2003 | Akiyama | |
| 6,566,744 B2 | 5/2003 | Gengel | |
| 6,580,151 B2 | 6/2003 | Vandeputte et al. | |
| 6,586,338 B2 | 7/2003 | Smith et al. | |
| 6,590,346 B1 | 7/2003 | Hadley et al. | |
| 6,606,079 B1 | 8/2003 | Smith | |
| 6,606,247 B2 | 8/2003 | Credelle et al. | |
| 6,608,370 B1 | 8/2003 | Chen et al. | |
| 6,623,579 B1 | 9/2003 | Smith et al. | |
| 6,639,578 B1 | 10/2003 | Comiskey et al. | |
| 6,655,286 B2 | 12/2003 | Rogers | |
| 6,657,289 B1 | 12/2003 | Craig et al. | |
| 6,661,037 B2 | 12/2003 | Pan et al. | |
| 6,665,044 B1 | 12/2003 | Jacobsen et al. | |
| 6,666,821 B2 | 12/2003 | Keimel | |
| 6,683,663 B1 | 1/2004 | Hadley et al. | |
| 6,693,384 B1 | 2/2004 | Vicentini et al. | |
| 6,706,402 B2 | 3/2004 | Ruckes et al. | |
| 6,720,469 B1 | 4/2004 | Curtis et al. | |
| 6,723,576 B2 | 4/2004 | Nozawa et al. | |
| 6,730,990 B2 | 5/2004 | Kondo et al. | |
| 6,731,353 B1 | 5/2004 | Credelle et al. | |
| 6,743,982 B2 | 6/2004 | Biegelsen et al. | |
| 6,780,696 B1 | 8/2004 | Schatz | |
| 6,784,450 B2 | 8/2004 | Pan et al. | |
| 6,787,052 B1 | 9/2004 | Vaganov | |
| 6,814,898 B1 | 11/2004 | Deeman et al. | |
| 6,816,380 B2 | 11/2004 | Credelle et al. | |
| 6,844,673 B1 | 1/2005 | Bernkopf | |
| 6,848,162 B2 | 2/2005 | Arneson et al. | |
| 6,850,312 B2 | 2/2005 | Jacobsen et al. | |
| 6,856,830 B2 | 2/2005 | He | |
| 6,863,219 B1 | 3/2005 | Jacobsen et al. | |
| 6,864,435 B2 | 3/2005 | Hermanns et al. | |
| 6,864,570 B2 | 3/2005 | Smith | |
| 6,872,645 B2 | 3/2005 | Duan et al. | |
| 6,878,871 B2 | 4/2005 | Scher et al. | |
| 6,881,979 B2 | 4/2005 | Starikov et al. | |
| 6,887,450 B2 | 5/2005 | Chen et al. | |
| 6,900,094 B2 | 5/2005 | Hammond et al. | |
| 6,917,061 B2 | 7/2005 | Pan et al. | |
| 6,936,181 B2 | 8/2005 | Bulthaup et al. | |
| 6,949,199 B1 | 9/2005 | Gauzner et al. | |
| 6,949,206 B2 | 9/2005 | Whiteford | |
| 6,950,220 B2 | 9/2005 | Abramson et al. | |
| 6,984,934 B2 | 1/2006 | Moller et al. | |
| 6,989,285 B2 | 1/2006 | Ball | |
| 7,029,951 B2 | 4/2006 | Chen et al. | |
| 7,033,961 B1 | 4/2006 | Smart et al. | |
| 7,067,903 B2 | 6/2006 | Tachibana et al. | |
| 7,116,318 B2 | 10/2006 | Amundson et al. | |
| 7,132,313 B2 | 11/2006 | O'Connor et al. | |
| 7,148,512 B2 | 12/2006 | Leu et al. | |
| 7,158,277 B2 | 1/2007 | Berggren et al. | |
| 7,169,546 B2 | 1/2007 | Suzuki et al. | |

(56) References Cited

U.S. PATENT DOCUMENTS

| | | |
|---|---|---|
| 7,169,669 B2 | 1/2007 | Blakers et al. |
| 7,170,164 B2 | 1/2007 | Chen et al. |
| 7,186,624 B2 | 3/2007 | Welser et al. |
| 7,190,051 B2 | 3/2007 | Mech et al. |
| 7,192,997 B2 | 3/2007 | Papathomas |
| 7,195,733 B2 | 3/2007 | Rogers et al. |
| 7,223,609 B2 | 5/2007 | Anvar et al. |
| 7,253,442 B2 | 8/2007 | Huang et al. |
| 7,255,919 B2 | 8/2007 | Sakata et al. |
| 7,291,540 B2 | 11/2007 | Mech et al. |
| 7,374,968 B2 | 5/2008 | Kornlivich et al. |
| 7,425,523 B2 | 9/2008 | Ikemizu et al. |
| 7,521,292 B2 | 4/2009 | Rogers et al. |
| 7,557,367 B2 | 7/2009 | Rogers et al. |
| 7,604,663 B1 | 10/2009 | Reimink et al. |
| 7,605,062 B2 | 10/2009 | Kahen |
| 7,622,367 B1 | 11/2009 | Nuzzo et al. |
| 7,629,691 B2 | 12/2009 | Roush et al. |
| 7,635,755 B2 | 12/2009 | Kaplan et al. |
| 7,674,882 B2 | 3/2010 | Kaplan et al. |
| 7,700,402 B2 | 4/2010 | Wild et al. |
| 7,704,684 B2 | 4/2010 | Rogers et al. |
| 7,705,280 B2 | 4/2010 | Nuzzo et al. |
| 7,709,961 B2 | 5/2010 | Greenberg et al. |
| 7,727,575 B2 | 6/2010 | Kaplan et al. |
| 7,799,699 B2 | 9/2010 | Nuzzo et al. |
| 7,842,780 B2 | 11/2010 | Kaplan et al. |
| 7,932,123 B2 | 4/2011 | Rogers et al. |
| 7,943,491 B2 | 5/2011 | Nuzzo et al. |
| 7,972,875 B2 | 7/2011 | Rogers et al. |
| 7,982,296 B2 | 7/2011 | Nuzzo et al. |
| 8,039,847 B2 | 10/2011 | Nuzzo et al. |
| 8,198,621 B2 | 6/2012 | Rogers et al. |
| 8,217,381 B2 | 7/2012 | Rogers et al. |
| 8,327,532 B2 | 12/2012 | Xu et al. |
| 8,367,035 B2 | 2/2013 | Rogers et al. |
| 8,394,706 B2 | 3/2013 | Nuzzo et al. |
| 8,440,546 B2 | 5/2013 | Nuzzo et al. |
| 8,470,701 B2 | 6/2013 | Rogers et al. |
| 8,552,299 B2 | 10/2013 | Rogers et al. |
| 8,562,095 B2 | 10/2013 | Alleyene et al. |
| 8,664,699 B2 | 3/2014 | Nuzzo et al. |
| 8,666,471 B2 | 3/2014 | Rogers et al. |
| 8,679,888 B2 | 3/2014 | Rogers et al. |
| 8,722,458 B2 | 5/2014 | Rogers et al. |
| 8,729,524 B2 | 5/2014 | Rogers et al. |
| 8,754,396 B2 | 6/2014 | Rogers et al. |
| 8,865,489 B2 | 10/2014 | Rogers et al. |
| 8,895,406 B2 | 11/2014 | Rogers et al. |
| 8,905,772 B2 | 12/2014 | Rogers et al. |
| 8,934,965 B2 | 1/2015 | Rogers et al. |
| 8,946,683 B2 | 2/2015 | Rogers et al. |
| 9,057,994 B2 | 6/2015 | Rogers et al. |
| 9,061,494 B2 | 6/2015 | Rogers et al. |
| 9,105,555 B2 | 8/2015 | Rogers et al. |
| 9,105,782 B2 | 8/2015 | Rogers et al. |
| 9,117,940 B2 | 8/2015 | Rogers et al. |
| 9,278,522 B2 | 3/2016 | Rogers et al. |
| 9,324,733 B2 | 4/2016 | Rogers et al. |
| 9,349,900 B2 | 5/2016 | Rogers et al. |
| 9,442,285 B2 | 9/2016 | Rogers |
| 9,450,043 B2 | 9/2016 | Nuzzo et al. |
| 9,487,002 B2 | 11/2016 | Rogers et al. |
| 9,496,229 B2 | 11/2016 | Rogers et al. |
| 9,515,025 B2 | 12/2016 | Rogers et al. |
| 9,554,484 B2 | 1/2017 | Rogers et al. |
| 9,555,644 B2 | 1/2017 | Rogers et al. |
| 9,601,671 B2 | 3/2017 | Rogers et al. |
| 9,613,911 B2 | 4/2017 | Rogers et al. |
| 9,647,171 B2 | 5/2017 | Rogers et al. |
| 9,691,873 B2 | 6/2017 | Rogers et al. |
| 9,761,444 B2 | 9/2017 | Nuzzo et al. |
| 9,765,934 B2 | 9/2017 | Rogers et al. |
| 9,768,086 B2 | 9/2017 | Nuzzo et al. |
| 2002/0021445 A1 | 2/2002 | Bozhevolnyi et al. |
| 2002/0110766 A1 | 8/2002 | Tsai et al. |
| 2003/0003759 A1 | 1/2003 | Kudelka |
| 2003/0006527 A1 | 1/2003 | Rabolt et al. |
| 2003/0032892 A1 | 2/2003 | Erlach et al. |
| 2003/0082889 A1 | 5/2003 | Maruyama et al. |
| 2003/0087476 A1 | 5/2003 | Oohata et al. |
| 2003/0138704 A1 | 7/2003 | Mei et al. |
| 2003/0149456 A1 | 8/2003 | Rottenberg et al. |
| 2003/0178316 A1 | 9/2003 | Jacobs et al. |
| 2003/0227116 A1 | 12/2003 | Halik et al. |
| 2004/0005723 A1 | 1/2004 | Empedocles et al. |
| 2004/0026684 A1 | 2/2004 | Empedocles et al. |
| 2004/0079464 A1 | 4/2004 | Kumakura |
| 2004/0081384 A1 | 4/2004 | Datesman et al. |
| 2004/0095658 A1 | 5/2004 | Buretea et al. |
| 2004/0112964 A1 | 6/2004 | Empedocles et al. |
| 2004/0136866 A1 | 7/2004 | Pontis et al. |
| 2004/0146560 A1 | 7/2004 | Whiteford et al. |
| 2004/0155290 A1 | 8/2004 | Mech et al. |
| 2004/0178390 A1 | 9/2004 | Whiteford |
| 2004/0192082 A1 | 9/2004 | Wagner et al. |
| 2004/0200734 A1 | 10/2004 | Co et al. |
| 2004/0206448 A1 | 10/2004 | Dubrow |
| 2004/0211458 A1 | 10/2004 | Gui et al. |
| 2004/0211459 A1 | 10/2004 | Suenaga et al. |
| 2004/0176312 A1 | 11/2004 | Gillis |
| 2004/0250950 A1 | 12/2004 | Dubrow |
| 2004/0252559 A1 | 12/2004 | Gupta |
| 2005/0020094 A1 | 1/2005 | Forbes et al. |
| 2005/0038498 A1 | 2/2005 | Dubrow et al. |
| 2005/0082526 A1 | 4/2005 | Bedell et al. |
| 2005/0124712 A1 | 6/2005 | Anderson et al. |
| 2005/0133954 A1 | 6/2005 | Homola |
| 2005/0214962 A1 | 9/2005 | Daniels et al. |
| 2005/0227389 A1 | 10/2005 | Bhattacharya et al. |
| 2005/0233546 A1 | 10/2005 | Oohata et al. |
| 2005/0238967 A1 | 10/2005 | Rogers et al. |
| 2005/0149158 A1 | 11/2005 | Skiba et al. |
| 2005/0255686 A1 | 11/2005 | Yamano et al. |
| 2005/0260706 A1 | 11/2005 | Kaplan et al. |
| 2005/0261561 A1 | 11/2005 | Jones et al. |
| 2006/0038182 A1 | 2/2006 | Rogers et al. |
| 2006/0049485 A1 | 3/2006 | Pan et al. |
| 2006/0076561 A1 | 4/2006 | Hioki et al. |
| 2006/0084012 A1 | 4/2006 | Nuzzo et al. |
| 2006/0085976 A1 | 4/2006 | Eldridge et al. |
| 2006/0100478 A1 | 5/2006 | Connors et al. |
| 2006/0102525 A1 | 5/2006 | Volkel et al. |
| 2006/0119853 A1 | 6/2006 | Baumberg et al. |
| 2006/0127817 A1 | 6/2006 | Ramanujan et al. |
| 2006/0129056 A1 | 6/2006 | Leuthardt et al. |
| 2006/0132025 A1 | 6/2006 | Gao et al. |
| 2006/0134893 A1 | 6/2006 | Savage et al. |
| 2006/0141617 A1 | 6/2006 | Desai et al. |
| 2006/0159837 A1 | 7/2006 | Kaplan et al. |
| 2006/0169989 A1 | 8/2006 | Bhattacharya et al. |
| 2006/0173364 A1 | 8/2006 | Clancy et al. |
| 2006/0177479 A1 | 8/2006 | Giachelli et al. |
| 2006/0178655 A1 | 8/2006 | Santini et al. |
| 2006/0244105 A1 | 11/2006 | Forbes et al. |
| 2006/0255341 A1 | 11/2006 | Pinnington et al. |
| 2006/0273279 A1 | 12/2006 | Kaplan et al. |
| 2006/0279191 A1 | 12/2006 | Gehegan et al. |
| 2006/0286488 A1 | 12/2006 | Rogers et al. |
| 2006/0286785 A1 | 12/2006 | Rogers et al. |
| 2007/0009968 A1 | 1/2007 | Cunningham et al. |
| 2007/0031607 A1 | 2/2007 | Dubson et al. |
| 2007/0032089 A1 | 2/2007 | Nuzzo et al. |
| 2007/0043416 A1 | 2/2007 | Callas et al. |
| 2007/0058254 A1 | 3/2007 | Kim |
| 2007/0073130 A1 | 3/2007 | Finch et al. |
| 2007/0085078 A1 | 4/2007 | Kuroda et al. |
| 2007/0187862 A1 | 8/2007 | Kaplan et al. |
| 2007/0212730 A1 | 9/2007 | Vepari et al. |
| 2007/0227586 A1 | 10/2007 | Zapalac |
| 2007/0233208 A1 | 10/2007 | Kurtz et al. |
| 2008/0038236 A1 | 2/2008 | Gimble et al. |
| 2008/0041617 A1 | 2/2008 | Chen et al. |
| 2008/0055581 A1 | 3/2008 | Rogers et al. |

(56) References Cited

U.S. PATENT DOCUMENTS

| | | |
|---|---|---|
| 2008/0085272 A1 | 4/2008 | Kaplan et al. |
| 2008/0090097 A1 | 4/2008 | Shaw et al. |
| 2008/0090322 A1 | 4/2008 | Mech et al. |
| 2008/0102096 A1 | 5/2008 | Molin et al. |
| 2008/0108171 A1 | 5/2008 | Rogers et al. |
| 2008/0142870 A1 | 6/2008 | Watanabe |
| 2008/0152281 A1 | 6/2008 | Lundquist et al. |
| 2008/0000871 A1 | 7/2008 | Suh et al. |
| 2008/0157235 A1 | 7/2008 | Rogers et al. |
| 2008/0183076 A1 | 7/2008 | Witte et al. |
| 2008/0203431 A1 | 8/2008 | Garcia et al. |
| 2008/0212102 A1 | 9/2008 | Nuzzo et al. |
| 2008/0219122 A1 | 9/2008 | Detzler et al. |
| 2008/0239755 A1 | 10/2008 | Parker et al. |
| 2008/0243217 A1 | 10/2008 | Wildon |
| 2008/0280360 A1 | 11/2008 | Kaplan et al. |
| 2008/0288037 A1 | 11/2008 | Neysmith et al. |
| 2008/0293919 A1 | 11/2008 | Kaplan et al. |
| 2008/0306359 A1 | 12/2008 | Zdeblick et al. |
| 2009/0004737 A1 | 1/2009 | Borenstein et al. |
| 2009/0028910 A1 | 1/2009 | Desimone et al. |
| 2009/0149930 A1 | 6/2009 | Schecnk |
| 2009/0163895 A1 | 6/2009 | Ausiello et al. |
| 2009/0198293 A1 | 8/2009 | Cauller et al. |
| 2009/0199960 A1 | 8/2009 | Nuzzo et al. |
| 2009/0202614 A1 | 8/2009 | Kaplan et al. |
| 2009/0208555 A1 | 8/2009 | Kuttler et al. |
| 2009/0221896 A1 | 9/2009 | Rickert et al. |
| 2009/0232963 A1 | 9/2009 | Kaplan et al. |
| 2009/0234026 A1 | 9/2009 | Kaplan et al. |
| 2009/0289246 A1 | 11/2009 | Schneider et al. |
| 2009/0294803 A1 | 12/2009 | Nuzzo et al. |
| 2010/0002402 A1 | 1/2010 | Rogers et al. |
| 2010/0028451 A1 | 2/2010 | Kaplan et al. |
| 2010/0046902 A1 | 2/2010 | Kaplan et al. |
| 2010/0052112 A1 | 3/2010 | Rogers et al. |
| 2010/0055438 A1 | 3/2010 | Kaplan et al. |
| 2010/0059863 A1 | 3/2010 | Rogers et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0072577 A1 | 3/2010 | Nuzzo et al. |
| 2010/0096763 A1 | 4/2010 | Kaplan et al. |
| 2010/0120116 A1 | 5/2010 | Kaplan et al. |
| 2010/0121420 A1 | 5/2010 | Fiset et al. |
| 2010/0160999 A1 | 6/2010 | Epstein et al. |
| 2010/0176705 A1 | 7/2010 | Van Herpen et al. |
| 2010/0178304 A1 | 7/2010 | Wang et al. |
| 2010/0191328 A1 | 7/2010 | Kaplan et al. |
| 2010/0195367 A1 | 8/2010 | Kato |
| 2010/0196447 A1 | 8/2010 | Kaplan et al. |
| 2010/0200752 A1 | 8/2010 | Lee et al. |
| 2010/0203226 A1 | 8/2010 | Kaplan et al. |
| 2010/0252840 A1 | 10/2010 | Ibbetson et al. |
| 2010/0279112 A1 | 11/2010 | Kaplan et al. |
| 2010/0283069 A1 | 11/2010 | Rogers et al. |
| 2010/0289124 A1 | 11/2010 | Nuzzo et al. |
| 2010/0317132 A1 | 12/2010 | Rogers et al. |
| 2011/0068672 A1 | 3/2011 | Hasnain |
| 2011/0147715 A1 | 6/2011 | Rogers et al. |
| 2011/0170225 A1 | 7/2011 | Rogers et al. |
| 2011/0171813 A1 | 7/2011 | Rogers et al. |
| 2011/0187798 A1 | 8/2011 | Rogers et al. |
| 2011/0220890 A1 | 9/2011 | Nuzzo et al. |
| 2011/0230747 A1* | 9/2011 | Rogers .............. A61B 5/05 600/377 |
| 2011/0245914 A1 | 10/2011 | Santini, Jr. et al. |
| 2011/0266561 A1 | 11/2011 | Rogers et al. |
| 2011/0276124 A1 | 11/2011 | Doerr et al. |
| 2011/0277813 A1 | 11/2011 | Rogers et al. |
| 2011/0291078 A1 | 12/2011 | Hwang et al. |
| 2011/0316120 A1 | 12/2011 | Rogers et al. |
| 2012/0035740 A1 | 2/2012 | Koo et al. |
| 2012/0083099 A1 | 4/2012 | Rogers et al. |
| 2012/0105528 A1 | 5/2012 | Alleyene et al. |
| 2012/0157804 A1 | 6/2012 | Rogers et al. |
| 2012/0165759 A1 | 6/2012 | Rogers et al. |
| 2012/0223293 A1 | 9/2012 | Borenstein et al. |
| 2012/0261551 A1 | 10/2012 | Rogers et al. |
| 2012/0320581 A1 | 12/2012 | Rogers et al. |
| 2012/0321785 A1 | 12/2012 | Rogers et al. |
| 2012/0327608 A1 | 12/2012 | Rogers et al. |
| 2013/0036928 A1 | 2/2013 | Rogers et al. |
| 2013/0041235 A1* | 2/2013 | Rogers .............. A61B 5/1107 600/306 |
| 2013/0072775 A1 | 3/2013 | Rogers et al. |
| 2013/0100618 A1 | 4/2013 | Rogers et al. |
| 2013/0140649 A1 | 6/2013 | Rogers et al. |
| 2013/0320503 A1 | 12/2013 | Rogers et al. |
| 2013/0333094 A1 | 12/2013 | Rogers et al. |
| 2014/0092158 A1 | 4/2014 | Rogers et al. |
| 2014/0140020 A1 | 5/2014 | Rogers et al. |
| 2014/0163390 A1 | 6/2014 | Rogers et al. |
| 2014/0191236 A1 | 7/2014 | Nuzzo et al. |
| 2014/0216524 A1 | 8/2014 | Rogers et al. |
| 2014/0220422 A1 | 8/2014 | Rogers et al. |
| 2014/0305900 A1 | 10/2014 | Rogers et al. |
| 2014/0323968 A1* | 10/2014 | Rogers .............. H01L 21/0228 604/113 |
| 2014/0361409 A1 | 12/2014 | Rogers et al. |
| 2014/0373898 A1 | 12/2014 | Rogers et al. |
| 2014/0374872 A1 | 12/2014 | Rogers et al. |
| 2015/0001462 A1 | 1/2015 | Rogers et al. |
| 2015/0080695 A1 | 3/2015 | Rogers et al. |
| 2015/0132873 A1 | 5/2015 | Rogers et al. |
| 2015/0141767 A1 | 5/2015 | Rogers et al. |
| 2015/0181700 A1 | 6/2015 | Rogers et al. |
| 2015/0207012 A1 | 7/2015 | Rogers et al. |
| 2015/0237711 A1 | 8/2015 | Rogers et al. |
| 2015/0290938 A1 | 10/2015 | Borenstein et al. |
| 2015/0373831 A1 | 12/2015 | Rogers et al. |
| 2015/0380355 A1 | 12/2015 | Rogers et al. |
| 2016/0005700 A1 | 1/2016 | Rogers et al. |
| 2016/0027737 A1 | 1/2016 | Rogers et al. |
| 2016/0050750 A1 | 2/2016 | Rogers et al. |
| 2016/0066789 A1 | 3/2016 | Rogers et al. |
| 2016/0072027 A1 | 3/2016 | Rogers et al. |
| 2016/0133843 A1 | 5/2016 | Rogers et al. |
| 2016/0136877 A1 | 5/2016 | Rogers et al. |
| 2016/0284544 A1 | 9/2016 | Nuzzo et al. |
| 2016/0293794 A1 | 10/2016 | Nuzzo et al. |
| 2016/0381789 A1 | 12/2016 | Rogers et al. |
| 2017/0020402 A1 | 1/2017 | Rogers et al. |
| 2017/0128015 A1 | 5/2017 | Rogers et al. |
| 2017/0164482 A1 | 6/2017 | Rogers et al. |
| 2017/0179085 A1 | 6/2017 | Rogers et al. |
| 2017/0179100 A1 | 6/2017 | Rogers et al. |
| 2017/0179356 A1 | 6/2017 | Rogers et al. |
| 2017/0181704 A1 | 6/2017 | Rogers et al. |
| 2017/0200679 A1 | 7/2017 | Rogers et al. |
| 2017/0200707 A1 | 7/2017 | Rogers et al. |
| 2017/0210117 A1 | 7/2017 | Rogers et al. |
| 2017/0224257 A1 | 8/2017 | Rogers et al. |
| 2017/0231571 A1 | 8/2017 | Rogers et al. |

FOREIGN PATENT DOCUMENTS

| | | |
|---|---|---|
| CN | 1802705 | 7/2006 |
| CN | 1992084 | 7/2007 |
| CN | 101772348 | 7/2010 |
| DE | 4241045 | 5/1994 |
| DE | 19748173 | 5/1999 |
| EP | 0 929 097 | 7/1999 |
| EP | 1 025 988 | 8/2000 |
| EP | 1 357 773 | 10/2003 |
| EP | 1 467 224 | 10/2004 |
| EP | 1 477 230 | 11/2004 |
| EP | 1 498 456 | 1/2005 |
| EP | 1 511 096 | 3/2005 |
| EP | 1 558 444 | 8/2005 |
| EP | 1 613 796 | 1/2006 |
| EP | 1 773 240 | 4/2007 |
| EP | 1 915 436 | 4/2008 |

(56) References Cited

FOREIGN PATENT DOCUMENTS

| | | |
|---|---|---|
| EP | 1 726 329 | 8/2009 |
| EP | 2 086 749 | 8/2009 |
| EP | 2 101 975 | 9/2009 |
| EP | 2 107 964 | 10/2009 |
| EP | 2 109 634 | 10/2009 |
| EP | 2 129 772 | 12/2009 |
| EP | 2 206 017 | 7/2010 |
| EP | 2 211 876 | 8/2010 |
| EP | 2 249 886 | 11/2010 |
| JP | H01-135853 | 5/1989 |
| JP | H06-118441 | 4/1994 |
| JP | H06-163365 | 6/1994 |
| JP | H11-026344 | 1/1999 |
| JP | H11-123791 | 5/1999 |
| JP | H11-142878 | 5/1999 |
| JP | H11-183854 | 7/1999 |
| JP | H11-514252 | 12/1999 |
| JP | 2000-180969 | 6/2000 |
| JP | 2001-007340 | 1/2001 |
| JP | 2001-147301 | 5/2001 |
| JP | 2002-092984 | 3/2002 |
| JP | 2004-006540 | 1/2004 |
| JP | 2004-237077 | 8/2004 |
| JP | 2004-307661 | 11/2004 |
| JP | 2006-504450 | 2/2006 |
| JP | 2006-119424 | 5/2006 |
| JP | 2006-163719 | 6/2006 |
| JP | 2006-186294 | 7/2006 |
| JP | 2007-515391 | 6/2007 |
| JP | 2008-502739 | 1/2008 |
| JP | 2009-536422 | 10/2009 |
| JP | 2010-508852 | 3/2010 |
| JP | 2010-509593 | 3/2010 |
| JP | 2010-509644 | 3/2010 |
| JP | 2010-509645 | 3/2010 |
| JP | 2010-522583 | 7/2010 |
| JP | 2010-529230 | 8/2010 |
| KR | 10-2008-0069553 | 7/2008 |
| TW | 367570 | 8/1999 |
| TW | 494257 | 7/2002 |
| TW | 200836353 | 9/2008 |
| WO | WO 1996/021245 | 7/1996 |
| WO | WO 1997/010784 | 3/1997 |
| WO | WO 1998/049936 | 11/1998 |
| WO | WO 1999/045860 | 9/1999 |
| WO | WO 2000/046854 | 8/2000 |
| WO | WO 2000/049421 | 8/2000 |
| WO | WO 2000/049658 | 8/2000 |
| WO | WO 2000/055915 | 9/2000 |
| WO | WO 2000/055916 | 9/2000 |
| WO | WO 2001/031082 | 5/2001 |
| WO | WO 2001/033621 | 5/2001 |
| WO | WO 2001/066833 | 9/2001 |
| WO | WO 2001/098838 | 12/2001 |
| WO | WO 2002/027701 | 4/2002 |
| WO | WO 2002/043032 | 5/2002 |
| WO | WO 2002/045160 | 6/2002 |
| WO | WO 2002/071137 | 9/2002 |
| WO | WO 2002/073699 | 9/2002 |
| WO | WO 2002/092778 | 11/2002 |
| WO | WO 2002/097724 | 12/2002 |
| WO | WO 2004/099068 | 12/2002 |
| WO | WO 2003/030194 | 4/2003 |
| WO | WO 2003/032240 | 4/2003 |
| WO | WO 2003/049201 | 6/2003 |
| WO | WO 2003/063211 | 7/2003 |
| WO | WO 2003/085700 | 10/2003 |
| WO | WO 2003/085701 | 10/2003 |
| WO | WO 2003/092073 | 11/2003 |
| WO | WO 2004/000915 | 12/2003 |
| WO | WO 2004/001103 | 12/2003 |
| WO | WO 2004/003535 | 1/2004 |
| WO | WO 2004/022637 | 3/2004 |
| WO | WO 2004/022714 | 3/2004 |
| WO | WO 2004/023527 | 3/2004 |
| WO | WO 2004/024407 | 3/2004 |
| WO | WO 2004/027822 | 4/2004 |
| WO | WO 2004/032190 | 4/2004 |
| WO | WO 2004/032191 | 4/2004 |
| WO | WO 2004/032193 | 4/2004 |
| WO | WO 2004/034025 | 4/2004 |
| WO | WO 2004/062697 | 7/2004 |
| WO | WO 2004/086289 | 10/2004 |
| WO | WO 2004/094303 | 11/2004 |
| WO | WO 2004/100252 | 11/2004 |
| WO | WO 2004/105456 | 12/2004 |
| WO | WO 2004/107973 | 12/2004 |
| WO | WO 2005/000483 | 1/2005 |
| WO | WO 2005/005679 | 1/2005 |
| WO | WO 2005/012606 | 2/2005 |
| WO | WO 2005/015480 | 2/2005 |
| WO | WO 2005/017962 | 2/2005 |
| WO | WO 2005/022120 | 3/2005 |
| WO | WO 2005/029578 | 3/2005 |
| WO | WO 2005/031724 | 4/2005 |
| WO | WO 2005/033786 | 4/2005 |
| WO | WO 2005/033787 | 4/2005 |
| WO | WO 2005/054119 | 6/2005 |
| WO | WO 2005/065576 | 7/2005 |
| WO | WO 2005/099310 | 10/2005 |
| WO | WO 2005/104756 | 11/2005 |
| WO | WO 2005/106934 | 11/2005 |
| WO | WO 2002/097708 | 12/2005 |
| WO | WO 2005/122285 | 12/2005 |
| WO | WO 2005/123114 | 12/2005 |
| WO | WO 2006/028996 | 3/2006 |
| WO | WO 2006/042287 | 4/2006 |
| WO | WO 2006/076711 | 7/2006 |
| WO | WO 2006/104069 | 10/2006 |
| WO | WO 2006/130558 | 12/2006 |
| WO | WO 2006/130721 | 12/2006 |
| WO | WO 2007/000037 | 1/2007 |
| WO | WO 2007/016524 | 2/2007 |
| WO | WO 2007/028003 | 3/2007 |
| WO | WO 2007/056183 | 5/2007 |
| WO | WO 2007/126412 | 11/2007 |
| WO | WO 2007/132390 | 11/2007 |
| WO | WO 2008/030666 | 3/2008 |
| WO | WO 2008/030960 | 3/2008 |
| WO | WO 2008/036837 | 3/2008 |
| WO | WO 2008/038197 | 4/2008 |
| WO | WO 2008/055054 | 5/2008 |
| WO | WO 2008/085904 | 7/2008 |
| WO | WO 2008/103464 | 8/2008 |
| WO | WO 2008/106485 | 9/2008 |
| WO | WO 2008/108838 | 9/2008 |
| WO | WO 2008/118133 | 10/2008 |
| WO | WO 2008/118211 | 10/2008 |
| WO | WO 2008/127401 | 10/2008 |
| WO | WO 2008/127402 | 10/2008 |
| WO | WO 2008/127403 | 10/2008 |
| WO | WO 2008/127404 | 10/2008 |
| WO | WO 2008/127405 | 10/2008 |
| WO | WO 2008/140562 | 11/2008 |
| WO | WO 2008/143635 | 11/2008 |
| WO | WO 2008/150861 | 12/2008 |
| WO | WO 2009/011709 | 1/2009 |
| WO | WO 2009/023615 | 2/2009 |
| WO | WO 2009/061823 | 5/2009 |
| WO | WO 2009/075625 | 6/2009 |
| WO | WO 2009/076088 | 6/2009 |
| WO | WO 2009/090398 | 7/2009 |
| WO | WO 2009/100280 | 8/2009 |
| WO | WO 2009/111641 | 9/2009 |
| WO | WO 2009/114115 | 9/2009 |
| WO | WO 2009/114689 | 9/2009 |
| WO | WO 2009/118678 | 10/2009 |
| WO | WO 2009/126689 | 10/2009 |
| WO | WO 2009/140588 | 11/2009 |
| WO | WO 2009/155397 | 12/2009 |
| WO | WO 2010/005707 | 1/2010 |
| WO | WO 2010/036807 | 4/2010 |
| WO | WO 2010/036992 | 4/2010 |
| WO | WO 2010/040528 | 4/2010 |

(56) References Cited

FOREIGN PATENT DOCUMENTS

| WO | WO 2010/042798 | 4/2010 |
|---|---|---|
| WO | WO 2010/049881 | 5/2010 |
| WO | WO 2010/057142 | 5/2010 |
| WO | WO 2010/065957 | 6/2010 |
| WO | WO 2010/126640 | 11/2010 |
| WO | WO 2010/132552 | 11/2010 |
| WO | WO 2010/141133 | 12/2010 |
| WO | WO 2011/005381 | 1/2011 |
| WO | WO 2011/006133 | 1/2011 |
| WO | WO 2011/008842 | 1/2011 |
| WO | WO 2011/011347 | 1/2011 |
| WO | WO 2011/026101 | 3/2011 |
| WO | WO 2011/038401 | 3/2011 |
| WO | WO 2011/041395 | 4/2011 |
| WO | WO 2011/046652 | 4/2011 |
| WO | WO 2011/084450 | 7/2011 |
| WO | WO 2011/112931 | 9/2011 |
| WO | WO 2011/115643 | 9/2011 |
| WO | WO 2011/130335 | 10/2011 |
| WO | WO 2014/124044 | 8/2014 |
| WO | WO 2014/124049 | 8/2014 |
| WO | WO 2014/126927 | 8/2014 |
| WO | WO 2014/138465 | 9/2014 |
| WO | WO 2014/165686 | 10/2014 |
| WO | WO 2016/054348 | 4/2016 |
| WO | WO 2016/196673 | 12/2016 |
| WO | WO 2016/196675 | 12/2016 |
| WO | WO 2017/004531 | 1/2017 |
| WO | WO 2017/004576 | 1/2017 |

OTHER PUBLICATIONS

Hwang, Suk-Won, et al. "A Physically Transient Form of Silicon Electronics." Science, American Association for the Advancement of Science, Sep. 28, 2012, science.sciencemag.org/content/337/6102/1640. (Year: 2012).*

[Authors unknown] (1996) "National Nosocomial Infections Surveillance (NNIS) Report, Data Summary from Oct. 1986-Apr. 1996, Issued May 1996. A Report from the National Nosocomial Infections Surveillance (NNIS) System," Am. J. Infect. Control. 24:380-388.

Abbaschian et al. (Dec. 2005) "High Pressure-High Temperature Growth of Diamond Crystals Using Split Sphere Apparatus," Diamond Relat. Mater. 14(1112):1916-1919.

Adachi et al (1982) "Chemical Etching of InGaAsP/InP DH Wafer," J. Electrochem. Soc. 129:1053-1062.

Adachi et al. (1983) "Chemical Etching Characteristics of (001)GaAs," J. Electrochem. Soc. 130:2427-2435.

Adeyeye et al. (2002) "Viscoelastic evaluation of topical creams containing microcrystalline cellulose/sodium carboxymethyl cellulose as stabilizer," AAPS PharmSciTech 3(2):16-25.

Adrega et al. (2010) "Stretchable Gold Conductors Embedded in PDMS and Patterned by Photolithography: Fabrication and Electromechanical Characterization," J. Micromech. Microeng. 20:055025.

Ago et al. (2005) "Aligned Growth of Isolated Single-Walled Carbon Nanotubes Programmed by Atomic Arrangement of Substrate Surface," Chem. Phys. Lett. 408:433-438.

Ago et al. (2006) "Synthesis of Horizontally-Aligned Single-Walled Carbon Nanotubes with Controllable Density on Sapphire Surface and Polarized Raman Spectroscopy," Chem. Phys. Lett. 421:399-403.

Aharoni (1972) "Electrical Resistivity of a Composite of Conducting Particles in an Insulating Matrix," Journal of Applied Physics. 43:2463.

Ahmed et al. (Web Release Oct. 11, 2005) "Extending the 3ω-Method to the MHz Range for Thermal Conductivity Measurements of Diamond Thin Films," Diamond Relat. Mater. 15(2-3):389-393.

Ahn et al. (2006) "Heterogeneous three-dimensional electronics by use of printed semiconductor nanomaterials," Science. 314:1754-1757.

Ahn et al. (2006) "High-speed mechanically flexible single-crystal silicon thin-film transistors on plastic substrates," IEEE Elect. Dev. Lett. 27:460-462.

Ahn et al. (2007) "Bendable integrated circuits on plastic substrates by use of printed ribbons of single-crystalline silicon," Appl. Phys. Lett. 90:213501.

Ahn et al. (2009) "Omnidirectional Printing of Flexible, Stretchable, and Spanning Silver Microelectrodes," Science. 323:1590-1593.

Alavi et al. (1992), "Fabrication of Microchannels by Laser Machining and Anisotropic Etching of Silicon", Sensors and Actuators A, vol. A32, No. 1/3, pp. 299-302.

Al-Halhouli et al. (2008) "Nanoindentation Testing of SU-8 Photoresist Mechanical Properties," Microelectronic Eng. 85:942-944.

Al-Hardan et al. (2010) "The effect of oxygen ratio on the crystallography and optical emission properties of reactive RF sputtered ZnO films," Physica B. 405:1081-1085.

Aliot, E. M. et al. (2009) "EHRA/HRS Expert Consensus on Catheter Ablation of Ventricular Arrhythmias: Developed in a partnership with the European Heart Rhythm Association (EHRA), a Registered Branch of the European Society of Cardiology (ESC), and the Heart Rhythm Society (HRS); in collaboration with the American College of Cardiology (ACC) and the American Heart Association (AHA)," Europace 11:771-817.

Alivisatos et al. (1996) "Semiconductor Clusters, Nanocrystals, and Quantum Dots," Science 271:933-937.

Alivisatos et al. (1998) "From Molecules to Materials: Current Trends and Future Directions," Adv. Mater. 10:1297-1336.

Allam et al. (1967) "The structure of evaporated silicon oxide films and its effect on the electrical and optical properties," Thin Solid Films. 68:245-254.

Allen et al. (Feb. 20, 2006) "Nanomaterial Transfer Using Hot Embossing for Flexible Electronic Devices," Appl. Phys. Lett. 88:083112.

Al-Sarawi et al. (Feb. 1998) "A Review of 3-D Packaging Technology," IEEE Trans.Comp. Packag. Manufac. Technol. B 21(1):2-14.

Altman et al. (2003) "Silk-Based Biomaterials," Biomaterials 24:401-416.

Amano et al. (Feb. 3, 1986) "Metalorganic Vapor Phase Epitaxial Growth of a High Quality GaN Film Using an AlN Buffer Layer," Appl. Phys. Lett. 48(5):353-355.

Ambat et al. (2000) "Studies on the influence of chloride ion and pH on the corrosion and electrochemical behaviour of AZ91D magnesium alloy," J. Appl. Electrochem. 30(7):865-874.

Ambrose et al. (2004) "Bioabsorbable implants: review of clinical experience in orthopedic surgery," Ann. Biomed. Eng. 32:171-177.

Ambrosy et al. (1996) "Silicon Motherboards for Multichannel Optical Modules," IEEE Trans. Compon. Pack. A 19:34-40.

Amir et al. (2000) "The Influence of Helium-Neon Irradiation on the Viability of Skin Flaps in the Rat," Br. J. Plast. Surg. 53:58-62.

Amsden et al. (Nov. 9, 2009) "Spectral Analysis of Induced Color Change on Periodically Nanopatterned Silk Films," Opt. Express 17(23):21271-21279.

Andersen et al. (2004) "Selecting the Signals for a Brain—Machine Interface," Curr. Opin. Neurobiol. 14:720-726.

Anderson et al. (2009) "Clinical and Financial Outcomes Due to Methicillin Resistant *Staphylococcus aureus* Surgical Site Infection: A Multi-Center Matched Outcomes Study," PLoS One. 4(12):1-8.

Andersson et al. (Oct. 16, 2002) "Active Matrix Displays Based on All-Organic Electrochemical Smart Pixels Printed on Paper," Adv. Mater. 14:1460-1464.

Ando et al. (2004) "Self-Aligned Self-Assembly Process for Fabricating Organic Thin-Film Transistors," Appl. Phys. Lett. 85:1849-1851.

Andosca et al. (May 2012) "Experimental and theoretical studies on MEMS piezoelectric vibrational energy harvesters with mass loading," Sensors and Actuators A. 178:76-87.

Angadi et al. (Web Release Jun. 1, 2006) "Thermal Transport and Grain Boundary Conductance in Ultrananocrystalline Diamond Thin Films," J. Appl. Phys. 99:114301.

(56) References Cited

OTHER PUBLICATIONS

Angelopoulos et al. (Sep. 17-21, 2012) "Manufacturing aspects of an ultra-thin chip technology," In; The Proceedings of the European Solid-State Device Research Conference (ESSDERC) 2012. Bordeaux, France. Ed.: Yann Deval. pp. 141-144.
Anik et al. (2002) "Effect of pH on the Anodic Behavior of Tungsten," Journal of the Electrochemical Society. 149(6):B224-B233.
Anik et al. (2006) "Dissolution kinetics of WO3 in acidic solutions," J. Appl. Electrochem. 36(5):603-608.
Aoki et al. (2003) "Microassembly of Semiconductor Three Dimensional Photonic Crystals," Nat. Mater. 2:117-121.
APC International, Ltd. (2011) Piezoelectric Ceramics: Principles and Applications. APC International. p. 16.
Arai et al. "Biodegradation of Bombyx mori silk fibroin fibers and films," J. Appl. Polym. 91:2383-2390.
Arnold et al. (2003) "Field-Effect Transistors Based on Single Semiconducting Oxide Nanobelts," J. Phys. Chem. B 107(3):659-663.
Athanasiou et al. (1998) "Orthopaedic applications for PLA-PGA biodegradable polymers," Arthroscopy 14:726-737.
Ayón et al. (Jan. 1999) "Characterization of a Time Multiplexed Inductively Coupled Plasma Etcher," J. Electrochem. Soc. 146(1):339-349.
Babcock et al. (2001) "Analog characteristics of metal-insulator-metal capacitors using PECVD nitride dielectrics," IEEE Electron Device Lett. 22:230-232.
Baca et al. (2007) "Printable Single-Crystal Silicon Micro/Nanoscale Ribbons, Platelets and Bars Generated from Bulk Wafers," Adv. Funct. Mater. 17:3051-3062.
Baca et al. (2008) "Semiconductor Wires and Ribbons for High-Performance Flexible Electronics," Angew. Chem. Int. Ed. 47:5524-5542.
Bachtold et al. (Nov. 9, 2001) "Logic Circuits with Carbon Nanotube Transistors," Science 294:1317-1320.
Badawy et al. (1998) "Corrosion and passivation behaviors of molybdenum in aqueous solutions of different pH," Electrochimica Acta. 44(4):693-702.
Bae et al. (Jul. 1, 2002) "Single-Crystalline Gallium Nitride Nanobelts," Appl. Phys. Lett. 81(1):126-128.
Bal et al. (Apr. 26, 2012) "Orthopedic applications of silicon nitride ceramics," Acta Biomater. 8:2889-2898.
Ball et al. (2004) "Towards an Implantable Brain-Machine Interface Based on Epicortical Field Potentials," Biomed. Tech. 49:756-759.
Balmer et al. (2005) "Diffusion of Alkanethiols in PDMS and Its Implications on Microcontact Printing (µCP)," Langmuir 21(2):622-632.
Banerjee et al. (2006) "Low-Temperature Deposition of ZnO Thin Films on PET and Glass Substrates by DC-Sputtering Technique," Thin Solid Films. 496:112-116.
Banerjee et al. (May 2001) "3-D ICs: A Novel Chip Design for Improving Deep-Submicrometerinterconnect Performance and Systems-on-Chip Integration," Proc. IEEE 89(5):602-633.
Bao et al. (1997) "High-Performance Plastic Transistors Fabricated by Printing Techniques," Chem. Mater. 9:1299-1301.
Bao et al. (1999) "Printable Organic and Polymeric Semiconducting Materials and Devices," J. Mater. Chem. 9:1895-1904.
Barbottin et al. (1989) "Instabilities in Field Effect Transistors," Ch. 15. In; Instabilities in Silicon Devices. vol. 2. Elsevier. Amsterdam, The Netherlands.
Barceloux et al. (1999) "Molybdenum," Journal of Toxicology: Clinical Toxicology. 37(2):231-237.
Barquins, M. (1992) "Adherence, Friction and Wear of Rubber-Like Materials," Wear 158:87-117.
Barreca et al. (2001) "A Study of Nanophase Tungsten Oxides Thin Films by XPS," Surface Science Spectra. 8(4):258-267.
Barreca et al. (2001) "Chemical Vapor Deposited Fe2O3 Thin Films Analyzed by XPS," Surface Science Spectra. 8(3):240-245.
Baskoutas et al. (2011) "Transition in the Optical Emission Polarization of ZnO Nanorods," J. Phys. Chem. C. 115:15862-15867.

Bates, F.S. (1991) "Polymer-Polymer Phase Behavior," Science 251:898-905.
Battaglia et al. (2003) "Colloidal Two-Dimensional Systems: CdSe Quantum Shells and Wells," Angew. Chem. Int. Ed. 442:5035-5039.
Bauer et al. (2004) "Biological Applications of High Aspect Ratio Nanoparticles," J. Mater. Chem. 14:517-526.
Bayarri et al. (2009) "Viscoelastic properties of aqueous and milk systems with carboxymethyl cellulose," Food Hydrocolloids. 23:441-450.
Bayliss et al. (1999) "The culture of neurons on silicon," Sensors and Actuators A: Physical. 74(1-3):139-142.
Becker et al. (2004) "Opinion of The Scientific Panel on Dietetic Products, Nutrition and Allergies on a Request from the Commission Related to the Tolerable Upper Intake Level of Silicon," The EFSA Journal 60:1-11.
Berg et al. (2003) "Tailored Micropatterns Through Weak Polyelectrolyte Stamping," Langmuir 19:2231-2237.
Bergstrom et al. (1990) "Surface chemistry of silicon nitride powders: Electrokinetic behaviour and ESCA studies," Colloid Surf. A. 49:183-197.
Bernard et al. (1998) "Printing Patterns of Proteins," Langmuir 14(9):2225-2229.
Bernardini et al. (1997) "Spontaneous polarization and piezoelectric constants of III-V nitrides," Physical Review B. 56:R10024.
Bett et al. (Aug. 1999) "III-V Compounds for Solar Cell Applications," Appl. Phys. A. Mater. Sci. 69(2):119-129.
Bettinger et al. (2010) "Biomaterials-based organic electronic devices," Polym Int. 59:563-567.
Bettinger et al. (2010) "Organic thin-film transistors fabricated on resorbable biomaterial substrates," Adv. Mater. 22:651-655.
Bevers et al. (2009) "The bioinorganic chemistry of tungsten," Coordination Chemistry Reviews. 253(3-4):269-290.
Bhrany et al. (Jan. 1, 2013) "Evaluation of a Sphere-Templated Polymeric Scaffold as a Subcutaneous Implant," JAMA Facial Plast. Surg. 15:29-33.
Bhunia et al. (2004) "Free-Standing and Vertically Aligned InP Nanowires Grown by Metalorganic Vapor Phase Epitaxy," Physica E 21:583-587.
Bhushan et al. (Nov. 2004) "Multiwalled Carbon Nanotube AFM Probes for Surface Characterization of Micro/Nanostructures," Microsyst. Technol. 10(8-9):633-639.
Bietsch et al. (Oct. 1, 2000) "Conformal Contact and Pattern Stability of Stamps Used for Soft Lithography," J. Appl. Phys. 88(7):4310-4318.
Biran et al. (2005) "Neuronal cell loss accompanies the brain tissue response to chronically implanted silicon microelectrode arrays," Experimental neurology. 195:115-126.
Biran et al. (2007) "The brain tissue response to implanted silicon microelectrode arrays is increased when the device is tethered to the skull," Journal Biomedical Materials Research, Part A. 82:169-178.
Bishay et al. (2000) "Temperature Coefficient of the Surface Resistivity of Two-Dimensional Island Gold Films," J. Phys. D. Appl. Phys. 33(18):2218-2222.
Blanchet et al. (2003) "Large Area, High Resolution, Dry Printing of Conducting Polymers for Organic Electronics," Appl. Phys. Lett. 82:463-465.
Blanchet et al. (2003) "Printing Techniques for Plastic Electronics," J. Imag. Sci. Tech. 47(4):296-303.
Blawert et al. (2009) "Different Underlying Corrosion Mechanism for Mg Bulk Alloys and Mg Thin Films," Plasma Processes and Polymers. 6:S690-S694.
Blazdell et al. (Nov. 1999) "Preparation of Ceramic Inks for Solid Freeforming Using a Continuous Jet Printer," J. Mat. Syn. Process. 7(6):349-356.
Block et al. (1998) "Association of Serum Phosphorus and Calcium X Phosphate Product with Mortality Risk in Chronic Hemodialysis Patients: A National Study," Am. J. Kidney Dis. 31(4):607-61.
Blom et al. (1990) "Thin-film ZnO as micromechanical actuator at low frequencies," Sensors and Actuators. 21:226-228.
Boltau et al. (1998) "Surface-Induced Structure Formation of Polymer Blends on Patterned Substrates," Nature 391:877-879.

(56) References Cited

OTHER PUBLICATIONS

Boncheva et al. (Mar. 15, 2005) "Magnetic Self-Assembly of Three-Dimensional Surfaces from Planar Sheets," Proc. Natl. Acad. Sci. USA 102(11):3924-3929.
Boncheva et al. (Mar. 8, 2005) "Templated Self-Assembly: Formation of Folded Structures by Relaxation of Pre-Stressed, Planar Tapes," Adv. Mater. 17(5):553-557.
Bourzac, K. (May/Jun. 2010) "TR10: Implantable Electronics," Technology Review, Published by MIT, http://www.technologyreview.com/biomedicine/25086/?a=f.
Bowden et al. (1997) "Self Assembly of Mesoscale Objects into Ordered Two-Dimensional Arrays," Science 276:233-235.
Bowden et al. (1998) "Spontaneous Formation of Ordered Structures in Thin Films of Metals Supported on an Elastomeric Polymer," Nature 393:146-149.
Bowden et al. (2001) "Molecule-Mimetic Chemistry and Mesoscale Self-Assembly," Acc. Chem. Res. 34:231-238.
Bowen et al. (May 14, 2013) "Zinc exhibits ideal physiological corrosion behavior for bioabsorbable stents," Advanced Materials. 25(18):2577-2582.
Bower et al. (2009) "Transfer-Printed Microscale Integrated Circuits," In; The Proc. 59th Elec. Comp. Tech. Conf (59th ECTC). San Diego, California. p. 618.
Bracher et al. (2009) "Shaped Films of Ionotropic Hydrogels Fabricated Using Templates of Patterns Paper," Adv. Mater. 21:445-450.
Bradley et al. (2003) "Flexible Nanotube Electronics," Nano Lett., vol. 3, No. 10, pp. 1353-1355.
Bramson et al. (2003) "Enabling Topical Immunization Via Microporation: A Novel Method for Pain-Free and Needle-Free Delivery of Adenovirus-Based Vaccines," Gene Ther. 10:251-260.
Braun et al. (1999) "Electrochemically Grown Photonic Crystals," Nature 402:603-604.
Briscoe (Aug. 30, 2012) "Measured efficiency of a ZnO nanostructured diode piezoelectric energy harvesting device," App. Phys. Lett. 101:093902.
Britton et al. (Web Release Oct. 25, 2005) "Microstructural Defect Characterization of a Si:H Deposited by Low Temperature HW-CVD on Paper Substrates," Thin Solid Films 501(1-2):79-83.
Brown et al. (2005) "Evaluation of Polydimethylsiloxane Scaffolds with Physiologically-Relevant Elastic Moduli: Interplay of Substrate Mechanics and Surface Chemistry Effects on Vascular Smooth Muscle Cell Response," Biomaterials 26:3123-3129.
Brown et al. (Dec. 19, 2001) "Heterogeneous Materials Integration: Compliant Substrates to Active Device and Materials Packaging," Mater. Sci. Eng. B 87(3):317-322.
Brown, H.R. (1991) "The Adhesion Between Polymers," Ann. Rev. Mater. Sci. 21:463-489.
Brugger et al. (1999) "Self-Aligned 3D Shadow Mask Technique for Patterning Deeply Recessed Surfaces of Micro-Electro-Mechanical Systems Devices," Sensors and Actuators. 76:329-334.
Bruschi et al. (2001) "Micromachined Silicon Suspended Wires With Submicrometric Dimensions," Microelectron. Eng. 57-58:959-965.
Buchanan (1999) "Scaling the gate dielectric: Materials, integration, and reliability," IBM J. Res. Develop. 43:245-264.
Buma et al. (2001) "High-Frequency Ultrasound Array Element Using Thermoelastic Expansion in an Elastomeric Film," Appl. Phys. Lett. 79:548-550.
Burdinski et al. (2005) "Single Etch Patterning of Stacked Silver and Molybdenum Alloy Layers on Glass Using Microcontact Wave Printing," J. Am. Chem. Soc. 127(31):10786-10787.
Burdinski, D. (non-dated) "Soft Lithography and Microcontact Wave Printing," http://www.research.philips.com/technologies/light_dev_microsys/softlitho/index.html, Downloaded May 23, 2007.
Burge et al. (Jun. 25, 1997) "X-Ray Holography for VLSI Using Synthetic Bilevel Holograms," Proc. Int. Soc. Opt. Eng. 3183:2-13.
Burghartz et al. (2009) "A New Fabrication and Assembly Process for Ultrathin Chips," IEEE Trans. Electron Dev. 56:321-327.
Burgin et al. (2000) "Large Area Submicrometer Contact Printing Using a Contact Aligner," Langmuir 16:5371-5375.
Burns et al. (2003) "Printing of Polymer Thin-Film Transistors for Active-Matrix-Display Applications," J. Soc. Inf. Display 11:599-604.
Butler et al. (2000) "In Vivo Degredation of Tungsten Embolisation Coils," The British Journal of Radiology. 73:601-603.
Bylander et al. (2005) "Current measurement by real-time counting of single electrons," Nature. 434(7031):361-364.
Camacho et al. (2011) "Structural, optical and electrical properties of ZnO thin films grown by radio frequency (rf) sputtering in oxygen atmosphere," International Journal of the Physical Sciences. 6:6660-6663.
Campbell et al. (1999) "Dynamics of Oxidation of Aluminum Nanoclusters using Variable Charge Molecular-Dynamics Simulations on Parallel Computers," Phys. Rev. Lett. 82:4866-4869.
Campbell et al. (2000) "Fabrication of Photonic Crystals for the Visible Spectrum by Holographic Lithography," Nature 404:53-56.
Cao et al. (2006) "Bilayer Organic-Inorganic Gate Dielectrics for High-Performance, Low-Voltage, Single-Walled Carbon Nanotube Thin-Film Transistors, Complementary Logic Gates, and p-n Diodes on Plastic Substrates," Adv. Funct. Mater. 16:2355-2362.
Cao et al. (2006) "Highly Bendable,Transparent Thin-Film Transistors That Use Carbon-Nanotube-Based Conductors and Semiconductors with Elastomeric Dielectrics," Adv. Mater. 18(3):304-309.
Cao et al. (2006) "Transparent flexible organic thin-film transistors that use printed single-walled carbon nanotube electrodes," Applied Physics Letters 88:113511.
Cao et al. (Jan. 5, 2009) "Ultrathin Films of Single-Walled Carbon Nanotubes for Electronics and Sensors: A Review of Fundamental and Applied Aspects," Adv. Mater. 21(1):29-53.
Cao et al. (Jul. 24, 2008) "Medium-Scale Carbon Nanotube Thin-Film Integrated Circuits on Flexible Plastic Substrates," Nature 454:495-500.
Capala et al. (2003) "Boron Neutron Capture Therapy for Glioblastoma Multiforme: Clinical Studies in Sweden," J. Neuro-Oncol. 62:135-144.
Capelli et al. (2011) "Integration of Silk Protein in Organic and Light Emitting Transistors," Organic Electronics. 12:1146-1151.
Carcia et al. (2006) "High-performance ZnO thin-film transistors on gate dielectrics grown by atomic layer deposition," Appl. Phys. Lett. 88:123509.
Carlson et al. (Aug. 31, 2012) "Transfer Printing Techniques for Materials Assembly and Micro/Nanodevice Fabrication," Adv. Mater. 24:5284-5318.
Carr et al. (1998) "Measurement of Nanomechanical Resonant Structures in Single-Crystal Silicon," J. Vac. Sci. Technol. B 16:3821-3824.
Cavusoglu et al. (2005) "Resorbable plate-screw systems: Clinical applications," Ulus. Travma Acil Cerrahi Derg. 11:43-48.
Ceiler et al. (1995) "Plasma-Enhanced Chemical Vapor Deposition of Silicon Dioxide Deposited at Low Temperatures," J. Electrochem. Soc. 142:2067-2071.
Chang et al. (1994) "Process Techniques," "Lithography," and "Device-Related Physics and Principles," In; GaAs High-Speed Devices: Physics, Technology and Circuit Application, John Wiley and Sons, New York, pp. 115-278.
Chang et al. (2010) "Direct-write piezoelectric polymeric nanogenerator with high energy conversion efficiency," Nano Lett. 10:726-731.
Chaudhury et al. (1991) "Direct Measurement of Interfacial Interactions Between Semispherical Lenses and Flat Sheets of Poly(dimethylsiloxane) and their Chemical Derivatives," Langmuir 7:1013-1025.
Chen et al. (2003) "Characterization of Pd—GaAs Schottly Diodes Prepared by the Electrodes Plating Technique," Semiconductor. Sci. Technol. 18:620-626.
Chen et al. (2003) "Electronic Paper: Flexible Active-Matrix Electronics Ink Display," Nature 423:136.
Chen et al. (2005) "Humidity Sensors: A Review of Materials and Mechanisms," Sensor Letters. 3:274-295.
Chen et al. (2005) "InGaN Nanorings and Nanodots by Selective Area Epitaxy," Appl. Phys. Lett. 87:143111.

(56) References Cited

OTHER PUBLICATIONS

Chen et al. (2005) "The Role of Metal-Nanotube Contact in the Performance of Carbon Nanotube Field-Effect Transistors," Nano Lett. 5(7):1497-1502.
Chen et al. (Feb. 27, 2006) "Complementary Carbon Nanotube-Gated Carbon Nanotube Thin-Fim Transistor," Appl. Phys. Lett. 88:093502.
Chen et al. (Jun. 2002) Effect of Process Parameters on the Surface Morphology and Mechanical Performance of Silicon Structures After Deep Reactive Ion Etching (DRIE) J. Microelectromech. Syst. 11(3):264-275.
Chen et al. (Mar. 2004) "A Family of Herringbone Patterns in Thin Films," Scripta Materialia 50(6):797-801.
Chen et al. (Mar. 24, 2006) "An Integrated Logic Circuit Assembled on a Single Carbon Nanotube," Science 311:1735.
Chen et al. (Sep. 2004) "Herringbone Buckling Patterns of Compressed Thin Films on Compliant Substrates," J. Appl. Mech. 71:597-603.
Cheng (2011) "Effects of Post-Deposition Rapid Thermal Annealing on Aluminum-Doped ZnO Thin Films Grown by Atomic Layer Deposition," Appl. Surf. Sci. 258:604-607.
Cheng et al. (2005) "Ink-Jet Printing, Self-Assembled Polyelectrolytes, and Electroless Plating: Low Cost Fabrication of Circuits on a Flexible Substrate at Room Temperature," Macromol. Rapid Commun. 26:247-264.
Chern et al. (1980) "A new method to determine MOSFET channel length," IEEE Electron. Dev. Lett. 1:170-173.
Chiappini et al. (2010) "Biodegradable Porous Silicon Barcode Nanowires with Defined Geometry," Adv. Funct. Mater. 20:2231-2239.
Childs et al. (2002) "Decal Transfer Microlithography: A New Soft-Lithographic Patterning Method," J. Am. Chem. Soc. 124:13583-13596.
Childs et al. (2005) "Masterless Soft-Lithography: Patterning UV/Ozone-Induced Adhesion on Poly(dimethylsiloxane) Surfaces," Langmuir 21:10096-10105.
Childs et al. (Aug. 14, 2004) "Patterning of Thin-Film Microstructures on Non-Planar Substrate Surfaces Using Decal Transfer Lithography," Adv. Mater. 16(15):1323-1327.
Chiu et al. (1995) "Effects of polymer degradation on drug released—mechanistic study of morphology and transport properties in 50:50 poly(dl-lactide-co-glycolide)," Int. J. Pharm. 126:169-178.
Cho et al. (1999) "UV-photoassisted etching of GaN in KOH," J. Electron. Mater. 28:290-294.
Cho et al. (2009) "Characterization of the Biaxial Textures of MgO Thin Films Grown By E-Beam Evaporation," Journal of the European Ceramic Society. 30:481-484.
Choi et al. (2003) "Investigation of Gate-Induced Drain Leakage (GIDL) Current in Thin Body Devices: Single-Gate Ultra-Thin Body, Symmetrical Double-Gate, and Asymmetrical Double-Gate MOSFETs," Jpn. J. Appl. Phys. 42:2073-2076.
Choi et al. (2007) "Biaxially Stretchable 'Wavy' Silicon Nanomembranes," Nano Lett. 7(6):1655-1663.
Choi et al. (2009) "The Effects of Rapid Thermal Annealing on the Performance of ZnO Thin-Film Transistors," J. Kor. Phys. Soc. 55:1925-1930.
Choi et al. (Web Release Jan. 25, 2005) "Simple Detachment Patterning of Organic Layers and Its Applications to Organic Light-Emitting Diodes," Adv. Mater. 17(2):166-171.
Choi-Yim et al. (1998) "The effect of silicon on the glass forming ability of the Cu47Ti34Zr11Ni8 bulk metallic glass forming alloy during processing of composites," J. Appl. Phys. 83:7993.
Chou et al. (1996) "Imprint Lithography with 25 Nanometer Resolution," Science. 272(5258):85-87.
Chou et al. (2004) "An Orientation-Controlled Pentacene Film Aligned by Photoaligned Polyimide for Organic Thin-Film Transistor Applications," Adv. Func. Mater. 14:811-815.
Chou et al. (Jun. 8, 1999) "Micromachining on (111)-Oriented Silicon," Sens. Actuators A 75(3):271-277.

Chu et al. (2005) "High-Performance Organic Thin-Film Transistors with Metal Oxide/Metal Bilayer Electrode," Appl. Phys. Lett. 87:193508.
Chung et al. (2000) Silicon Nanowire Devices Appl. Phys. Lett. 76(15):2068-2070.
Chung et al. (2003) "Nanoscale Gap Fabrication by Carbon Nanotube-Extracted Lithography (CEL)," Nano Lett. 3(8):1029-1031.
Chung et al. (2011) "Fabrication of Releasable Single-Crystal Silicon-Metal Oxide Field-Effect Devices and Their Deterministic Assembly on Foreign Substrates," Adv. Func. Mater. 21:3029-3036.
Chung et al. (Jul. 1, 2003) "A Study on Formation of Al and Al2O3 on the Porous Paper by DC Magnetron Sputtering," Surf. Coat. Technol. 171(1-3):65-70.
Clerc, L. (1976) "Directional Differences of Impulse Spread in Trabecular Muscle from Mammalian Heart," J. Physiol. 255:335-346.
Cohen-Karni et al. (2009) "Flexible Electrical Recording from Cells Using Nanowire Transistor Arrays," Proc. Natl. Acad. Sci. USA 106:7309-7313.
Cole et al. (2008) "Patterned Growth and Transfer of ZnO Micro- and Nanocrystals with Size and Location Control," Adv. Mater. 20:1474-1478.
Collins et al. (Apr. 27, 2001) "Engineering Carbon Nanotubes and Nanotube Circuits Using Electrical Breakdown," Science 292:706-709.
Cong et al. (2010) "CNT-Based Photopatternable Nanocomposites with High Electrical Conductivity and Optical Transparency," J. Micromech. Microeng. 20:025002.
Corazza et al. (2007) "Photobiomodulation on the Angiogenesis of Skin Wounds in Rats Using Different Light Sources," Photomedicine Laser Surg. 25:102-106.
Costner et al. (2009) "Nanoimprint Lithography Materials Development for Semiconductor Device Fabrication," Annu. Rev. Mater. Res. 39:155-180.
Cox, H. L. (1952) "The Elasticity and Strength of Paper and Other Fibrous Materials," Br. J. Appl. Phys. 3:72-79.
Creagh et al. (2003) "Design and Performance of Inkjet Print Heads for Non-Graphic-Arts Applications," MRS Bull. 28:807-811.
Crone et al. (Feb. 3, 2000) "Large-Scale Complementary Integrated Circuits Based on Organic Transistors," Nature 403:521-523.
Crowder et al. (1998) "Low-Temperature Single-Crystal Si TFTs Fabricated on Si Films Processed via Sequential Lateral Solidification," IEEE Electron. Dev. Lett. 19:306-308.
Csutak et al. (2002) "CMOS-compatible high-speed planar silicon photodiodes fabricated on SOI substrates," IEEE Journal of Quantum Electronics. 38:193-196.
Cui et al. (2001) "Nanowire Nanosensors for Highly Sensitive and Selective Detection of Biological and Chemical Species," Science 293:1289-1292.
Czekalla et al. (2008) "Spatial fluctuations of optical emission from single ZnO/MgZnO nanowire quantum wells," Nanotechnology. 19:115202.
Dagdeviren et al. (Apr. 19, 2013) "Transient, Biocompatible Electronics and Energy Harvesters Based on ZnO," Small. 9(20):3398-3404.
Dai et al. (2002) "Gallium Oxide Nanoribbons and Nanosheets," J. Phys. Chem. B 106(5):902-904.
Dai et al. (2003) "Novel Nanostructures of Functional Oxides Synthesized by Thermal Evaporation," Adv. Funct. Mater. 13:9-24.
Dameron et al. (2008) "Gas Diffusion Barriers on Polymers Using Multilayers Fabricated by Al2O3 and Rapid SiO2 Atomic Layer Deposition," J. Phys. Chem. C. 112:4573-4580.
Danckwerts (1950) "Absorption by Simultaneous Diffusion and Chemical Reaction," Tran. Faraday Soc. 46:300-304.
Darhuber et al. (2003) "Microfluidic Actuation by Modulation of Surface Stresses," Appl. Phys. Lett. 82(4):657-659.
Davenward et al. (Jan. 1, 2013) "Silicon-rich mineral water as a non-invasive test of the aluminum hypothesis' in Alzheimer's disease," J Alzheimers Dis. 33:423-430.
David et al. (Apr. 26, 2012) "Dissolution Kinetics and Solubility of ZnO Nanoparticles Followed by AGNES," J. Phys. Chem. 116:11758-11767.

(56) References Cited

OTHER PUBLICATIONS

Davidson et al. (2004) "Supercritical Fluid-Liquid-Solid Synthesis of Gallium Arsenide Nanowires Seeded by Alkanethiol-Stabilized Gold Nanocrystals," Adv. Mater. 16:646-649.

De Gans (2004) "Inkjet Printing of Polymers: State of the Art and Future Developments," Adv. Mater. 16(3):203-213.

De Rosa et al. (2004) "The wet corrosion of molybdenum thin film —. Part I: Behavior at 25° C.," Materials and Corrosion. 55(8):602-609.

De Sio et al. (Web Release May 18, 2005) "Electro-Optical Response of a Single-Crystal Diamond Ultraviolet Photoconductor in Transverse Configuration," Appl. Phys. Lett. 86:213504.

DeBoer et al. (2004) "Organic Single-Crystal Field-Effect Transistors," Phys. Stat. Sol. 201:1302-1331.

Deen et al. (2004) "Electrical Characterization of Polymer-Based FETs Fabricated By Spin-Coating Poly(3-alkylthiophene)s," IEEE Trans. Electron Devices 51:1892-1901.

Delmerche et al. (1997) "Stability of Molded Polydimethylsiloxane Microstructures," Adv. Mat. 9:741-746.

Deng et al. (2007) "Distribution of PBDEs in air particles from an electronic waste recycling site compared with Guangzhou and Hong Kong, South China," Environment International. 33:1063-1069.

Deruelle et al. (1995) "Adhesion at the Solid-Elastomer Interface: Influence of Interfacial Chains," Macromol. 28:7419-7428.

Derycke et al. (Sep. 2001) "Carbon Nanotube Inter- and Intramolecular Logic Gates," Nano Lett. 1(9):453-456.

Desai et al. (Feb. 1999) "Nanopore Technology for Biomedical Applications," Biomed. Microdevices 2(1):11-40.

Dharmadasa et al. (Apr. 8, 2014) "Intense Pulsed Light Sintering of Electrodeposited CdS Thin Films," Advanced Engineering Materials. 16(11):1351-1361.

Diao et al. (2010) "Reduced Low Frequency Noise in Electron Beam Evaporated MgO Magnetic Tunnel Junctions," Appl. Phys. Lett. 96:202506.

Dick et al. (Jun. 2004) "Synthesis of Branched 'Nanotrees' by Controlled Seeding of Multiple Branching Events," Nat. Mater. 3:380-384.

Dickey et al. (2008) "Fabrication of Arrays of Metal and Metal Oxide Nanotubes by Shadow Evaporation," ACS. Nano. 2(4):800-808.

Dickey et al. (2010) "Transistors Formed from a Single Lithography Step Using Information Encoded in Topography," Small. 6(18):2050-2057.

Diftis et al. (2003) "Improvement of emulsifying properties of soybean protein isolate by conjugation with carboxymethyl cellulose," Food Chemistry. 81(1):1-6.

DiLorenzo et al. (Nov. 7, 2014) "Chronic Recording Electrocorticography Guided Resective Epilepsy Surgery: Overview and Future Directions," Journal of Nuerosurgery. 120:1402-1414.

Dimroth et al. (Mar. 2007) "High Efficiency Multijunction Solar Cells," MRS Bull. 32:230-235.

Ding et al. (Oct. 4, 2004) "Self Catalysis and Phase Transformation in the Formation of CdSe Nanosaws," Adv. Mater. 16(19):1740-1743.

Dinsmore et al. (2002) "Colloidosomes: Selectively Permeable Capsules Composed of Colloidal Particles," Science 298:1006-1009.

Divliansky et al. (2003) "Fabrication of Three-Dimensional Polymer Photonic Crystal Structures Using Single Diffraction Element Interference Lithography," Appl. Phys. Lett. 82(11):1667-1669.

Dodabalapur A. (Apr. 2006) "Organic and Polymer Transistors for Electronics," Mater Today 9(4):24-30.

Dodabalapur et al. (1995) "Organic Transistors: Two-Dimensional Transport and Improved Electrical Characteristics," Science 268:270-271.

Dolan (1977) "Offset Masks for Lift—Off Photoprocessing," Appl. Phys. Lett. 31(5):337-339.

Dong et al. (2011) "Initiation and repassivation of pitting corrosion of carbon steel in carbonated concrete pore solution," Corrosion Science. 53(4):1322-1330.

Dove (1999) "The dissolution kinetics of quartz in aqueous mixed cation solutions," Geochim. Cosmochim. Acta. 63:3715-3727.

Dove et al. (1997) "The influence of the alkaline earth cations, magnesium, calcium,.And barium on the dissolution kinetics of quartz," Geochim. Cosmochim. Acta. 61:3329-3340.

Duan et al. (2000) "General Synthesis of Compound Semiconductor Nanowires," Adv. Mater. 12(4):298-302.

Duan et al. (2003) "High-performance Thin-Film Transistors Using Semiconductor Nanowires and Nanoribbons," Nature 425:274-278.

Duan X. (2003) "Semiconductor Nanowires: From Nanoelectronics to Macroelectronics," Abstract from a presentation given at the 11th Foresight Conference on Molecular Nanotechnology, Oct. 10-20, Burlingame, CA.

Duboz et al. (1998) "Transistors and Detectors Based on GaN-Related Materials," In; Group III Nitride Semiconductor Compounds, Gill, B. ed., Clarendon, Oxford, pp. 343-387.

Ducéré et al. (2005) "A capacitive humidity sensor using crosslinked cellulose acetate butyrate," Sensors and Actuators B: Chemical. 106:331-334.

Duesberg et al. (2000) "Polarized Raman Spectroscopy on Isolated Single-Wall Carbon Nanotubes," Phys. Rev. Lett., vol. 85, No. 25, pp. 5436-5439.

Duffy et al. (1998) "Rapid Prototyping of Microfluidic Systems in Poly(dimethylsiloxane)," Anal. Chem. 70:4974-4984.

Dupuis et al. (2008) "History, Development, and Applications of High-Brightness Visible Light-Emitting Diodes," IEEE J. Lightwave Tech. 26:1154-1171.

Durkop et al. (2004) "Extraordinary Mobility in Semiconducting Carbon Nanotube," Nano Lett. 4(1):35-39.

Eder et al. (Apr. 5, 2004) "Organic Electronics on Paper," Appl. Phys. Lett. 84(14):2673-2675.

Edrington et al. (2001) "Polymer-Based Photonic Crystals," Adv. Mater. 13:421-425.

Edwards et al. (2012) "Optically monitoring and controlling nanoscale topography during semiconductor etching," Light Sci. Appl. 1:e30.

Efimenko et al. (Oct. 15, 2002) "Surface Modification of Sylgard-184 Poly(dimethyl Siloxane) Networks by Ultraviolet and Ultraviolet/Ozone Treatment," J. Colloid Interface Sci. 254(2):306-315.

Eftekhari, G. (1993) "Variation in the Effective Richardson Constant of Metal—GaAs and Metal—InP Contacts Due to the Effect of Processing Parameters," Phys. Status Solid A—Appl. Res. 140:189-194.

Egger et al. (2005) "Dynamic Shadow Mask Technique: A Universal Tool for Nanoscience," Nano Lett. 5(1):15-20.

Ensell, G. (1995) "Free Standing Single-Crystal Silicon Microstructures," J. Micromech. Microeng. 5:1-4.

Erogbogbo et al. (2008) "Biocompatible Luminescent Silicon Quantum Dots for Imaging of Cancer Cells," ACS Nano. 2(5):873-878.

Erogbogbo et al. (2010) "Biocompatible Magnetofluorescent Probes: Luminescent Silicon Quantum Dots Coupled with Superparamagnetic Iron(III) Oxide," ACS Nano. 4(9):5131-5138.

Escabi et al. (Jun. 11, 2014) "A high-density, high-channel count, multiplexed 1-1ECoG array for auditory-cortex recordings," Journal of neurophysiology. 112:1566-1583.

Faez et al. (1999) "An Elastomeric Conductor Based on Polyaniline Prepared by Mechanical Mixing," Polymer 40:5497-5503.

Farra et al. (2012) "First-in-Human Testing of a Wirelessly Controlled Drug Delivery Microchip," Sci. Trans. Med. 4(122). pp. 1-10.

Feigner et al. (1996) "Flexural Rigidity of Microtubules Measured with the Use of Optical Tweezers," J. Cell Sci. 109:509-516.

Fink et al. (1999) "Block Copolymers as Photonic Bandgap Materials," J. Lightwave Tech. 17:1963-1969.

Fink et al. (2002) "Enhancement of device performance in vertical sub-100 nm MOS devices due to local channel doping," Solid State Electron. 46:387-391.

Flanders (1979) "X-ray Lithography at <100 Å Linewidths Using X-Ray Masks Fabricated by Shadowing Techniques," J. Vac. Sci. Technol. 16(6):1615-1619.

(56) References Cited

OTHER PUBLICATIONS

Flewitt et al. (2005) "Low-Temperature Deposition of Hydrogenated Amorphous Silicon in an Electron Cyclotron Resonance Reactor for Flexible Displays," Proc. IEEE 93:1364-1373.
Folch et al. (1999) "Wafer-Level In-Registry Microstamping," J. Microelectromech. Syst. 8:85-89.
Fontes et al. (Oct. 2012) "Electrodes for bio-application: recording and stimulation," J. Phys. Cont. Ser. 421:012019.
Forment et al. (2004) "Influence of Hydrogen Treatment and Annealing Processes Upon the Schottky Barrier Height of Au/n-GaAs and Ti/n-GaAs Diodes," Semicond. Sci. Technol. 19:1391-1396.
Forrest et al. (2004) "The Path to Ubiquitous and Low-Cost Organic Electronic Appliances on Plastic," Nature 428:911-918.
Fortunato et al. (2005) "Flexible a-Si: H Position-Sensitive Detectors," Proc. IEEE 93:1281-1286.
Fortunato et al. (Sep. 2008) "High-Performance Flexible Hybrid Field-Effect Transistors Based on Cellulose Fiber Paper," IEEE Electron. Dev. Lett. 29(9):988-990.
Fosmire (1990) "Zinc toxicity," Am. J. Clin. Nutr. 51:225-227.
Freeman et al. (2000) "Spatial Spectral Analysis of Human Electrocardiograms Including the Alpha and Gamma Bands," J. Neurosci. Methods 95:111-121.
Freire et al. (1999) "Thermal Stability of Polyethylene Terephthalate (PET): Oligomer Distribution and Formation of Volatiles," Packag. Technol. Sci. 12:29-36.
Freund, L.B. (2000) "The Mechanics of Electronic Materials," Int. J. Solids Struct. 37:185-196.
Friedman et al. (2005) "High-Speed Integrated Nanowire Circuits," Nature 434:1085.
Frizzel et al. (1995) "Cure, Morbidity, and Mortality Associated with Embolization of Brain Arteriovenous Malformations: A Review of 1246 Patients in 32 Series over a 35-Year Period," Neurosurgery. 37:1031-1040.
Fu et al. (Jan. 10, 2003) "Patterning of Diamond Microstructures on Si Substrate by Bulk and Surface Micromachining," J. Mater. Process. Technol. 132(1-3):73-81.
Fukushima et al. (2010) "Surface tension-driven chip self-assembly with load-free hydrogen fluoride-assisted direct bonding at room temperature for three-dimensional integrated circuits," Appl. Phys. Lett. 96:154105.
Fulati et al. (2009) "Miniaturized pH Sensors Based on Zinc Oxide Nanotubes/Nanorods," Sensors. 9:8911-8923.
Furneaux et al. (1989) "The Formation of Controlled-Porosity Membranes from Anodically Oxidized Aluminum," Nature 337:147-149.
Gabriel et al. (2006) "The dielectric properties of biological tissues: I. Literature survey," Phys. Med. Biol. 41:2231-2249.
Gabriel et al. (2009) "Electrical conductivity of tissue at frequencies below 1 MHz," Phys. Med. Biol. 54:4863-4878.
Gad et al. (2008) "Formulation and Evaluation of PLA and PLGA In Situ Implants Containing Secnidazole and/or Doxycycline for Treatment of Periodontitis," AAPS PharmSciTech. 9:878-884.
Gan et al. (2002) "Preparation of Thin-Film Transistors With Chemical Bath Deposited CdSe and CdS Thin Films," IEEE Trans. Electron. Dev. 49:15-18.
Gao et al. (Sep. 9, 2005) "Conversion of Zinc Oxide Nanobelts into Superlattice-Structures Nanohelices," Science 309:1700-1704.
Garcia et al. (2004) "Etchant Anisotropy Controls the Step Bunching Instability in KOH Etching of Silicon," Phys. Rev. Lett. 93(16):166102.
Gardner et al. (1965) "Physical Aspects of the Internal Water Relations of Plant Leaves," Plant Physiol. 40:705-710.
Garnier et al. (1994) "All-Polymer Field-Effect Transistor Realized by Printing Techniques," Science 265:1684-1686.
Gatti et al. (2004) "Detection of micro- and nano-sized biocompatible particles in the blood," Journal of Materials Science: Materials in Medicine. 15(4):469-472.
Geim et al. (Mar. 2007) "The Rise of Graphene," Nature Mater. 6:183-191.

Geissler et al. (2003) "Fabrication of Metal Nanowires Using Microcontact Printing," Langmuir 19(15):6301-6311.
Geissler et al. (Jun. 2003) "Selective Wet-Etching of Microcontact-Printed Cu Substrates with Control Over the Etch Profile," Microelec. Eng. 67-68:326-332.
Gelinck et al. (2000) "High-Performance All-Polymer Integrated Circuits," Appl. Phys. Lett. 77:1487-1489.
Gelinck et al. (2004) "Flexible Active-Matrix Displays and Shift Registers Based on Solution-Processed Organic Transistors," Nat. Mater. 3:106-110.
Gentile et al. (Feb. 28, 2014) "An overview of poly(lactic-coglycolic) acid (PLGA)-based biomaterials for bone tissue engineering," Int. J. Mol. Sci. 15:3640-3659.
Georgakilas et al. (2002) "Wafer-Scale Integration of GaAs Optoelectronic Devices with Standard Si Integrated Circuits Using a Low-Temperature Bonding Procedure," Appl. Phys. Lett. 81:5099-5101.
Gerischer et al. (1992) "Chemical dissolution of zinc oxide crystals in aqueous electrolytes—An analysis of the kinetics," Electrochimica Acta. 37:827-835.
Givargizov, E.I. (1991) "Applications," In; Oriented Crystallization on Amorphous Substrates, Plenum Press, New York, pp. 341-363.
Goetting et al. (1999) "Microcontact Printing of Alkanephosphonic Acids on Aluminum: Pattern Transfer by Wet Chemical Etching," Langmuir 15:1182-1191.
Goldman et al. (1996) "Correlation of Buffer Strain Relaxation Modes with Transport Properties of Two-Dimensional Electron Gases," J. Appl. Phys. 80:6849-6854.
Goldmann et al. (2004) "Hole Mobility in Organic Single Crystals Measured by a "Flip-Crystal" Field-Effect Technique," J. Appl. Phys. 96:2080-2086.
Goldsmith, T.H. (Sep. 1990) "Optimization, Constraint, and History in the Evolution of Eyes," Quart. Rev. Biol. 65(3):281-322.
Gracias et al. (2000) "Forming Electrical Networks in Three Dimensions by Self-Assembly," Science. 289:1170-1172.
Grant et al. (Oct. 30, 2013) "Health consequences of exposure to e-waste: a systematic review," The Lancet Global Health. 1:e350-e361.
Gratz et al. (1991) "Atomic Force Microscopy of Atomic-Scale Ledges and Etch Pits Formed During Dissolution of Quartz," Science, 251:1343-1346.
Gray et al. (Dec. 2001) "Screen Printed Organic Thin Film Transistors (OTFTs) on a Flexible Substrate," Proc. SPIE 4466:89-94.
Gray et al. (Mar. 5, 2004) "High-Conductivity Elastomeric Electronics," Adv. Mater. 16(5):393-397.
Grayson, T. (2002) "Curved Focal Plane Wide Field of View Telescope Design," Proc. SPIE 4849:269-274.
Grosjean et al. (2006) "Hydrolysis of Mg-salt and MgH2-salt mixtures prepared by ball milling for hydrogen production," Journal of Alloys and Compounds. 416:296-302.
Gruen et al. (Mar. 21, 1994) "Fullerenes as Precursors for Diamond Film Growth Without Hydrogen or Oxygen Additions," Appl. Phys. Lett. 65(12):1502-1504.
Gu et al. (2009) "In Vitro Corrosion and Biocompatibility of Binary Magnesium Alloys," Biomaterials. 30:484-498.
Gudiksen et al. (Web Release Apr. 18, 2001) "Synthetic Control of the Diameter and Length of Single Crystal Semiconductor Nanowires," J. Phys. Chem. B 105:4062-4064.
Gullapalli et al. (2010) "Flexible Piezoelectric ZnO-Paper Nanocomposite Strain Sensor," Small. 6:1641-1646.
Guo (2004) "Recent Progress in Nanoimprint Technology and its Applications," J. Phys. D: Appl. Phys. 37:R123-R141.
Guo et al. (Aug. 19, 2002) "Metal-Insulator-Semiconductor Electrostatics of Carbon Nanotubes," Appl. Phys. Lett. 81(8):1486-1488.
Gupta et al. (2010) "Development of gas sensors using ZnO nanostructures," J. Chem. Sci. 122:57-62.
Gur et al. (2005) "Air-Stable All-Inorganic Nanocrystal Solar Cells Processed from Solution," Science 310:462-465.
Gurbuz et al. (Jul. 2005) "Diamond Semiconductor Technology for RF Device Applications." Solid State Electron. 49(7):1055-1070.

(56) References Cited

OTHER PUBLICATIONS

Haisma et al. (2002) "Contact Bonding, Including Direct-Bonding in a Historical and Recent Context of Materials Science and Technology, Physics and Chemistry," Mater. Sci Eng. 37:1-60.
Halik et al. (2004) "Low-Voltage Organic Transistors with an Amorphous Molecular Gate Dielectric," Nature 431:963-966.
Hamedi et al. (May 2007) "Towards Woven Logic from Organic Electronic Fibres," Nat. Mater. 6:357-362.
Hamer et al. (2009) "AMOLED Displays Using Transfer-Printed Integrated Circuits," In; sid 2009 International Symposium Digest of Technical Papers. 15:947-950.
Hamer et al. (2009) "AMOLED Displays Using Transfer-Printed Integrated Circuits," SID 2009 International Symposium Digest of Technical Papers. 15:947-950.
Hamilton et al. (2004) "Field-Effect Mobility of Organic Polymer Thin-Film Transistors," Chem. Mater. 16:4699-4704.
Han et al. (2005) "Template-Free Directional Growth of Single-Walled Carbon Nanotues on a- and r-Plane Sapphire," J. Am. Chem. Soc. 127:5294-5295.
Han et al. (2010) "Potential Dissolution and Photo-Dissolution of ZnO Thin Films," Journal of Hazardous Materials. 178:115-122.
Hao et al. (2002) "Comparison of the Properties for ZnO: Al Films Depositied on Polyimide and Glass Substrates," Mater. Sci. Eng. B. 90:50-54.
Harada et al. (2001) "Catalytic Amplification of the Soft Lithographic Patterning of Si. Nonelectrochemical Orthogonal Fabrication of Photoluminescent Porous Si Pixel Arrays," J. Am. Chem. Soc. 123:8709-8717.
Haran et al. (Dec. 15-17, 2008) "22 nm Technology Compatible Fully Functional 0.1 µm2 6T-SRAM Cell," In; Electron Devices Meeting, 2008. IEDM 2008. IEEE International. San Francisco, California.
Harkonen et al. (Jun. 8, 2006) "4 W Single-Transverse Mode VECSEL Utilizing Intra-Cavity Diamond Heat Spreader," Electron Lett. 42(12):693-694.
Hawkeye et al. (2007) "Glancing Angle Deposition: Fabrication, Properties, and.Applications of Micro- and Nanostructured Thin Films," J. Vac. Sci. Technol. A. 25:1317-1335.
Hawtin et al. (1964) "The Role of In-Pore Mass Transport Resistance in The Reaction of Porous Solids with Gases," Chemical Engineering Science. 19:819-834.
Hayase et al. (2001) "Photoangioplasty with Local Motexafin Lutetium Delivery Reduces Macrophages in a Rabbit Post-Balloon Injury Model," Cardiovascular Res. 49:449-455.
He et al. (2005) "Si Nanowire Bridges in Microtrenches: Integration of Growth into Device Fabrication," Adv. Mater. 17:2098-2102.
Hebeish et al. (Jan. 30, 2013) "Development of CMC hydrogels loaded with silver nano-particles for medical applications," Carbohydrate Polymers. 92:407-413.
Heffelfinger et al. (1997) "Steps and the structure of the (0001) α-alumina surface," Surf. Sci., 370:L168-L172.
Heo et al. (2007) "Effects of O2 Ambient on the Properties of MgO Thin Films Deposited by E-Beam Evaporation," J. Electrochem. Soc. 154(11):J352-J356.
Hermawan et al. (2010) "Fe—Mn alloys for metallic biodegradable stents: Degradation and cell viability studies," Acta Biomaterialia. 6(5):1852-1860.
Hierlemann (2005) In; Integrated Chemical Microsensor Systems in CMOS Technology. Springer Berlin. Heidelberg, Germany. pp. 1-229.
Hillbrog et al. (Web Release Dec. 30, 2003) "Nanoscale Hydrophobic Recovery: A Chemical Force Microscopy Study of UV/Ozone-Treated Cross-Linker Poly(dimethylsiloxane)," Langmuir 20(3):785-794.
Hines et al. (2005) "Nanotransfer Printing of Organic and Carbon Nanotube Thin-Film Transistors on Plastic Substrates," Appl. Phys. Lett. 86:163101.
Hiramatsu et al. (2007) "Influence of Thermal Annealing on Microstructure of Zinc Oxide Films Deposited by Magnetron Sputtering," Jpn. J. Appl. Phys. 46:3319-3323.
Hixson et al. (1995) "Valence-band and core photoelectron spectroscopic studies of molybdenum aqueous oxidation and the influence of argon-ion etching," Journal of the Chemical Society, Faraday Transactions. 91(20):3593-3601.
Hoffman et al. (2003) "ZnO-based transparent thin-film transistors," Appl. Phys. Lett. 82:733.
Holdeman et al. (1985) "An Approach to Fabricating Sub-Half-Micrometer-Length Gates for GaAs Metal-Semiconductor Field-Effect Transistors," J. Vac. Sci. Technol. B. 3(4):956-958.
Hölke et al. (1999), "Ultra-deep anisotropic etching of (110) silicon", Journal of Micromechanics & Microengineering, vol. 9, No. 1, pp. 51-57.
Hollenberg et al. (2006) "A MEMS Fabricated Flexible Electrode Array for Recording Surface Field Potentials," J. Neurosci. Methods 153:147-153.
Holmes et al. (Feb. 25, 2000) "Control of Thickness and Orientation of Solution-Grown Silicon Nanowires," Science 287:1471-1473.
Horan et al. (Jun. 2005) "In Vitro Degradation of Silk Fibroin," Biomaterials 26(17):3385-3393.
Horn et al. (1992) "Contact Electrification and Adhesion Between Dissimilar Materials," Science 256:362-364.
House et al. (1992) "Dissolution kinetics of silica between 5 and 35 ° C. Application of a titrimetric method," J. Chem. Soc. Faraday, Trans. 88:2021-2026.
Hoyer, P. (1996) "Semiconductor Nanotube Formation by a Two-Step Template Process," Adv. Mater. 8:857-859.
Hsia et al. (2005) "Collapse of Stamps for Soft Lithography Due to Interfacial Adhesion," Appl. Phys. Lett. 86:154106.
Hsu et al. (2002) "Amorphous Si TFTs on Plastically Deformed Spherical Domes," J. Non-Crystalline Solids 299-302:1355-1359.
Hsu et al. (2003) "Nature of Electrical Contacts in a Metal-Molecule-Semiconductor System," J. Vac. Sci. Technol. B 21(4):1928-1935.
Hsu et al. (Jan. 15, 2004) "Spherical Deformation of Compliant Substrates with Semiconductor Device Islands," J. Appl. Phys. 95(2):705-712.
Hsu et al. (Mar. 2004) "Effects of Mechanical Strain on TFT's on Spherical Domes," IEEE Trans. Electron Dev. 51(3):371-377.
Hu et al. (1997) "Using Soft Lithography to Fabricate GaAs/AlGaAs Heterostructure Field Effect Transistors," Appl. Phys. Lett. 71:2020-2022.
Hu et al. (1999) Chemistry and Physics in One Dimension: Synthesis and Properties of Nanowires and Nanotubes, Acc. Chem. Res. 32:435-445.
Hu et al. (2004) "Percolation in Transparent and Conducting Carbon Nanotube Networks," Nano Lett., vol. 4, No. 12, pp. 2513-2517.
Hu et al. (2008) "Dynamic Protein Water Relationships During Beta Sheet Formation," Macromolecules. 41:3939-3948.
Hu et al. (2009) "Highly Conductive Paper for Energy-Storage Devices," Proc. Natl. Acad. Sci. USA 106:21490-21494.
Hu et al. (2009) "Microphase Separation Controlled Beta Sheet Crystallization Kinetics in Fibrous Proteins," Macromolecules. 42:2079-2087.
Hu et al. (2010) "Stretchable, Porous, and Conductive Energy Textiles," Nano Lett. 10:708-714.
Hu et al. (2011) "Regulation of Silk Material Structure by Temperature-Controlled Water Vapor Annealing," Biomacromolecules. 12:1686-1696.
Hua et al. (2004) "Polymer Imprint Lithography with Molecular-Scale Resolution," Nano. Lett. 4(12):2467-2471.
Huang et al. (2001) "Directed Assembly of One-Dimensional Nanostructures into Functional Networks," Science 291:630-633.
Huang et al. (2001) "Room-Temperature Ultraviolet Nanowire Nanolasers," Science 292:1897-1899.
Huang et al. (2003) "Growth of Millimeter-Long and Horizontally Aligned Single-Walled Carbon Nanotubes on Flat Substrates," J. Am. Chem. Soc., 125:5636-5637.
Huang et al. (2004) "Long and Oriented Single-Walled Carbon Nanotubes Grown by Ethanol Chemical Vapor Deposition," J. Phys. Chem. B. 108:16451-16456.
Huang et al. (2004) "Self-Organizing High-Density Single-Walled Carbon Nanotube Arrays from Surfactant Suspensions," Nanotechnol. 15:1450-1454.

(56) References Cited

OTHER PUBLICATIONS

Huang et al. (2005) "Nanomechanical Architecture of Strained Bilayer Thin Films: From Design Principles to Experimental Fabrication," Adv. Mater. 17(23):2860-2864.
Huang et al. (2005) "Nanowires for Integrated Multicolor Nanophotorics," Small 1(1):142-147.
Huang et al. (2005) "Nonlinear Analyses of Wrinkles in a Film Bonded to a Compliant Substrate," J. Mech. Phys. Solids 53:2101-2118.
Huang et al. (2005) "Stamp Collapse in Soft Lithography," Langmuir 21:8058-8068.
Huang et al. (2009) "Recycling of waste printed circuit boards: A review of current technologies and treatment status in China," Journal of Hazardous Materials. 164:399-408.
Huang et al. (2011) "A flexible pH sensor based on the iridium oxide sensing film," Sensors and Actuators A: Physical. 169:1-11.
Huang et al. (Apr. 6, 2014) "Stretchable, Wireless Sensors and Functional Substrates for Epidermal Characterization of Sweat," Small. 10(15):3083-3090.
Huang et al. (Aug. 23, 2012) "Epidermal differential impedance sensor for conformal skin hydration monitoring," Biointerphases. 7:52.
Huang et al. (Jan. 16, 2001) "Catalytic Growth of Zinc Oxide Nanowires by Vapor Transport," Adv. Mater. 13(2):113-116.
Huang et al. (Mar. 2, 2014) "Materials and Designs for Wireless Epidermal Sensors of Hydration and Strain," Advanced Functional Materials. 24:3846-3854.
Huang et al. (Sep. 22, 2014) "Biodegradable Materials for Multilayer Transient Printed Circuit Boards," Advanced Materials. 26(43):7371-7377.
Huck et al. (2000) "Ordering of Spontaneously Formed Buckles on Planar Surfaces," Langmuir 16:3497-3501.
Hudson et al. (2008) "The biocompatibility of mesoporous silicates," Biomaterials. 29:4045-4055.
Huie, J.C. (2003) "Guided Molecular Self Assembly: A review of Recent Efforts," Smart Mater. Struct. 12:264-271.
Huitema et al. (2001) "Plastic Transistors in Active-Matrix Displays," Nature 414:599.
Hur et al. (2005) "Organic Nanodielectrics for Low Voltage Carbon Nanotube Thin Film Transistors and Complementary Logic Gates," J. Am. Chem. Soc. 127:13808-13809.
Hur et al. (2005) "Printed thin-film transistors and complementary logic gates that use polymer-coated single-walled carbon nanotube networks," J. Appl. Phys., 98, 114302.
Hur et al. (Dec. 2004) "Nanotransfer Printing by Use of Noncovalent Surface.Forces: Applications to Thin-Film Transistors that Use Single-Walled Carbon Nanotube Networks and Semiconducting Polymers," Appl. Phys. Lett. 85(23):5730-5732.
Hur et al. (Jun. 13, 2005) "Extreme Bendability of Single Walled Carbon Nanotube Networks Transferred From High-Temperature Growth Substrates to Plastic and Their Use in Thin-Film Transistors," Appl. Phys. Lett. 243502.
Hutchinson et al. (1992) "Mixed Mode Cracking in Layered Materials," Adv. Appl. Mech. 29:63-191.
Hutmacher (2001) "Scaffold design and fabrication technologies for engineering tissues—state of the art and future perspectives," J. Biomater. Sci. Polymer Edn. 12:107-124.
Hwang et al. (2008) "The Effects of the Microstructure of ZnO Films on the Electrical Performance of Their Thin Film Transistors," Appl. Phys. Lett. 93:222104.
Hwang et al. (Apr. 11, 2013) "Materials and Fabrication Processes for Transient and Bioresorbable High-Performance Electronics," Adv. Funct. Mater. 23(33):4087-4093.
Hwang et al. (Mar. 31, 2014) "Dissolution chemistry and biocompatibility of singlecrystalline silicon nanomembranes and associated materials for transient electronics," ACS Nano. 8:5843-5851.
Hwang et al. (May 17, 2013) "Materials for bioresorbable radio frequency electronics," Adv. Mater. 25:3526-3531.
Hwang et al. (Sep. 28, 2012) "A Physically Transient Form of Silicon Electronics, With Integrated Sensors, Actuators and Power Supply," Science 337(6102):1640-1644.
Icenhower et al. (2000) "The dissolution kinetics of amorphous silica into sodium chloride solutions: effects of temperature and ionic strength," Geochim. Cosmochim. Acta. 64:4193-4203.
Iler (1973) "Effect of Adsorbed Alumina on the Solubility of Amorphous Silica in Water," J. of Colloid Interf. Sci. 43:399-408.
Ilican et al. (2008) "Preparation and characterization of ZnO thin films deposited by sol-gel spin coating method ," Journal of Optoelectronics and Advance Materials. 10:2578-2583.
Im et al. (2007) "Evolution in LTPS AMLCD Manufacturing via Advances in Laser Crystallization Techniques and Systems," Information Display. vol. 23. No. 09.
Imparato et al. (2005) "Excimer Laser Induced Crystallization of Amorphous Silicon on Flexible Polymer Substrates," Thin Solid Films 487:58-62.
Irimia-Vladu (2010) "Environmentally sustainable organic field effect transistors," Organic Electronics. 11:1974-1990.
Irimia-Vladu et al. (2010) "Biocompatible and Biodegradable Materials for Organic-Field Transistors," Adv. Mater. 20:4069-4076.
Irimia-Vladu et al. (2010) "Environmentally Sustainable Organic Field Effect Transistors," Org. Electron. 11:1974-1990.
Isberg et al. (Sep. 6, 2002) "High Carrier Mobility in Single-Crystal Plasma-Deposited Diamond," Science 297:1670-1672.
Islam et al. (Jan. 16, 2003) "High Weight Fraction Surfactant Solubilization of Single-Wall Carbon Nanotubes in Water," Nano Lett. 3(2):269-273.
Ismach et al. (2004) "Atomic-Step-Templated Formation of Single Wall Carbon Nanotube Patterns," Angew. Chem. Int. Ed. 43:6140-6143.
Israelachvili (1997) "The different faces of poly(ethylene glycol)," Proceedings of the National Academy of Sciences USA. 94:8378-8379.
Itoh et al. (1991) "Cathodoluminescence Properties of Undoped and Zn-Doped AlxGa1-xN Grown by Metalorganic Vapor Phase Epitaxy," Jap. J. Appl. Phys. 30:1604-1608.
Jabbour et al. (2001) "Screen Printing for the Fabrication of Organic Light-Emitting Devices," IEEE J. Select. Top. Quantum. Electron. 7:769-773.
Jackman et al. (Aug. 4, 1995) "Fabrication of Submicrometer Features on Curved Substrates by Microcontact Printing," Science 269:664-666.
Jacobs et al. (2001) "Submicrometer Patterning of Charge in Thin-Film Electrets," Science 291:1763-1766.
Jacobs et al. (2002) "Fabrication of a Cylindrical Display by Patterned Assembly," Science 296:323-325.
Jain et al. (2000) "III-Nitrides: Growth, Characterization, and Properties," J. Appl. Phys. 87:965-1006.
Jain et al. (2005) "Flexible Electronics and Displays: High-Resolution, Roll-to-Roll, Projection Lithography and Photoablation Processing Technologies for High-Throughput Production," Proc. IEEE 93:1500-1510.
James et al. (1998) "Patterned Protein Layers on Solid Substrates by This Stamp Microcontact Printing," Langmuir 14:742-744.
Jang et al. (2003) "Lateral Growth of Aligned Multiwalled Carbon Nanotubes Under Electric Fields," Solid State Commun. 126:305-308.
Jang et al. (2006) "Low-Voltage and High-Field-Effect Mobility Organic Transistors with a Polymer Insulator," Appl. Phys. Lett. 88:072101.
Jang et al. (Mar. 25, 2013) "Effect of Biologically Relevant Ions on the Corrosion Products formed on Alloy AZ31B: An Improved Understanding of Magnesium Corrosion," Acta Biomaterialia, (9):8761-8770.
Javey et al. (2002) "High-κ Dielectrics for Advanced Carbon-Nanotube Transistors and Logic Gates," Nature Mater. 1:241-246.
Javey et al. (2004) "From the Cover: Ten to 50-nm-Long Quasi-Ballistic Carbon Nanotube Devices Obtained Without Complex Lithography," Proc. Nat. Acad. Sci. USA. 101(37):13408-13410.
Javey et al. (2005) "High Performance n-Type Carbon Nanotube Field-Effect Transistors with Chemically Doped Contacts," Nano Lett., vol. 5, No. 2, pp. 345-348.

(56) References Cited

OTHER PUBLICATIONS

Javey et al. (Aug. 7, 2003) "Ballistic Carbon Nanotube Field-Effect Transistors," Nature 424:654-657.
Jenkins et al. (1994) "Gallium Arsenide Transistors: Realization Through a Molecularly Designed Insulator," Science 263:1751-1753.
Jeon et al. (1995) "Patterning of Dielectric Oxide Thin Layers by Microcontact Printing of Self-Assembled Monolayers," J. Mater. Res. 10:2996-2999.
Jeon et al. (2003) "Structural and Mechanical Properties of Woven Fabrics Employing Peirce's Model," Textile Res. J. 73:929-933.
Jeon et al. (2004) "Fabricating Complex Three-Dimensional Nanostructures with.High Resolution Conformable Phase Masks," Proc. Natl. Acad. Sci. USA 101:12428-12433.
Jeon et al. (2007) "Low-Voltage Zinc-Oxide Thin-Film Transistors on a Conventional SiO2 Gate Insulator Grown by Radio-Frequency Magnetron Sputtering at Room Temperature," J. Kor. Phys. Soc. 51:1999-2003.
Jeon et al. (Aug. 4, 2004) "Three Dimensional Nanofabrication with Rubber Stamps and Conformable Photomasks," Adv. Mater. 16(15):1369-1375.
Jeong et al. (2007) "Flexible Full-Color AMOLED on Ultrathin Metal Foil," IEEE Elect. Dev. Lett. 28:389-391.
Jiang et al. (1999) "Preparation of Macroporous Metal Films from Colloidal Crystals," J. Am. Chem. Soc. 121:7957-7958.
Jiang et al. (2002) "Polymer-on-Polymer Stamping: Universal Approaches to Chemically Patterned Surfaces," Langmuir 18:2607-2615.
Jiang et al. (2007) "Mechanical Properties of Robust Ultrathin Silk Fibroin Films," Adv. Funct. Mater. 17:2229-2237.
Jiang et al. (Oct. 2, 2007) "Finite Deformation Mechanics in Buckled Thin Films on Compliant Supports," Proc. Natl. Acad. Sci. USA 104(40):15607-15612.
Jimbo et al. (2008) "Gastric-fluid-utilizing micro battery for micro medical devices," Sensors Actuators B: Chem. 134:219-224.
Jin et al. (2004) "Scalable Interconnection and Integration of Nanowire Devices Without Registration," Nano Lett. 4:915-919.
Jin et al. (2004) "Soft Lithographic Fabrication of an Image Sensor Array on a Curved Substrate," J. Vac. Sci. Technol. B 22(5):2548-2551.
Jin et al. (Aug. 2005) "Water-Stable Silk Films with Reduced β-Sheet Content," Adv. Funct. Mater. 15(8):1241-1247.
Jin et al. (Web Release Jan. 23, 2004) "Biomaterial Films of Bombyx mori Silk Fibroin with Poly(ethylene oxide)," Biomacromolecules 5(3):711-717.
Joachim et al. (Nov. 30, 2000) "Electronics Using Hybrid-Molecular and Mono-Molecular Devices," Nature 408:541-548.
Johnson et al. (1999) "Ordered Mesoporous Polymers of Tunable Pore Size from Colloidal Silica Templates," Science 283:963-965.
Jones et al. (1987) "Preparation and Characterization of Molecule-Based Transistors with a 50-Nanometer Source-Drain Separation with Use of Shadow Deposition Techniques. Toward Faster, More Sensitive Molecule-Based Devices," J. Am. Chem. Soc. 109(18):5526-5528.
Jones et al. (Jul./Aug. 2004) "Stretchable Wavy Metal Interconnects," J. Vac. Sci. Technol. A 22(4):1723-1725.
Joo et al. (2006) "Low-Temperature Solution-Phase Synthesis of Quantum Well Structures CdSe Nanoribbons," J. Am. Chem. Soc. 128(17):5632-5633.
Jortner et al. (2002) "Nanostructured Advanced Materials Perspectives and Directions," Pure Appl. Chem. 74(9):1491-1506.
Joselevich (2002) "Vectorial Growth of Metallic and Semiconducting Single-Wall Carbon Nanotubes," Nano Lett., vol. 2, No. 10, pp. 1137-1141.
Jugdaohsingh et al. (2002) "Dietary silicon intake and absorption," Am. J. Clin. Nutr. 75:887-893.
Jurkic et al (Jan. 8, 2013) "Biological and therapeutic effects of ortho-silicic acid and some ortho-silicic acid-releasing compounds: new perspectives for therapy," Nutr. Metab. 10:2-12.
Kadish et al. (1988) "Interaction of Fiber Orientation and Direction of Impulse.Propagation with Anatomic Barriers in Anisotropic Canine Myocardium," Circulation. 78:1478-1494.
Kagan (1999) "Organic-Inorganic Hybrid Materials as Semiconducting Channels in Thin-Film Field-Effect Transistors," Science 286:945-947.
Kagan et al. (2001) "Patterning Organic-Inorganic Thin-Film Transistors Using Microcontact Printed Templates," Appl. Phys Lett. 79(21):3536-3538.
Kagan et al. (2003) Thin Film Transistors, Dekker, New York, pp. 1-34.
Kamath et al. (1993) "Biodegradable hydrogels in drug delivery," Adv. Drug Delivery Rev. 11:59-84.
Kane et al. (2000) "Analog and Digital Circuits Using Organic Thin-Film Transistors on Polyester Substrates," IEEE Electron. Dev. Lett. 21:534-536.
Kang et al. (2004) "Avoiding Cu Hillocks During the Plasma Process," J. Electrochem. Soc. 151(6):G391-G395.
Kang et al. (2005) "Electronic waste recycling: A review of U.S. infrastructure and technology options," Resources, Conservation and Recycling. 45:368-400.
Kang et al. (2007) "High-Performance Electronics Using Dense, Perfectly Aligned Arrays of Single-Walled Carbon Nanotubes," Nat. Nanotechnol. 2(4):230-236.
Kang et al. (2007) "Printed Multilayer Superstructures of Aligned Single-Walled Carbon Nanotubes for Electronic Applications," Nano Lett. 7(11):3343-3348.
Kang et al. (Apr. 22, 2013) "Potential Environmental and Human Health Impacts of.Rechargeable Lithium Batteries in Electronic Waste," Environmental Science & Technology. 47:5495-5503.
Kang et al. (Feb. 4, 2016) "Bioresorbable silicon electronic sensors for the brain," Nature. 530:71-76.
Kang et al. (Jan. 12, 2015) "Biodegradable thin metal foils and spin-on glass materials for transient electronics," Adv. Funct. Mater. 7:9297-9305.
Kang et al. (Jul. 23, 2014) "Dissolution Behaviors and Applications of Silicon Oxides and Nitrides in Transient Electronics," Adv. Funct. Mater. 24:4427-4434.
Kanicki et al. (2003) "Hydrogenated Amorphous Silicon Thin-Film Transistors," Ch. 3 In; Thin Film Transistors. Eds.: Kagan, C. R.; Andry, P. Marcel-Dekker. New York, New York. pp. 71-137.
Kar et al. (2005) "Controlled Synthesis and Photoluminescence Properties of ZnS Nanowires and Nanoribbons," J. Phys. Chem. B 109(8):3298-3302.
Kar et al. (2005) "Synthesis and Optical Properties of CdS Nanoribbons," J. Phys. Chem B. 109(41):19134-19138.
Kar et al. (2006) "Shape Selective Growth of CdS One-Dimensional Nanostructures by a Thermal Evaporation Process," J. Phys. Chem. B. 110(10):4542-4547.
Karnik et al. (2003) "Lateral Polysilicon p+-p-n+ and p+-n-n+ Diodes," Solid-State Electronics 47:653-659.
Karnik et al. (2003) "Multiple Lateral Polysilicon Diodes as Temperature Sensors for Chemical Microreaction Systems," Jpn. J. Appl. Phys. 42:1200-1205.
Kato et al. (2004) The Characteristic Improvement of Si(111) Metal-Oxide-Semiconductor Field-Effect Transistor by Long-Time Hydrogen Annealing, Jpn. J. Appl. Phys. 43(10):6848-6853.
Katz et al. (2001) "Synthetic Chemistry for Ultrapure, Processable, and High-Mobility Organic Transistor Semiconductors," Acc. Chem. Res. 34:359-369.
Katz, H.E. (2004) "Recent Advances in Semiconductor Performance and Printing Processes for Organic Transistor-Based Electronics," Chem. Mater. 16:4748-4756.
Kawahara et al. (2011) "Link between aluminum and the pathogenesis of Alzheimer's Disease: the integration of the aluminum and amyloid cascade hypotheses," Int. J. Alzheimer's Dis. 2011:276393.
Kawata et al. (2001) "Finer Features for Functional Microdevices," Nature 412:697-698.
Keim et al. (2011) "Control of magnesium corrosion and biocompatibility with biomimetic coatings," Journal of Biomedical Materials Research Part B: Applied Biomaterials. 96B:84-90.

(56) References Cited

OTHER PUBLICATIONS

Kellis et al. (2009) "Human Neocortical Electrical Activity Recorded on Nonpenetrating Microwire Arrays: Applicability for Neuroprostheses," Neurosurg. Focus 27(1):E9.

Kendall, D.L. (1979) "Vertical Etching of Silicon at Very High Apect Ratios," Ann. Rev. Mater. Sci. 9:373-403.

Kerber et al. (2009) "Reliability Challenges for CMOS Technology Qualifications With Hafnium Oxide/Titanium Nitride Gate Stacks," IEEE Trans. Device Mater. Reliab. 9:147-162.

Khakani et al. (2006) "Lateral Growth of Single Wall Carbon Nanotubes on Various Substrates by Means of an 'All-Laser' Synthesis Approach," Diamond Relat. Mater. 15:1064-1069.

Khan et al. (1993) "High Electron Mobility Transistor Based on a GaN-AlxGa1-xN Heterojunction," Appl. Phys. Lett. 63:1214-1215.

Khang et al. (2006) "A Stretchable Form of Single-Crystal Silicon for High-Performance Electronics on Rubber Substrates," Science 311:208-212.

Khodagholy et al. (Dec. 22, 2014) "NeuroGrid: recording action potentials from the surface of the brain," Nature Neurosci. 18:310-315.

Khodagholy et al. (Mar. 12, 2013) "In vivo recordings of brain activity using organic transistors," Nature Commun. 4:1575.

Kilby, J.S. (1976) "Invention of the Integrated Circuit," IEEE Trans. Electron. Dev. 23:648-654.

Kim et al. (1999) "Direct Observation of Electron Emission Site on Boron-Doped Polycrystalline Diamond Thin Films Using an Ultra-High-Vacuum Scanning Tunneling Microscope," Appl. Phys. Lett. 75(20):3219-3221.

Kim et al. (2000) "Field Emission from Carbon Nanotubes for Displays," Diamond and Related Mater. 9(3-6):1184-1189.

Kim et al. (2002) "Nanolithography Based on Patterned Metal Transfer and Its Application to Organic Electronic Devices," Appl. Phys. Lett. 80:4051-4053.

Kim et al. (2003) "Epitaxial Self-Assembly of Block Copolymers on Lithographically Defined Nanopatterned Substrates," Nature 424:411-414.

Kim et al. (2004) "Organic TFT Array on a Paper Substrate," IEEE Electron. Dev. Lett. 25(10):702-704.

Kim et al. (2008) "Complementary Logic Gates and Ring Oscillators Plastic Substrates by Use of Printed Ribbons Single-Crystalline Silicon," IEEE Electron. Dev. Lett. 29(1):73-76.

Kim et al. (2008) "Complementary Metal Oxide Silicon Integrated Circuits Incorporating Monolithically Integrated Stretchable Wavy Interconnects," Appl. Phys. Lett. 93(4):044102.

Kim et al. (2008) "Highly Emissive Self-Assembled Organic Nanoparticles Having Dual Color Capacity for Targeted Immunofluorescence Labeling," Adv. Mater. 20(6):1117-1121.

Kim et al. (2008) "Materials and Noncoplanar Mesh Designs for Integrated Circuits with Linear Elastic Responses to Extreme Mechanical Deformations," Proc. Natl. Acad. Sci. USA 105(48):18675-18680.

Kim et al. (2008) "Stretchable and Foldable Silicon Integrated Circuits," Science 320:507-511.

Kim et al. (2008) "Stretchable Electronics: Materials Strategies and Devices," Adv. Mater. 20:4887-4892.

Kim et al. (2009) "Electrically interconnected assemblies of microscale device components by printing and molding," Appl. Phys. Lett. 95:214101.

Kim et al. (2009) "Emerging Technologies for the Commercialization of AMOLED TVs," Information Display. vol. 25. No. 09.

Kim et al. (2009) "Integrated Wireless Neural Interface Based on the Utah Electrode array," Biomed. Microdevices 11:453-466.

Kim et al. (2009) "Intense pulsed light sintering of copper nanoink for printed electronics," Appl. Phys. A. 97:791-798.

Kim et al. (2009) "Optimized Structural Designs for Stretchable Silicon Integrated Circuits," Small 5(24):2841-2847.

Kim et al. (2009) "Roll-To-Roll Manufacturing of Electronics on Flexible Substrates Using Self-Aligned Imprint Lithography (SAIL)," J. Soc. Inf. Disp. 17(11):963-970.

Kim et al. (2009) "Self-assembled nanodielectrics and silicon nanomembranes for low voltage, flexible transistors, and logic gates on plastic substrates," Appl. Phys. Lett. 95:183504.

Kim et al. (2009) "Silicon Electronics on Silk as a Path to Bioresorbable, Implantable Devices," Appl. Phys. Lett. 95:133701.

Kim et al. (2009) "Ultrathin Silicon Circuits with Strain-Isolation Layers and Mesh Layouts for High-Performance Electronics on Fabric, Vinyl, Leather and Paper," Adv. Mater. 21(36):3703-3707.

Kim et al. (2010) "Dissolvable Films of Silk Fibroin for Ultrathin Conformal Bio Integrated Electronics," Nature Materials. 9(6):511-517.

Kim et al. (2010) "Microstructured Elastomeric Surfaces with Reversible Adhesion and Examples of Their Use in Deterministic Assembly by Transfer Printing," Proc. Nat. Acad. Sci. USA 107(40):17095-17100.

Kim et al. (2010) "Waterproof AlInGaP optoelectronics on stretchable substrates with applications in biomedicine and robotics," Nature Materials 9:929-937.

Kim et al. (Dec. 9, 2013) "Biologically derived melanin electrodes in aqueous sodium-ion energy storage devices," Proceedings of the National Academy of Sciences. 110(52):20912-20917.

Kim et al. (Mar. 7, 2013) "Self-deployable current sources fabricated from edible materials," Journal of Materials Chemistry B. 1:3781-3788.

Kim et al. (May 7, 2013) "Deterministic assembly of releasable single crystal silicon-metal oxide field-effect devices formed from bulk wafers," 102:182104.

Kim et al. (Nov. 11, 2012) "Silk Inverse Opals," Nature Photonics. 6:818-823.

Kim, Y.S. (2005) "Microheater-Integrated Single Gas Sensor Array Chip Fabricated on Flexible Polyimide Substrate," Sens. Actuators B 114(1):410-417.

King-Stephens et al. (May 19, 2015) "Lateralization of mesial temporal lobe epilepsy with chronic ambulatory electrocorticography," Epilepsia. 56:959-967.

Kirkland et al. (Mar. 2012) "Assessing the corrosion of biodegradable magnesium implants: A critical review of current methodologies and their limitations," Acta Biomaterialia. 8(3): p. 925-936.

Kirkpatrick (1973) "Percolation and Conduction," Reviews of Modern Physics. 45:574.

Klauk et al. (2002) "High-Mobility Polymer Gate Dielectric Pentacene Thin Film Transistors," J. Appl. Phys. 92:5259-5263.

Klein-Wiele et al. (2003) "Fabrication of Periodic Nanostructures by Phase-Controlled Multiple-Beam Interference," Appl. Phys. Lett. 83(23):4707-4709.

Knauss et al. (1998) "The dissolution kinetics of quartz as a function of pH and time at 70 degrees Celsius," Geochim. Cosmochim. Acta. 52:43-53.

Kneer et al. (1997) "Electrochemical Measurements During the Chemical-Mechanical Polishing of Tungsten Thin-Films," Journal of the Electrochemical Society.144(9):3041-3049.

Knipp et al. (2003) "Pentacine Thin Film Transistors on Inorganic Dielectrics: Morphology, Structural Properties, and Electronic Transport," Appl. Phys. Lett. 93:347-355.

Knuesel et al. (2010) "Self-assembly of microscopic chiplets at a liquid-liquid-solid interface forming a flexible segmented monocrystalline solar cell," Proc. Natl. Acad. Sci. USA. 107:993-998.

Ko et al. (2006) "Bulk Quantities of Single-Crystal Silicon Micro-/Nanoribbons Generated from Bulk Wafers," Nano Lett. 6(10):2318-2324.

Ko et al. (2008) "A Hemispherical Electronic Eye Camera Based on Compressible Silicon Optoelectronics," Nature 454:748-753.

Ko et al. (2009) "Curvilinear Electronics Formed Using Silicon Membrane Circuits and Elastomeric Transfer Elements," Small 5(23):2703-2709.

Ko et al. (2010) "Flexible Carbon Nanofiber Connectors with Anisotropic Adhesion Properties," Small 6:22-26.

Ko et al. (2010) "Ultrathin compound semiconductor on insulator layers for high-performance nanoscale transistors," Nature. 468:286-289.

(56) References Cited

OTHER PUBLICATIONS

Kocabas et al. (2004) "Aligned Arrays of Single-Walled Carbon Nanotubes Generated from Random Networks by Orientationally Selective Laser Ablation," Nano Lett., vol. 4, No. 12, pp. 2421-2426.
Kocabas et al. (2005) "Guided Growth of Large-Scale, Horizontally Aligned Arrays of Single-Walled Carbon Nanotubes and Their Use in Thin-Film Transistors," Small 1(11):1110-1116.
Kocabas et al. (2006) "Large Area Aligned Arrays of SWNTs for High Performance Thin Film Transistors," American Physical Society, APS Mar. Meeting, Mar. 13-17, Abstract # W31.004.
Kocabas et al. (2006) "Spatially Selective Guided Growth of High-Coverage Arrays and Random Networks of Single-Walled Carbon Nanotubes and Their Integration into Electronic Devices," J. Am. Chem. Soc. 128:4540-4541.
Kocabas et al. (2007) "Experimental and Theoretical Studies of Transport Through Large Scale, Partially Aligned Arrays of Single-Walled Carbon Nanotubes in Thin Film Type Transistors," Nano Lett. 7(5):1195-1202.
Kocabas et al. (Feb. 5, 2008) "Radio Frequency Analog Electronics Based on Carbon Nanotube Transistors," Proc. Natl. Acad. Sci. USA 105(5):1405-1409.
Kodambaka et al. (2006) "Control of Si Nanowire Growth by Oxygen," Nano Lett. 6(6):1292-1296.
Kohler et al. (1999) "Direct Growth of Nanostructures by Deposition Through an Si 3N 4 Shadow Mask," Physica E. 4:196-200.
Koide et al. (2000) "Patterned Luminescence of Organic Light-Emitting Diodes by Hot Microcontact Printing (HμCP) of Self-Assembled Monolayers," J. Am. Chem. Soc. 122:11266-11267.
Konagai et al. (1978) "High Efficiency GaAs Thin Film Solar Cells by Peeled Film Technology," J. Cryst. Growth 45:277-280.
Kong et al. (2004) "Single-Crystal Nanorings Formed by Epitaxial Self-Coating of Polar Nanobelts," Science 303:1348-1351.
Kong et al. (Jan. 28, 2000) "Nanotube Molecular Wires as Chemical Sensors," Science 287:622-625.
Kong et al. (Oct. 2003) "Structure of Indium Oxide Nanobelts," Solid State Commun. 128(1):1-4.
Kong et al. (Oct. 29, 1998) "Synthesis of Individual Single-Walled Carbon Nonotubes on Patterned Silicon Wafers," Nature 395:878-881.
Kosiorek et al. (2004) "Shadow Nanosphere Lithography: Simulation and Experiment," Nano Lett. 4:1359-1363.
Kozai et al. (Nov. 11, 2012) "Ultrasmall implantable composite microelectrodes with bioactive surfaces for chronic neural interfaces," Nat. Mater. 11:1065-1073.
Kozicki et al. (Nov. 10, 2005) "Programmable Metallization Cell Memory Based on Ag—Ge—S and Cu—Ge—S Solid Electrolytes," In; Non-Volatile Memory Technology Symposium 2005, Dallas, Texas. pp. 83-89.
Krejčiřík et al. (2007) "Non-Hermitian spectral effects in a PT-symmetric waveguide," Nanotechnology. 18:475-504.
Kringelbach et al. (2007) "Translational principles of deep brain stimulation," Nat. Rev. Neurosci. 8(8):623-635.
Kudo et al. (Web Release Jun. 13, 2006) "A Flexible and Wearable Glucose Sensor Based on Functional Polymers with Soft-MEMS Techniques," Biosens. Bioelectron. 22:558-562.
Kue et al. (1999) "Enhanced proliferation and osteocalcin production by human osteoblast-like MG63 cells on silicon nitride ceramic discs," Biomater. 20:1195-1201.
Kulkarni et al. (2002) "Mesoscale Organization of Metal Nanocrystals," Pure Appl. Chem 74(9):1581-1591.
Kumar et al. (1993) "Features of Gold Having Micrometer to Centimeter Dimensions can be Formed Through a Combination of Stamping with an Elastomeric Stamp and an Alkanethiol "Ink" Followed by Chemical Etching," Appl. Phys. Lett. 63(4):2002-2004.
Kumar et al. (1994) "Patterning Self-Assembled Monolayers: Applications in Materials Science," Langmuir 10:1498-1511.
Kumar et al. (2002) "Polyanhydrides: an overview," Adv. Drug Del. Rev. 54:889-910.
Kumar et al. (2002) "Thermally-Stable Low-Resistance Ti/Al/Mo/Au Multilayer Ohmic Contacts on n-GaN," J. Appl. Phys. 92:1712-1714.
Kumar et al. (2005) "Percolating in Finite Nanotube Networks," Phys. Rev. Lett., 95, 066802.
Kumar et al. (2006) "Ultrasensitive DNA sequence detection using nanoscale ZnO sensor arrays," Nanotechnology. 17:2875-2881.
Kumar et al. (2011) "ZnO nanoparticle as catalyst for efficient green one-pot synthesis of coumarins through Knoevenagel condensation," J. Chem. Sci. 123:615-621.
Kuo (2004) "Deposition of Dielectric Thin Films for a-Si:H TFT," Ch. 6 In; Thin Film.Transistors Materials and Processe. vol. 1. Klewer Academic. Norwell, Massachusetts.
Kuo et al. (1985) "Effect of Mismatch Strain on Band Gap in III-V Semiconductors," J. Appl. Phys. 57:5428-5432.
Kuoni et al. (2003) "Polyimide Membrane with ZnO Piezoelectric Thin Film Pressure Transducers as a Differential Pressure Liquid Flow Sensor," J. Micromech. Microeng. 13:S103-S107.
Kurzweil (2009) "Metal Oxides and Ion-Exchanging Surfaces as pH Sensors in Liquids: State-of-the-Art and Outlook," Sensors (Basel). 9:4955-4985.
Kuykendall et al. (Aug. 2004) "Crystallographic Alignment of High Density Gallium Nitride Nanowire Arrays," Nat. Mater. 3:524-528.
Kuzum et al. (Oct. 20, 2014) "Transparent and flexible low noise graphene electrodes for simultaneous electrophysiology and neuroimaging," Nat. Commun. 5:5259.
Kwadwo et al. (2010) "Layer-by-Layer Assembly of Charged Particles in Nonpolar Media," Langmuir. 26(12), 9974-9980.
Laarz et al. (2000) "Dissolution and Deagglomeration of Silicon Nitride in Aqueous Medium" J. Am. Ceram. Soc. 83:2394-2400.
Lacour et al. (2003) "Stretchable Gold Conductors on Elastomeric Substrates," Appl. Phys. Lett. 82(15):2404-.
Lacour et al. (2004) "An Elastically Stretchable TFT Circuit," IEEE Electron Dev. Lett. 25(12):792-794.
Lacour et al. (2004) "Design and Performance of Thin Metal Film Interconnects for Skin-Like Electronic Circuits," IEEE Electron. Dev. Lett. 25(4):179-181.
Lacour et al. (2005) "Stretchable Interconnects for Elastic Electronic Surfaces," Proc. IEEE 93:1459-1467.
Lacour et al. (2006) "Mechanisms of Reversible Stretchability of Thin Metal Films on Elastomeric Substrates," Appl. Phys. Lett. 88:204103.
Lacour et al. (2006) "Stiff Subcircuit Islands of Diamondlike Carbon for Stretchable Electronics," J. Appl. Phys. 100:014913.
Lacour et al. (2010) "Flexible and Stretchable Micro-Electrodes for in Vitro and n Vivo Neural Interfaces," Med. Biol. Eng. Comput. 48:945-954.
Laimer et al. (Mar. 1997) "Diamond Growth in a Direct-Current Low-Pressure Supersonic Plasmajet," Diamond Relat. Mater. 6:406-410.
Lam et al. (2008) "Dynamics of in vitro polymer degradation of polycaprolactone-based scaffolds: accelerated versus simulated physiological conditions," Biomed. Mater. 3:034108.
Lambacher et al. (2004) "Electrical Imaging of Neuronal Activity by Multi-Transistor-Array (MTA) Recording at 7.8 μm Resolution," Appl. Phys. A 79:1607-1611.
Landes et al. (2002) "Some Properties of Spherical and Rod-Shaped Semiconductor and Metal Nanocrystals," Pure Appl. Chem. 74(9):1675-1692.
Lang et al. (1986) "Salting-out of oxygen from aqueous electrolyte solutions: prediction and measurement," Industrial & Engineering Chemistry Fundamentals. 25(4):775-782.
Larson et al. (2008) "Silica Nanoparticle Architecture Determines Radiative Properties of Encapsulated Fluorophores," Chemistry of Materials. 20(8):2677-2684.
Laurencin et al. (1999) "Tissue engineering: orthopedic applications," Annu. Rev. Biomed. Eng. 1:19-46.
Law et al. (2004) "Semiconductor Nanowires and Nanotubes," Ann. Rev. Mater. Res. 34:83-122.
Law et al. (Aug. 27, 2004) "Nanoribbon Waveguides for Subwavelength Photonics Integration," Science 305:1269-1273.
Lawrence et al. (2008) "Bioactive Silk Protein Biomaterial Systems for Optical Devices," Biomacromolecules 9:1214-1220.

(56) References Cited

OTHER PUBLICATIONS

Lay et al. (2004) "Simple Route to Large-Scale Ordered Arrays of Liquid-Deposited Carbon Nanotubes," Nano Lett., vol. 4, No. 4, pp. 603-606.
Leclercq et al. (1998) "III-V Micromachined Devices for Microsystems," Microelectronics J. 29:613-619.
Lecomte et al. (Apr. 2006) "Degradation Mechanism of Diethylene Glycol Units in a Terephthalate Polymer," Polym. Degrade. Stab. 91(4):681-689.
Lee (2009) "Effects of Sputtering Pressure and Thickness on Properties of ZnO: Al Films Deposited on Polymer Substrates," J. Electroceram. 23:512-518.
Lee et al. (1999) "The Surface/Bulk Micromachining (SBM) Process: A New Method For Fabricating Released MEMS in Single Crystal Silicon," J. Microelectromech. Syst. 8(4):409-416.
Lee et al. (2000) "Thin Film Transistors for Displays on Plastic Substrates," Solid State Electron. 44:1431-1434.
Lee et al. (2001) "Application of Carbon Nanotubes to Field Emission Displays," Diamond and Related Mater. 10(2):265-270.
Lee et al. (2001) "Thickness Effect on Secondary Electron Emission of MgO Layers," Appl. Surf. Sci. 174:62-69.
Lee et al. (2003) "High-Performance Poly-Si TFTs on Plastic Substrates Using a Nano-Structured Separation Layer Approach," IEEE Elec. Dev. Lett. 24:19-21.
Lee et al. (2004) "Organic Light-Emitting Diodes Formed by Soft Contact Lamination," Proc. Natl. Acad. Sci. USA 101(2):429-433.
Lee et al. (2005) "A Printable Form of Single-Crystalline Gallium Nitride for Flexible Optoelectronic Systems," Small 1:1164-1168.
Lee et al. (2005) "Dielectrophoresis and Chemically Mediated Directed Self-Assembly of Micrometer-Scale Three-Terminal Metal Oxide Semiconductor Field-Effect Transistors," Adv. Mater. 17:2671-2677.
Lee et al. (2005) "Effect of nano-sized silver particles on the resistivity of polymeric conductive adhesives," International Journal of Adhesion and Adhesives. 25:437-441.
Lee et al. (2005) "Fabrication of Stable Metallic Patterns Embedded in Poly(dimethylsiloxane) and Model Applications in Non-Planar Electronic and Lab-on-a-Chip Device Patterning," Adv. Funct. Mater. 15(4):557-566.
Lee et al. (2005) "Large-Area, Selective Transfer of Microstructured Silicon (μs-Si): A Printing-Based Approach to High-Performance Thin-Film Transistors Supported on Flexible Substrates," Adv. Mater. 17:2332-2336.
Lee et al. (2005) "Weave Patterned Organic Transistors on Fiber for E-Textiles," IEEE Trans. Electron. Dev. 52(2):269-275.
Lee et al. (2006) "Micron and Submicron Patterning of Polydimethylsiloxane Resists on Electronic Materials by Decal Transfer Lithography and Reactive Ion-Beam Etching: Application to the Fabrication of High-Mobility, Thin-Film Transistors," Appl. Phys. Lett. 100:084907/1-7.
Lee et al. (2010) "Fabrication of microstructured silicon (μs-Si) from a bulk Si wafer and its use in the printing of high-performance thin-film transistors on plastic substrates," J. Micromech. Microeng. 20:075018.
Lee et al. (2010) "Mechanically flexible thin film transistors and logic gates on plastic substrates by use of single-crystal silicon wires from bulk wafers," Appl. Phys. Lett. 96:173501.
Lee et al. (2011) "Pulsed light sintering characteristics of inkjet-printed nanosilver films on a polymer substrate," Journal of Micromechanics and Microengineering. 21:125023.
Legnani et al. (2008) "Bacterial Cellulose Membrane as Flexible Substrate for Organic Light Emitting Devices," Thin Film Solids. 517:1016-1020.
Lendlein et al. (2002) "Biodegradable, Elastic Shape-Memory Polymers for Potential Biomedical Applications," Science. 296:1673-1676.
Leong et al. (2009) "Tetherless Thermobiochemicall Actuated Microgrippers," Proc. Natl. Acad. Sci. USA 106:703-709.
Létant et al. (Jun. 2003) "Functionalized Silicon Membranes for Selective Bio-Organisms Capture," Nat. Mater. 2:391-395.

Leung et al. (2006) "Environmental contamination from electronic waste recycling at Guiyu, southeast China," Journal of Material Cycles and Waste Management. 8:21-33.
Levine (2005) Molecular Reaction Dynamics. Cambridge University Press. Cambridge, United Kingdom.
Li et al. (2002) "High-Resolution Contact Printing with Dendrimers," Nano Lett. 2(4):347-349.
Li et al. (2002) "ZnO Nanobelts Grown on Si Substrate," Appl. Phys. Lett. 81:144-146.
Li et al. (2003) "Ultrathin Single-Crystalline-Silicon Cantilever Resonators: Fabrication Technology and Significant Specimen Size effect on Young's Modulus," Appl. Phys. Lett. 83:3081-3083.
Li et al. (2004) "Electrospinning of Nanofibers: Reinventing the Wheel," Adv. Mater.16(14):1151-1170.
Li et al. (2005) "Compliant Thin Film Patterns of Stiff Materials as Platforms for Stretchable Electronics," J. Mater. Res. 20(12):3274-3277.
Li et al. (2005) "Enhanced ionic conductivity of poly(ethylene oxide) (PEO) electrolyte by adding mesoporous molecular sieve LiAlSBA," J. Solid State Electrochem. 9:609-615.
Li et al. (2005) "Facile Synthesis of Silver Nanoparticles Useful for Fabrication of High-Conductivity Elements for Printed Electronics," J. Am. Chem. Soc. 127:3266-3267.
Li et al. (2006) "Catalyst-Assisted Formation of Nanocantilever Arrays on ZnS Nanoribbons by Post-Annealing Treatment," J. Phys. Chem. B 110(13):6759-6762.
Li et al. (2007) "Recycle Technology for Recovering Resources and Products from Waste Printed Circuit Boards," Environmental Science & Technology. 41:1995-2000.
Li et al. (2008) "Cellular Level Biocompatibility and Biosafety of ZnO Nanowires," J. Phys. Chem. C. 112:20114-20117.
Li et al. (Jan. 21, 2013) "An Analytical Model of Reactive Diffusion for Transient Electronics," Adv. Funct. Mater. 23:3106-3114.
Lieber, C. (2001) "The Incredible Shrinking Circuit," Sci. Am. 285(3):58-64.
Lieber, C.M. (2003) "Nanoscale Science and Technology: Building a Big Future from Small Things," MRS Bull. 28:486-491.
Lillard et al. (1998) "The Nature of Oxide Films on Tungsten in Acidic and Alkaline Solutions," Journal of the Electrochemical Society. 145(8):2718-2725.
Lim et al. (2005) "Flexible Membrane Pressure Sensor," Sens. Act. A 119:332-335.
Lim et al. (2007) "Au Micro-Pattern Fabrication on Cellulose Paper: Comparison of μ-Contact Printing and Liftoff Techniques," J. Micromech.Microeng. 17:1415-1419.
Lima et al. (2007) "Creating Micro- and Nanostructures on Tubular and Spherical Surfaces," J. Vac. Sci. Technol. B 25(6):2412-2418.
Lin et al. (2010) "ZnO and ε-Zn(OH)2 Composite Nanoparticles by Pulsed Laser Ablation on Zn in Water," The Journal of Physical Chemistry C. 115(12):5003-5010.
Lin et al. (2012) "Optimizing the organic/inorganic barrier structure for flecible plastic substrate encapsulation," Int. J. Eng. Tech. Innovation. 2:184-194.
Lin et al. (Sep. 2005) "High-Performance Carbon Nanotube Field-Effect Transistor With Tunable Polarities," IEEE Trans. Nano 4(5):481-489.
Linder et al. (1994) "Fabrication Technology for Wafer Through-Hole Interconnections and Three-Dimensional Stacks of Chips and Wafers," Proc. IEEE Micro. Electro Mech. Syst. 349-354.
Ling et al. (2004) "Thin Film Deposition, Patterning, and Printing in Organic Thin Film Transistors," Chem. Mater. 16:4824-4840.
Litt et al. (2001) "Epileptic seizures may begin hours in advance of clinical onset: a report of five patients," Neuron. 30:51-64.
Liu et al. (1999) "Controlled deposition of individual single-walled carbon nanotubes on chemically functionalized templates," Chem. Phys. Lett., 303:125-129.
Liu et al. (2009) "A first quantitative XPS study of the surface films formed, by exposure to water, on Mg and on the Mg—Al intermetallics: Al3Mg2 and Mg17Al12," Corrosion Science. 51(5):1115-1127.
Long et al. (1990) "Heterostructure FETs and Bipolar Transistors," In; Gallium Arsenide Digital Integrated Circuit Design, McGraw-Hill, New York, pp. 58-69.

(56) References Cited

OTHER PUBLICATIONS

Longobardo (2010) "Glass Fibers for Printed Circuit Boards," In; Fiberglass and Glass Technology. Eds: Wallenberger et al. Springer. pp. 175-196.
Loo et al. (2002) "Additive, Nanoscale Patterning of Metal Films with a Stamp and a Surface Chemistry Mediated Transfer Process: Applications in Plastic Electronics," Appl. Phys. Lett. 81:562-564.
Loo et al. (2002) "High-Resolution Transfer Printing on GaAs Surfaces Using Alkane Dithiol Monolayers," J. Vac. Sci. Technol. B 20(6):2853-2856.
Loo et al. (2002) "Interfacial Chemistries for Nanoscale Transfer Printing," J. Am. Chem. Soc. 124:7654-7655.
Loo et al. (2002) "Soft, Conformable Electrical Contacts for Organic Semiconductors: High-Resolution Plastic Circuits by Lamination," Proc. Natl. Acad. Sci. USA 99(16):10252-10256.
Loo et al. (2003) "Electrical Contacts to Molecular Layers by Nanotransfer Printing," Nano Lett. 3(7):913-917.
Lopes et al. (Sep. 2004) "Thermal Conductivity of PET/(LDPE/Al) Composites Determined by MDSC," Polym. Test. 23(6):637-643.
Lou et al. (Aug. 20, 2012) "Imprint Lithography with Degradable Elastomeric Polyanhydrides," ACS Applied Materials & Interfaces. 4:4457-4460.
Low et al. (2009) "The Biocompatibility of Porous Silicon in Tissues of the Eye," Biomaterials. 30(15):2873-2880.
Lu et al. (Apr. 2010) "Water-Insoluble Silk Films with Silk I Structure," Acta Biomater. 6(4):1380-1387.
Lu et al. (Dec. 2006) "Electronic Materials-Buckling Down for Flexible Electronics," Nat. Nanotechnol. 1:163-164.
Lu et al. (Jul. 19, 2005) "One Dimensional Hole Gas in Germanium/Silicon Nanowire Heterostructures," Proc. Nat. Acad. Sci. USA 102(29):10046-10051.
Lu et al. (Nov. 2008) "Nanowire Transistor Performance Limits and Applications," IEEE Trans Electron Dev. 55(11):2859-2876.
Luan et al. (1992) "An Experimental Study of the Source/Drain Parasitic Resistance Effects in Amorphous Silicon Thin Film Transistors," J. Appl. Phys. 72:766-772.
Luther (2010) Managing Electronic Waste: Issues with Exporting E-Waste. CRS Report for Congress. Document No. 7-5700.
Ma et al. (2004) "Single-Crystal CdSe Nanosaws," J. Am. Chem. Soc. 126(3):708-709.
Mack et al. (2006) "Mechanically Flexible Thin-Film Transistors that Use Ultrathin Ribbons of Silicon Derived from Bulk Wafers," Appl. Phys. Lett. 88:213101.
Madou, M. (1997) "Etch-Stop Techniques," In; Fundamentals of Microfabrication, CRC Press, New York, pp. 193-199.
Magda Gioia et al. (2007) "Characterization of the Mechanisms by which Gelatinase A, Neutrophil Collagenase, and Membrane-Type Metalloproteinase MMP-14 Recognize Collagen I and Enzymatically Process the Two Alpha-Chains," J. Mol. Biol. 368(4):1101-13.
Maher et al. (2000) "Smooth wet etching by ultraviolet-assisted photoetching and its application to the fabrication of AlGaN/GaN heterostructure field-effect transistors," Appl. Phys. Lett. 77:3833.
Maikap et al. (2004) "Mechanically Strained-Si NMOSFETs," IEEE Electron. Dev. Lett. 25:40-42.
Makadia et al. (2011) "Poly Lactic-co-Glycolic Acid (PLGA) as Biodegradable Controlled Drug Delivery Carrier," Polymers. 3:1377-1397.
Makadia et al. (Aug. 26, 2011) "Poly Lactic-co-Glycolic Acid (PLGA) as Biodegradable Controlled Drug Delivery Carrier," Polymers. 3:1377-1397.
Maldovan et al. (2004) "Diamond-Structured Photonic Crystals," Nature Materials 3:593-600.
Mandlik et al. (Aug. 2006) "Fully Elastic Interconnects on Nanopatterned Elastomeric Substrates," IEEE Electron Dev. Lett. 27(8):650-652.
Mann et al. (1977) "Catalytic oxidation of methanol over molybdenum oxide-tungsten oxide," Journal of Applied Chemistry and Biotechnology. 27:198-204.

Manna et al. (Web Release May 25, 2003) "Controlled Growth of Tetrapod-Branched Inorganic Nanocrystals," Nat. Mater. 2:382-385.
Mannsfeld et al. (2010) "Highly sensitive flexible pressure sensors with microstructured rubber dielectric layers," Nat. Mater. 9:859-864.
Markovich et al. (1999) "Architectonic Quantum Dot Solids," Acc. Chem. Res. 32:415-423.
Marquette et al. (2004) "Conducting Elastomer Surface Texturing: A Path to Electrode Spotting Application to the Biochip Production," Biosens. Bioelectron. 20:197-203.
Martensson et al. (2004) "Nanowire Arrays Defined by Nanoimprint Lithography," Nano Lett. 4:699-702.
Martin, C.R. (1995) "Template Synthesis of Electronically Conductive Polymer Nanostructures," Acc. Chem. Res. 28:61-68.
Martinez-Boubeta et al. (2010) "Self-Assembled Multifunctional Fe/Mgo Nanospheres for Magnetic Resonance Imaging and Hyperthermia," Nanomedicine: Nanotechnology, Biology, and Medicine. 6:362-370.
Mas-Torrent et al. (2006) "Large Photoresponsivity in High-Mobility Single-Crystal Organic Field-Effect Phototransistors," ChemPhysChem 7:86-88.
Mastrangeli et al. (2009) "Self-assembly from milli- to nanoscales: methods and applications," J. Micromech. Microeng. 19:083001.
Masuda et al. (2000) "Fabrication of Ordered Diamonds/Metal Nanocomposite Structures," Chem. Lett. 10:1112-1113.
Masuda et al. (2003) "Transparent thin film transistors using ZnO as an active channel layer and their electrical properties," J. Appl. Phys. 93:1624.
Matsunaga et al. (2003) "An Improved GaAs Device Model for the Simulation of Analog Integrated Circuit," IEEE Trans. Elect. Dev. 50:1194-1199.
Mayevsky et al. (1998) "Real-time multi parametric monitoring of the injured human cerebral cortex—a new approach," Acta Neurochir. Suppl. 71:78-81.
McAlpine et al. (2003) "High-Performance Nanowire Electronics and Photonics on Glass and Plastic Substrates," Nano Lett. 3:1531-1535.
McAlpine et al. (2005) "High-Performance Nanowire Electronics and Photonics and Nanoscale Patterning on Flexible Plastic Substrates," Proc. IEEE 93:1357-1363.
McCaldin et al. (1971) "Diffusivity and Solubility of Si in the Al Metallization of Integrated Circuits," Appl. Phys. Lett. 19:524-517.
Mckhann et al. (2000) "Intraoperative hippocampal electrocorticography to predict the extent of hippocampal resection in temporal lobe epilepsy surgery," Journal of Neurosurgery. 93:44-52.
Mcnett et al. (Dec. 2014) "International multidisciplinary consensus conference on multi modality monitoring: ICU processes of care," Neurocrit Care. 21:215-228.
Medina-Montes et al. (2011) "Effects of Sputtered ZnO Layers on Behavoir of Thin-Film Transistors Deposited at Room Temperature in a Nonreactive Atmosphere," J. Electr. Mater. 40:1461-1469.
Mehring C. et al. (2003) Inference of hand movements from local field potentials in monkey motor cortex. Nature Neurosci. 6, 1253-1254.
Meisel et al. (2004) "Three-Dimensional Photonic Crystals by Holographic Lithography Using the Umbrella Configuration: Symmetries and Complete Photonic Band Gaps," Phys. Rev. B. 70:165101:1-10.
Meitl et al. (2004) "Solution Casting and Transfer Printing Single-Walled Carbon Nanotube Films," Nano Lett. 4:1643-1647.
Meitl et al. (2006) "Transfer Printing by Kinetic Control of Adhesion to an Elastomeric Stamp," Nat. Mater. 5:33-38.
Meitl et al. (Web Release Feb. 22, 2007) "Stress Focusing for Controlled Fracture in Microelectromechanical Systems," Appl. Phys. Lett. 90:083110.
Melosh et al. (2003) "Ultrahigh-Density Nanowire Lattices and Circuits," Science 300:112-115.
Menard et al. (2004) "A Printable Form of Silicon for High Performance Thin Film Transistors on Plastic Substrates," Appl. Phys. Lett. 84:5398-5400.

(56) References Cited

OTHER PUBLICATIONS

Menard et al. (2004) "High-Performance n- and p-Type Single-Crystal Organic Transistors with Free-Space Gate Dielectrics," Adv. Mat. 16:2097-2101.

Menard et al. (2004) "Improved Surface Chemistries, Thin Film Deposition Techniques, and Stamp Designs for Nanotransfer Printing," Langmuir 20:6871-6878.

Menard et al. (2005) "Bendable Single Crystal Silicon Thin Film Transistors Formed by Printing on Plastic Substrates," Appl. Phys. Lett. 86(093507):1-3.

Menard et al. (2007) Micro- and Nanopatterning Techniques for Organic Electronic and Optoelectronic Systems, Chem. Rev. 107:1117-1160.

Meyer et al. (2009) "Al2O3/ZrO2 Nanolaminates as Ultrahigh Gas-Diffusion Barriers—A Strategy for Reliable Encapsulation of Organic Electronics," Adv. Mater. 21:1845-1849.

MG Chemicals (2015) "Silver Conductive Epoxy: 10 Mins. Working Time / High Conductivity," MG Chemicals. Accessible on the Internet at URL: http://www.mgchemicals.com/products/adhesives/electrically-conductive/silver-conductive-epoxy-8331/. [Last Accessed Nov. 10, 2015].

Miao et al. (2003) "Micromachining of Three-Dimensional GaAs Membrane Structures Using High-Energy Nitrogen Implantation," J. Micromech. Microeng. 13:35-39.

Michalske et al. (1985) "Closure and Repropagation of Healed Cracks in Silicate Glass," J. Am. Ceram. Soc. 68:586-590.

Michel et al. (2001) Printing Meets Lithography: Soft Approaches to High-Resolution Printing, IBM J. Res. Dev. 45:697-719.

Middleton et al. (2000) "Synthetic biodegradable polymers as orthopedic devices," Biomaterials. 21:2335-2346.

Miller et al. (2002) "Direct Printing of Polymer Microstructures on Flat and Spherical Surfaces Using a Letterpress Technique," J. Vac. Sci. Technol. B 20(6):2320-2327.

Milliron et al. (2004) "Colloidal Nanocrystal Heterostructures with Linear and Branched Topology," Nature 430:190-195.

Min, G. (Apr. 4, 2003) "Plastic Electronics and Their Packaging Technologies," Syn. Metals. 135:141-143.

Minev et al. (2010) "Impedance Spectroscopy on Stretchable Microelectrode Arrays," Appl. Phys. Lett. 97:043707.

Minsky et al. (1996) "Room-temperature photoenhanced wet etching of GaN," Appl. Phys. Lett. 68:1531.

Mirkin et al. (2001) "Emerging Methods for Micro- and Nanofabrication," MRS Bulletin 26(7):506-507.

Misewich et al. (May 2, 2003) "Electronically Induced Optical Emission from a Carbon Nanotube FET," Science 300:783-786.

Mishra et al. (2002) "AlGaN/GaN HEMTs—an Overview of Device Operation and Applications," Proc. IEEE 90:1022-1031.

Mitzi et al. (2004) "High-Mobility Ultrathin Semiconducting Films Prepared by Spin Coating," Nature 428:299-303.

Miyake et al. (1994) "Formation of iron film by ion beam deposition," Surface and Coatings Technology. 65(1-3):208-213.

Miyamoto et al. (2004) "High-electron-mobility ZnO epilayers grown by plasma-assisted molecular beam epitaxy," Journal of Crystal Growth. 265:34-40.

Momose et al. (2002) "Ultrathin gate oxide CMOS on (111) surface-oriented Si substrate," IEEE Trans. Electron. Dev. 49:1597-1605.

Mondal et al. (2008) "Preparation of Al-Doped ZnO (AZO) Thin Film by SILAR," Journal of Physical Sciences. 12:221-229.

Moon et al. (2002) "Ink-Jet Printing of Binders for Ceramic Components," J. Am. Ceram. Soc. 85:755-762.

Moore et al. (1959) "II. Diffusion of zinc and oxygen in zinc oxide," Discussions of the Faraday Society. 28:86-93.

Moore et al. (Sep. 9, 2003) "Individually Suspended Single-Walled Carbon Nanotubes in Various Surfactants," Nano Lett. 3(10):1379-1382.

Morales et al. (Jan. 9, 1998) "A Laser Ablation Method for the Synthesis of Crystalline Semiconductor Nanowires," Science 279:208-211.

Moravej et al. (2011) "Biodegradable Metals for Cardiovascular Stent Application: Interests and New Opportunities," Int. J. Mol. Sci. 12:4250-4270.

Morent et al. (2007) "Adhesion Enhancement by a Dielectric Barrier Discharge of PDMS used for Flexible and Stretchable Electronics," J. Phys. D. Appl. Phys. 40:7392-7401.

Mori et al. (1978) "A New Etching Solution System, H3PO4—H2O2—H2O, for GaAs and Its Kinetics," J. Electrochem. Soc. 125:1510-1514.

Morita et al. (1990) "Growth of Native Oxide on a Silicon Surface," J. Appl. Phys. 68:1272-1281.

Morkoc et al. (1995) "High-Luminosity Blue and Blue-Green Gallium Nitride Light-Emitting Diodes," Science 267:51-55.

Morkved et al. (1994) "Mesoscopic Self-Assembly of Gold Islands on Diblock-Copolymer Films," Appl. Phys. Lett. 64:422-424.

Morra et al. (1990) "On the Aging of Oxygen Plasma-Treated Polydimthylsiloxane Surfaces," J. Colloid Interface Sci. 137:11-24.

Mudunkotuwa et al. (Nov. 28, 2011) "Dissolution of ZnO Nanoparticles at Circumneutral pH: A Study of Size Effects in the Presence and Absence of Citric Acid," Langmuir. 28:396-403.

Mueller et al. (Nov. 2012) "Histological and molecular evaluation of iron as degradable medical implant material in a murine animal model," Journal of Biomedical Materials Research Part A. 100A(11):2881-2889.

Murakami et al. (2005) "Polarization Dependence of the Optical Absorption of Single-Walled Carbon Nanotubes," Phys. Rev. Lett., 94, 087402.

Murphy et al. (2008) "Modification of Silk Fibroin Using Diazonium Coupling Chemistry and the Effects on hMSC Proliferation and Differentiation," Biomaterials 29:2829-2838.

Naghii et al. (2011) "Comparative Effects of Daily and Weekly Boron Supplementation on Plasma Steroid Hormones and Proinflammatory Cytokines," J. Trace Elem. Med. Bio. 25:54-58.

Namazu et al. (2000) "Evaluation of Size Effect on Mechanical Properties of Single Crystal Silicon by Nanoscale Bending Test Using AFM," J. MEMS 9:450-459.

Nath et al. (2002) "Nanotubes of the Disulfides of Groups 4 and 5 Metals," Pure Appl. Chem. 74(9):1545-1552.

Nathan et al. (2000) "Amorphous Silicon Detector and Thin Film Transistor Technology for Large-Area Imaging of X-Rays," Microelectron J. 31:883-891.

Nathan et al. (2002) "Amorphous Silicon Technology for Large Area Digital X-Ray and Optical Imaging," Microelectronics Reliability 42:735-746.

National Academy of Sciences (Last Updated Nov. 4, 2016) "Dietary Reference Intakes Tables and Application," Accessible on the Internet at URL: http://www.nationalacademies.org/hmd/Activities/Nutrition/SummaryDRIs/DRI-tables.aspx. [Last Accessed Mar. 14, 2017].

Newman et al. (2004) "Introduction to Organic Thin Film Transistors and Design of n-Channel Organic Semiconductors," Chem. Mater. 16:4436-4451.

Ng et al. (2010) "Effect of pH on the in vitro corrosion rate of magnesium degradable implant material," Materials Science and Engineering: C. 30(6):898-903.

Nicholas et al. (Oct. 7, 2011) "The mechanism for hydrothermal growth of zinc oxide," CrystEngComm. 14(4):1232-1240.

Nie et al. (2010) "In vitro corrosion, cytotoxicity and hemocompatibility of bulk nanocrystalline pure iron," Biomedical Materials. 5(6):065015.

Nirmal et al. (1999) "Luminescence Photophysics in Semiconductor Nanocrystals," Acc. Chem. Res. 32:407-414.

Noda et al. (1996) "New Realization Method for Three-Dimensional Photonic Crystal in Optical Wavelength Region," Jpn. J. Appl. Phys. 35:L909-L912.

Nomura et al. (2004) "Room-Temperature Fabrication of Transparent Flexible Thin-Film Transistors Using Oxide Semiconductors," Nature 432:488-492.

Novoselov et al. (Oct. 22, 2004) "Electric Field Effect in Atomically Thin Carbon Films," Science 306:666-669.

O'Connell et al. (Jul. 26, 2002) "Bang Gap Fluorescence from Individual Single-Walled Carbon Nanotubes," Science 297:593-596.

(56) References Cited

OTHER PUBLICATIONS

O'Riordan et al. (2004) "Field Configured Assembly: Programmed Manipulation and Self-Assembly at the Mesoscale," Nano Lett. 4:761-765.
Odom et al. (2002) "Improved Pattern Transfer in Soft Lithography Using Composite Stamps," Langmuir 18(13):5314-5320.
Ohzono et al. (2004) "Ordering of Microwrinkle Patterns by Compressive Strain," Phys. Rev. B 69(13):132202.
Ohzono et al. (Web Release Jul. 7, 2005) "Geometry-Dependent Stripe Rearrangement Processes Induced by Strain on Preordered Microwrinkle Patterns," Langmuir 21(16):7230-7237.
Oikawa (1975) "Ellipsometric Investigation of Corrosion of Deposited Thin Molybdenum Film," Japanese Journal of Applied Physics. 14(5):629-635.
Okonkwo et al. (Jul. 31, 2012) "Oxidation states of molybdenum in oxide films formed in sulphuric acid and sodium hydroxide," Thin Solid Films. 520(19):6318-6327.
Omenetto et al. (2008) "A New Route for Silk," Nature Photon. 2:641-643.
Ondo-Ndong et al. (2003) "Electrical properties of zinc oxide sputtered thin films," Microelectronics Journal. 34:1087-1092.
Ong et al. (2004) "High-Performance Semiconducting Polythiophenes for Organic Thin-Film Transistors," J. Am. Chem. Soc. 126:3378-3379.
Ong et al. (2005) "Design of High-Performance Regioregular Polythiophenes for Organic Thin-Film Transistors," Proc. IEEE 93:1412-1419.
Origin Energy (May 2004) "Fact Sheet—Sliver Cells," www.orginenergy.com.au/sliver.
Oskam et al. (1998) "Electrochemical deposition of metals onto silicon," J. Phys. D: Appl. Phys. 31:1927-1949.
Ouyang et al. (2002) "High-Performance, Flexible Polymer Light-Emitting Diodes Fabricated by a Continuous Polymer Coating Process," Adv. Mat. 14:915-918.
Ouyang et al. (2004) "Polymer Optoelectronic Devices with High-Conductivity Poly(3,4-Ethylenedioxythiophene) Anodes," Journal of Macromolecular Science. 41(12):1497-1511.
Ouyang et al. (2008) "High Frequency Properties of Electro-Textiles for Wearable Antenna Applications," IEEE Trans. Antennas Propag. 56(2):381-389.
Ouyang et al. (Web Release Mar. 20, 2000) "Conversion of Some Siloxane Polymers to Silicon Oxide by UV/Ozone Photochemical Processes," Chem. Mater. 12(6):1591-1596.
Overholt et al. (2005) "Photodynamic Therapy for Esophageal Cancer using a 180° Windowed Esophageal Balloon," Lasers in Surg. Med. 14:27-33.
Ozisik et al. (1971) "Carbon Loss from Graphite Cylinders Exposed to Steam for Short Times," Nuclear Science and Engineering. 44:310-319.
Pal et al. (2006) "Development of carboxymethyl cellulose acrylate for various biomedical applications," Biomedical Materials. 1:85-91.
Pan et al. (2001) "Nanobelts of Semiconducting Oxides," Science 291:1947-1949.
Pan et al. (2010) "Design and Fabrication of Flexible Piezo-Microgenerator by Depositing ZnO Thin Films on PET Substrates," Sensors and Actuators A. 159:96-104.
Pandy et al. (1998) "Experimental Investigation of High Si/Al Selectivity During Anisotropic Etching in Tetra-Methyl Ammonium Hydroxide," J. Vac. Sci. Technol. A. 16(2):868-872.
Panev et al. (2003) "Sharp Excitation from Single InAs Quantum Dots in GaAs Nanowires," Appl. Phys. Lett. 83:2238-2240.
Pang et al. (Jul. 29, 2012) "A flexible and highly sensitive strain-gauge sensor using reversible interlocking of nanofibres," Nat. Mater. 11:795-801.
Panilaitis et al. (2003) "Macrophage responses to silk," Biomaterials. 24:3079-3085.
Pardo et al. (2000) "Application of Screen Printing in the Fabrication of Organic Light-Emitting Devices," Adv. Mater. 12(17):1249-1252.
Park et al. (1997) "Block Copolymer Lithography: Periodic Arrays of ~1011 Holes in 1 Square Centimeter," Science 276:1401-1404.
Park et al. (1998) "Fabrication of Three-Dimensional Macroporous Membranes with Assemblies of Microspheres as Templates," Chem. Mater. 10:1745-1747.
Park et al. (1999) "Fabrication of Metallic Electrodes with Nanometer Separation by Electromigration," Appl. Phys. Lett. 75:301-303.
Park et al. (2003) "Electrocatalytic Enhancement of Methanol Oxidation at Pt—WOx Nanophase Electrodes and In-Situ Observation of Hydrogen Spillover Using Electrochromism," The Journal of Physical Chemistry B. 107:4352-4355.
Park et al. (2005) "Wireless Thermal Micro-Ablation of Skin for Transdermal Drug Delivery," In; The 13th International Conference on Solid-state Sensors, Actuators and Microsystems. 2:1238-1241.
Park et al. (2007) "High Resolution Electrohydrodynamic Jet Printing," Nature Materials. 6:782-789.
Park et al. (2008) "High Aspect-Ratio Cylindrical Nanopore Arrays and Their Use for Templating Titania Nanoposts," Adv. Mater. 20:738-742.
Park et al. (2008) "Nanoscale Patterns of Oligonucleotides Formed by Electrohydrodynamic Jet Printing with Applications in Biosensing and Nanomaterials Assembly," Nano Lett. 8:4210-4216.
Park et al. (2008) "Theoretical and Experimental Studies of Bending of Inorganic Electronic Materials on Plastic Substrates," Adv. Funct. Mater. 18:2673-2684.
Park et al. (2009) "Biodegradable Luminescent Porous Silicon Nanoparticles for in Vivo Applications," Nature Mater. 8:331-336.
Park et al. (2009) "Printed Assemblies of Inorganic Light-Emitting Diodes for Deformable and Semitransparent Displays," Science 325:977-981.
Park et al. (2010) "Nanoscale, Electrified Liquid Jets for High-Resolution Printing of Charge," Nano Lett. 10:584-591.
Park et al. (Oct. 26, 2013) "Inorganic/organic multilayer passivation incorporating alternating stacks of organic/inorganic multilayers for long-term air-stable organic light-emitting diodes," Org. Electron. 14:3385-3391.
Parker et al. (2009) "Biocompatible Silk Printed Optical Waveguides," Adv. Mater. 21:2411-2415.
Patolsky et al. (2006) "Stimulation, and Inhibition of Neuronal Signals with High-Density Nanowire Transistor Arrays," Science 313:1100-1104.
Patrick et al. (2011) "Corrosion of tungsten microelectrodes used in neural recording applications," Journal of Neuroscience Methods. 198(2)158-171.
Patton et al. (Mar. 1998) "Effect of Diamond like Carbon Coating and Surface Topography on the Performance of Metal Evaporated Magnetic Tapes," IEEE Trans Magn. 34(2):575-587.
Paul et al. (Apr. 2003) "Patterning Spherical Surfaces at the Two Hundred Nanometer Scale Using Soft Lithography," Adv. Func. Mater. 13(4):259-263.
Pearce et al. (Feb. 15, 2014) "Spike-wave discharges in adult Sprague-Dawley rats and their implications for animal models of temporal lobe epilepsy," Epilepsy & Behavior. 32:121-131.
Pearton et al. (1999) "GaN: Processing, Defects, and Devices," J. Appl. Phys. 86:1-78.
Peng et al. (Mar. 2, 2000) "Shape Control of CdSe Nanocrystals," Nature 404:59-61.
Pennington (1991) "Silicon in foods and diets Food," Addit. Contam. 8:97-118.
Perry et al. (2008) "Nano- and Micropatterning of Optically Transparent, Mechanically Robust, Biocompatible Silk Fibroin Films," Adv. Mater. 20:3070-3072.
Petrova et al. (2011) "Mechanism of anodic oxidation of molybdenum in nearly-neutral electrolytes studied by electrochemical impedance spectroscopy and X-ray photoelectron spectroscopy," Electrochimica Acta. 56(23):7899-7906.
Peuster et al. (2001) "A Novel Approach to Temporary Stenting: Degradable Cardiovascular Stents Produced from Corrodible Metal-Results 6-18 Months After Implantation Into New Zealand White Rabbits," Heart. 86:563-569.

(56) References Cited

OTHER PUBLICATIONS

Peuster et al. (2003) "Biocompatibility of Corroding Tungsten Coils: In Vitro Assessment of Degradation Kinetics and Cytotoxicity on Human Cells." Biomaterials. 24:4057-4061.
Peuster et al. (2003) "Degradation of Tungsten Coils Implanted Into the Subclavian Artery of New Zealand White Rabbits is not Associated with Local or Systemic Toxicity," Biomaterials. 24:393-399.
Peuster et al. (2006) "Long-term biocompatibility of a corrodible peripheral iron stent in the porcine descending aorta," Biomaterials. 27(28):4955-4962.
Pham et al. (2012) "Fast phase reconstruction in white light diffraction phase microscopy," Appl. Opt. 52:A97-A101.
Philipp et al. (1999) "Shadow Evaporation Method for Fabrication of Sub 10 nm Gaps Between Metal Electrodes," Microelectron. Eng. 46:157-160.
Piazza et al. (2005) "Protective Diamond-Like Carbon Coatings for Future Optical Storage Disks," Diamond Relat. Mater. 14:994-999.
Pierret (1996) "MOSFETs —The Essentials," Ch. 17 In; Semiconductor Device Fundamentals. Addison-Wesley. Natick, Massachusetts. pp. 611-645.
Pierret (1996) "Non Ideal MOS," Ch. 18 In; Semiconductor Device Fundamentals. Addison-Wesley. Natick, Massachusetts. pp. 645-690.
Piispanen et al. (1995) "Complex Formation Equilibria of Some Aliphatic alpha-Hydroxycarboxylic Acids. 1. The Determination of Protonation Constants and the Study of Calcium(II) and Magnesium(II) Complexes," Acta Chemica Scandinavica. 49:235-240.
Pimparkar et al. (Feb. 2007) "Current-Voltage Characteristics of Long-Channel Nanobundle Thin-Film Transistors: A 'Bottom-Up' Perspective," IEEE Electron Dev. Lett. 28(2):157-160.
Pique et al. (2006) "Embedding electronic circuits by laser direct-write," Microelect. Eng. 83:2527-2533.
Podzorov et al. (2005) "Hall Effect in the Accumulation Layers on the Surface of Organic Semiconductors," Phys. Rev. lett. 95:226601.
Polikov et al. (2005) "Response of brain tissue to chronically implanted neural electrodes," Journal of neuroscience methods. 148:1-18.
Ponnusamy et al. (Apr. 1, 2012) "In vitro degradation and release characteristics of spin coated thin films of PLGA with a 'breath figure' morphology" Biomatter. 2:77-86.
Popescu et al. (2006) "Diffraction phase microscopy for quantifying cell structure and dynamics," Optics Letters. 31:775-777.
Preechatiwong et al. (1996) "Electrical conductivity of poly(ethylene oxide)—alkali metal salt systems and effects of mixed salts and mixed molecular weights," Polymer 37:5109-5116.
Proteus® Digital Health (2014) "Digital Health Feedback System," Proteus® Digital Health Accessible on the Internet at URL: http://www.proteus.com/. [Last Accessed Nov. 5, 2014].
Pushpa et al. (2002) "Stars and Stripes. Nanoscale Misfit Dislocation Patterns on Surfaces," Pure Appl. Chem. 74(9):1663-1671.
Qian et al. (2006) "Scaling Effects of Wet Adhesion in Biological Attachment Systems," Acta Biomaterialia 2:51-58.
Qing et al. (2010) "Nanowire transistor arrays for mapping neural circuits in acute brain slices," Proc. Natl Acad. Sci. 107:1882-1887.
Quake et al. (2000) "From Micro- to Nanofabrication with Soft Materials," Science 290:1536-1540.
Racz et al. (2004) "Nanofabrication Using Nanotranslated Stencil Masks and Lift Off," J. Vac. Sci. Technol. B. 22(1):74-76.
Rácz et al. (2007) "Characterization and Control of Unconfined Lateral Diffusion Under Stencil Masks," J. Vac. Sci. Technol. B. 25:857-861.
Radtke et al. (Feb. 5, 2007) "Laser-Lithography on Non-Planar Surfaces," Opt. Exp. 15(3):1167-1174.
Raicu et al. (2000) "A quantitative approach to the dielectric properties of the skin," Phys. Med. Biol. 45:L1.
Raman et al. (1989) "Study of Mesa Undercuts Produced in GaAs with H3PO4-Based Etchants," J. Electrochem. Soc. 136:2405-2410.
Randall et al. (2005) "Permeation-driven flow in poly(dimethylsiloxane) microfluidic devices," Proc. Nat. Acad. Sci. USA 102(31):10813-10818.

Rao et al. (2003) "Large-scale assembly of carbon nanotubes," Nature, 425:36-37.
Razavi et al. (2009) "Three Dimensional Nanopillar Array Photovoltaics on Low Cost and Flexible Substrates," Nature Materials 8:648-653.
Razeghi et al. (1994) "High-Power Laser Diode Based on InGaAsP Alloys," Nature 369:631-633.
Razouk et al. (Sep. 1979) "Dependence of Interface State Density on Silicon Thermal Oxidation Process Variables," J. Electrochem. Soc. 126(9):1573-1581.
Reed et al. (Dec. 9, 2011) "Solubility of nano-zinc oxide in environmentally and biologically important matrices," Environ. Toxicol. Chem. 31:93-99.
Reiner et al. (2010) "Crystalline Oxides on Silicon," Adv. Mater. 22:2919-2938.
Reuss et al. (Jul. 2005) "Macroelectronics: Perspectives on Technology and Applications," Proc. IEEE 93(7):1239-1256.
Reuss et al. (Jun. 2006) "Macroelectronics," MRS Bull. 31:447-454.
Ribas et al. (1998) "Bulk Micromachining Characterization of 1.2 μm HEMT MMIC Technology for GaAs MEMS Design," Mater. Sci. Eng. B 51:267-273.
Richter et al. (2008) "Review on Hydrogel-based pH Sensors and Microsensors," Sensors. 8:561-581.
Ridley et al. (1999) "All-Inorganic Field Effect Transistors Fabricated by Printing," Science 286:746-749.
Rimstidt et al. (1980) "Kinetics of Silica-Water Reactions," Geochim. Cosmochim. Ac. 44:1683-1699.
Robbie et al. (1997) "Sculptured Thin Films and Glancing Angle Deposition: Growth Mechanics and Applications," J. Vac. Sci. Technol. A. 15(3):1460-1465.\.
Robbie et al. (1998) "Advanced Techniques for Glancing Angle Deposition," J. Vac. Sci. Technol. B. 16(3):1115-1122.
Roberts et al. (1979) "Looking at Rubber Adhesion," Rubber Chem. Technol. 52:23-42.
Roberts et al. (Mar. 2006) "Elastically Relaxed Free-Standing Strained-Silicon Nanomembranes," Nat. Mater. 5:388-393.
Robertson (2004) "High dielectric constant oxides," Eur. Phys. J. Appl. Phys. 28:265-291.
Robertson (2006) "High dielectric constant gate oxides for metal oxide Si transistor," Rep. Prog. Phys. 69:327-396.
Robertson (2008) "Maximizing performance for higher K gate dielectrics," J. Appl. Phys. 104:124111.
Robinson (2009) "E-waste: an assessment of global production and environmental impacts," Science of The Total Environment. 408:183-191.
Robinson et al. (1983) "GaAs Readied for High-Speed Microcircuits," Science 219:275-277.
Rodgers et al. (Jun. 17, 2015) "Progressive, seizure-like, spike-wave discharges are common in both injured and uninjured sprague-dawley rats: implications for the fluid percussion injury model of post-traumatic epilepsy," The Journal of Neuroscience. 35:9194-9204.
Rodriguez et al. (2007) "Dual-frequency resonance-tracking atomic force microscopy," Nanotechnology. 18:475-504.
Roelkens et al. (Dec. 2005) "Integration of InP/InGaAsP Photodetectors onto Silicon-on-Insulator Waveguide Circuits," Optics Express 13(25):10102-10108.
Rogers et al. (1997) "Using an Elastomeric Phase Mask for Sub-100 nm Photolithography in the Optical Near Field," Appl. Phys. Lett. 70:2658-2660.
Rogers et al. (1998) "Generating ~90 Nanometer Features Using Near Field Contact Mode Photolithography with an Elastomeric Phase Mask," J. Vac. Sci. Technol. 16(1):59-68.
Rogers et al. (1998) "Quantifying Distortions in Soft Lithography," J. Vac. Sci. Technol. 16:88-97.
Rogers et al. (1998) "Using Printing and Molding Techniques to Produce Distributed Feedback and Bragg Reflector Resonators for Plastic Lasers," Appl. Phys. Lett. 73:1766-1768.
Rogers et al. (1999) Printing Process Suitable for Reel-to-Reel Production of High-Performance Organic Transistors and Circuits, Adv. Mater. 11(9):741-745.

(56) References Cited

OTHER PUBLICATIONS

Rogers et al. (2000) "Organic Smart Pixels and Complementary Inverter Circuits Formed on Plastic Substrates by Casting and Rubber Stamping," IEEE Electron Dev. Lett. 21(3):100-103.
Rogers et al. (2002) "Paper-Like Electronic Displays: Large-Area Rubber-Stamped Plastic Sheets of Electronics and Microencapsulated Electrophoretic Inks," Proc. Nat. Acad. Sci. USA 98:4835-4840.
Rogers et al. (2002) "Printed Plastic Electronics and Paperlike Displays," J. Polym. Sci. Part A. Polym. Chem. 40:3327-3334.
Rogers et al. (2010) "Materials and Mechanics for Stretchable Electronics," Science. 327:1603-1607.
Rogers et al. (2011) "Synthesis, assembly and applications of semiconductor nanomembranes," Nature. 477:45-53.
Rogers, J.A. (2001) "Rubber Stamping for Plastic Electronics and Fiber Optics," MRS Bulletin 26(7):530-534.
Rogers, J.A. (2001) "Toward Paperlike Displays," Science 291:1502-1503.
Roney et al. (Sep. 2004) "Toxicological Profile for Ammonia," Agency for Toxic Substances and Disease Registry. Ammonia. 1-223.
Rosenblatt et al. (2002) "High Performance Electrolyte Gated Carbon Nanotube Transistors," Nano Lett. 2(8):869-872.
Rosink et al. (2005) "Ultra-Thin Encapsulation for Large-Area OLED Displays," SID 05 Digest of Technical Papers. Paper No. 34.1. pp. 1272-1275.
Rotkin et al. (2003) "Universal Description of Channel Conductivity for Nanotube and Nanowire Transistors," Appl. Phys. Lett. 83:1623-1625.
Roundy et al. (2003) "Photonic Crystal Structure with Square Symmetry within Each Layer and a Three-Dimensional Band Gap," Appl. Phys Lett. 82:3835-3837.
Rubehn et al. (2009) "A MEMS based Flexible Multichannel ECoG-Electrode Array," J. Neural Eng. 6:036003.
Ruchehoeft et al. (2000) "Optimal Strategy for Controlling Linewidth on Spherical Focal Surface Arrays," J. Vac. Sci. Technol. B 18(6):3185-3189.
Rutherglen (2010) "Polyanhydride Networks from Thiol-Ene Polymerizations," Macromolecules. 43:10297-10303.
Ryu et al. (2009) "Human Cortical Prostheses: Lost in Translation?" Neurosurg Focus 27(1):E5.
Saad et al. (2008) "Characterization of various zinc oxide catalysts and their activity in the dehydration-dehyrogenation of isobutanol," J. Serb. Chem. Soc. 73:997-1009.
Sabir et al. (2009) "A review on biodegradable polymeric materials for bone tissue," J. Mater. Sci. 44:5713-5724.
Saha et al. (2010) "Highly doped polycrystalline silicon microelectrodes reduce noise in neuronal recordings in vivo," IEEE Trans Neural Sys Rehab Eng. 18:489-97.
Samaniego et al. (Mar. 2013) "Combined effect of composition and surface condition on corrosion behaviour of magnesium alloys AZ31 and AZ61," Corrosion Science. 68:66-71.
Sammoura et al. (2004) "Water-activated disposable and long shelf life microbatteries," Sensors and Actuators A: Physical. 111:79-86.
Samuelson et al. (2004) "Semiconductor Nanowires for Novel One-Dimensional Devices," Physica E 21:560-567.
Sancaktar et al. (2011) "Electrically Conductive Epoxy Adhesives," Polymers. 3:427-466.
Sang et al. (2011) "Thin Film Encapsulation for OLED Display using Silicon Nitride.and Silicon Oxide Xomposite Film," In; The Proceedings of the Int. Conf. Electronic Packaging Technology & High Density Packaging. Shanghai, China 2011. pp. 1175-1178.
Sangwal et al. (1997) "Nature of multilayer steps on the {100} cleavage planes of MgO single crystals," Surf. Sci., 383:78-87.
Sankir et al. (2008) "Electrical and Morphological Characterization of Polyaniline/Sulfonated Poly(Arylene ether Sulfone) Composite Films," J. Mater. Sci.: Mater. El. 19(4):389-392.

Santamaria et al. (2007) "Initial surface film on magnesium metal: a.characterization by X-ray photoelectron spectroscopy (XPS) and photocurrent spectroscopy (PCS)," Electrochimica Acta. 53(3):1314-1324.
Santin et al. (1999) "In vitro Evaluation of the Inflammatory Potential of the Silk Fibroin," J. Biomed. Mater. Res. 46:382-389.
Santra et al. (2010) "Silicon on Insulator Diode Temperature Sensor—A Detailed Analysis for Ultra-High Temperature Operation," IEEE Sens. J. 10(5):997-1003.
Sanyal et al. (2002) "Morphology of Nanostructured Materials," Pure Appl. Chem. 74(9):1553-1570.
Sato et al. (1999) "Anisotropic etching rates of single-crystal silicon for TMAH water solution as a function of crystallographic orientation," Sens. Actuators A. 73:131-137.
Sazonov et al. (2005) "Low-Temperature Materials and Thin-Film Transistors for Flexible Electronics," Proc. IEEE 93:1420-1428.
Scherlag et al. (1969) "Catheter Technique for Recording His Bundle Activity in Man," Circulation 39:13-18.
Schermer et al. (Web Release Apr. 28, 2005) "Thin-Film GaAs Epitaxial Lift-Off Solar Cells for Space Applications," Prog. Photovoltaics: Res. Applic. 13:587-596.
Schermer et al. (Web Release Jan. 19, 2006) "Photon Confinement in High-Efficiency, Thin-Film III-V Solar Cells Obtained by Epitaxial Lift-Off," Thin Solid Films 511-512:645-653.
Schift (2008) "Nanoimprint Lithography: An Old Story in Modern Times? A Review," J. Vac. Sci. Technol. B. 26(2):458-480.
Schindl et al. (2003) "Direct Stimulatory Effect of Low-Intensity 670-nm Laser Irradiation on Human Endothelial Cell Proliferation," Br. J. Dermatol. 148:334-336.
Schlegel et al. (2002) "Structures of quartz (1010)- and (1011)-water interfaces determined by X-ray reflectivity and atomic force microscopy of natural growth surfaces," Geochim. Cosmochim. Acta, vol. 66, No. 17, pp. 3037-3054.
Schlom et al. (2008) "Gate Oxides Beyond SiO2," MRS Bulletin. 33:1017-1025.
Schluter et al. (2010) "Comparison of the corrosion behaviour of bulk and thin film magnesium alloys," Corrosion Science. 52(12):3973-3977.
Schmickler et al. (2010) "Thermodynamics of ideal polarizable interfaces," Ch. 11 in; Interfacial Electrochemistry. Springer, Berlin Heidelberg.
Schmid et al. (1998) "Light- Coupling Masks for Lensless, Sub-wavelength Optical Lithography," Appl. Phys. Lett. 72(19):2379-2381.
Schmid et al. (2000) "Siloxane Polymers for High-Resolution, High-Accuracy Soft Lithography," Macromolecules 33(8):3042-3049.
Schmid et al. (2003) "Preparation of Metallic Films on Elastomeric Stamps and Their Application on Contact Processing and Contact Printing," Adv. Funct. Mater. 13:145-153.
Schmidt et al. (2001) "Thin Solid Films Roll up into Nanotubes," Nature 410:168.
Schnable et al. (1969) "Aluminum Metallization; Advantages and Limitations for Integrated Circuit Applications," IEEE 57:1570-1580.
Schneider et al. (2008) "Mechanical Properties of Silicones for MEMS," J. Micromech. Microeng. 18:065008.
Schoenfeld (2007) "Contemporary Pacemakers and Defibrillator Device Therapy," Circulation.115:638-653.
Schon et al. (1995) "Ambipolar Pentacene Field-Effect Transistors and Inverters," Science 287:1022-1023.
Schroder (2006) "Mobility," Ch. 8 In; Semiconductor Materials and Device Characterization. 3rd Ed. Wiley. Hoboken, New Jersey.
Schwertmann (1991) "Solubility and dissolution of iron oxides," Plant and Soil. 130(1-2):1-25.
Scorzoni et al. (Oct. 4, 2004) "On the Relationship Between the Temperature Coefficient of Resistance and the Thermal Conductance of Integrated Metal Resistors," Sens Actuators A 116(1):137-144.
Seidel et al. (1990) "Anisotropic etching of crystalline silicon in alkaline solutions: I. orientation dependence and behavior of passivation layers," J. Electrochem. Soc. 137:3612-3626.

(56) References Cited

OTHER PUBLICATIONS

Seidel et al. (1990) "Anisotropic etching of crystalline silicon in alkaline solutions: II. influence of dopants," J. Electrochem. Soc. 737:3626-3632.
Seidel et al. (2004) "High-Current Nanotube Transistors," Nano Lett., vol. 4, No. 5, pp. 831-834.
Sekitani et al. (2005) "Bending Experiment on Pentacene Field-Effect Transistors on Plastic Films," Appl. Phys. Lett. 86:073511.
Sekitani et al. (2008) "A Rubberlike Stretchable Active Matrix Using Elastic Conductors," Science 321:1468-1472.
Sekitani et al. (2008) "Organic transistors manufactured using inkjet technology with subfemtoliter accuracy," Proc. Nat. Acad. Sci. 105:4976-4980.
Sekitani et al. (2009) "Stretchable Active-Matrix Organic Light-Emitting Diode Display Using Printable Elastic Conductors," Nature Mater. 8:494-499.
Sekitani et al. (Mar. 2012) "Stretchable organic integrated circuits for large-area electronic skin surface," MRS Bull. 37:236-245.
Semprius.com (2014) "Semprius," Semprius, Inc. Accessible on the Internet at URL: http://www.semprius.com/. [Last Accessed Dec. 9, 2015].
Sen et al. (2002) "Nonequilibrium Processes for Generating Silicon Nanostructures in Single-Crystalline Silicon," Pure Appl. Chem. 74(9):1631-1641.
Serikawa et al. (May 1, 2000) "High-Mobility Poly-Si Thin Film Transistors.Fabricated on Stainless-Steel Foils by Low-Temperature Processes Using Sputter-Depositions," Jpn. J. Appl. Phys. 39:L393-L395.
Servanti et al. (2005) "Functional Pixel Circuits for Elastic AMOLED displays," Proc. IEEE 93:1257-1264.
Service, R.F. (Aug. 15, 2003) "Electronic Textiles Charge Ahead," Science 301:909-911.
Shahrjerdi et al. (Dec. 18, 2012) "Extremely Flexible Nanoscale Ultrathin Body Silicon Integrated Circuits on Plastic," Nano Lett. 13:315-320.
Shan et al. (2004) "From Si Source Gas Directly to Positioned, Electrically Contained Si Nanowires: The Self-Assembling 'Grow-in-Place' Approach," Nano Lett. 4(11):2085-2089.
Shapiro et al. (Oct. 27, 2011) "Stentsupported aneurysm coiling: a literature survey of treatment and follow-up," American Journal of Neuroradiology. 33:159-163.
Sharp et al. (2003) "Holographic Photonic Crystals with Diamond Symmetry," Phys. Rev. B 68:205102/1-205102/6.
Shaw (2004) "Is spontaneous high-voltage rhythmic spike discharge in Long Evans rats an absence-like seizure activity?" Journal of neurophysiology. 91:63-77.
Shelanski et al. (1948) "Physiological Action OP Sodium Carboxymethyl-Cellulose on Laboratory Animals and Humans," Journal of Food Science. 13:29-35.
Shen et al. (2007) "Submicron Particles of SBA-15 Modified with MgO as Carriers for Controlled Drug Delivery," Chem. Pharm. Bull. 55(7):985-991.
Sheraw et al. (2002) "Organic Thin-Film Transistor-Driven Polymer-Dispersed.Liquid Crystal Displays on Flexible Polymeric Substrates," Appl. Phys. Lett. 80:1088-1090.
Sherif et al. (2010) "In situ Raman spectroscopy and electrochemical techniques for studying corrosion and corrosion inhibition of iron in sodium chloride solutions," Electrochimica Acta. 55(11):3657-3663.
Shetty et al. (2005) "Formation and Characterization of Silicon Films on Flexible Polymer Substrates," Mater. Lett. 59:872-875.
Shi et al. (2001) "Free-Standing Single Crystal Silicon Nanoribbons," J. Am. Chem. Soc. 123(44):11095-11096.
Shi et al. (Sep. 2000) "Synthesis of Large Areas of Highly Oriented, Very Long Silicon Nanowires," Adv. Mater. 12(18):1343-1345.
Shimizu et al. (Jun. 2012) "Letter: Zinc Oxide Paste as Sunscreen in the Postoperative Period," Dermatologic Surgery. 38:965-966.
Shimizu et al. (Jun. 2012) "Zinc Oxide Paste as Sunscreen in the Postoperative Period," Dermatologic Surgery. 38:965-966.
Shin et al. (2003) "PDMS-Based Micro PCR Chip with Parylene Coating," J. Micromech. Microeng. 13:768-774.
Shipp et al. (2009) "Elastomeric and degradable polyanhydride network polymers by step-growth thiol—ene photopolymerization," Chem. Commun. pp. 6415-6417.
Shipak et al. (2007) "XPS studies of active elements surface of gas sensors based on WO3-x nanoparticles," Journal of Electron Spectroscopy and Related Phenomena. 156:172-175.
Shtein et al. (Oct. 15, 2004) "Direct Mask-Free Patterning of Molecular Organic Semiconductors Using Organic Vapor Jet Printing," J. Appl. Phys. 96(8):4500-4507.
Shull et al. (1998) "Axisymmetric Adhesion Tests of Soft Materials," Macromol. Chem. Phys. 199:489-511.
Siegel et al. (2009) "lightweight, Foldable Thermochromic Displays on Paper," Lab Chip 9:2775-2781.
Siegel et al. (2010) "Foldable Printed Circuit Boards on Paper Substrates," Adv. Funct. Mater. 20:28-35.
Siegel et al. (Web Release Feb. 7, 2007) "Microsolidics: Fabrication of Three-Dimensional Metallic Microstructures in Poly(dimethylsiloxane)," Adv. Mater.19(5):727-733.
Sim et al. (1993) "An Analytical Back-Gate Bias Effect Model for Ultrathin SOI CMOS Devices," IEEE Trans. Elec. Dev. 40:755-765.
Singhal et al. (1998) "Absorbable Suture Materials: Preparation and Properties," Polym. Rev. 28:475-502.
Sirringhaus et al. (2003) "Inkjet Printing of Functional Materials," MRS Bull. 28:802-806.
Sirringhaus et al. (Dec. 15, 2000) "High-Resolution Inkjet Printing of All-Polymer Transistor Circuits," Science 290:2123-2126.
Sirringhaus, H. (2005) "Device Physics of Solution-Processed Organic Field-Effect Transistors," Adv. Mater. 17:2411-2425.
Smay et al. (2002) "Colloidal Inks for Directed Assembly of 3-D Periodic Structures," Langmuir 18:5429-5437.
Smith et al. (2000) "Electric-Field Assisted Assembly and Alignment of Metallic Nanowires," Appl. Phys. Lett. 77(9):1399-1401.
Snow et al. (2003) "Random networks of carbon nanotubes as an electronic material," Appl. Phys. Lett., vol. 82, No. 13, pp. 2145-2147.
Snow et al. (2005) "High-mobility carbon-nanotube transistors on a polymeric substrate," Appl. Phys. Lett., 86, 033105.
So et al. (2008) Organic Light-Emitting Devices for Solid-State Lighting, MRS Bull. 33:663-669.
Sofia et al. (2001) "Functionalized Silk-Based Biomaterials for Bone Formation," J. Biomed. Mater. Res. 54:139-148.
Solorio et al. (Nov. 8, 2012) "Noninvasive characterization of the effect of varying PLGA molecular weight blends on in situ forming implant behavior using ultrasound imaging," 2(11):1064-1077.
Someya et al. (2004) "A Large-Area, Flexible, Pressure Sensor Matrix with Organic.Field-Effect Transistors for Artificial Skin Applications," Proc. Nat. Acad. Sci. USA 101(27):9966-9970.
Someya et al. (2005) "Conformable, Flexible, Large-Area Networks of Pressure and Thermal Sensors with Organic Transistor Active Matrixes," Proc. Nat. Acad. Sci. USA 102:12321-12325.
Someya et al. (2005) "Integration of Organic FETs with Organic Photodiodes for a Large Area, Flexible, and Lightweight Sheet Image Scanners," IEEE Trans. Electron Devices 52:2502-2511.
Song (2007) "Control of Biodegradation of Biocompatible Magnesium Alloys," Corrosion Science. 49:1696-1701.
Song et al. (2003) "Understanding Magnesium Corrosion—A Framework for Improved Alloy Performance," Advanced Engineering Materials. 5:837-858.
Song et al. (2009) "Mechanics of noncoplanar mesh design for stretchable electronic circuits," Journal of Applied Physics. 105:123516.
Soole et al. (Mar. 1991) "InGaAs Metal-Semiconductor-Metal Photodetectors for Long Wavelength Optical Communications," IEEE J. Quantum Electron. 27(3):737-752.
Soong et al. (1984) "Adverse Reactions to Virgin Silk Sutures in Cataract Surgery," Ophthalmology 91:479-483.
Soppimatha et al. (2001) "Biodegradable polymeric nanoparticles as drug delivery devices," J. Controlled Release. 70(1-2):1-20.
Sordan et al. (2001) "Removable Template Route to Metallic Nanowires and Nanogaps," Appl. Phys. Lett. 79(13):2073-2075.

(56) References Cited

OTHER PUBLICATIONS

Spi© Supplies (2015) "Conductive (Silver) Expoxies," Structure Probe, Inc. Accessible on the Internet at URL: http://www.2spi.com/category/conductive-epoxies/. [Last Accessed Nov. 10, 2015].
Srinivasan et al. (Web Release Mar. 26, 2007) "Piezoelectric/Ultrananocrystalline Diamond Heterostructures for High-Performance Multifunctional Micro/Nanoelectromechanical Systems," Appl. Phys. Lett. 90:134101.
Stacey et al. (2008) "Technology insight: neuroengineering and epilepsy-designing devices for seizure control," Nat. Clin. Pract. Neural. 4:190-201.
Stafford et al. (Aug. 2004) "A Buckling-Based Metrology for Measuring the Elastic Moduli of Polymeric Thin Films," Nature Mater. 3:545-550.
Staiger et al. (2006) "Magnesium and its alloys as orthopedic biomaterials: a review," Biomaterials. 27:1728-1734.
Star et al. (2004) "Nanotube Optoelectric Memory Devices," Nano Lett., vol. 4, No. 9, pp. 1587-1591.
Stathis et al. (2006) "The negative bias temperature instability in MOS devices: A review," Microelec. Rel. 46:270-286.
Stauth et al. (2006) "Self-assembled single-crystal silicon circuits on plastic," Proc. Natl. Acad. Sci. USA. 19:13922-13927.
Stefaniak (2010) "Persistence of tungsten oxide particle/fiber mixtures in artificial human lung fluids," Particle and Fibre Toxicology. 7:38.
Storm et al. (Aug. 2003) "Fabrication of Solid-State Nanopores with Single-Nanometre Precision," Nat. Mater. 2:537-540.
Streetman et al. (2000) "Intrinsic Material," In; Solid State Electronic Devices, 5th Ed., Prentice Hall; Upper Saddle River, NJ; pp. 74-75.
Strigul (2010) "Does speciation matter for tungsten ecotoxicology?" Ecotoxicology and Environmental Safety. 73(6):1099-1113.
Strukov et al. (2005) "CMOL FPGA: A Reconfigurable Architecture for Hybrid Digital Circuits with Two-Terminal Nanodevices," Nanotechnology 16:888-900.
Su et al. (2000) "Lattice-Oriented Growth of Single-Walled Carbon Nanotubes," J. Phys. Chem. B 104(28):6505-6508.
Su et al. (Dec. 1, 2011) "Postbuckling analysis and its application to stretchable electronics," Journal of the Mechanics and Physics of Solids. 60:487-508.
Sum et al. (2009) "Near-Infrared Spectroscopy for the Detection of Lipid Core Coronary Plaques," Curr. Cardiovasc. Imag. Rep. 2:307-315.
Sumant et al. (Apr. 2005) "Toward the Ultimate Tribological Interface: Surface Chemistry and Nanotribology of Ultrananocrystalline Diamond," Adv. Mater. 17(8):1039-1045.
Sun et al. (1980) "Electron Mobility in Inversion and Accumulation Layers on Thermally Oxidized Silicon Surfaces," IEEE J. Solid-State Circuits 5:562-573.
Sun et al. (2004) "Fabricating Semiconductor Nano/Microwires and Transfer Printing Ordered Arrays of Them onto Plastic Substrates," Nano Lett. 4:1953-1959.
Sun et al. (2005) "Advances in Organic Field-Effect Transistors," J. Mater. Chem. 15:53-65.
Sun et al. (2005) "Bendable GaAs Metal-Semiconductor Field-Effect Transistors Formed with Printed GaAs Wire Arrays on Plastic Substrates," Appl. Phys. Lett. 87:083501.
Sun et al. (2005) "Photolithographic Route to the Fabrication of Micro/Nanowires of III-V Semiconductors," Adv. Fuct. Mater. 15:30-40.
Sun et al. (2006) "Buckled and Wavy Ribbons of GaAs for High-Performance Electronics on Elastomeric Substrates," Adv. Mater. 18(21):2857-2862.
Sun et al. (2007) "Controlled Buckling of Semiconductor Nanoribbons for Stretchable Electronics," Nat. Nanotechnol. 1:201-207.
Sun et al. (2007) "Inorganic Semiconductors for Flexible Electronics," Adv. Mater. 19(15):1897-1916.
Sun et al. (2007) "Nano- to Microscale Porous Silicon as a Cell Interface for Bone-Tissue Engineering," Advanced Materials. 19(7):921-924.
Sun et al. (2007) "Structural Forms of Single Crystal Semiconductor Nanoribbons for High-Performance Stretchable Electronics," J. Mater Chem. 17:832-840.
Sunaga et al. (2002) "Measurement of the electrical properties of human skin and the variation among subjects with certain skin conditions," Phys. Med. Biol. 47:N11-N15.
Sundar et al. (2004) "Elastomeric Transistor Stamps: Reversible Probing of Charge Transport in Organic Crystals," Science 303:1644-1646.
Suo et al. (Feb. 22, 1999) "Mechanics of Rollable and Foldable Film-on-Foil Electronics," Appl. Phys. Lett. 74(8):1177-1179.
Suzuki et al. (2000) "XPS study of oxides formed on the surface of high-purity iron exposed to air," Surface and Interface Analysis. 30(1):372-376.
Swain et al. (2004) "Curved CCD Detector Devices and Arrays for Multi-Spectral Astrophysical Application and Terrestrial Stereo Panoramic Cameras," Proc. SPIE 5499:281-301.
Sze et al. (1985) Semiconductor Devices, Physics and Technology, 2nd ed., Wiley, New York, pp. 190-192.
Sze, S. (1985) Semiconductor Devices: Physics and Technology, New York: Wiley, pp. 428-467.
Sze, S. (1988) VLSI Technology, Mcgraw-Hill, 327-374, 566-611.
Sze, S. (1994) Semiconductor Sensors, John Wiley and Sons: New York, pp. 17-95.
Tabata et al. (1992) "Anisotropic etching of silicon in TMAH solutions," Sens. Actuators, A. 34:51-57.
Taheri et al. (Jun. 2012) "Analysis of the surface film formed on Mg by exposure to water using a FIB cross-section and STEM-EDS," Corrosion Science. 59:222-228.
Takagi et al. (1994) "On the universality of inversion layer mobility in Si MOSFET's: Part II—effects of surface orientation," IEEE Trans. Electron Dev. 41:2363-2368.
Takamoto et al. (Jan. 20, 1997) "Over 30% Efficient InGaP/GaAs Tandem Solar Cells," Appl. Phys. Lett. 70(3):381-383.
Takei et al. (2010) "Nanowire active-matrix circuitry for low-voltage macroscale artificial skin," Nat. Mater. 9:821-826.
Talapin et al. (Oct. 7, 2005) "PbSe Nanocrystal Solids for n- and p-Channel Thin Film Field-Effect Transistors," Science 310:86-89.
Tamboli et al. (1999) "Studies of Passivation Behavior of Tungsten in Application to Chemical Mechanical Polishing," J. Vac. Sci. Technol. A-Vac. Surf. Films. 17(4):1168-1173.
Tan et al. (Apr. 12, 2004) "Performance Enhancement of InGaN Light Emitting Diodes by Laser-Lift-off and Transfer from Sapphire to Copper Substrate," Appl. Phys. Lett. 84(15):2757-2759.
Tanase et al. (2002) "Magnetic Trapping and Self-Assembly of Multicomponent Nanowires," J. Appl. Phys. 91:8549-8551.
Tang et al. (2005) "One-Dimensional Assemblies of Nanoparticles: Preparation, Properties, and Promise," Adv. Mater. 17:951-962.
Tao et al. (2003) "Langmuir-Blodgett Silver Nanowire Monolayers for Molecular Sensing Using Surface-Enhanced Raman Spectroscopy," Nano Lett. 3:1229-1233.
Tao et al. (2010) "Gold Nanoparticle-Doped Biocompatible Silk Films as a Path to Implantable Thermo-Electrically Wireless Powering Devices," Appl. Phys. Lett. 97:123702.
Tao et al. (Nov. 27, 2012) "Implantable, Multifunctional, Bioresorbable Optics," Proc. Natl. Acad. Sci. USA. 109(48):19584-19589.
Tate et al. (2000) "Anodization and Microcontact Printing on Electroless Silver: Solution-Based Fabrication Procedures for Low-Voltage Electronic Systems with Organic Active Components," Langmuir 16:6054-6060.
Terazono et al. (2006) "Current status and research on E-waste issues in Asia," Journal of Material Cycles and Waste Management. 8:1-12.
Teshima et al. (2001) "Room-Temperature Deposition of High-Purity Silicon Oxide Films by RF Plasma-Enhanced CVD," Surf. Coat. Technol. 146-147:451-456.
Theiss et al. (1998) "PolySilicon Thin Film Transistors Fabricated at 1000C on a Flexible Plastic Substrate," IEDM 98:257-260.
Thornwood et al. (Oct. 1, 1990) "Utilizing Olptical Lithography in the Sub-Micron Dimensional Regime," IBM Tech. Disc. Bull. 33(5):187-188.
Tian et al. (2010) "Three-dimensional, flexible nanoscale field-effect transistors as localized bioprobes," Science. 329:830-834.

(56) References Cited

OTHER PUBLICATIONS

Tie et al. (2010) "XPS Studies of Magnesium Surfaces after Exposure to Dulbecco's Modified Eagle Medium, Hank's Buffered Salt Solution, and Simulated Body Fluid," Advanced Engineering Materials. 12(12):B699-B704.
Timko et al. (2009) "Electrical Recording from Hearts with Flexible Nanowire Device Arrays," Nano Lett. 9:914-918.
Toader et al. (2001) "Proposed Square Spiral Microfabrication Architecture for Large Three-Dimensional Photonic Band Gap Crystals," Science. 292(5519):1113-1136.
Toader et al. (2004) "Photonic Band Gap Architectures for Holographic Lithography," Phy. Rev. Lett. 043905/1-043905/4.
Toader et al. (2004) "Photonic Band Gaps Based on Tetragonal Lattices of Slanted Pores," Phys. Rev. Lett. 90:233901/1-233901/4.
Tomozawa et al. (1999) "Time Dependent Diffusion Coefficient of Water Into Silica Glass at Low Temperatures," Mater. Sci. Eng. A. 272:114-119.
Tong (1999) Semiconductor Wafer Bonding: Science and Technology, John Wiley; New York, pp. 187-221.
Trau et al. (1997) "Microscopic Patterning of Orientated Mesoscopic Silica Through Guided Growth," Nature 390:674-676.
Trentler et al. (1995) "Solution-Liquid-Solid Growth of Crytalline III-V Semiconductors: An Analogy to Vapor-Liquid-Solid Growth," Science 270:1791-1794.
Trewyn et al. (2008) "Biocompatible Mesoporous Silica Nanoparticles with Different Morphologies for Animal Cell Membrane Penetration," Chemical Engineering Journal. 137:23-29.
Trumbo et al. (2001) "Dietary Reference Intakes," Journal of the American Dietetic Association. 101(3):294-301.
Tseng et al. (Web Release Dec. 19, 2003) "Monolithic Integration of Carbon Nanotube Devices with Silicon MOS Technology" Nano Lett. 4(1):123-127.
U.S. Department of Health and Human Services (2004) "Toxicological Profile for Ammonia," ATSDR.
Ucjikoga, S. (2002) "Low-Temperature Polycrystalline Silicon Thin-Film Transistor Technologies for System-on-Glass Displays," MRS Bull. 27:881-.
University of Illinois (Sep. 27, 2012) "Biocompatible Electronic Devices Dissolve in the Body Environment," Phys.org. http://www.phys.org/news/2012-09-transient-electronics-biocompatible-electronic-devices.html. [Last accessed Jul. 30, 2014].
University of Illinois (Sep. 27, 2012) "Transient Electronics: UI Researcher demonstrates transient electronics," Youtube.com. http://www.youtube.com/watch?=NnmHZXvJhlk. [Last accessed Jul. 30, 2014].
Urruchi et al. (2000) "Etching of DLC Films Using a Low Intensity Oxygen Plasma Jet," Diamond Relat. Mater. 9:685-688.
Valtiner et al. (2008) "Stabilization and Acidic Dissolution Mechanism of Single-Crystalline ZnO(0001) Surfaces in Electrolytes Studied by In-Situ AFM Imaging and Ex-Situ LEED," Langmuir. 24:5350-5358.
Van Assche et al. (2004) "A Thin-Film Encapsulation Stack for PLED and OLED Displays," SID 04 Digest of Technical Papers. Paper No. P-111. pp. 695-697.
17811781188118811981198120812O8-Assisted Etching of p-Type Semiconductors, J. Electrochem. Soc. 138(11):3401-3406.
Van der Wilt et al. (2006) "Low-Temperature Polycrystalline Silicon Thin-Film Transistors and Circuits on Flexible Substrates," MRS Bulletin. 31:461-465.
Vanhollenbeke et al. (2000) "Compliant Substrate Technology: Integration of.Mismatched Materials for Opto-Electronic Applications," Prog. Cryst. Growth Charact. Mater. 41(1-4):1-55.
Vazquez-Mena et al. (2008) "Metallic Nanowires by Full Wafer Stencil Lithography," Nano Lett. 8:3675-3682.
Velev et al. (1997) "Porous silica via colloidal crystallization," Nature 389:447-448.
Vepari et al. (Aug. Sep. 2007) "Silk as a Biomaterial," Prog. Polym. Sci. 32(8-9):991-1007.
Vilan et al. (2000) "Molecular Control Over Au/GaAs Diodes," Nature 404:166-168.

Vinck et al. (2003) "Increased Fibroblast Proliferation Induced by Light Emitting Diode and Low Power Laser Irradiation," Lasers Med. Sci. 18:95-99.
Vitale et al. (Mar. 24, 2015) "Neural stimulation and recording with bidirectional, soft carbon nanotube fiber microelectrodes," ACS Nano. 9:4465-4474.
Viventi et al. (2011) "Flexible, foldable, actively multiplexed, high-density electrode array for mapping brain activity in vivo," Nature Neurosci. 14:1599-1605.
Viventi et al. (Mar. 2010) "A Conformal, Bio-Interfaced Class of Silicon Electronics for Mapping Cardiac Electrophysiology," Sci. Trans. Med. 2(24):24ra22.
Vlasov et al. (2001) "On-Chip Natural Assembly of Silicon Photonic Bandgap Crystals," Nature 414:289-293.
Vojtěch et al. (2011) "Mechanical and Corrosion Properties of Newly Developed Biodegradable Zn-Based Alloys for Bone Fixation," Acta Biomaterialia. 7:3515-3522.
Voss, D. (2000) "Cheap and Cheerful Circuits," Nature 407:442-444.
Vuorilehto (2003) "An environmentally friendly water-activated manganese dioxide battery," J. Appl. Electrochem. 33:15-21.
Wagner et al. (2003) "Silicon for Thin-Film Transistors," Thin Solid Films 430:15-19.
Wagner et al. (2005) "Electronic Skin: Architecture and Components," Physica E 25:326-334.
Wagner et al. (Mar. 1, 1964) "Vapor-Liquid-Solid Mechanism of Single Crystal Growth," Appl. Phys. Lett. 4(5):89-90.
Waksman et al. (2008) "Photopoint Photodynamic Therapy Promotes Stabilization of Atherosclerotic Plaques and Inhibits Plaque Progression," J. Am. Coll. Cardiol. 52:1024-1032.
Wales et al. (2003) "Stationary points and dynamics in high-dimensional systems," J. Chem. Phys. 119:12409-12416.
Walker et al. (Feb. 14, 2012) "Magnesium alloys: Predicting in vivo corrosion with in vitro immersion testing," Journal of Biomedical Materials Research Part B: Applied Biomaterials. 100B(4):1134-1141.
Wang et al. (1999) "Electromechanical coupling and output efficiency of piezoelectric bending actuators," IEEE Transactions on Ultrasonics, Ferroelectrics and Frequency Control. 46:638-646.
Wang et al. (2003) "A Solution-Phase, Precursor Route to Polycrystalline $SnO_2$ Nanowires that can be Used for Gas Sensing under Ambient Conditions," J. Am. Chem. Soc. 125:16176-16177.
Wang et al. (2005) "Electronically Selective Chemical Functionalization of Carbon Nanotubes: Correlation between Raman Spectral and Electrical Responses," J. Am. Chem. Soc., 127:11460-11468.
Wang et al. (2005) "Oxidation Resistant Germanium Nanowires: Bulk Synthesis, Long Chain Alkanethiol Functionalization, and Langmuir-Blodgett Assembly," J. Am. Chem. Soc. 127(33):11871-11875.
Wang et al. (2006) "Direct Synthesis and Characterization of CdS Nanobelts," Appl. Phys. Lett. 89:033102.
Wang et al. (2006) "Neural Stimulation with a Carbon Nanotube Microelectrode Array," Nano Lett. 6:2043-2048.
Wang et al. (2008) "In Vivo Degradation of Three-Dimensional Silk Fibroin Scaffolds," Biomaterials 29(24-25):3415-3428.
Wang et al. (2009) "Self-Aligned Fabrication of 10 nm Wide Asymmetric Trenches for Si/SiGe Heterojunction Tunneling Field Effect Transistors Using Nanoimprint Lithography, Shadow Evaporation, and Etching," J. Vac. Sci. Technol. B. 27(6):2790-2794.
Wang et al. (2009) "The nucleation and growth of metastable pitting on pure iron," Corrosion Science. 51(1):181-185.
Wang et al. (2011) "In vitro biodegradation behavior of magnesium and magnesium alloy," Journal of Biomedical Materials Research Part B: Applied Biomaterials. 98B(2):203-209.
Waxman et al. (2009) "In vivo Validation of a Catheter-Based Near-Infrared Spectroscopy System for Detection of Lipid Core Coronary Plaques: Initial Results of the Spectacl Study," J. Am. Coll. Cardiol. Img. 2:858-868.
Waxman, S. (2008) "Near-Infrared Spectroscopy for Plaque Characterization," J. Interv. Cardiol. 21:452-458.
Weber et al. (1993) "Fabrication of Narrow Lines by Shadow-Evaporated Lift-Off Masks," Physica Status Solidi (A). 136(1):K41-K45.

(56) References Cited

OTHER PUBLICATIONS

Weber et al. (Jan. 2004) "A Novel Low-Cost, High Efficiency Micromachined Silicon Solar Cell," IEEE Electron Device Lett. 25(1):37-39.
Weber et al. (May 2012) "Temperature responsive bio-compatible polymers based on poly(ethylene oxide) and poly(2-oxazoline)s," Progress in Polymer Science. 37:686-714.
Wegner et al. (2006) "In situ formation and hydrolysis of Zn nanoparticles for H2 production by the 2-step ZnO/Zn water-splitting thermochemical cycle," International Journal of Hydrogen Energy. 31:55-61.
Weimann et al. (2001) "Four-Angle Evaporation Method for the Preparation of Single Electron Tunneling Devices," Microelectron. Eng. 57-58:915-918.
Wen et al. (Web Release Dec. 4, 2004) "Controlled Growth of Large-Area, Uniform, Vertically Aligned Arrays of α-Fe2O2 Nanobelts and Nanowires," J. Phys. Chem. B 109(1):215-220.
Whang et al. (2003) "Large-Scale Hierarchical Organization of Nanowire Arrays for Integrated Nanosystems," Nano Lett. 3(9):1255-1259.
Whitmer et al. (Jun. 4, 2012) "High frequency deep brain stimulation attenuates subthalamic and cortical rhythms in Parkinson's disease," Frontiers in human neuroscience. 6:155.
Whitten et al. (2007) "Free Standing Carbon Nanotube Composite Bio-electrodes." J. Biomed. Mater. Res. B. 82:37-43.
Wholey et al. (2000) "Global experience in cervical carotid artery stent placement," Catheterization and Cardiovascular Interventions. 50:160-167.
Widmer et al. (2005) "Global perspectives on e-waste," Environmental Impact Assessment Review. 25:436-458.
Wieczorek et al. (1998) "Effect of Salt Concentration on the Conductivity of Peo-Based Composite Polymeric Electrolytes," The Journal of Physical Chemistry B. 102:8725-8731.
Wilcock et al. (1997) "Development of a seawater battery for deep-water applications," J. Power Sources 66:71-75.
Williams et al. (2003) "Etch rates for micromachining processing—Part II," J. Microelectromech. Sys. 12:761-778.
Williams et al. (Oct. 2006) "Growth and Properties of Nanocrystalline Diamond Films," Phys. Stat. Sol. A 203(13):3375-3386.
Williams et al. (Web Release Jan. 23, 2006) "Comparison of the Growth and Properties of Ultrananocrystalline Diamond and Nanocrystalline Diamond," Diamond Relat. Mater. 15:654-658.
Willner et al. (2002) "Functional Nanoparticle Architectures for Senoric, Optoelectronic, and Bioelectronic Applications," Pure Appl. Chem. 74(9):1773-1783.
Wilson (2009) "A Decade of Step and Flash Imprint Lithography," J. Photopolym. Sci. Technol. 22(2):147-153.
Wilson et al. (2006) "ECoG Factors Underlying Multimodal Control of a Brain-Computer Interface," IEEE Trans. Neural Syst. Rehabil. Eng. 14:246-250.
Wind et al. (May 20, 2002) "Vertical Scaling of Carbon Nanotube-Field-Effect Transistors Using Top Gate Electrodes," Appl. Phys. Lett. 80(20):3871-3819.
Wise et al. (Jul. 2008) "Microelectrodes, Microelectronics, and Implantable Neural Microsystems," Proc. IEEE 96(7):1184-1202.
Witte (2010) "The History of Biodegradable Magnesium Implants," Acta. Biomater. 6:1680-1692.
Witte et al. (2008) "Degradable Biomaterials Based on Magnesium Corrosion," Current Opinion in Solid State and Materials Science. 12:63-72.
Won et al. (2004) "Effect of Mechanical and Electrical Stresses on the Performance of an a-Si:H TFT on Plastic Substrate," J. Electrochem. Soc. 151:G167-G170.
Won et al. (2011) "Piezoresistive Strain Sensors and Multiplexed Arrays Using Assemblies of Single-Crystalline Silicon Nanoribbons on Plastic Substrates," IEEE T. Electron. Dev. 58(11):4074-4078.
Wong-Riley et al. (2005) "Photobiomodulation Directly Benefits Primary Neurons Functionally Inactivated by Toxins," J. Biol. Chem. 280:4761-4771.
Woodburn et al. (1996) "Phototherapy of Cancer and Atheromatous Plaque with Texaphyrins," J. Clin. Laser Med. Surg. 14:343-348.
Woodruff et al. (2010) "The return of a forgotten polymer—Polycaprolactone in the 21st century," Prog. Polym. Sci. 35:1217-1256.
Worley (1994) "Dissolution kinetics and mechanisms in quartz- and grainite-water systems," Ph. D. Thesis, Massachusetts Institute of Technology.
Wu et al. (2001) "Amorphous Silicon Crystallization and Polysilicon Thin Film Transistors on SiO2 Passivated Steel Foil Substrates," Appl. Surf. Sci 175-176:753-758.
Wu et al. (2001) "Direct Observation of Vapor-Liquid-Solid Nanowire Growth," J. Am. Chem. Soc. 123(13):3165-3166.
Wu et al. (2001) "Synthesis, characterization, biodegradation, and drug delivery application of biodegradable lactic/glycolic acid polymers. Part II: Biodegradation," J. Biomater. Sci. Polymer Edn. 12:21-34.
Wu et al. (2001) "Thermal Oxide of Polycrystalline Silicon on Steel Foil as a Thin-Film Transitor Gate Dielectric," Appl. Phys. Lett. 78:3729-2731.
Wu et al. (2002) "Block-by-Block Growth of Single-Crystalline Si/SiGe Superlattice Nanowires," Nano Lett. 2(2):83-86.
Wu et al. (2002) "Complementary Metal-Oxide-Semiconductor Thin-Film Transistor Circuits from a High-Temperature Polycrystalline Silicon Process on Steel Foil Substrates," IEEE Trans. Electr. Dev. 49(11):1993-2000.
Wu et al. (2002) "Growth of Au-Catalyzed Ordered GaAs Nanowire Arrays by Molecular-Beam Epitaxy," Appl. Phys. Lett. 81:5177-5179.
Wu et al. (2002) "Inorganic Semiconductor Nanowires: Rational Growth, Assembly, and Novel Properties," Chem. Eur. J. 8(6):1261-1268.
Wu et al. (2003) "Growth, Branching, and Kinking of Molecular-Beam Epitaxial (110) GaAs Nanowires," Appl. Phys. Lett. 83:3368-3370.
Wu et al. (2004) "Single-Crystal Metallic Nanowires and Metal/Semiconductor Nanowire Heterostructures," Nature 430:61-65.
Wu et al. (2008) "Biomolecule-Assisted Synthesis of Water-Soluble Silver Nanoparticles and Their Biomedical Applications," Inorg. Chem. 47:5882-5888.
Wu et al. (2010) "Surface microstructurization of a sputtered magnesium thin film via a solution-immersion route," Materials Letters. 64(3):475-478.
Xia et al. (1996) "Complex Optical Surfaces Formed by Replica Molding Against Elastomeric Masters," Science 273:347-349.
Xia et al. (1996) "Shadowed Sputtering of Gold on V-Shaped Microtrenches Etched in Silicon and Applications in Microfabrication," Adv. Mater. 8(9):765-768.
Xia et al. (1998) "Soft Lithography," Angew. Chem. Int. Ed. 37:550-575.
Xia et al. (1998) "Soft Lithography," Annu. Rev. Mater. Sci. 28:153-184.
Xia et al. (1999) "Unconventional Methods for Fabricating and Patterning Nanostructures," Chem. Rev. 99:1823-1848.
Xia et al. (2003) "One-Dimensional Nanostructures: Synthesis, Characterization and Applications," Adv. Mater. 15:353-389.
Xiang et al. (2007) "Printed circuit board recycling process and its environmental impact assessment," Int. J. Adv. Manuf. Technol. 34:1030-1036.
Xiang et al. (Mar. 25, 2006) "Ge/Si Nanowire Heterostructures as High-Performance Field-Effect Transistors," Nature 441:489-493.
Xiang et al. (May 14, 2014) "Ultra-thin flexible polyimide neural probe embedded in a dissolvable maltose-coated microneedle," J. Micromech. Microeng. 24:065015.
Xiao et al. (2003) "High-mobility thin-film transistors based on aligned carbon nanotubes," Appl. Phys. Lett., vol. 83, No. 1, pp. 150-152.
Xie et al. (2012) "XPS studies on surface reduction of tungsten oxide nanowire film by Ar+ bombardment," Journal of Electron Spectroscopy and Related Phenomena. 185(3-4):112-118.
Xie et al. (May 2003) "Polymer-Controlled Growth of Sb2Se3 Nanoribbons Via a Hydrothermal Process," J. Cryst. Growth 252(4):570-574.

(56) References Cited

OTHER PUBLICATIONS

Xin et al. (Jun. 2005) "Evaluation of Polydimethylsiloxane Scaffolds with Physiologically-Relevant Elastic Moduli: Interplay of Substrate Mechanics and Surface Chemistry Effects on Vascular Smooth Muscle Cell Response," Biomaterials 26(16):3123-3129.
Xu et al. (2002) "Nanoditches Fabricated Using a Carbon Nanotube as a Contact Mask," Nano Lett. 2(10):1061-1065.
Xu et al. (2004) "Fabrication of Free-Standing Metallic Pyramidal Shells," Nano. Lett. 4(12):2509-2511.
Xu et al. (2005) "Approaching Zero: Using Fractured Crystals in Metrology for Replica Molding," J. Am. Chem. Soc. 127(3):854-855.
Xu et al. (2007) "Fabrication of Large-Area Patterned Nanostructures for Optical Applications by Nanoskiving," Nano Lett. 7(9):2800-2805.
Xu et al. (2008) "Nanoskiving: A New Method to Produce Arrays of Nanostructures," Account. Chem. Res. 41(12):1566-1577.
Xu et al. (2012) "Birth outcomes related to informal e-waste recycling in Guiyu, China," Reproductive Toxicology. 33:94-98.
Yamagata et al. (2003) "Preparation of a Copoly (dl-lactic/glycolic acid)-Zinc Oxide Complex and its Utilization to Microcapsules Containing Recombinant Human Growth Hormone," International Journal of Pharmaceuticals. 251:133-141.
Yan et al. (2006) "Magnesium Oxide as a Candidate High-κ Gate Dielectric," Appl. Phys. Lett. 88:142901.
Yang et al. (1997) "Mesoporous Silica with Micrometer-Scale Designs," Adv. Mater. 9:811-814.
Yang et al. (2000) "Stability of Low-Temperature Amorphous Silicon Thin Film Transistors Formed on Glass and Transparent Plastic Substrates," J. Vac. Sci. Technol. B 18:683-689.
Yang et al. (2002) "Creating Periodic Three-Dimensional Structures by Multibeam Interface of Visible Laser," Chem. Mater. 14:2831-2833.
Yang et al. (Dec. 2007) "RFID Tag and RF Structures on a Paper Substrate Using Inkjet-Printing Technology," IEEE Trans. Microw. Theory Tech. 55(12):2894-2901.
Yang, P. (2005) "The Chemistry and Physics of Semiconductor Nanowires," MRS Bull. 30:85-.
Yanina et al. (2002) "Terraces and ledges on (001) spinel surfaces," Surf. Sci., 513:L402-L412.
Yao et al. (2000) "An XPS investigation of the oxidation/corrosion of melt-spun Mg," Applied Surface Science. 158(1-2):112-119.
Yao et al. (2008) "Seeing Molecules by Eye: Surface Plasmon Resonance Imaging at Visible Wavelengths with High Spatial Resolution and Submonolayer Sensitivity," Angew. Chem. 47:5013-5017.
Yao et al. (2010) "Functional Nanostructured Plasmonic Materials," Adv. Mater. 22:1102-1110.
Yao et al. (Mar. 2000) "High-Field Effect Electrical Transport in Single-Walled Carbon Nanotubes," Phys. Rev. Lett. 84(13):2941-2944.
Yeager et al. (Aug. 30, 2008) "Characterization of Flexible ECoG Electrode Arrays for Chronic Recording in Awake Rats," J. Neurosci. Methods 173(2):279-285.
Yeh et al. (1994) "Fluidic Self-Assembly for the Integration of GaAs Light Emitting Diodes on Si Substrates," IEEE Photon. Techn. Lett. 6:706-708.
Yin (Mar. 20, 2014) "Materials, Designs, and Operational Characteristics for Fully Biodegradable Primary Batteries," Advanced Materials. 26(23):3879-3884.
Yin et al. (2000) "A Soft Lithography Approach to the Fabrication of Nanostructures of Single Crystalline Silicon with Well-Defined Dimensions and Shapes," Adv. Mater. 12:1426-1430.
Yin et al. (2005) "Colloidal Nanocrystal Synthesis and the Organic-Inorganic Interface," Nature 437:664-670.
Yin et al. (Sep. 25, 2013) "Dissolvable Metals for Transient Electronic," Adv. Funct. Mater. 24:645-658.
Yoon et al. (2005) "Low-Voltage Organic Field-Effect Transistors and Inverters Enabled by Ultrathin Cross-Linked Polymers as Gate Dielectrics," J. Am. Chem. Soc. 127:10388-10395.

Young et al. (1997) Dietary Reference Intakes for Calcium, Phosphorus, Magnesium, Vitamin D, and Fluoride. National Academy Press, Washington, D.C.
Youssef et al. (2004) "Improved corrosion behavior of nanocrystalline zinc produced by pulse-current electrodeposition," Corrosion Science. 46(1):51-64.
Yu et al. (2000) "Silicon Nanowires: Preparation, Device Fabrication, and Transport Properties," J. Phys. Chem. B 104(50):11864-11870.
Yu et al. (2003) "Solution-Liquid-Solid Growth of Soluble GaAs Nanowires," Adv. Mater. 15:416-419.
Yu et al. (2003) "Two-Versus Three-Dimensional Quantum Confinement in Indium Phosphide Wires and Dots," Nat. Mater. 2:517-520.
Yu et al. (2004) "The Yield Strength of Thin Copper Films on Kapton," J. Appl. Phys. 95:2991-2997.
Yu et al. (2004) "Triangular Profile Imprint Molds in Nanograting Fabrication," Nano Lett. 4(2):341-344.
Yu et al. (Apr. 18, 2016) "Bioresorbable silicon electronics for transient spatiotemporal mapping of electrical activity from the cerebral cortex," Nature Materials. 15(7):782-791.
Yuan et al. (2006) "High-Speed Strained-Single-Crystal-Silicon Thin-Film Transistors on Flexible Polymers," J. Appl. Phys. 100:013708.
Yurelki et al. (Jul. 24, 2004) "Small-Angle Neutron Scattering from Surfactant-Assisted Aqueous Dispersions of Carbon Nanotubes," J. Am. Chem. Soc. 126(32):9902-9903.
Zainal et al. (2011) "Corrosion of high purity Mg, AZ91, ZE41 and Mg2Zn0.2Mn in Hank's solution at room temperature," Corrosion Science. 53(3):862-872.
Zakhidov et al. (1998) "Carbon Structure with Three-Dimensional Periodicity at Optical Wavelengths," Science 282:897-901.
Zaumseil et al. (2003) "Contact resistance in organic transistors that use source and drain electrodes formed by soft contact lamination," J. Appl. Phys. 93:6117-6124.
Zaumseil et al. (2003) "Nanoscale Organic Transistors that use Source/Drain Electrodes Supported by High Resolution Rubber Stamps," Appl. Phys. Lett. 82(5):793-795.
Zaumseil et al. (2003) "Three-Dimensional and Multilayer Nanostructures Formed by Nanotransfer Printing," Nano Lett. 3(9):1223-1227.
Zeng et al. (2008) "Progress and Challenge for Magnesium Alloys as Biomaterials," Advanced Engineering Materials. 10(8):B3-B14.
Zhai et al. (Oct. 23, 2012) "High-Performance Flexible Thin-Film Transistors Exfoliated from Bulk Wafer," Nano Lett. 12:5609-5615.
Zhang (1996) Corrosion and Electrochemistry of Zinc. Plenum Press. New York, New York. pp. 1-474.
Zhang et al. (2001) "Electric-field-directed growth of aligned single-walled carbon nanotubes," Appl. Phys. Lett., vol. 79, No. 19. pp. 3155-3157.
Zhang et al. (2005) "Low-Temperature Growth and Photoluminescence Property of ZnS Nanoribbons," J. Phys. Chem. B 109(39):18352-18355.
Zhang et al. (2006) "Anomalous Coiling of SiGe/Si and SiGe/Si/Cr Helical Nanobelts," Nano Lett. 6(7):1311-1317.
Zhang et al. (2010) "Fabrication and Comparative Study of Top-Gate and Bottom-Gate ZnO TFTs with Various Insulator Layers," J. Mater. Sci.: Mater. Electron. 21:671-675.
Zhang et al. (Apr. 2003) "Oxide-Assisted Growth of Semiconducting Nanowires," Adv. Mater. 15(7-8):635-640.
Zhang et al. (Apr. 5, 2004) "Structure and Photoiluminescence of ZnSe Nanoribbons Grown by Metal Organic Chemical Vapor Deposition," Appl. Phys. Lett. 84(14):2641-2643.
Zhang et al. (Feb. 9, 2006) "Electronic Transport in Nanometre-Scale Silicon-on-Insulator Membranes," Nature 439:703-706.
Zhao et al. (2002) "Novel Nano-Column and Nano-Flower Arrays by Glancing Angle Deposition," Nano. Lett. 2(4):351-354.
Zhao et al. (2004) "Piezoelectric Characterization of Individual Zinc Oxide Nanobelt Probed by Piezoresponse Force Microscope," Nano Lett. 4:587-590.
Zhao et al. (2004) "Synthesis and Properties of a Water-Soluble Single-Walled Carbon Nanotube-Poly(m-aminobenzene Sulfonic Acid) Graft Copolymer," Adv. Funct. Mater. 14(1):71-76.

(56) References Cited

OTHER PUBLICATIONS

Zhao et al. (2009) "An exploratory study of the corrosion of Mg alloys during interrupted salt spray testing," Corrosion Science. 51(6):1277-1292.

Zhao et al. (Mar. 2007) "Improved Field Emission Properties from Metal-Coated Diamond Films," Diamond Relat Mater. 16(3):650-653.

Zheng et al. (1998) "Sudden Cardiac Death in the United States, 1989 to 1998," Circulation 104, 2158-2163 (1998.

Zheng et al. (2004) "Shape-and Solder-Directed Self-Assembly to Package Semiconductor Device Segments," Appl. Phys. Lett. 85:3635-3637.

Zheng et al. (2009) "In vitro and in vivo biocompatibility studies of ZnO nanoparticles," International Journal of Modern Physics B. 23:1566.

Zheng et al. (Aug. 31, 2004) "Sequential Shape-and-Solder-Directed Self Assembly of Functional Microsystems," Proc. Natl. Acad. Sci. USA 101(35):12814-12817.

Zhmud et al. (1999) "Dissolution Kinetics of Silicon Nitride in Aqueous Suspension," J. Colloid Interface Sci. 218:582-584.

Zhou et al. (2002) "An Efficient Two-Photon-Generated Photoacid Applied to Positive-Tone 3D Microfabrication," Science 296:1106-1109.

Zhou et al. (2003) "Simple Fabrication of Molecular Circuits by Shadow Mask Evaporation," Nano Lett. 3(10):1371-1374.

Zhou et al. (2004) "p-Channel, n-Channel Thin Film Transistors and p-n Diodes Based on Single Wall Carbon Nanotube Networks," Nano Lett. 4:2031-2035.

Zhou et al. (2005) "Band Structure, Phonon Scattering, and the Performance Limit of Single-Walled Carbon Nanotube Transistors," Phys. Rev. Lett. 95:146805.

Zhou et al. (2005) "Mechanism for Stamp Collapse in Soft Lithography," Appl. Phys. Lett. 87:251925.

Zhou et al. (2006) "Dissolving Behavior and Stability of ZnO Wires in Biofluids: A Study on Biodegradability and Biocompatibility of ZnO Nanostructures," Adv. Mater. 18:2432-2435.

Zhou et al. (2008) "Flexible Piezotronic Strain Sensor," Nano. Lett. 8(9):3035-3040.

Zhou et al. (Feb. 18, 2013) "Fast flexible electronics with strained silicon nanomembranes," Scientific Reports. 3:1291.

Zhu et al. (2005) "Spin on Dopants for High-Performance Single Crystal Silicon Transistors on Flexible Plastic Substrates," Appl. Phys. Lett. 86(133507)1-3.

Zhu et al. (2009) "Biocompatibility of Pure Iron: In Vitro Assessment of Degradation Kinetics and Cytotoxicity on Endothelial Cells," Materials Science and Engineering C. 29:1589-1592.

Zhu et al. (2010) "Flexible High-Output Nanogenerator Based on Lateral ZnO Nanowire Array," Nano Lett. 10:3151-3155.

Zipes et al. (2006) "ACC/AHA/ESC 2006 Guidelines for Management of Patients With Ventricular Arrhythmias and the Prevention of Sudden Cardiac Death: A Report of the American College of Cardiology/American Heart Association Task Force and the European Society of Cardiology Committee for Practice Guidelines (Writing Committee to Develop Guidelines for Management of Patients With Ventricular Arrhythmias and the Prevention of Sudden Cardiac Death," Circulation 114:385-484.

\* cited by examiner

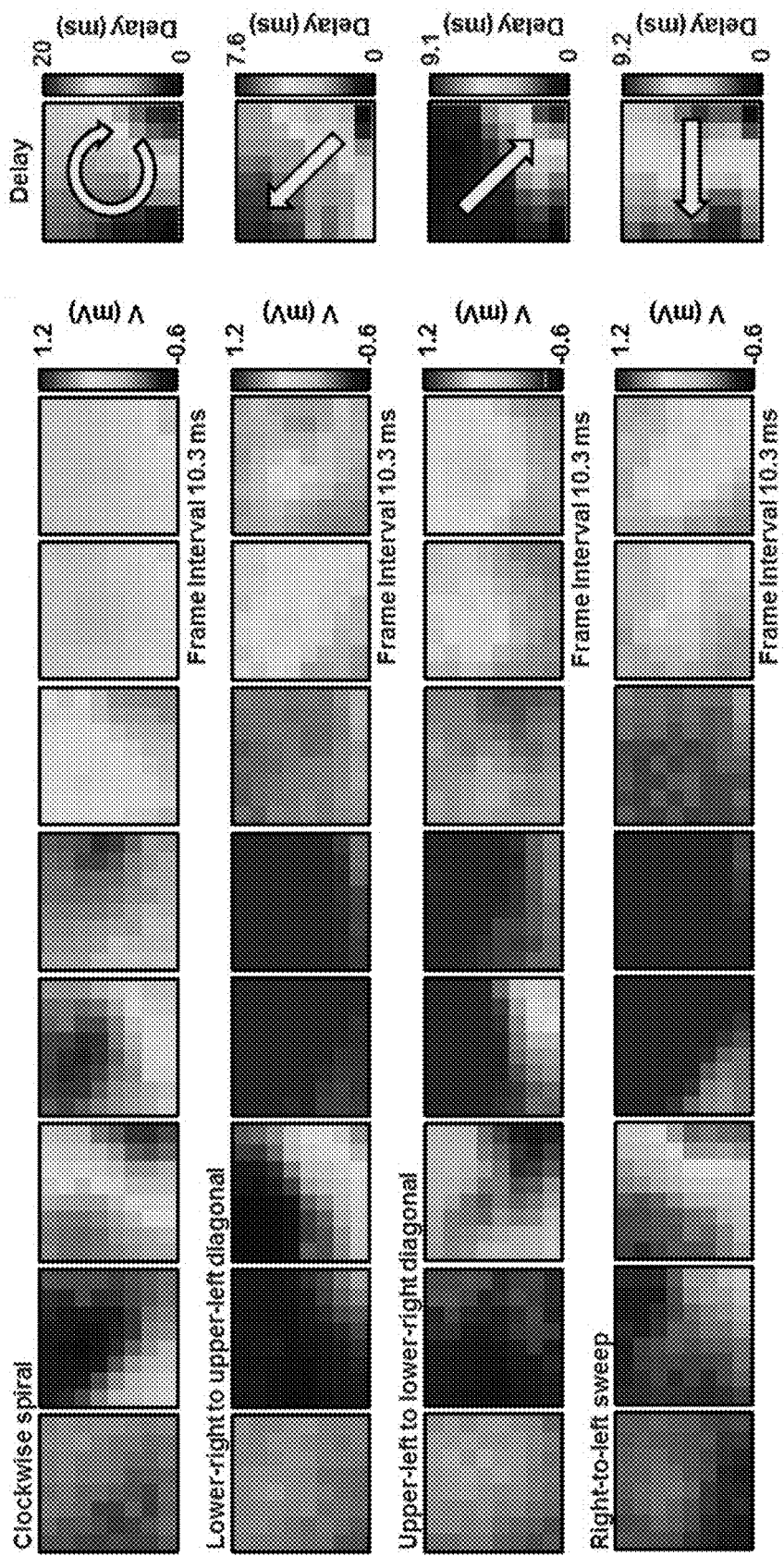

Day 32

BIORESORBABLE SILICON ELECTRONICS FOR TRANSIENT IMPLANTS

CROSS-REFERENCE TO RELATED APPLICATIONS

This application claims the benefit of priority from U.S. Provisional Patent Application No. 62/254,118 filed Nov. 11, 2015, which is hereby incorporated by reference in its entirety to the extent not inconsistent herewith.

STATEMENT REGARDING FEDERALLY SPONSORED RESEARCH OR DEVELOPMENT

Not applicable.

BACKGROUND OF INVENTION

With the continued advance of high performance electronic systems formed from device-grade, monocrystalline silicon as the semiconductor foundation, the ability to reliably deploy implantable monitoring systems has correspondingly increased. One disadvantage of such implantable devices is the need to remove them from the patient to avoid unwanted side effects, including due to the risk of an unwanted immune response, infection or irritation. Accordingly, effort has been devoted to designing implants and related sensors that are bioresorbable. See, for example, PCT/US16/40717 (filed Jul. 1, 2016); U.S. patent application Ser. No. 15/146,629 (filed May 4, 2016); and U.S. Pat. No. 8,666,471.

The focused effort toward an implantable and bioresorbable medical device is because such devices advantageously avoids the need for a separate surgical procedure to remove the implanted device. Instead, the device simply can be dissolved and removed from the implant site by natural biological and chemical processes.

A concern with implantable and bioresorbable medical devices is the ability to reliably control dissolution of the device after implantation so that device functionality is maintained over a desired device lifetime. For example, electronic circuits may have particular locations vulnerable to failure in a biological environment. The failure may be unforeseen and unpredictable, with minor variations in operating conditions leading to potentially wide changes in device lifetime, particularly for bioresorbable metals. In contrast, there is a concern regarding devices that are overly engineered to maintain functionality at the expense of the ability to bioresorb over a desired timeframe to minimize or avoid unwanted complications. Provided herein are devices and related methods that address this need in the art.

SUMMARY OF THE INVENTION

Devices and related methods provided herein utilize a specially configured membrane of silicon to form active electrodes that reliably interface with tissue while having a well-controlled dissolution rate. In particular, a highly doped and thin silicon membrane is processed and patterned to form an array of electrodes that can dissolve when contacted with a biofluid and achieve the desired bioresorption characteristics, thereby avoiding the need for medical intervention to remove the implanted device. Conventional corresponding bioresorbable metals, in contrast, suffer from comparatively fast dissolution kinetics, with tendency for uncontrolled degradation arising from cracking, fragmentation and flaking during bioresorption. The thin silicon membrane utilized herein not only forms the basis of active materials that electrically interface with tissue for sensing or for stimulation, but also can be used for the backplane transistors to access high-speed multiplexed addressing of the electrodes. In this manner, the silicon membrane may be thin, such as less than 10 µm, or less than 5 µm, or less than 1 µm, thereby providing desired dissolution characteristics. Similarly, various other components of the device, including substrate, insulators, encapsulating layers, electrical interconnects, may also have a thin layout configuration to further facilitate controlled dissolution, bioresorption and device mechanical parameters, such as flexibility, bendability, stretchability and/or rigidity, for implantation to a tissue of interest. The device physical properties of stretchability, net flexural rigidity, and bending modulus, may be selected to match an underlying tissue of interest.

Provided herein are implantable and bioresorbable medical devices and methods related thereto. For example, the device may comprise a bioresorbable substrate; an electronic circuit supported by the bioresorbable substrate, wherein the electronic circuit comprises a membrane of silicon ("Si membrane"), such as a membrane having a thickness less than or equal to 10 µm or 5 µm, or a thickness less than or equal to 1 µm. To reflect the small thickness of the Si membrane, the Si membrane is also referred herein as a "nanomembrane." The Si membrane may be processed and patterned to provide a desired circuit functionality and geometry, as described herein. For example, an array of dissolvable electrodes, including a multiplexed array, may be formed from the membrane of silicon. The electronic circuit is configured to conformally contact and electrically interface with a biological tissue, including detecting electrical activity of biological tissue during use. In this manner, the entire device may be similarly configured to ensure conformal contact is reliably achieved, including by selection of shape conformable components of the device, such as with thin and flexible bioresorbable substrates and additional elements of the electronic circuit, such as backplane transistors also formed from the Si membrane. The silicon membrane may be formed of thin films of amorphous, polycrystalline and single crystal semiconductor materials (e.g. polycrystalline silicon, amorphous silicon). The silicon membrane may comprise polycrystalline or single-crystalline silicon.

The dissolvable electrodes of any the systems provided herein may be configured to undergo hydrolysis upon contact with a biofluid.

The devices may also be described in terms of various additional circuit components to impart desired functionality and operating characteristics. For example, any of the devices may further comprise an array of backplane transistors formed from the membrane of silicon. The transistors may be in electrical contact with the array of dissolvable electrodes in order to achieve a desired high speed multiplexed addressing of the array of dissolvable electrodes. The transistors may be metal-oxide-semiconductor field-effect transistors (MOSFETs).

Examples of MOSFETs compatible with desired conformability and dissolution characteristics include those comprising a thin film of a metal, a gate dielectric and an interlayer dielectric. A MOSFET may include a metal layer comprising Mo having a thickness less than 500 nm; a gate dielectric comprising $SiO_2$ having a thickness less than 200 nm; and an interlayer dielectric comprising a multilayer stack of $SiO_2$ with a thickness less than 400 nm, $Si_3N_4$ with a thickness less than 500 nm, and $SiO_2$ with a thickness less than 400 nm.

Any of the devices may further comprise for each electrode: a buffer transistor electrically connected to the electrode for buffering of a measured tissue potential; and a multiplexing transistor electrically connected to the electrode for multiplexing of the array of electrodes.

To further facilitate multiplexed addressing and high-speed control and/or data acquisition, the devices may further comprise a second thin layer of metal to define column select lines electrically connected to the array of electrodes.

The membrane of silicon may be patterned to form a plurality of parallel silicon ribbons with an encapsulation layer having a plurality of passages that is aligned with the parallel silicon ribbons to form an array of exposed silicon corresponding to the active regions of the array of dissolvable electrodes electrically interconnected with regions of encapsulated silicon ribbons. In this manner, the electrodes may be electrically connected to external connectors, such as for connection to a power supply, controller, and/or wireless communicator.

Any of the devices may further comprise a plurality MOSFETs formed from the membrane of silicon, wherein the membrane of silicon serves as both an active semiconductor material and as a tissue interface electrode.

The devices may be described as having an active region at a distal end of the parallel silicon ribbons connected to external electrical connectors separated from the distal end by a longitudinal distance, such as a distance that is greater than or equal to 3 mm. "Active region" of the Si membrane refers to the portion of the electrode capable of electrically interfacing with biological tissue, specifically the unencapsulated and uninsulated portion that is exposed to the biological environment.

The electrodes may be configured for physical contact with underlying tissue and be in electrical contact with said backplane transistor through vertical interconnects. The vertical interconnects may comprise vias through which electronic signals pass, including through an electrical conductor positioned through the vias.

The devices may have one or more additional layers to achieve desired operating characteristics, depending on the application of interest. For example, encapsulation or barrier layers may be incorporated into the devices to achieve a desired operating lifetime and/or improve control or parameter measurement without sacrificing the ability to achieve the desired electrical interfacing.

Any of the devices may further comprise an encapsulation layer that covers the backplane transistors and the membrane of silicon. As desired, passages may be positioned to facilitate improved electrical contact with active electrode regions and underlying tissue. The encapsulation layer may have a thickness less than or equal to 2 µm. The encapsulation layer may comprise a trilayer of $SiO_2/Si_3N_4/SiO_2$. A plurality of passages may be positioned through the encapsulation layer and in spatial alignment with an active region of each of said electrodes. In this context, "spatial alignment" refers to the position of the passage or opening through the encapsulation layer such that reliable electrical contact between the active area of the electrode and the corresponding surface being measured is achieved. This may be further defined in a quantitative manner, wherein at least 80%, at least 90%, at least 99%, or all of the area of the active electrode has a vertical correspondence with an opening. Similarly, the passage opening area may have at least 80%, at least 90%, at least 99%, or all vertical correspondence to an underlying active electrode region. Accordingly, spatial alignment may also include entire correspondence between opening and active electrode region.

Any of the devices provided herein may also be described in terms of a device lifetime, such as a device configured for accurate measurement of a biological parameter over a device lifetime. Depending on the application of interest, the device is configured to have any of a wide range of device lifetimes. For example, a device lifetime for a chronic monitoring application may be greater than or equal to 10 days, such as lasting up to the order of 1 to 6 months. Alternatively, a device lifetime for an acute monitoring application may be less than or equal to 2 days. In this context, "accurate measurement" refers to a deviation from a measured value with a conventional system (e.g., non-dissolvable electrodes) that is less than 20%, less than 10%, or less than 5%. Accordingly, a bioresorption lifetime is generally longer than the device lifetime, reflecting that a portion of the device may still be observed at the implant site after the device is considered non-functional. For example, once the device lifetime has passed, it may take an additional day or week for the natural biochemical processes to result in no detectable portion of the device remaining at the implant site.

The membrane of silicon may have a thickness that decreases as a function of implant duration, wherein the device maintains functionality for a decrease in thickness of up to 70%. In this aspect, "functionality" refers to the ability for the device to reliably provide the desired functionality. For example, at least 80% of the electrodes in the array that are able to consistently measure electric potential and/or apply and electric potential at a value that is within at least 80% of desired.

The device lifetime may be controlled by a variety of physical parameter adjustments. For example, device lifetime may be increased with increasing dopant concentration and/or increasing Si membrane thickness.

The membrane of silicon may be doped with a high concentration of dopant. "High concentration" refers to an amount of dopant sufficient to provide desired functionality to the silicon membrane, including the ability to conduct charge for the electric potential sensing and/or electrical stimulation by the array of electrodes. The high concentration may also be described in quantitative amounts, such as greater than or equal to $5\times10^{16}/cm^3$ and less than or equal to $2\times10^{20}/cm^3$, or greater than about $10^{18}/cm^3$ and less than $2\times10^{20}/cm^3$. As desired, any number of dopant materials may be used, including a dopant selected from the group consisting of phosphorus and boron.

The devices may further comprise an insulation layer and electrical interconnects that electrically connect the electrodes, wherein the insulation layer electrically isolates interconnects from biofluids and biological tissue during use.

The insulation layer may comprise a layer of $SiO_2$ having a thickness less than or equal to 200 nm.

The membrane of silicon may further comprise terminal pads configured to electrically interface with a biological tissue. The terminal pads may correspond to exposed Si of membrane of Si. Other portions of the Si of membrane may be covered by an insulation layer.

Any of the devices provided herein may be configured to undergo bioresorption at least partially by controlled dissolution, including controlled dissolution of the membrane of Si. The controlled dissolution may be characterized by one or more of no observable: cracks, flakes, particulates, or decrease in surface smoothness over the time course of functional device lifetime. "No observable" may alternatively be expressed in quantitative terms, including less than 5% or less than 1% compared to an initial state of the material. In this manner, the bioresorption is relatively uniform and steady, and avoids cracking, flaking, particulate release and pitting associated with a rapid and sudden onset of device breakdown, including for electrodes formed of metal.

The controlled dissolution may be described as having an average dissolution rate characterized by a decrease in Si membrane thickness that is greater than or equal to 5 nm/day and less than or equal to 15 nm/day.

The dissolution rate for other non-Si membrane components of the device, including an insulating layer and/or substrate, may be between 3 nm/day and 12 nm/day.

The device may have one or more material parameters selected to obtain a desired dissolution time of the device, the material parameters including one or more of thickness, doping level, composition of polymer substrate.

The device may also be characterized in terms of biocompatibility during use, such as during use there is no detectable long-term adverse immune response.

The device may also be characterized in terms of its conformability, such as being capable of being bent from a planar configuration to a curved configuration with a radius of curvature up to 3 mm without adverse degradation of device functionality. In this context, "adverse degradation" may be defined in terms of deviation of a measured parameter, such as a deviation that is less than or equal to 20%, 10% or 5%, compared to the measure parameter in the planar configuration.

Any of the devices provided herein may be used for spatio-temporal mapping of electrical activity for a biological tissue, such as of the brain, including the cerebral cortex of brain.

Also provided herein are methods of electrically interfacing with biological tissue using any of the devices described herein. For example, the method may comprising the steps of: implanting an implantable and bioresorbable medical device described herein adjacent to a biological tissue; electrically interfacing the device with the biological tissue, wherein the interfacing is one or more of: electrically stimulating or electrically monitoring; and maintaining device functionality over a device lifetime; and dissolving the device so that after the device lifetime no detectable device remains at the implant site. The device lifetime may be selected for the application of interest, including short-term, acute to long-term chronic. After the desired device lifetime, sufficient dissolution has occurred that the device no longer reliably functions, including for example a 70% or greater dissolution of Si membrane thickness.

Also provided herein are methods of making any of the devices described herein.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 1A: Schematic exploded view illustration of the construction of a passive, bioresorbable neural electrode arrays for ECoG and subdermal EEG measurements. A photolithographically patterned, n-doped Si NMs (~300 nm thick) defines the electrodes and interconnects. A film of $SiO_2$ (~100 nm thick) and a foil of PLGA (~30 μm thick) serves as a bioresorbable encapsulating layer and substrate, respectively. The device connects to an external data acquisition (DAQ) system through an anisotropic conductive film interfaced to the Si NMs interconnects at contact pads at the edge. A magnified optical image of electrodes on the right highlights the sensing (Si NMs) and insulating ($SiO_2$) regions. FIG. 1B: Photographs of bioresorbable neural electrode arrays with 4 channels (top) and 256 (16×16 configuration) channels (bottom). FIG. 1C: Microscope image of a device on a hydrogel substrate immersed in an aqueous buffer solution (pH 7.4) at 37° C. FIG. 1D: Electrochemical impedance spectra measured at four different recording sites in an array configured for ECoG. FIG. 1E: Dissolution kinetics for phosphorus and boron doped Si NMs (~300 nm thick, dopant concentration $10^{20}/cm^3$) during immersion in artificial cerebrospinal fluid (aCSF) pH 7.4 at 37° C. FIG. 1F: Distribution of principal strains extracted from finite-element modeling (FEM) of a device bent to a radius of curvature of 1 mm (center) and corresponding displacement profile (left) and image of an array wrapped around a cylindrical tube with a radius of 2 mm (right). FIG. 1G: Images collected at several stages of accelerated dissolution induced by immersion in an aqueous buffer solution (pH 10) at 37° C.

FIG. 2A: Photograph of four-channel bioresorbable electrode array placed on the cortical surface of the left hemisphere of a rat. FIG. 2B: Sleep spindles recoded by a bioresorbable electrode and a nearby commercial stainless steel microwire electrode, as a control placed at 0.5 mm depth from the cortical surface. FIG. 2C: Interictal spiking activity captured by the bioresorbable electrode and the control electrode after topical application of bicuculine methodide. Both electrodes interface with the same hemisphere. Data were processed through a 0.1 Hz-5 kHz bandpass filter. Recordings by the bioresorbable electrode and the control electrode show consistent interictal spikes. FIG. 2D: Interictal spiking activity recorded by the bioresorbable electrode and the control electrode 30 minutes after topical application of bicuculine methodide. Both recordings exhibit high signal-to-noise ratio (Si: 42, Control electrodes: 32) for detecting epileptiform activity. FIG. 2E: Cartoon illustration of a bioresorbable array placed on the periosteum for subdermal EEG recordings. FIG. 2F: Theta oscillations and fast spindle-like oscillations recorded subdermally using bioresorbable electrodes during isoflurane anesthesia. FIG. 2G: Power density spectra of the theta oscillations recorded over a 5 min time window. The spectrum shows a clear peak at the expected frequency range.

FIG. 3A: Photograph of a four-channel bioresorbable electrode array implanted on left hemisphere of the brain of a rat, for chronic recordings, with a coating gelfoam and a layer of dental cement. The array connects to a custom-built circular interface board through a flexible ACF cable. The inset shows the array and craniaotomy after application of a first layer of dental cement.

FIG. 3B-3F: Representative ECoG signals recorded by the bioresorbable array and the control electrode on day 1, 8, 15, 30 and 33. Recordings from three electrodes from the bioresorbable array exhibit large scale oscillatory behavior consistent with small local and temporal variations. After functional dissolution (Day 33), signals from the bioresorbable array show no ECoG activity while the control electrode continues to show expected cortical potentials. FIG. 3G: High voltage rhythmic spikes observed during absence-like seizure activity recorded chronically.

FIG. 5A: Schematic exploded view illustration of an actively multiplexed sensing system for high resolution ECoG, in a fully bioresorbable construction. This 8×8 embodiment includes 128 metal-oxide-semiconductor field-effect transistors (MOSFETs) where Si NMs serve as both the active semiconductor material and the neural interface electrodes. The metallization, the gate dielectric and the interlayer dielectric rely on thin films of Mo (~300 nm thick) and $SiO_2$ (~100 nm thick) and trilayers of $SiO_2$ (~300 nm thick)/$Si_3N_4$ (~400 nm thick)/$SiO_2$ (~300 nm thick), respectively. A second layer of Mo (~300 nm thick) defines column interface lines. A similar trilayer serves as the encapsulation. A film of poly(lactide-co-glycolide) (PLGA, ~30 μm thick) forms the substrate. FIG. 5B: Optical micrograph images of a pair of unit cells at various stages of fabrication (left) and a picture of a complete system (right). FIG. 5C: The left frame shows linear (red) and log scale (blue) transfer curves for a representative n-channel MOSFET, for $V_g$ swept from −5 to +5 V. The channel length ($L_{ch}$), and width (W) are 15 μm and 80 μm, respectively. The threshold voltage, mobility and on/off ratio are ~1 V, ~400 $cm^2/V·s$ and ~$10^8$, respectively, with Mo for source, drain and gate electrodes, and $SiO_2$ for gate dielectrics. The right frame shows current-voltage characteristics, for $V_g$ from 0 to 2.5 V with 0.5 V steps. FIG. 5D: Output response of a unit cell with respect to an input sine wave (200 mV peak to peak) upon insertion in aqueous phosphate buffer solution (PBS, pH 7.4) at room temperature. FIG. 5E: Images collected at several stages of accelerated dissolution of a system immersed into an aqueous buffer solution (pH 12) at 37° C.

FIG. 6A-6G. Acute in vivo microscale electrocortigoraphy (μECoG) with a 64-channel, bioresorbable, actively multiplexed array of measurement electrodes. FIG. 6A: Data recorded from picrotoxin-induced spikes (clockwise spiral, lower-right to upper-left diagonal, upper-left to lower-right diagonal, and right-to-left sweep). The results correspond to measurements across the 64 channels of the array, and the average response (grey) from all channels. The waveforms are color-coded according to the relative latency of the spike maximum (blue is earliest, red is latest). FIG. 6B: Movie frames corresponding to each spike pattern, showing the varied spatial-temporal μECoG voltage patterns from all 64 electrodes at the labeled time. Blue indicates negative, and dark red indicates the highest peak-to-peak voltage observed for each electrode site. The frame interval and color scale are provided for each set of eight movie frames. FIG. 6C: Relative delay map for the band-pass filtered data of each spike activity from frame b, illustrating a clear phase singularity indicated by arrow. FIG. 6D: Illustration of the whisker stimulation locations (Stim. loc.: B1 and Stim. loc.: E3) in a rat model. FIG. 6E: Illustration of the barrel cortex and estimated relative location of the recording array based on evoked potential results. Visibly-activated whiskers indicated by color corresponding to the stimulation location. M=medial, C=caudal. FIG. 6F: Temporal characteristics of the potentials evoked by stimulation location 1 (left) and 2 (right). FIG. 6G: Spatial distribution of the potentials evoked by stimulation location 1 and 2. The color map indicates the evoked potential size, interpolated across the array.

FIG. 7A: Schematic illustrations of key processes for fabricating bioresorbable passive electrodes: (1) printing highly n-doped Si on temporary substrates, (2) defining the mesh structure, followed etching by RIE and immersion buffered oxide etchant (BOE), (3) retrieving the device onto a PDMS slab, (4) printing the device onto a bioresorbable substrate (PLGA), and (5) removing the top D-PI layer. FIG. 7B: Optical image of a complete device.

FIG. 9A: Schematic description of the equivalent circuit model used to fit EIS measurement results. $C_{PE}$ is the constant phase element representing the double-layer capacitance; $R_{CT}$ is the charge transfer resistance; and $R_S$ is the solution resistance. FIG. 9B: Results of measurement (solid lines) and fitting (dashed lines) for the impedance. FIG. 9C: Representative values of $C_{PE}$ and $R_{CT}$ for Au and Si.

FIG. 16A: Slow wave activity and FIG. 16B: k-complexes recorded using a bioresorbable electrode array and a control stainless steel microwire electrode.

DETAILED DESCRIPTION OF THE INVENTION

Figure 1A:
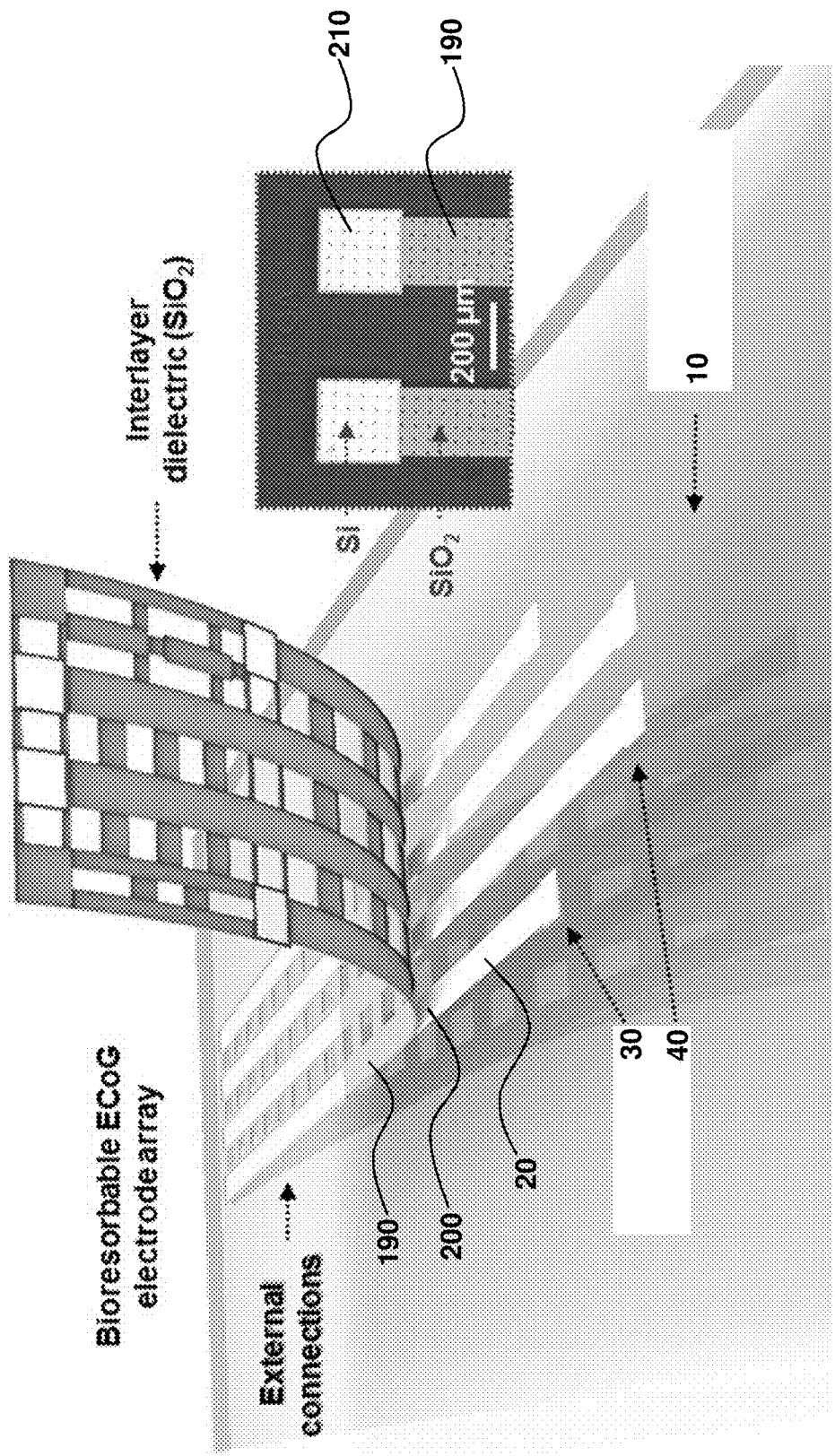
FIG. 1A-1G. Thin, flexible neural electrode arrays with fully bioresorbable construction based on patterned silicon nanomembranes (Si NMs) as the conducting component.

In general, the terms and phrases used herein have their art-recognized meaning, which can be found by reference to standard texts, journal references and contexts known to those skilled in the art. The following definitions are provided to clarify their specific use in the context of the invention.

"Spatio-temporally" or "spatio-temporal" refers to a parameter having a spatial pattern which may change over time. For example, electric potential over the brain surface changes with time, with different regions of the brain generating or propagating an electric potential under various conditions. A sleeping patient will have a different spatio-temporal waveform than an active person. A patient having a brain-generated seizure has a different spatio-temporal waveform than a patient not seizing. Accordingly, "spatio-temporally electrically interfacing" refers to spatial and temporal electrical connection between a device and a brain tissue, so that the spatio-temporal monitoring and/or actuation of the brain can occur.

"Electrically interfacing" refers to the ability to monitor and/or generate electrical potential with a biological tissue. The array and multiplex configuration allows for spatio-temporal monitoring and/or intervention with an applied electric field over a surface area. For example, electrical waveforms may be detected and/or applied, including for a detected waveform indicative of an adverse situation, depending on the tissue of interest. For brain, the adverse situation may be onset of a seizure. For heart, the adverse situation may be indicative of onset of a heart attack or failure. Of course, the devices are compatible with more passive monitoring and related transmission of data, including in real-time, for assessment and action by medical personnel.

"Brain tissue" refers to brain in the in vivo, in vitro, or the ex vitro environment. The brain may be from a human or a non-human, such as an animal.

"Conformable" refers to a device, material or substrate which has a bending stiffness sufficiently low to allow the device, material or substrate to adopt a desired contour profile, for example a contour profile allowing for conformal contact with a surface having a pattern of relief or recessed features. In certain embodiments, a desired contour profile is that of a tissue in a biological environment, for example heart tissue. "Deformable" is used similarly to conformable, and refers to a device, material or substrate can flex, bend, or conform without undue induced strain during deformation, specifically an induced strain below that required to induce mechanical fracture or permanent fatigue. In particular, the element is considered deformable if any induced stress associated with deformation is below the ultimate tensile stress or the yield stress.

"Electrical communication" or contact refers to an arrangement of two components of a device wherein electrical signal (e.g., current, potential) is passed between the two components. For example, each electrode in the array may be electrically connected to a pair of transistors, and the transistors may be connected to a current source or sink, and specifically, to a controller. The parts of the device that convey the electrical signal between the electrical components are herein referred to as "interconnects".

A "component" is used broadly to refer to a material or individual component used in a device. An "interconnect" is one example of a component and refers to an electrically conducting material capable of establishing an electrical connection with a component or between components. In particular, an interconnect may establish electrical contact between components that are separate and/or can move with respect to each other. Depending on the desired device specifications, operation, and application, an interconnect is made from a suitable material. For applications where a high conductivity is required, typical interconnect metals may be used, including but not limited to copper, silver, gold, aluminum and the like, and alloys. Suitable conductive materials further include semiconductors, such as silicon and GaAs and other conducting materials such as indium tin oxide.

An interconnect that is "stretchable" or "flexible" is used herein to broadly refer to an interconnect capable of undergoing a variety of forces and strains such as stretching, bending and/or compression in one or more directions without adversely impacting electrical connection to, or electrical conduction from, a device component. Accordingly, a stretchable interconnect may be formed of a relatively brittle material, such as GaAs, yet remain capable of continued function even when exposed to a significant deformatory force (e.g., stretching, bending, compression) due to the interconnect's geometrical configuration. In an exemplary embodiment, a stretchable interconnect may undergo strain larger than 1%, optionally 10% or optionally 30% or optionally up to 100% without fracturing. In an example, the strain is generated by stretching an underlying elastomeric substrate to which at least a portion of the interconnect is bonded. For certain embodiments, flexible or stretchable interconnects include interconnects having wavy, meandering or serpentine shapes.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material. A material made up of a plurality of components, e.g., substrate and barrier layers, electrical circuit, may be described in terms of a "net bending stiffness", which is a compilation and average of each component's bending stiffness.

"Conformal contact" refers to contact established between a device and a receiving surface, which may for example be a target tissue in a biological environment. In one aspect, conformal contact involves a macroscopic adaptation of one or more surfaces (e.g., contact surfaces) of an implantable device to the overall shape of a tissue surface. In another aspect, conformal contact involves a microscopic adaptation of one or more surfaces (e.g., contact surfaces) of an implantable device to a tissue surface resulting in an intimate contact substantially free of voids. In an embodiment, conformal contact involves adaptation of a contact surface(s) of the implantable device to a receiving surface(s) of a tissue such that intimate contact is achieved, for example, wherein less than 20% of the surface area of a contact surface of the implantable device does not physically contact the receiving surface, or optionally less than 10% of a contact surface of the implantable device does not physically contact the receiving surface, or optionally less than 5% of a contact surface of the implantable device does not physically contact the receiving surface. Conformal contact includes large area conformal contact, for example, wherein conformal contact between a tissue and device component is over an area greater than or equal to 1000 mm$^2$, and optionally greater than or equal to 10,000 mm$^2$. In an aspect, the tissue is brain tissue. Conformal contact may also be described in terms of the maximum separation distance between the device and the underlying brain tissue that the device is interfaced with, such as a distance that is less than or equal to 1 mm. In addition, the tissue may have an intervening thin film of brain fluid between the brain tissue and the device. Accordingly, physical contact with brain tissue includes physical contact between the device and any biological film, including brain fluid, surrounding the brain, so long as electrical contact between the device and brain is maintained.

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50% or optionally 90%, of the external surfaces of the structure is surrounded by one or more structures. "Completely encapsulated" refers to the orientation of one structure such that it is completely surrounded by one or more other structures. Devices may have partially or completely encapsulated inorganic semiconductor components, metallic conductor components and/or dielectric components, for example, via incorporation a polymer encapsulant, such as biopolymer, silk, a silk composite, or an elastomer encapsulant. The encapsulation may correspond to a substrate that supports an electronic device and a superstrate that covers the electronic device.

"Barrier layer" refers to a component spatially separating two or more other components or spatially separating a component from a structure, material, fluid or environment external to the device. In one embodiment, a barrier layer encapsulates one or more components. In some embodiments, a barrier layer separates one or more components from an aqueous solution, a biological tissue or both. The invention includes devices having one or more barrier layers, for example, one or more barrier layers positioned at the interface of the device with an external environment.

Devices and methods provided herein are useful for "monitoring" or "actuating" electrical spatio-temporal waveforms over the brain surface. Monitoring refers to measuring, and optionally encoding, spatio-temporal electrical waveform on the brain surface. Actuating refers to the electrodes of the device interacting with, stimulating, controlling, or otherwise affecting brain tissue, or a material (e.g., skull, skin) or fluid (e.g., cerebral fluid) in electrical contact therewith.

"Temporally adjacent time points" is a measure of the time resolution of the device. The ability to electrically detect changes in electrical potential in a brain location is constrained by how often the electrical measurement is made or the delay time between measurements. The ability to stimulate brain waveform change is similarly constrained.

"Electrical waveform" refers to a pattern of electric potential over the brain surface. A single waveform snapshot provides only limited information about the waveform at one single instance in time. Accordingly, a spatio-temporal profile requires monitoring of the waveform over a period of time. This provides information about the direction of travel of the waveform, how it initiates, propagates and terminates. That information is required to further identify a waveform as "abnormal" or "normal".

The terms "flexible" and "bendable" are used synonymously in the present description and refer to the ability of a material, structure, device or device component to be deformed into a curved or bent shape without undergoing a transformation that introduces significant strain, such as strain characterizing the failure point of a material, structure, device or device component. In an exemplary embodiment, a flexible material, structure, device or device component may be deformed into a curved shape without introducing strain larger than or equal to 5%, for some applications larger than or equal to 1%, and for yet other applications larger than or equal to 0.5% in strain-sensitive regions. A used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 100 microns, optionally less than 10 microns and optionally less than 1 micron) and device geometries such as thin film and mesh geometries.

"Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. A used herein, many stretchable structures are also flexible. Some stretchable structures (e.g., device components) are engineered to be able to undergo compression, elongation and/or twisting so as to be able to deform without fracturing. Stretchable structures include thin film structures comprising stretchable materials, such as elastomers; bent structures capable of elongation, compression and/or twisting motion; and structures having an island-bridge geometry. Stretchable device components include structures having stretchable interconnects, such as stretchable electrical interconnects.

"Semiconductor" refers to any material that is an insulator at a low temperature, but which has an appreciable electrical conductivity at a temperatures of about 300 Kelvin. In the present description, use of the term semiconductor is intended to be consistent with use of this term in the art of microelectronics and electronic devices. Useful semiconductors include those comprising element semiconductors, such as silicon, germanium and diamond, and compound semiconductors, such as group IV compound semiconductors such as SiC and SiGe, group III-V semiconductors such as AlSb, AlAs, Aln, AlP, BN, GaSb, GaAs, GaN, GaP, InSb, InAs, InN, and InP, group III-V ternary semiconductors alloys such as $Al_xGa_{1-x}As$, group II-VI semiconductors such as CsSe, CdS, CdTe, ZnO, ZnSe, ZnS, and ZnTe, group I-VII semiconductors CuCl, group IV-VI semiconductors such as PbS, PbTe and SnS, layer semiconductors such as $PbI_2$, $MoS_2$ and GaSe, oxide semiconductors such as CuO and $Cu_2O$. The term semiconductor includes intrinsic semiconductors and extrinsic semiconductors that are doped with one or more selected materials, including semiconductor having p-type doping materials and n-type doping materials, to provide beneficial electronic properties useful for a given application or device. The term semiconductor includes composite materials comprising a mixture of semiconductors and/or dopants. Specific semiconductor materials useful for in some embodiments include, but are not limited to, Si, Ge, SiC, AlP, AlAs, AlSb, GaN, GaP, GaAs, GaSb, InP, InAs, GaSb, InP, InAs, InSb, ZnO, ZnSe, ZnTe, CdS, CdSe, ZnSe, ZnTe, CdS, CdSe, CdTe, HgS, PbS, PbSe, PbTe, AlGaAs, AlInAs, AlInP, GaAsP, GaInAs, GaInP, AlGaAsSb, AlGaInP, and GaInAsP. Porous silicon semiconductor materials are useful for applications of aspects described herein in the field of sensors and light emitting materials, such as light emitting diodes (LEDs) and solid state lasers. Impurities of semiconductor materials are atoms, elements, ions and/or molecules other than the semiconductor material(s) themselves or any dopants provided to the semiconductor material. Impurities are undesirable materials present in semiconductor materials which may negatively impact the electronic properties of semiconductor materials, and include but are not limited to oxygen, carbon, and metals including heavy metals. Heavy metal impurities include, but are not limited to, the group of elements between copper and lead on the periodic table, calcium, sodium, and all ions, compounds and/or complexes thereof.

"Semiconductor element", "semiconductor structure" and "semiconductor circuit element" are used synonymously in the present description and broadly refer to any semiconductor material, composition or structure, and expressly includes high quality single crystalline and polycrystalline semiconductors, semiconductor materials fabricated via high temperature processing, doped semiconductor materials, organic and inorganic semiconductors and composite semiconductor materials and structures having one or more additional semiconductor components and/or non-semiconductor components, such as dielectric layers or materials, electrodes and/or conducting layers or materials.

"Active circuit" and "active circuitry" refers to one or more device components configured for performing a specific function. Useful active circuits include, but are not limited to, amplifier circuits, multiplexing circuits, logic circuits, CMOS circuits, processors, and current limiting circuits. Useful active circuit elements include, but are not limited to, transistor elements and diode elements.

"Electrical contact" refers to the ability of two or more materials and/or structures that are capable of transferring charge between them, such as in the form of the transfer of electrons or ions. Electrical communication refers to a configuration of two or more components such that an electronic signal or charge carrier can be directly or indirectly transferred from one component to another. As used herein, electrical communication includes one way and two way electrical communication. In some embodiments, components in electrical communication are in direct electrical communication wherein an electronic signal or charge carrier is directly transferred from one component to another. In some embodiments, components in electrical communication are in indirect electrical communication wherein an electronic signal or charge carrier is indirectly transferred from one component to another via one or more intermediate structures, such as circuit elements, separating the components.

"Dielectric" refers to a non-conducting or insulating material. In an embodiment, an inorganic dielectric comprises a dielectric material substantially free of carbon. Specific examples of inorganic dielectric materials include, but are not limited to, silicon nitride and silicon dioxide.

"Dopant" refers to ions, atoms, compounds, or any aggregates or combinations of these that are introduced into a material, usually in small quantities, to affect the material's chemical, electrical or physical properties. As used herein dopants include, atoms, compounds, or any aggregates or combinations of these that are introduced in a semiconductor to affect the semiconductor's electrical characteristics, such as the semiconductor's electrical conductivity and resistance. Dopants useful herein include p-type dopants such as boron, n-type dopants such as phosphorous, antimony and arsenic, and combinations of n-type dopants and p-type dopants.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, graft, tapered and other copolymers. Useful polymers include organic polymers or inorganic polymers and may be in amorphous, semi-amorphous, crystalline or partially crystalline states. Cross linked polymers having linked monomer chains are particularly useful for some applications. Polymers useable in the methods, devices and device components include, but are not limited to, plastics, elastomers, thermoplastic elastomers, elastoplastics, thermostats, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate, polymethylpentene, polyphenylene oxides and polyphenylene sulfides, polyphthalamide, polypropylene, polyurethanes, styrenic resins, sulfone based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomer" refers to a polymeric material which can be stretched or deformed and return to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers useful include, but are not limited to, thermoplastic elastomers, styrenic materials, olefenic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. In some embodiments, an elastomeric stamp comprises an elastomer. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefenic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a flexible polymer is a flexible elastomer.

"Conformable" refers to a device, material or substrate which has a bending stiffness sufficiently low to allow the device, material or substrate to adopt a desired contour profile, for example a contour profile allowing for conformal contact with a surface having a pattern of relief or recessed features. In certain embodiments, a desired contour profile is that of a tissue in a biological environment, for example heart tissue.

"Low modulus" refers to materials having a Young's modulus less than or equal to 10 MPa, less than or equal to 5 MPa, or optionally less than or equal to 1 MPa and optionally for some applications less than or equal to 0.1 MPa.

"Young's modulus" and "modulus" are used interchangeably and refer to a mechanical property of a material, device or layer which refers to the ratio of stress to strain for a given substance. Young's modulus may be provided by the expression;

$$E = \frac{(stress)}{(strain)} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied and A is the area over which the force is applied. Young's modulus may also be expressed in terms of Lame constants via the equation:

$$E = \frac{\mu(3\lambda + 2\mu)}{\lambda + \mu}, \quad (II)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably 10 times larger for some applications, more preferably 100 times larger for other applications and even more preferably 1000 times larger for yet other applications. "Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire layer of material.

"Biocompatible" refers to a material that does not elicit an immunological rejection or detrimental effect when it is disposed within an in-vivo biological environment. For example, a biological marker indicative of an immune response changes less than 10%, or less than 20%, or less than 25%, or less than 40%, or less than 50% from a baseline value when a biocompatible material is implanted into a human or animal. Similarly, "bioresorbable" refers to a biocompatible material that is configured for transient function, and after a certain time period, to be removed from the implant site by natural chemical processes, including breakdown with exposure to the biological environment and biofluid.

"Bioinert" refers to a material that does not elicit an immune response from a human or animal when it is disposed within an in-vivo biological environment. For example, a biological marker indicative of an immune response remains substantially constant (plus or minus 5% of a baseline value) when a bioinert material is implanted into a human or animal.

Described herein are conformable electrophysiology interface data acquisition and/or stimulating devices and related methods for acquiring electrophysiology data at high-speed and high-resolution. The devices disclosed herein include devices useful for diagnosing and treating medical conditions in real time and with high spatial precision. The disclosed devices and methods also include those suited for monitoring electrical, of tissues in-vivo as they undergo motion, for example the tissue of a beating heart or brain swelling or deformation associated with intra-cranial pressure changes. The disclosed devices and methods further include those especially suited for monitoring electrical characteristics of tissues having nonplanar surfaces.

Figures 7A, 7B:
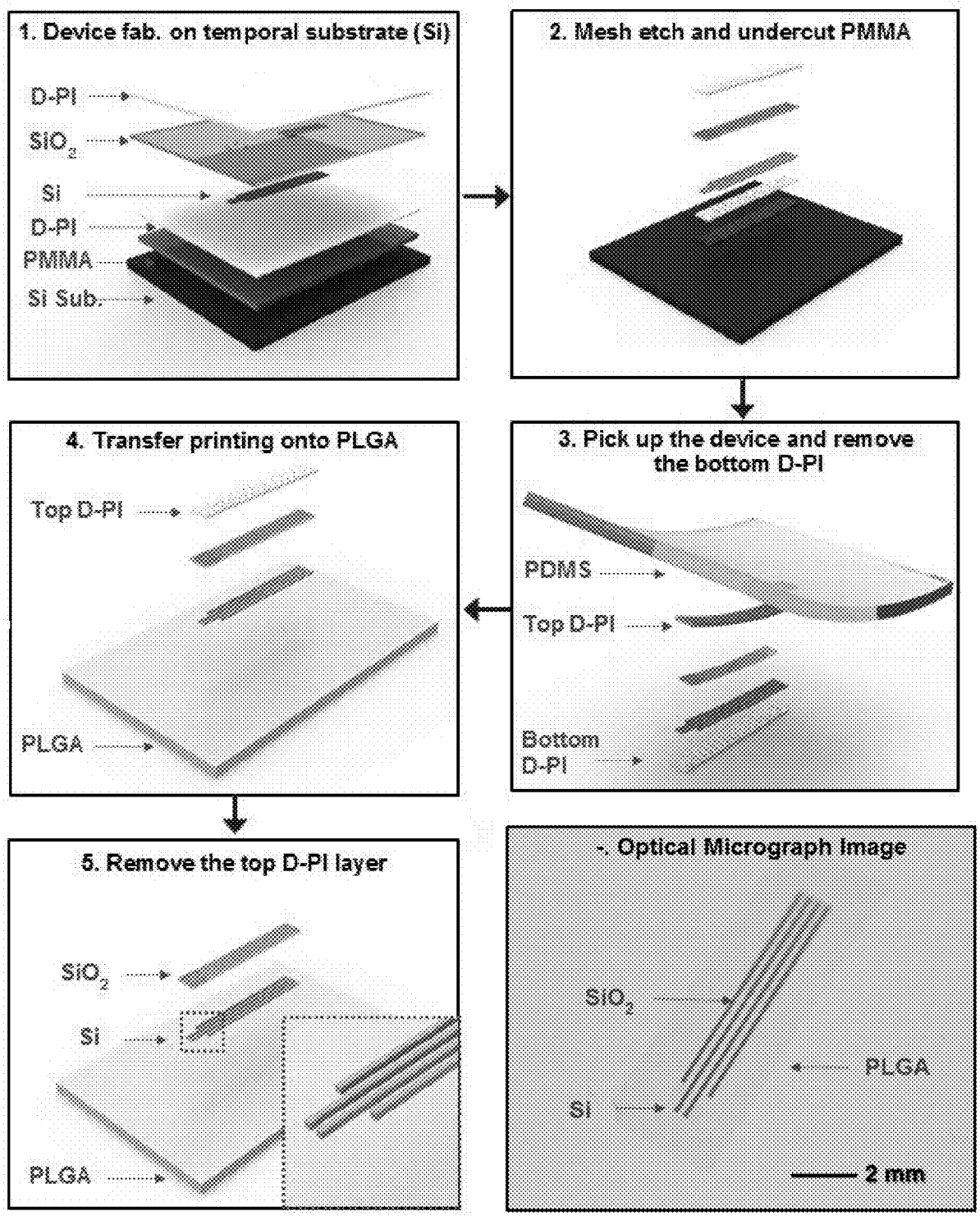
FIG. 7A-7B. Materials and procedures for fabricating bioresorbable passive electrodes on biodegradable substrates (PLGA) and a device image.

FIG. 1 illustrates an implantable and bioresorbable medical device comprising a bioresorbable substrate 10 (resorbable substrate of PLGA) and an electronic circuit 20 supported thereon. At least a portion of the electronic circuit corresponds to a membrane of silicon 30 (e.g., highly doped Si NMs) including a patterned membrane (see, e.g., FIG. 7A). A portion of the silicon membrane corresponds to dissolvable electrodes 40. An insulation layer 190 may electrically insulate interconnects 200 that electrically connect electrodes to external connections. The inset is a close-up view of the distal end of the device illustrating the electrodes as terminal pads 210 that are Si membrane portion not covered with the insulator layer 190.

Figure 5A:
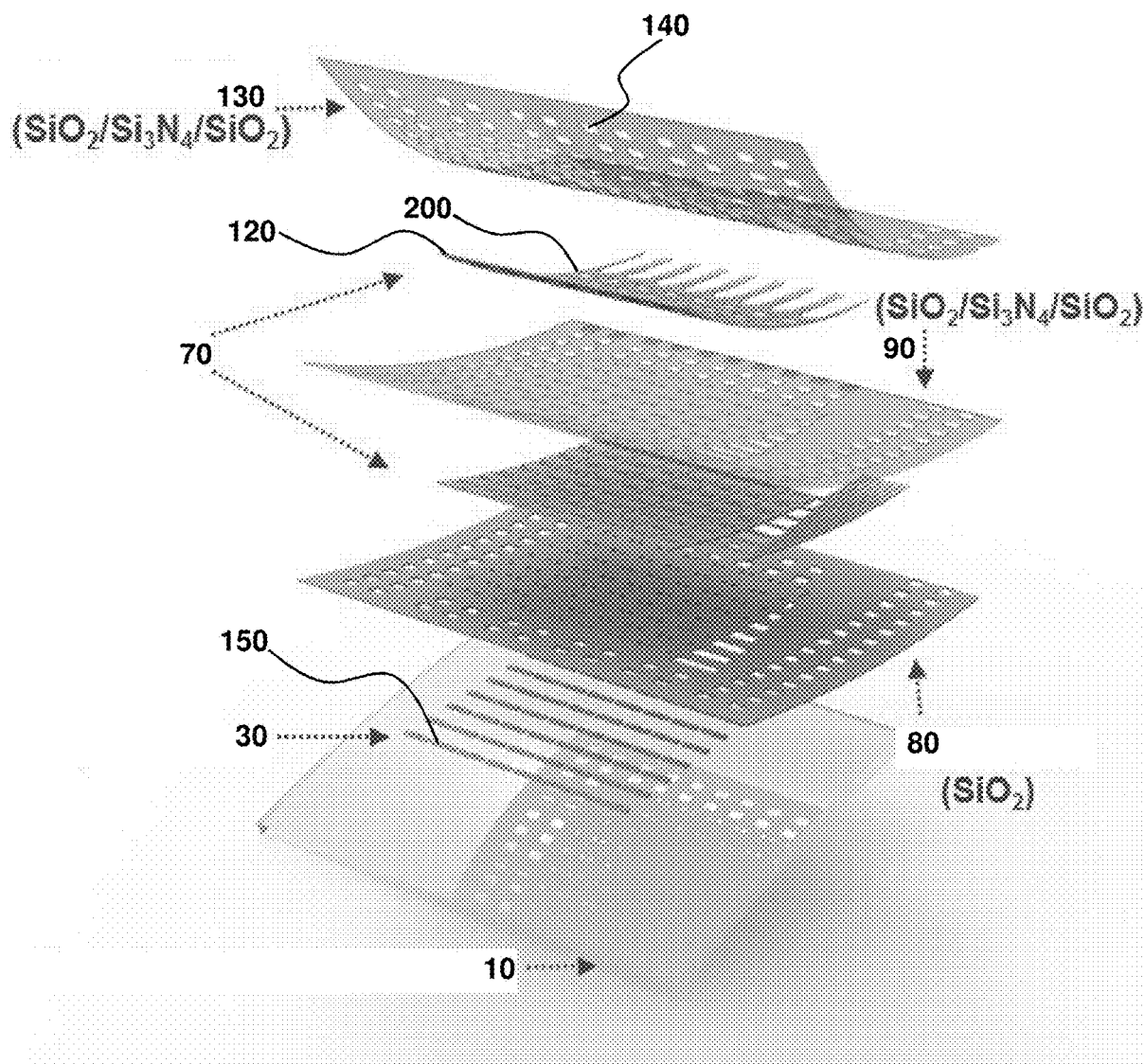
FIG. 5A-5E. Bioresorbable actively multiplexed neural electrode array.
Figure 5B:
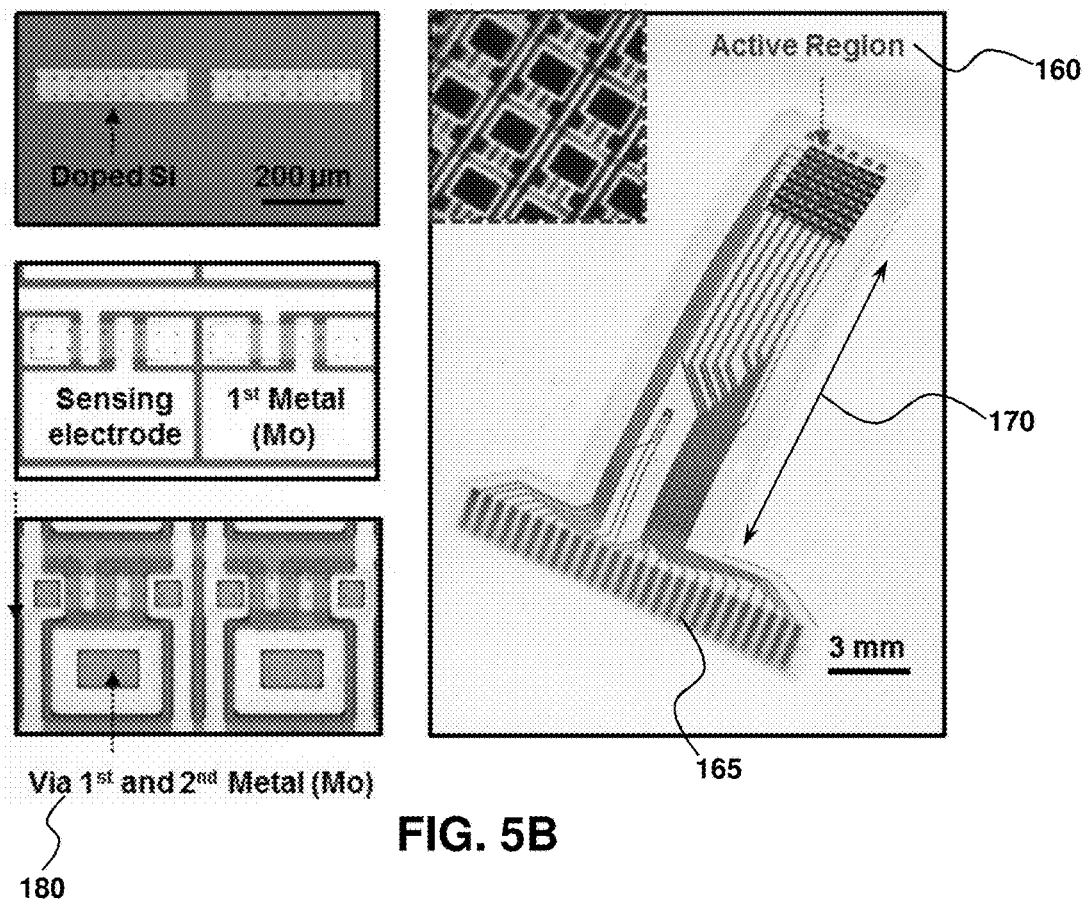

Various other components of the device are further illustrated in FIG. 5A. Bioresorbable substrate 10 formed from resorbable PLGA supports a silicon membrane 30, including a doped silicon membrane, and related electronic circuit components. Illustrated are layers of $SiO_2$ (gate oxide) as a gate dielectric 80, with passages to correspond to exposed silicon 150. Metal (Mo) in a thin film 70 and an interlayer dielectric (ILD) 90 formed of $SiO_2/Si_3N4/SiO_2$ with the gate dielectric can form a MOSFET. A second thin layer of metal 120 can be used to define, for example, column select lines 125 (see, e.g., FIG. 24). An encapsulation layer 130, may cover the system, with passages 140 in alignment with underlying silicon to define active regions that correspond to an array of dissolvable electrodes. Additional geometry is illustrated in FIG. 5B, with active regions 160 at a distal end and separated from external electrical connectors 165 by a longitudinal distance 170. Vertical interconnects 180, including vias, may connect electrodes to backplane transistors.

Figure 22:
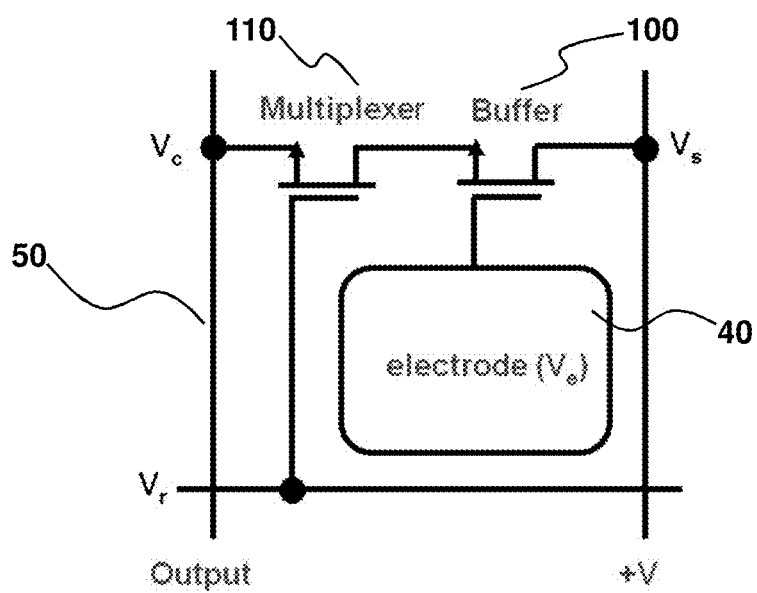
FIG. 22. Schematic circuit diagram of a single unit cell containing two matched n-MOS transistors in an actively multiplexed, bioresorbable electrode array.

A single unit cell of the multiplexed array 50 of dissolvable electrodes 40 is illustrated in FIG. 22. To facilitate current multiplexing, buffer transistor 100 and multiplexing transistor 110 are electrically connected to an electrode.

Bioresorbable silicon electronics: The devices provided herein offer unprecedented opportunities to deploy advanced implantable monitoring systems that eliminate risks, cost and discomfort associated with surgical extraction. Applications include post-operative monitoring and transient physiologic recording after percutaneous or minimally invasive placement of vascular, cardiac, orthopedic, neural or other devices. Present herein are examples of these materials in both passive and actively addressed arrays of bioresorbable silicon electrodes with multiplexing capabilities, that record in vivo electrophysiological signals from the cortical surface and the subgaleal space. The devices detect normal physiologic and epileptiform activity, both in acute and chronic recordings. Comparative studies show sensor performance comparable to standard clinical systems and reduced tissue reactivity relative to conventional clinical electrocorticography (ECoG) electrodes. This technology offers general applicability in neural interfaces, with additional potential utility in treatment of disorders where transient monitoring and modulation of physiologic function, implant integrity and tissue recovery or regeneration are required.

Neurophysiologic monitoring is commonly used for diagnosing and treating neurological disorders such as epilepsy, Parkinson's disease, depression, chronic pain and disorders of the peripheral nervous system[1,2]. Such capabilities are critically important for mapping and monitoring brain function during and in preparation for resective neurosurgery[3], such as for epilepsy and tumors, for assisting in neurodevice placement, such as for Parkinson's disease[4], epilepsy[5], and depression, and for guiding surgical procedures on complex, interconnected peripheral nerve structures such as the brachial, lumbar and sacral plexi[2]. Related functionality is also increasingly leveraged during intravascular procedures, such as aneurysm coiling[6], stent placement[7], AVM embolization[8], and endoscopic operations. Post-procedure monitoring typically occurs in an intensive care unit (ICU), where a variety of devices record physiologic activity, typically with limited temporal and spatial sampling, directly at the regions of interest, simply because these are exposed and accessible during surgery[9]. Intracranial monitors for post-operative seizures and recovery of brain function after surgery would also be useful, and potentially more sensitive than scalp monitoring[10]. These clinical needs motivate efforts to develop technologies for neurophysiologic monitoring that incorporate inorganic and organic nanomaterials in flexible formats[11-20]. Although it would be desirable for neuromonitoring in the ICU to offer the same high fidelity, high resolution performance as is available in the operating room, the morbidity and cost of associated with additional surgeries to remove implanted recording devices preclude this possibility in general practice. In certain cases, such as in invasive intracranial electrocorticographic monitoring for epilepsy surgery, recording electrodes remain in place for one to three weeks to localize epileptic networks[21]. Here, removal occurs in a second procedure, often with resection of brain involved in generating seizures. In other cases, electrodes are placed in staging procedures that do not end in resection, but rather are done for broad lateralization in preparation for more extensive implants or placement of implantable devices. Here, a second procedure to remove implants adds cost and risk. Recent evidence suggests that 1-3 months of ambulatory intracranial recording may be required to adequately localize seizures for epilepsy surgery or device placement, a period prohibitively long for current in-hospital approaches[22]. Using bioresorbable electrodes for such studies would eliminate the danger and cost of removing standard electrodes at the end of this period, during which standard devices may become fibrosed or adherent to underlying tissues. An ideal scenario would involve placement of temporary, bioresorbable monitoring devices capable of providing continuous streams of data for guiding medical care over predetermined periods of time before dissolving. Below we present a new class of technology that offers this mode of operation, with spatio-temporal resolution that matches or exceeds any existing alternative.

Recently reported bioresorbable sensors of pressure and temperature in the intracranial space provide distinct, complementary capabilities in single-point measurements of non-electrical characteristics of the cerebrospinal fluid in the intracranial space[23]. The results presented here introduce materials and device designs for direct electrical interfaces to the brain itself, including bioresorbable electrodes and multiplexing electronics for high speed spatio-temporal mapping of biological processes. The platform builds on recently described technologies that exploit nanomembranes of device-grade, monocrystalline silicon (Si NMs) as the semiconductor foundation of a high performance class of electronic systems. The key enabling chemistry involves hydrolysis of Si NMs upon immersion in biofluids, to yield end products that are biocompatible. The results presented here indicate that Si NMs, at high levels of doping[24], can additionally serve as the neural recording electrodes themselves, as a stable, yet ultimately transient, measurement interface. In addition to their established bioresorbability, the nanoscale thicknesses of Si NMs, when deployed with thin substrates, interconnect metals and dielectrics, yield devices with levels of mechanical flexibility necessary for conformal contact and chronically stable interfaces with neural tissues. The following describes means to exploit these concepts in materials, devices and system-level examples of bioresorbable Si electronic interfaces to the brain, with examples in passive and active matrix addressed recording in vivo. Evaluations include capture of ECoG and subdermal encephalograms (EEG) in live, awake animal models, where Si NMs serve as active materials both for the recording interface and for the backplane transistors that allow high speed multiplexed addressing across arrays of channels. Comprehensive in vitro and in vivo studies establish that these systems provide accurate and reproducible measurements of neural signals and physiological activity for acute (~hours) and chronic (up to 33 days) use. Biocompatibility studies reveal no overt tissue reactions compared to clinically approved commercial ECoG electrodes.

Figure 1B:
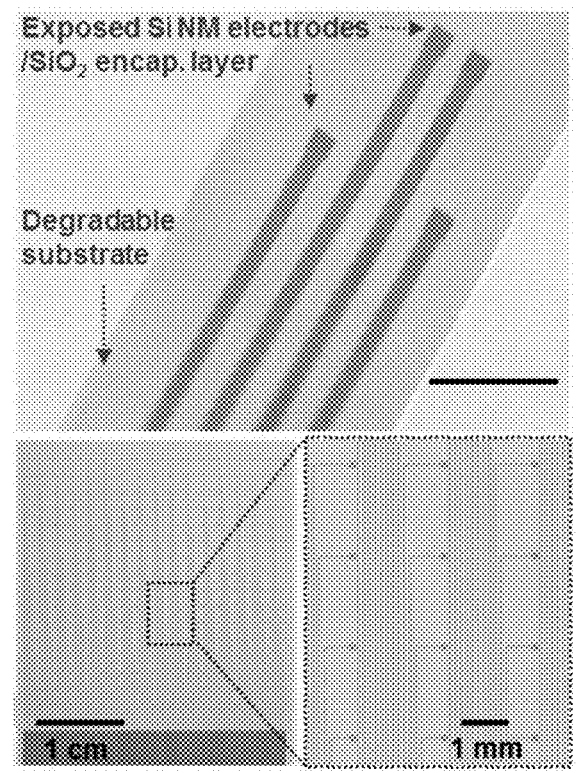
Figure 1C:
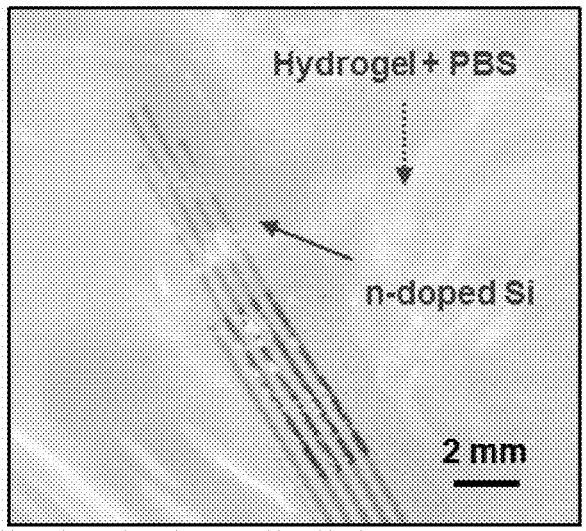
Figure 8:
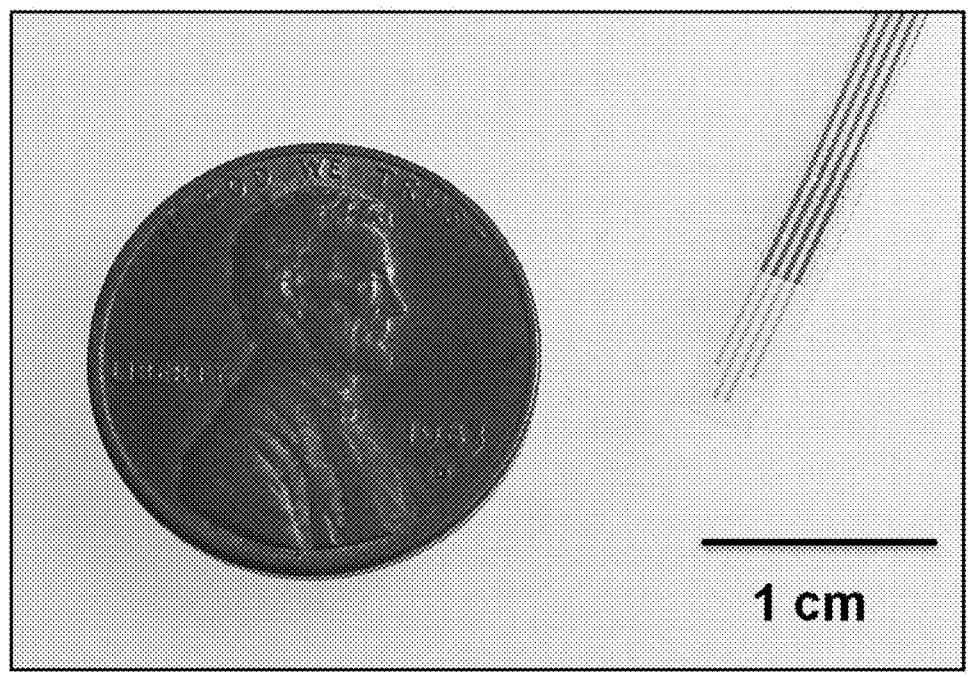
FIG. 8. A photograph of a bioresorbable passive electrode array with a penny.

FIG. 1A provides an exploded schematic diagram (left) of a magnified optical microscope image of the active sensing and the passivation regions (right) of a simplest embodiment of these concepts: a thin, flexible electrode array based on phosphorus doped (impurity concentrations: $\sim 10^{20}/cm^3$) collection of Si NM (thickness ~300 nm) structures. Here, a layer of $SiO_2$ (thickness ~100 nm) insulates the connection traces to isolate them from bio-fluids and adjacent tissue. The terminal pads comprise exposed Si, as the direct neural interface. A flexible sheet of the bioresorbable polymer poly(lactic-co-glycolic acid, PLGA, thickness ~30 μm) serves as the substrate. This array (3×4 mm²) allows chronic recordings from rat cortex at four measurement sites, each with dimensions of 250×250 μm². Such small arrays serve effectively in demonstrator experiments and studies of the fundamental issues in the materials science. The materials and fabrication schemes do, however, align with those used in the semiconductor industry and are, as a result, immediately scalable to much larger areas, higher channel counts and smaller/larger electrode sizes. As an illustration, FIG. 1B (bottom frames) presents a passive array that includes 256 independent channels, in a 16×16 configuration, with an overall area of 3 cm×3.5 cm. Multiplexing architectures, described subsequently, provide routes to scaling to even higher numbers of channels. The fabrication steps appear in the methods section and in FIG. 7A-7B. The lot and functional electrode yields are ~100% and >90%, respectively. FIG. 1B and FIG. 8 show micrographs of completed arrays. FIG. 1B (bottom) shows a scaled version of this same basic device architecture that includes 256 independent channels.

Figure 1D:
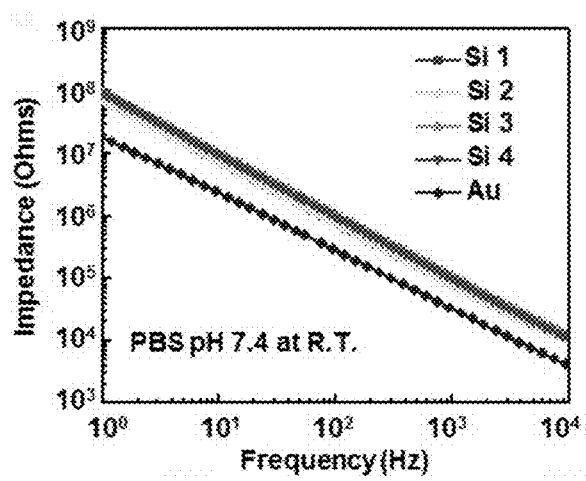
Figure 1D:
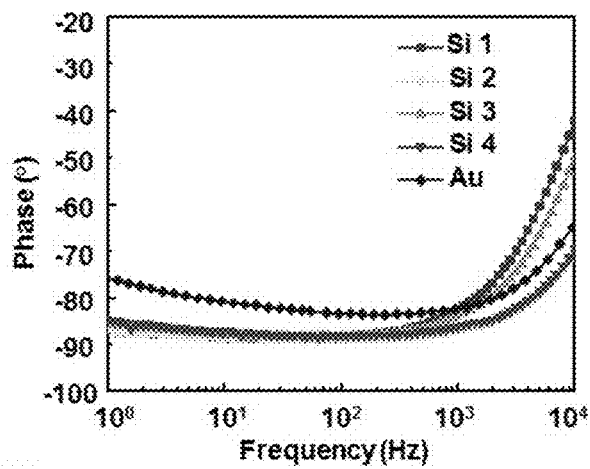
Figure 9A:
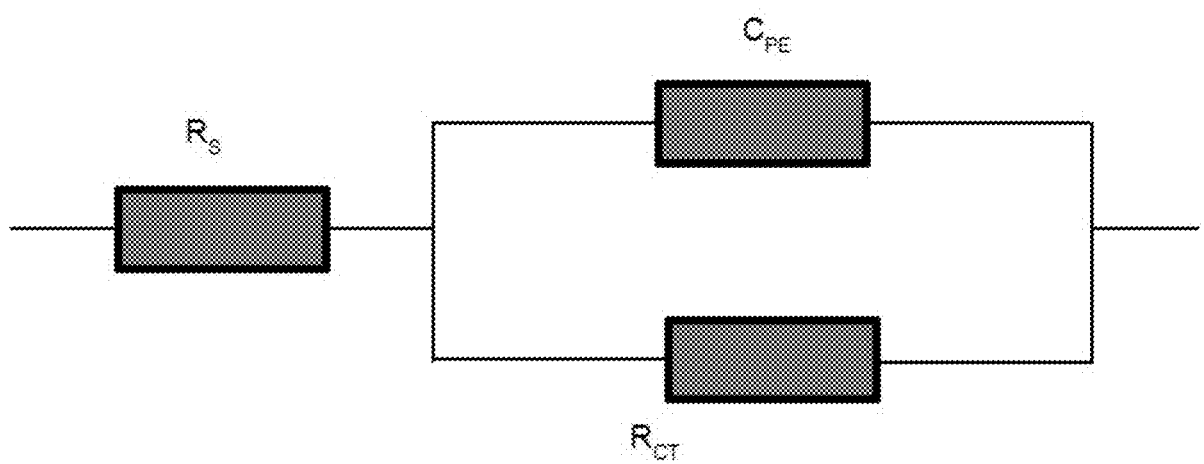
FIG. 9A-9C. EIS characterization of Si and Au.
Figure 9B:
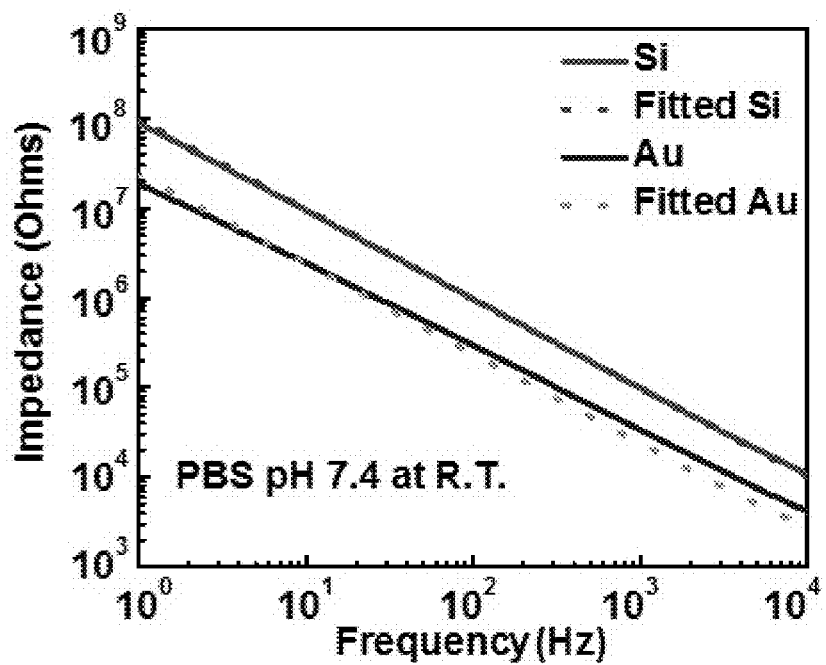
Figure 9C:
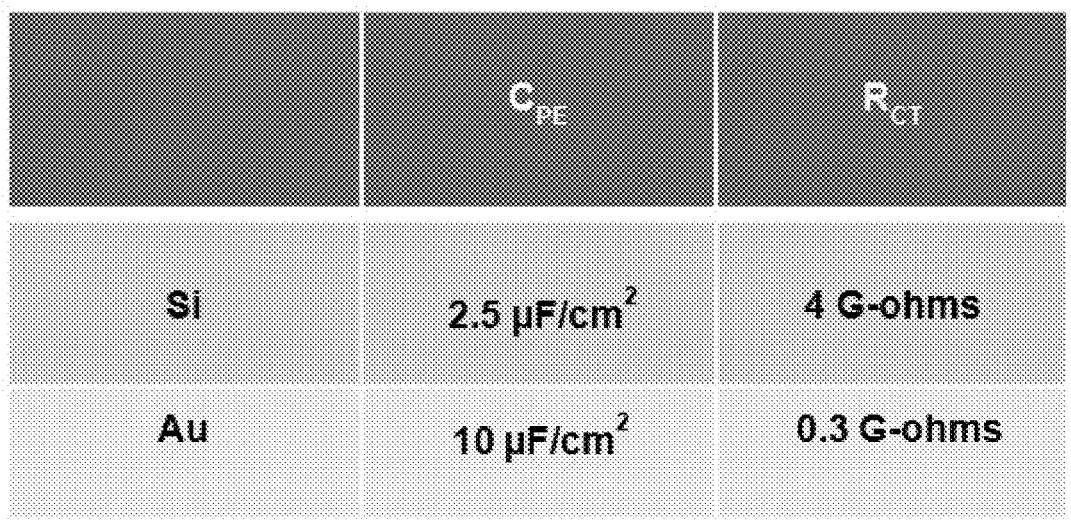

Placing an array onto a hydrogel substrate (FIG. 1C) and immersing the system in phosphate-buffered saline (PBS) at physiological pH (7.4) and at room temperature enables characterization of each of the electrodes by electrochemical impedance spectroscopy (EIS), across a range of frequencies most relevant to the studies described subsequently. In the recording of brain signals, the electrodes transduce ionic currents in the electrolyte to an electric current in the measurement system. The contact between an electrode and tissue has associated electrical impedance, where reductions in the impedance decrease the noise level, thereby increasing the signal to noise ratio (SNR) of the recordings[19,25]. The data in FIG. 1D correspond to the impedance (IZI) of each channel in the array, along with the response of a gold (Au) electrode with the same dimensions. The EIS data for Si can be fit to an equivalent Randles circuit model (FIG. 9A) that includes a double layer capacitance ($C_{PE}$) in parallel with a charge transfer resistance ($R_{CT}$), all of which is in series with a resistance ($R_S$) that corresponds to the surrounding electrolyte solution. This model quantitatively captures the EIS data for both Au (without the space charge layer) and Si electrodes, as shown in FIG. 9B. The fitted values of $C_{PE}$ are ~2.5 μF/cm² and ~10 μF/cm² for Si and Au, respectively; both values are in a range consistent with the literature[26,27]. The space charge layer lowers the capacitance of the Si electrode[28], causing the difference in capacitances for Au and Si electrodes (FIG. 1D). More details of in vitro experiments of the Si electrodes are described below and FIGS. 10-13.

In Vitro Experiments of Phosphorus Doped Si NM Electrodes.

Figure 10:
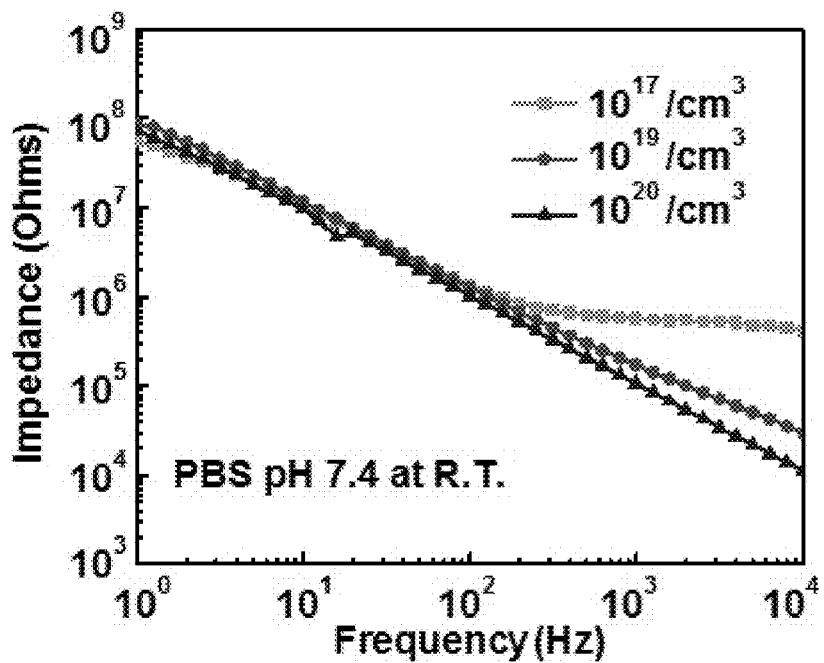
FIG. 10. Impedance spectra of phosphorus doped Si NM electrodes with different doping concentrations ($10^{17}/cm^3$, $10^{19}/cm^3$, $10^{20}/cm^3$).
Figure 11:
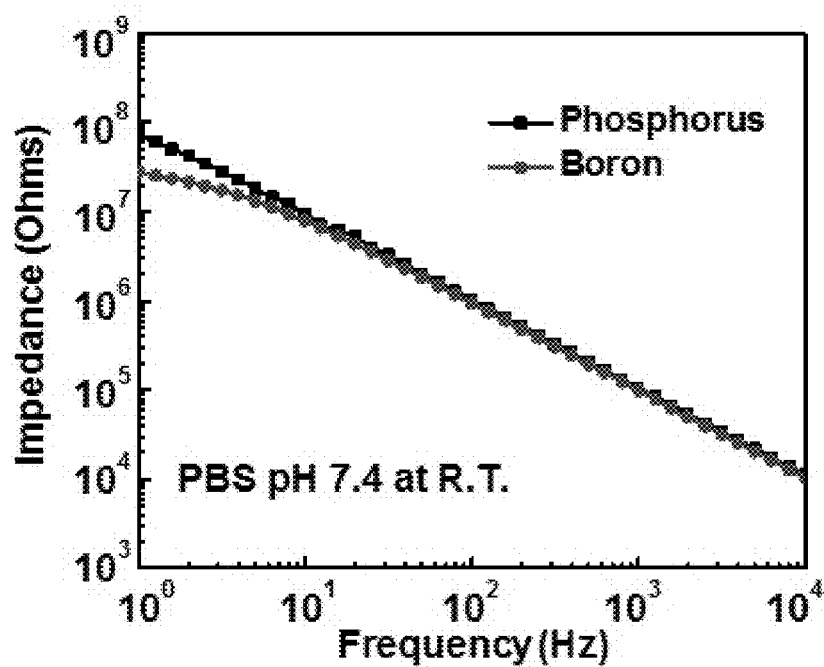
FIG. 11. Impedance spectra of boron and phosphorus doped Si NM electrodes with the same doping concentrations ($10^{20}/cm^3$) for both boron and phosphorus.
Figure 12:
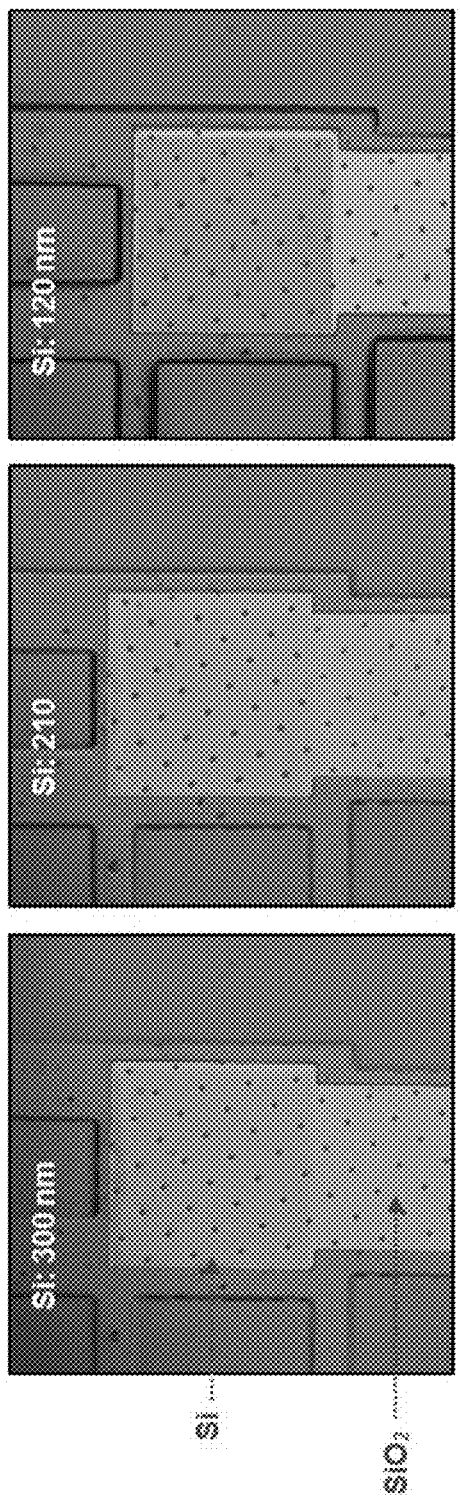
FIG. 12. Impedance spectra of different thicknesses (300 nm, 210 nm, 120 nm) of sites of Si.
Figure 12:
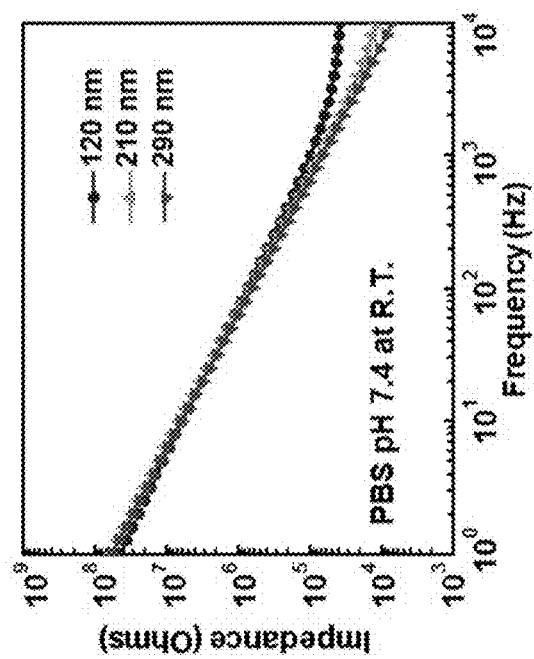
Figure 13:
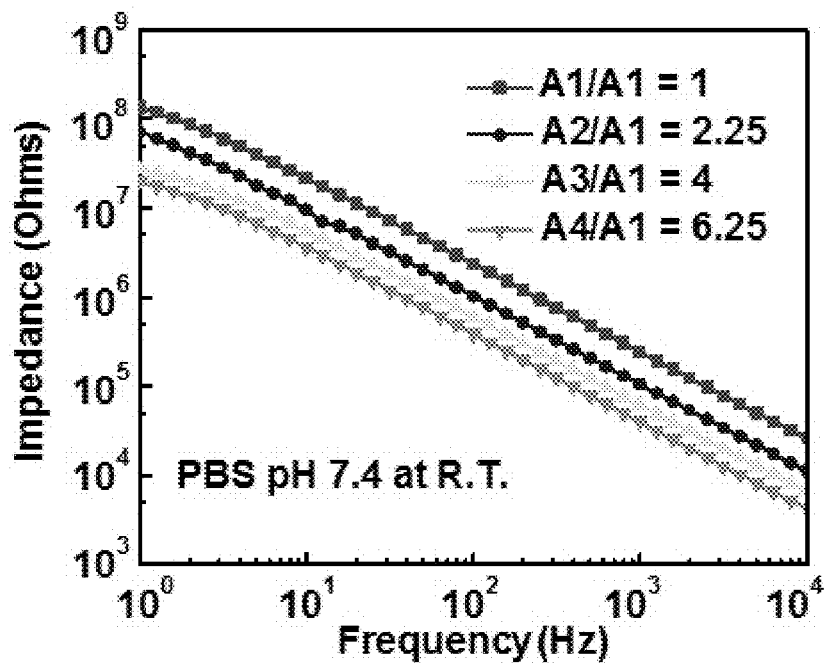
FIG. 13. Impedance spectra of phosphorus doped Si NM electrodes with the different areas (200×200 $\mu m^2$ (A1), 300×300 $\mu m^2$ (A2), 400×400 $\mu m^2$ (A3), 500×500 $\mu m^2$ (A4)) of sites.

Results of impedance measured on devices constructed using Si NMs with different dopant species and concentrations (phosphorus, between ~$10^{17}$ and ~$10^{20}$/cm³; and boron, at ~$10^{20}$/cm³) are comparable at all frequencies, up to ~1 kHz. (FIGS. 10 and 11). The impedances measured from Si NMs with different thicknesses across a relevant range also show similar values (FIG. 12), thereby suggesting an ability for continuous, reliable neural recording even as the electrodes dissolve over time. The doping level and the thickness do, however, strongly affect the time for complete dissolution, where increasing the level and thickness increases the lifetime. The impedance decreases, as expected, inversely with the areas of the electrodes (phosphorous, ~$10^{20}$/cm³), as illustrated in the data of FIG. 13 for dimensions of 200×200 μm² (A1), 300×300 μm² (A2), 400×400 μm² (A3), 500×500 μm² (A4).

Figure 1E:
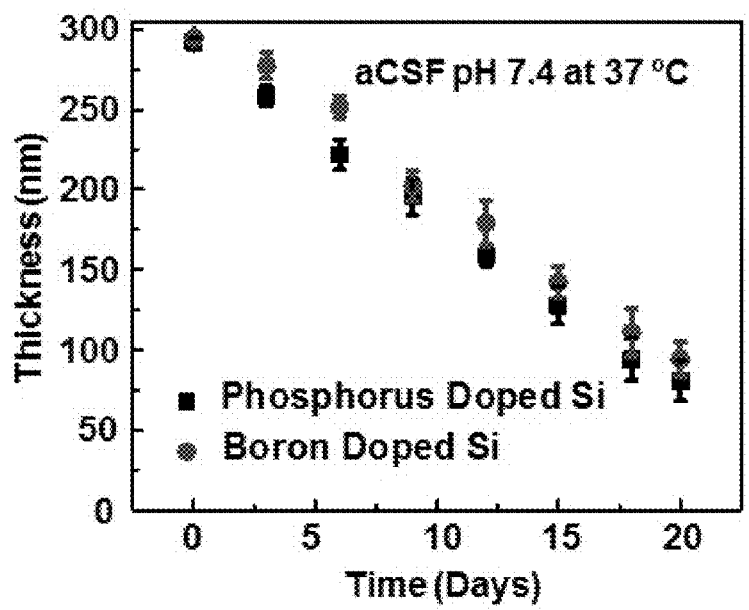
Figure 1F:
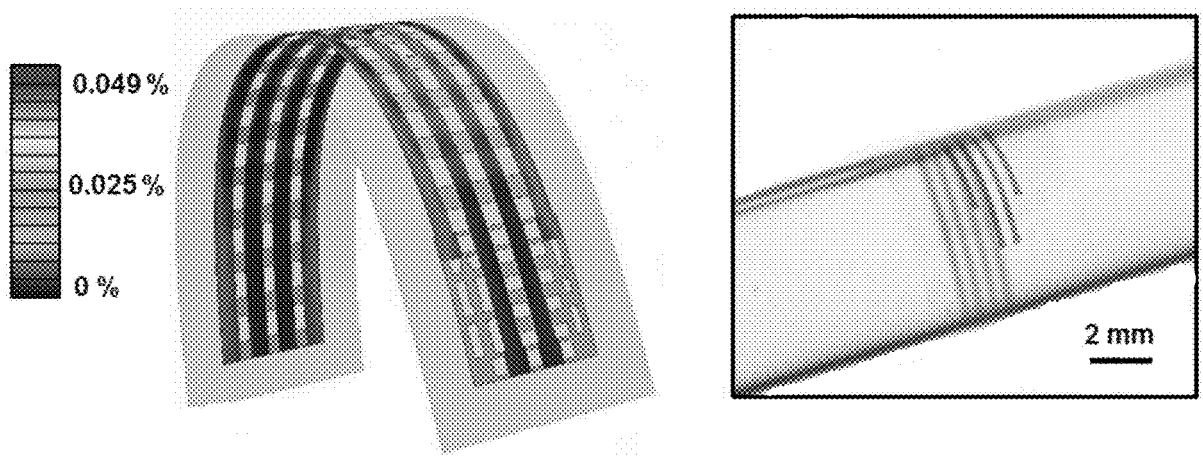
Figure 1G:
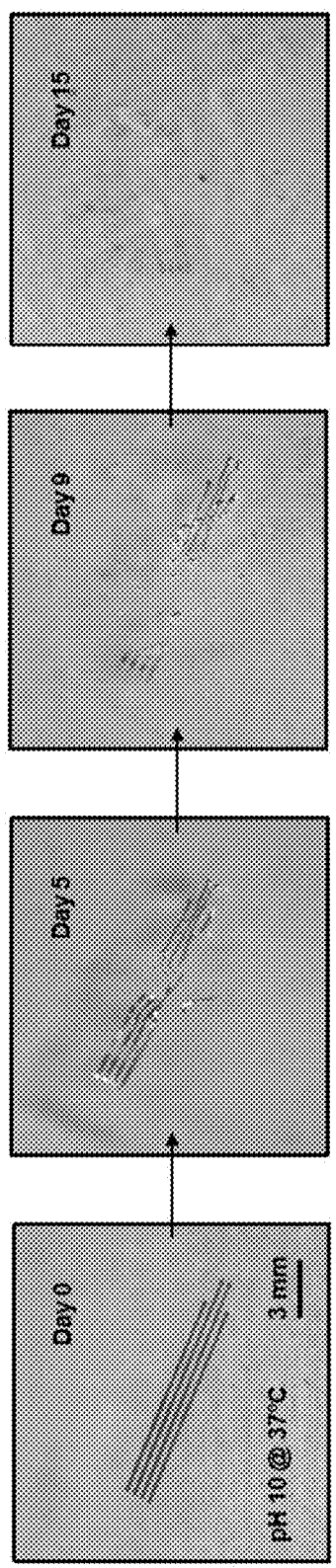
Figure 14:
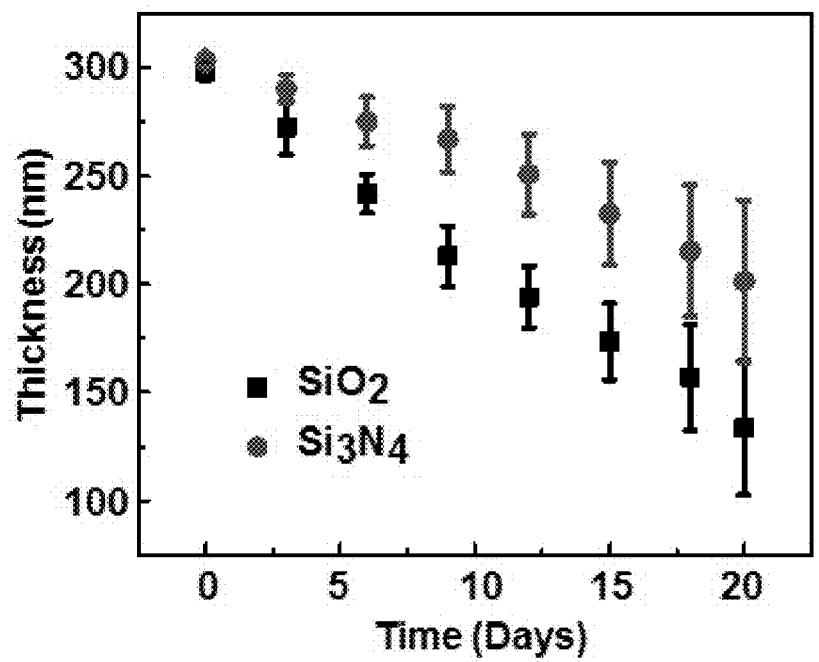
FIG. 14. Hydrolysis kinetics for $SiO_2$ and $Si_3N_4$ used in the devices. Thicknesses as a function of time during dissolution in artificial cerebrospinal fluid (ACSF) at 37° C. The initial thicknesses were 300 nm for both $SiO_2$ and $Si_3N_4$.

The slow, controlled dissolution of Si NMs is an important aspect in their use as bioresorbable neural interfaces. Bioresorbable metals are less attractive options due to their comparatively fast dissolution kinetics, and tendency to crack, fragment and flake during the process. Si dissolves under physiological conditions by hydrolysis to yield silicic acid, at rates that depend strongly on ionic content of the surrounding solution, pH, temperature and other factors, including the doping level. Specifically, Si forms neutral ortho-silicic acid $Si(OH)_4$ through an initial oxidation step to $SiO_2$ or through a direct equilibrium $Si+4H_2O \leftrightarrow Si(OH)_4+2H_2$[29,30]. FIG. 1E illustrates the dissolution kinetics for highly boron and phosphorus doped (concentration of ~$10^{20}$/cm³) Si NMs (~300 nm thick) in artificial cerebrospinal fluid (aCSF, pH 7.4) at physiological temperature (37° C.), evaluated by measuring the thicknesses at different time points by profilometry (Dektak, USA). Observations indicate that dissolution occurs in an exceptionally controlled, predictable process, without cracks, flakes, particulates or reduction in surface smoothness that often occurs in dissolution of metals. The dissolution rate exhibits a constant, thickness independent value of ~11 nm/day for these conditions. The dissolution characteristics of the other materials in the system, which for the case of the simple device in FIG. 1A-1G are $SiO_2$ and PLGA, are also important, although less critical than the Si NMs due to their passive role in the device operation. Measurements indicate that $SiO_2$ and PLGA (75:25)[31] dissolve in biofluids at 37° C. at rates of ~8.2 nm/day (FIG. 14), and complete dissolution time scales of ~4-5 weeks, respectively. Results of accelerated dissolution tests appear in FIG. 1G as a series of images of a complete device collected at various times after immersion in PBS pH 10 at 37° C. We estimate that the current device designs and material choices allow complete dissolution of the device in 2 months. Si and $SiO_2$ will dissolve within a month and 2 weeks, respectively, followed by PLGA. PLGA will dissolve in ~4-5 weeks. The materials parameters (i.e., thicknesses, doping levels for the Si, and ratio of lactide to glycolide for the PLGA) can be adjusted to achieve desired dissolution times.

Figure 15:
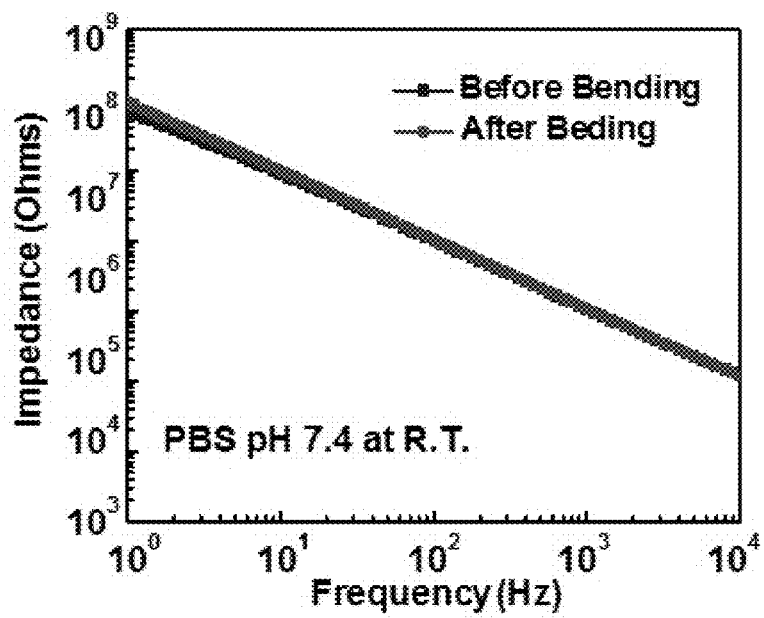
FIG. 15. Impedance spectra of before and after bending with 2 mm bending radius of a bioresorbable passive electrode array.

For conformal contact against the curved surface of the brain, thin geometries and optimized mechanical layouts are important. Three dimensional finite element modeling (FEM) reveals distributions of principle strain for bending perpendicular to the interconnect direction, as in FIG. 1F (left). Based on the layouts and the mechanical moduli, the maximum strains in the $SiO_2$, Si and PLGA are less than 0.03% for a bending radius of 1 mm, corresponding to the linear elastic regime for each of these materials. An optical image of a device wrapped around a glass rod with a radius of curvature of ~2 mm appears in FIG. 1F (right). Measurements before and after bending show negligible differences in impedance, consistent with expectation based both on FEM and analytical modeling results (FIG. 15).

Figure 2A:
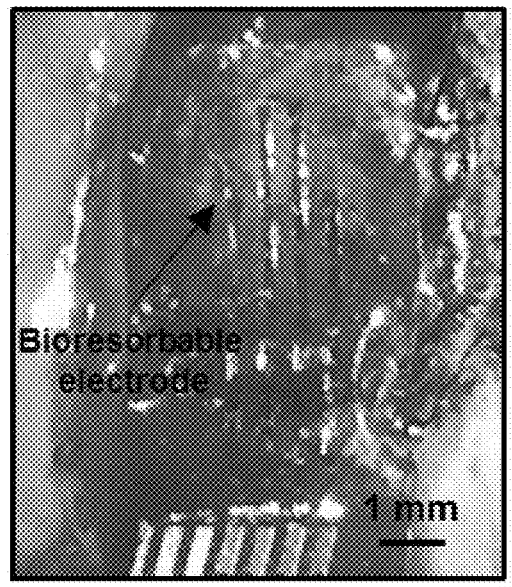
FIG. 2A-2G. In vivo neural recordings in rats using a passive, bioresorbable electrode array. The data presented here are representative of three separate acute experiments, each with a duration of ~5-6 hours.
Figure 2B:
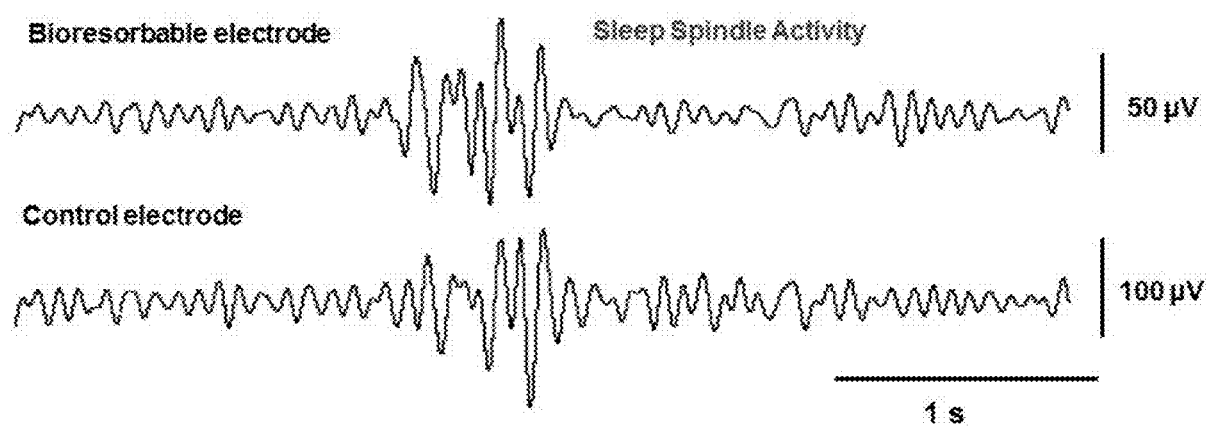
Figure 2C:
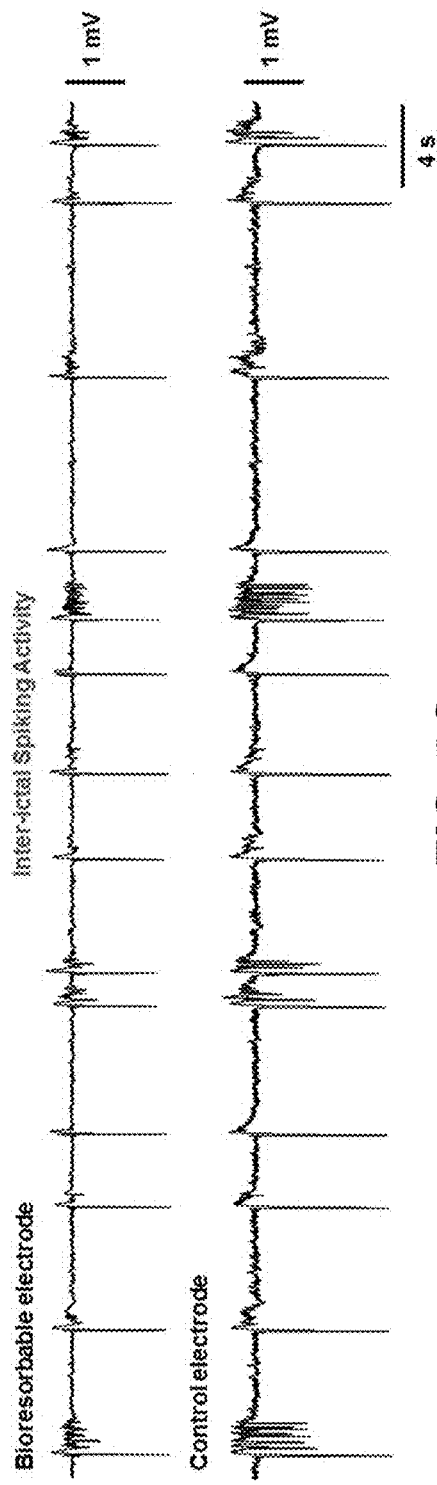
Figure 2D:
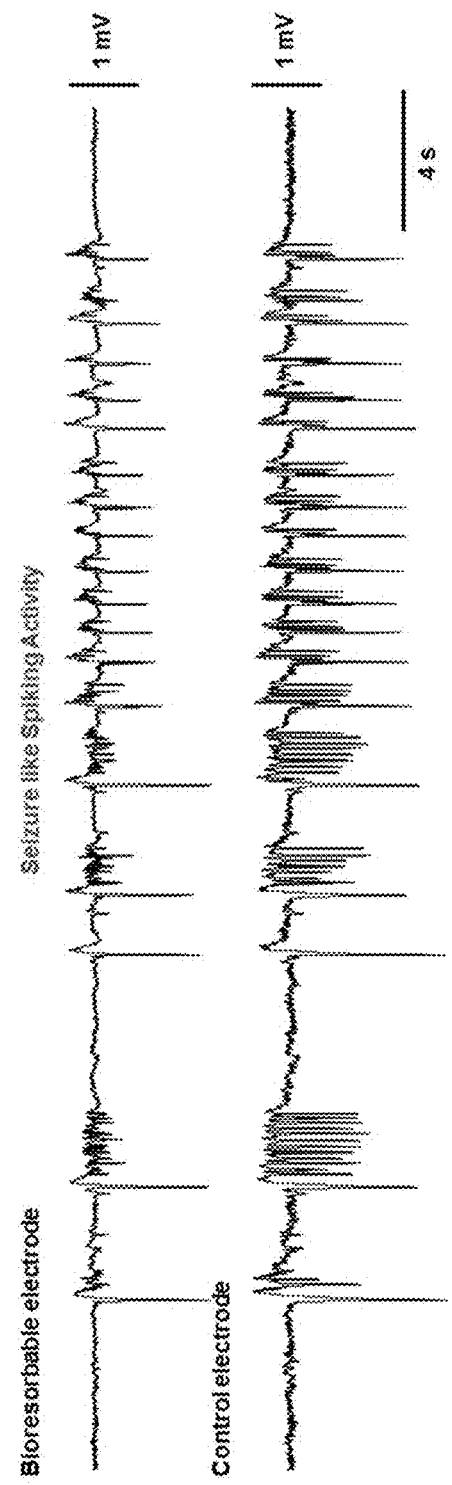
Figure 2E:
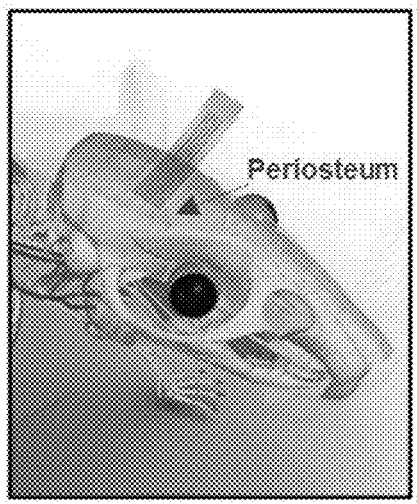
Figure 2F:
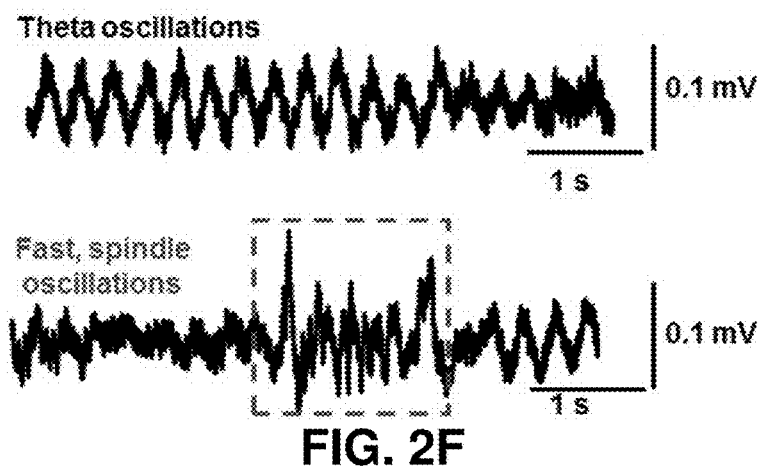
Figure 2G:
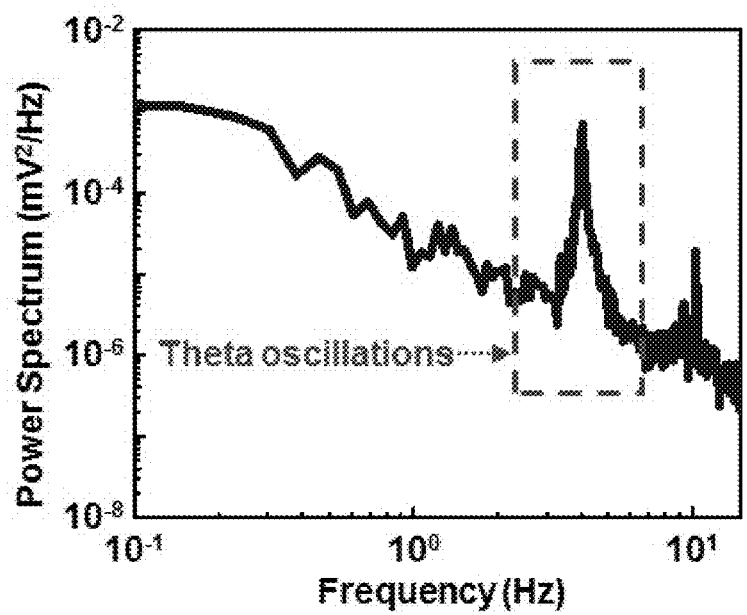
Figure 16A:
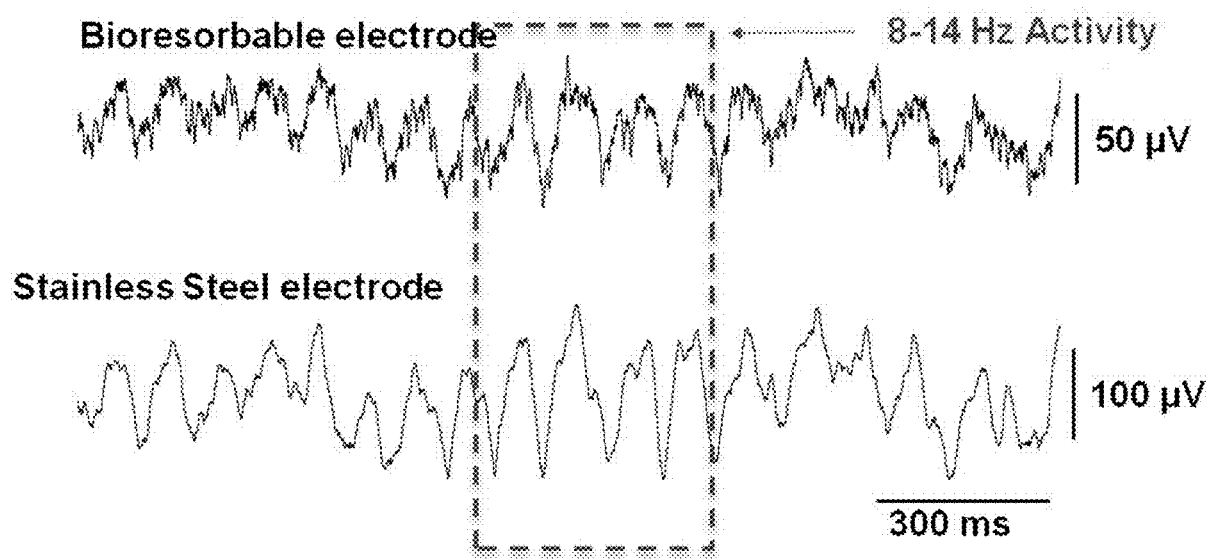
FIG. 16A-16B. In vivo neural recordings in rats.
Figure 16B:
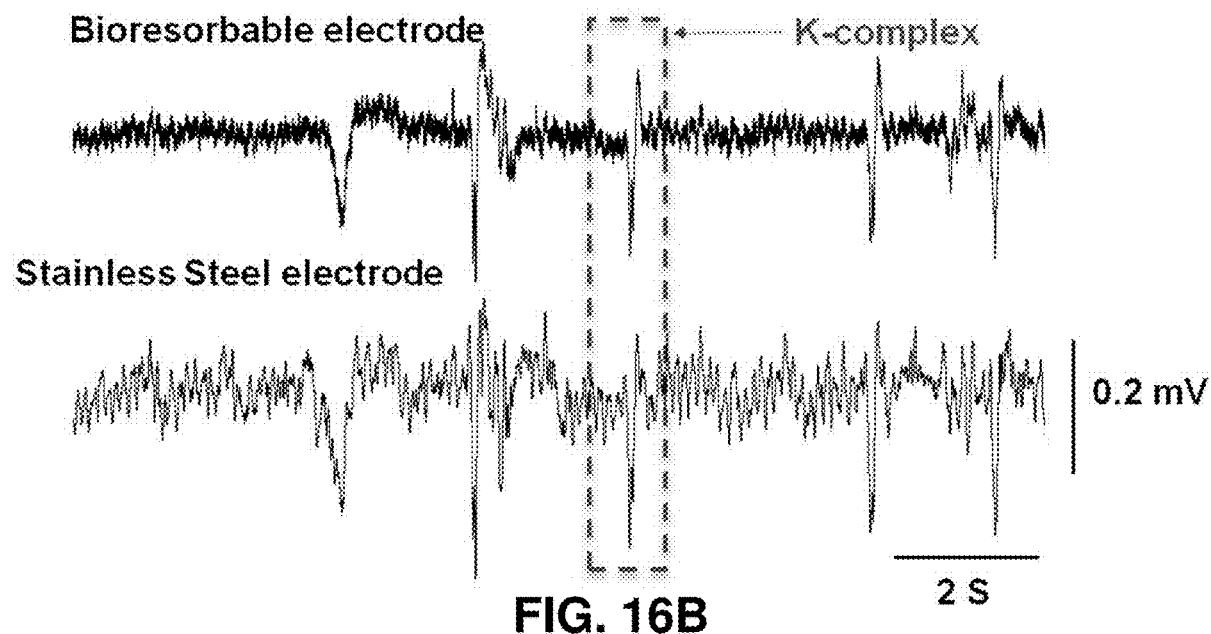
Figure 17:
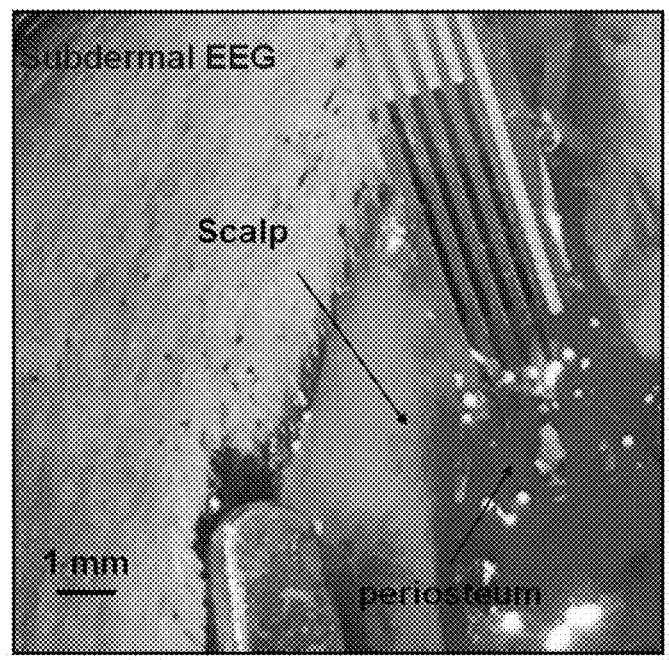
FIG. 17. A photograph of bioresorbable passive electrode array placed onto the periosteum of a rat.

In vivo neural recording experiments involved the bioresorbable devices of FIG. 1A-1G in adult rat animal models anesthetized and placed in a stereotaxic apparatus. A craniotomy exposed a 4×8 mm² region of cortex in left hemisphere (FIG. 2A), to allow positioning of a device on an area of the cortical surface next to a standard stainless steel microelectrode (7,850 μm²) as a control for recording physiological oscillations under isofluorene anesthesia. FIG. 2B shows representative sleep spindle activity captured by one of the channels in the bioresorbable array and the control electrode. FIG. 16A-16B show similar data for brain waves recorded during transition to deep anesthesia (FIG. 16A) and K-complexes (FIG. 16B) measured under anesthesia. Representative examples of pre-ictal and ictal-like spiking epileptiform activity induced by application of crystals of bicuculline methoxide recorded by the bioresorbable electrode and the control electrode appear in FIG. 2C and FIG. 2D, respectively. The frequency of the pre-ictal spikes (FIG. 2C) increases and the inter-spike duration decreases as the time progresses, terminating into after discharges and ictal-like early epileptic discharges (FIG. 2D). The bioresorbable arrays can also be utilized as subdermal implants for high fidelity, recording of EEG and evoked potentials. Devices implanted on periosteum as described in FIG. 2E and FIG. 17 yielded reliable recordings of theta waves (highlighted in power spectral analysis) and sleep spindles (FIG. 2F). Collectively, the results demonstrate that bioresorbable recording platforms can capture reliable physiological or pathological activity both intracortically and subdermally.

Figure 3A:
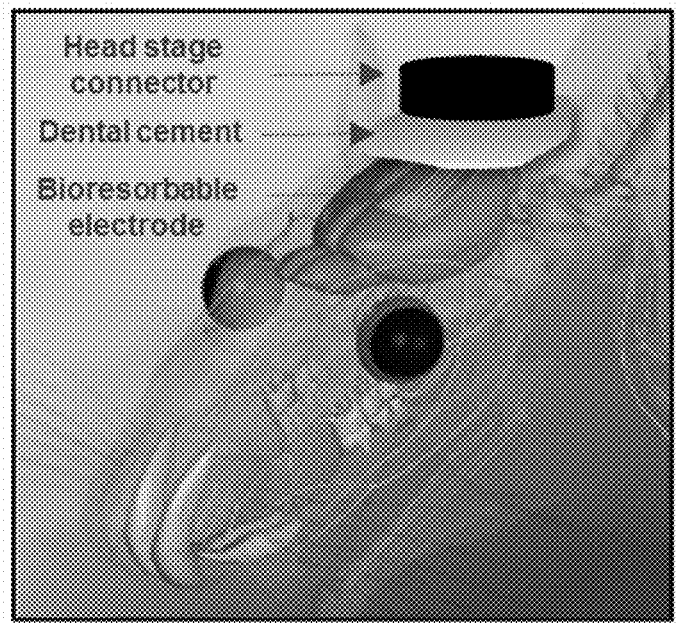
FIG. 3A-3G. In vivo chronic recordings in rats using a passive, bioresorbable electrode array. The data presented here is representative of chronic recording experiments with a duration of 30 days.
Figure 3B:
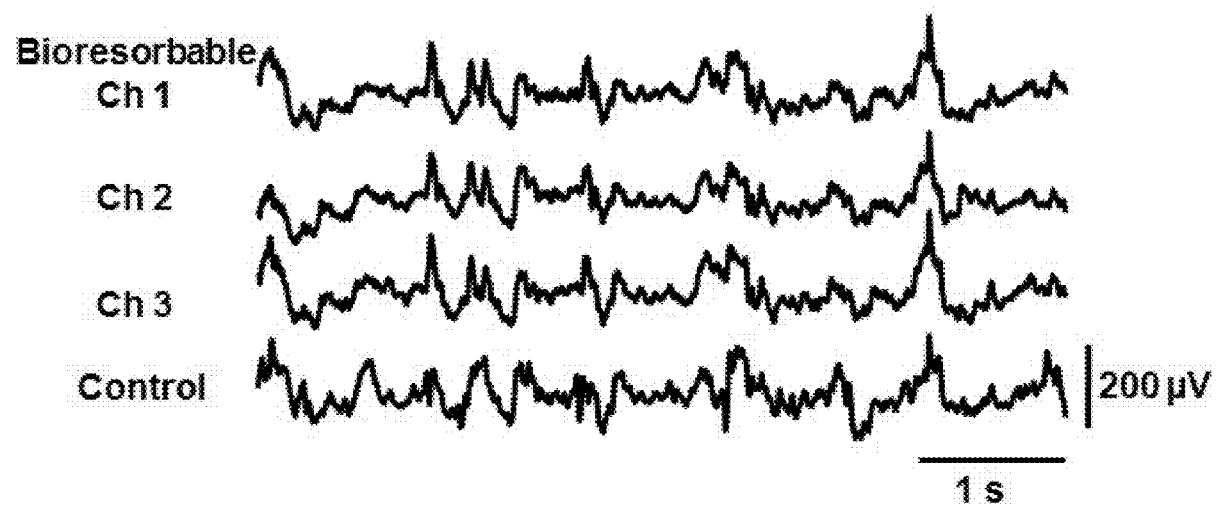
Figure 3C:
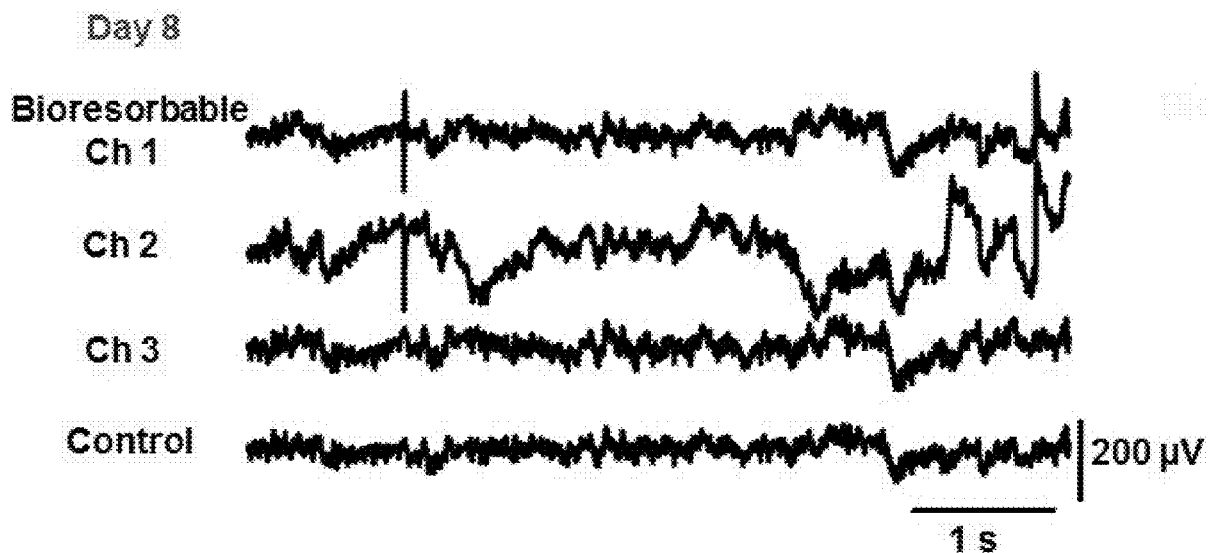
Figure 3D:
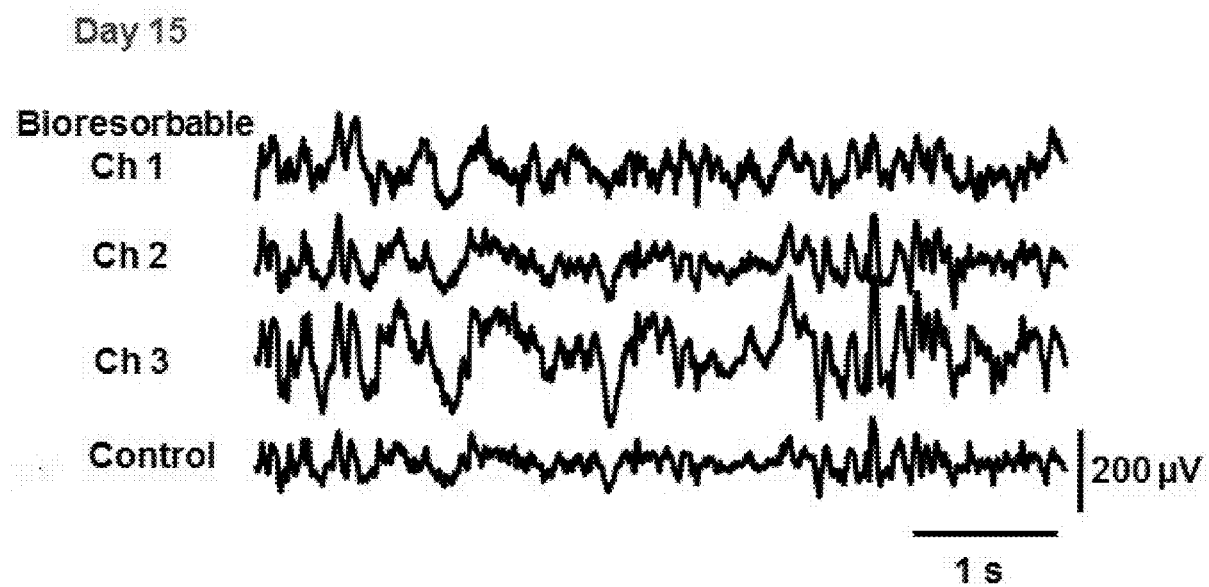
Figure 3E:
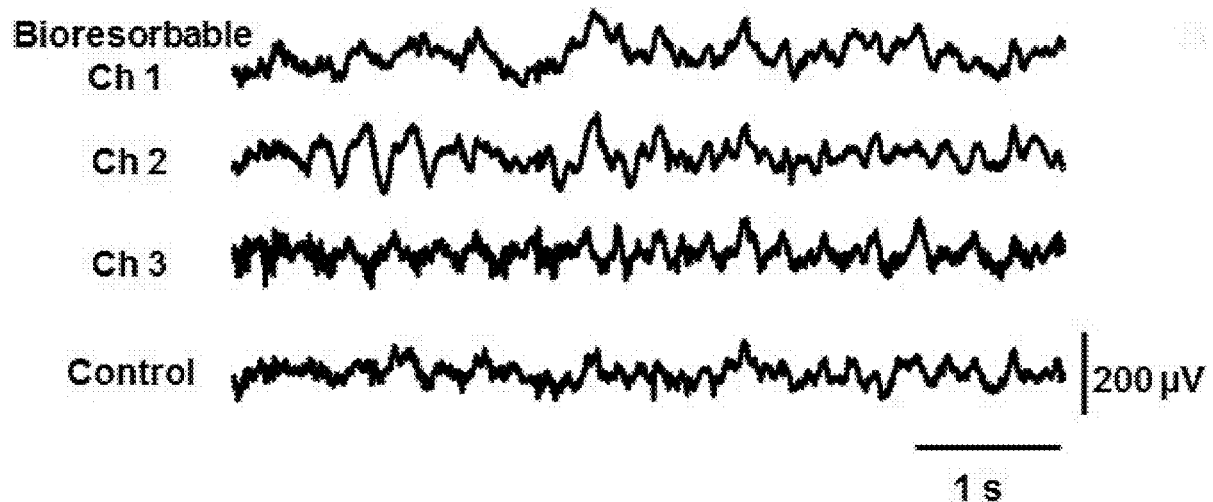
Figure 3F:
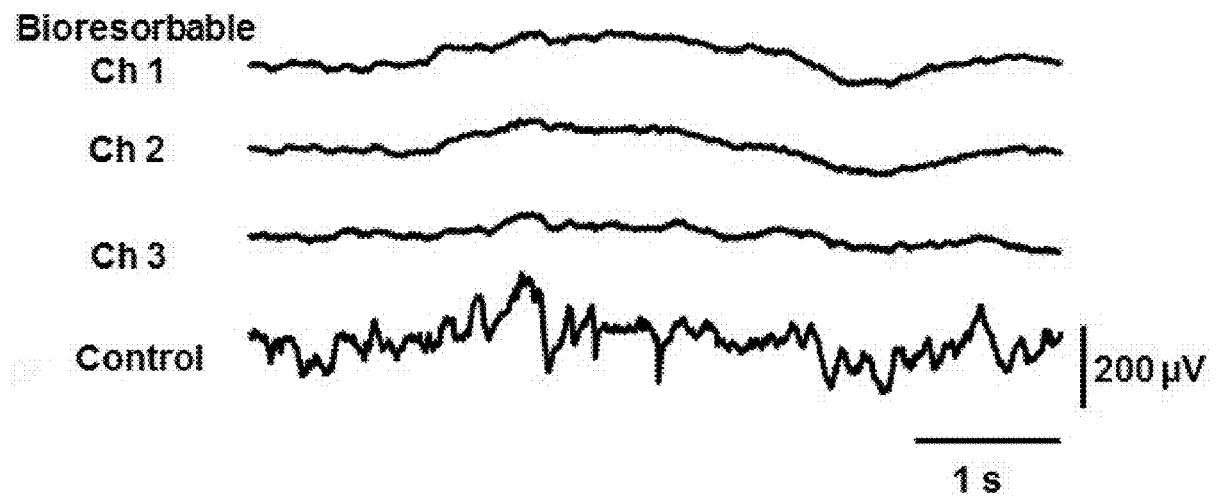
Figure 3G:
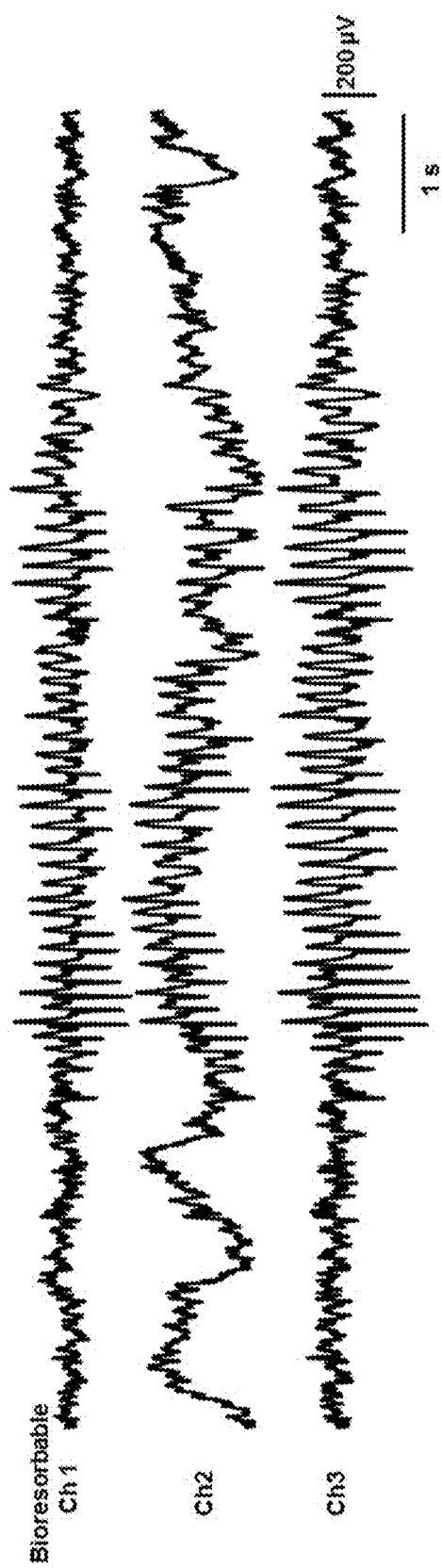
Figure 18:
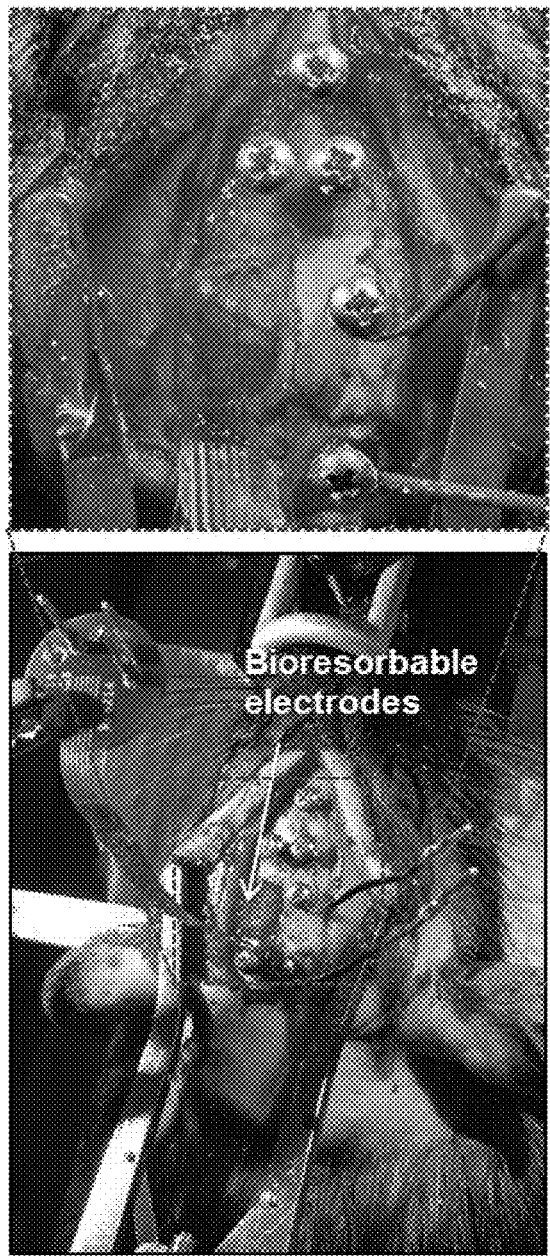
FIG. 18. Photographs of surgery associated with chronic recording experiments. Implanting the bioresorbable electrode arrays on a rat brain, applying the dental cement, and then burying the head stage board.
Figure 18:
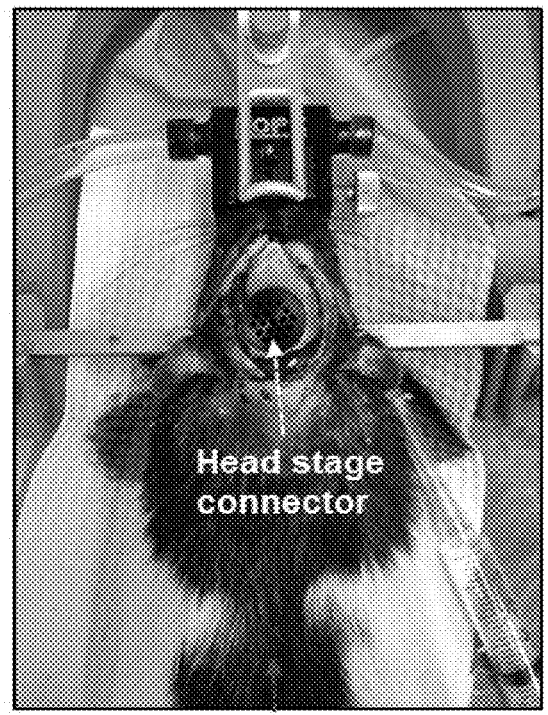
Figure 18:
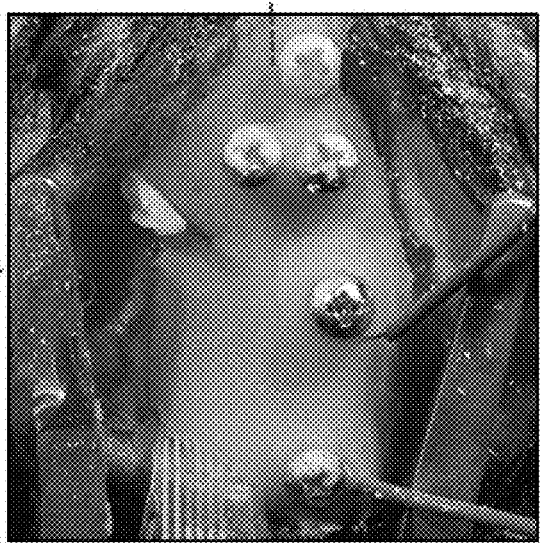
Figure 19:
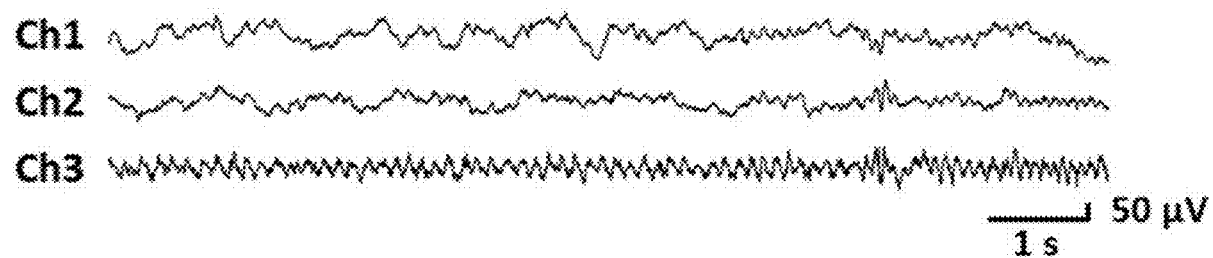
FIG. 19. Representative ECoG signals recorded by the bioresorbable array (Ch1, Ch2, and Ch3) and the control electrode on day 32.
Figure 20:
FIG. 20. A photograph after the surgery of the device implantation, showing freely moving rat with a head stage connector.

Chronic tests of ECoG recording indicate long-term stability in operation, where devices with increased thicknesses of $SiO_2$ (~300 nm) and Si NMs (~1000 nm) survive for more than one month. Such studies used a miniature interface board connected to the device via a flexible interconnect cable to a headstage (FIG. 18) designed for use with rats. Details are explained in the Methods section. FIG. 3A-3G summarizes representative cortical potentials recorded by three electrodes in the bioresorbable array and by a nearby screw electrode as a control, captured on Days 1, 8, 15, 30, 32 (FIG. 19), and 33 measured from the time of the surgical implantation. FIGS. 3A, 18 and 20 describe the surgical procedures and the post-surgical setups used in freely moving rats, respectively. ECoG potentials show physiological signals and brain oscillations with various temporal and spatial differences. High-amplitude seizure-like rhythmic spike discharges (FIG. 3G) appear occasionally, consistent with absence-like seizure activity observed in Long Evans Rats[32-34]. By all functional metrics (e.g. signal to noise ratio, ability to measure delta, theta, alpha, gamma, spindles and sometimes epileptic spikes), the devices operate in a stable fashion, largely without change in performance throughout the month of the study, until sudden failure, likely due to the development of an open circuit state in the vicinity of the interconnects. After day 33, signals from the bioresorbable device disappear; while those form the control persist, consistent with dissolution of at least some critical component of the device. For epilepsy patients the clinically relevant operational lifetime is several weeks. Here, bioresorbable devices could be embedded into particular clinical devices to monitor for early signs of failure during critical post-operative periods, such as measuring pressure and flow after intravascular aneurysm occlusion (coiling), placement of aortic or other vascular grafts, or procedures to seal cerebrospinal fluid (CSF) leaks. Currently monitoring is based upon clinical examination, or requires interventional radiology that is invasive, expensive and impractical for continuous monitoring over days to months.

Figures 4A, 4B:
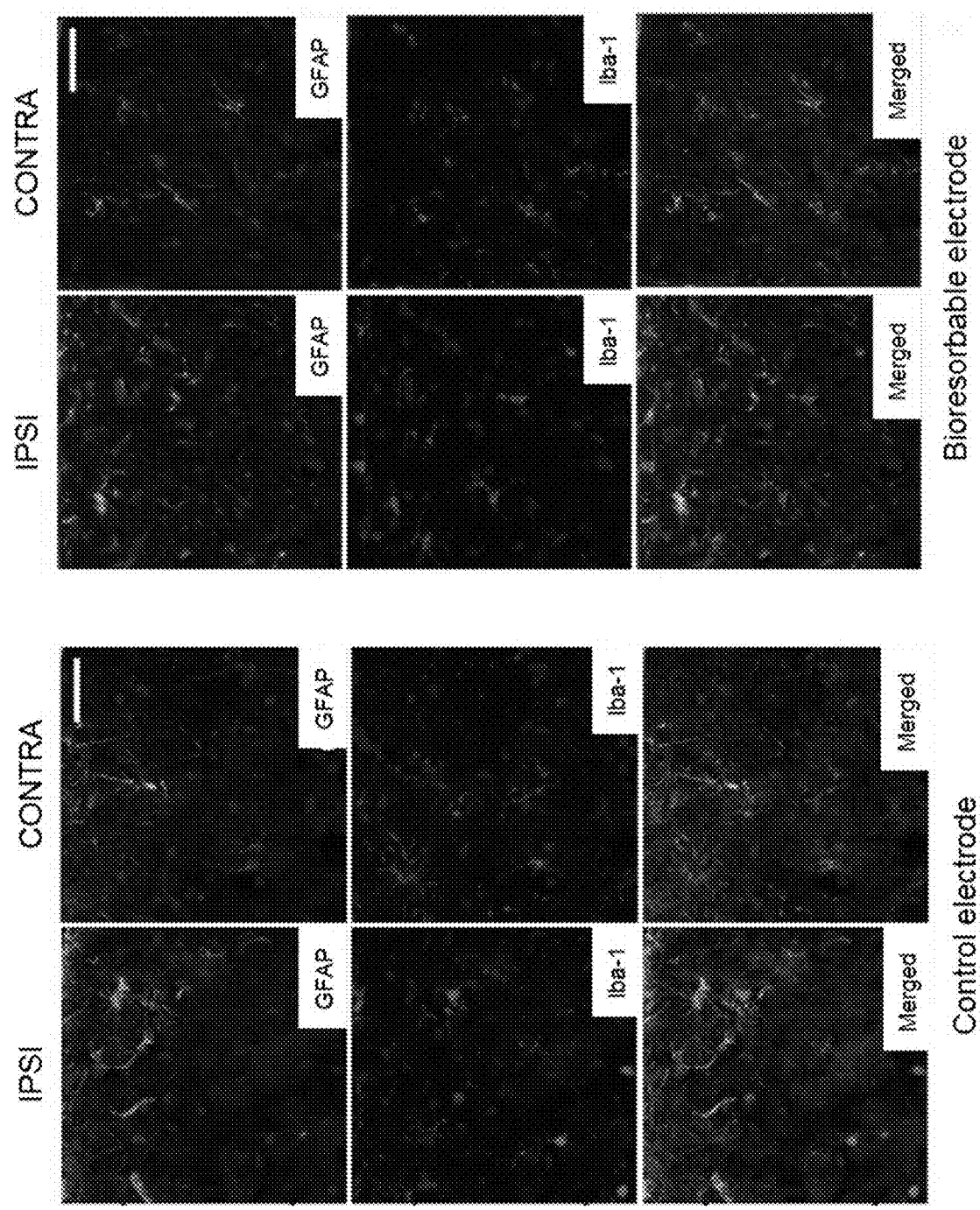
FIG. 4A-4B. Immunohistology analysis. Double labeling for astrocytic marker GFAP (green) and microglia/macrophages marker Iba-1 (red) demonstrates moderate subpial gliosis at the implantation sites of both control (FIG. 4A, upper left panels) and bioresorbable (FIG. 4B, upper right panels) electrodes and a marked increase in the densities of activated round microglial cells, exclusively underneath the control electrodes (middle left panels). Cell nuclei are visualized with DAPI stain (blue). Scale bars represent 30 μm.
Figure 21:
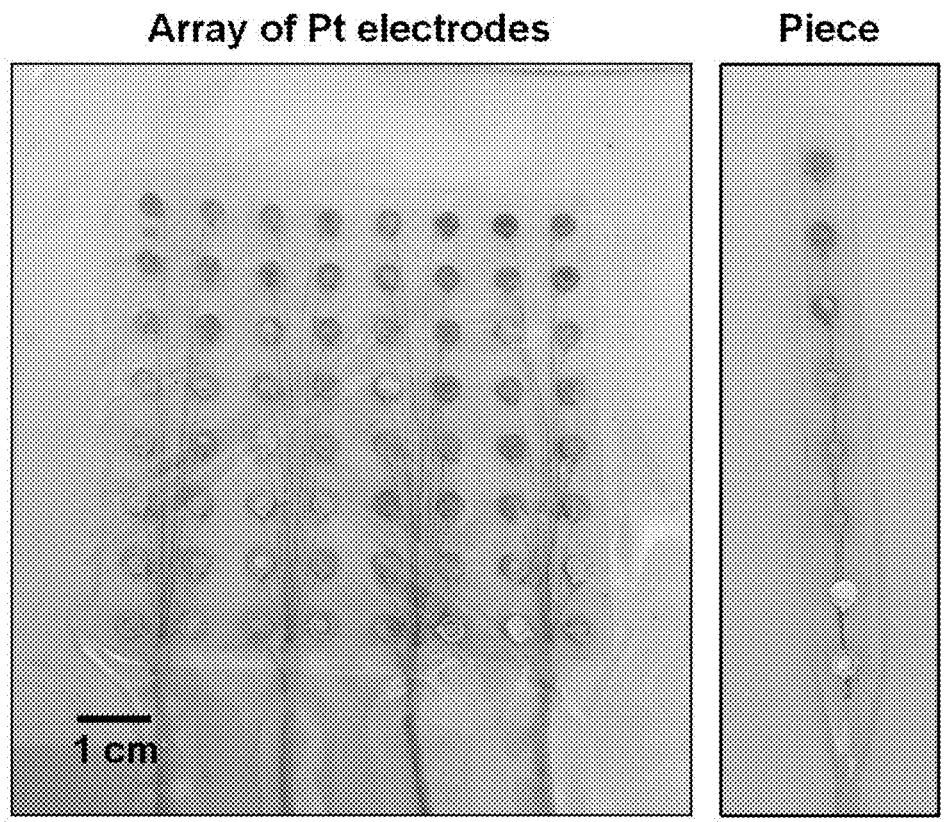
FIG. 21. Clinical platinum electrodes for ECoG, 8×8 Electrode Grid (left), and 1×8 Strip Electrode (right).

Understanding the reactive tissue response is important in assessing the potential for use in such clinical applications[35]. Tissue inflammation, encapsulation of the electrodes in fibrous tissue (glial scar) and neuronal death in the vicinity of the electrode are the most important issues related to clinical translation[36-38]. Studies of tissue reactions of bioresorbable electrode arrays involved chronic implants in 14 animals, with Pt electrodes cut into similar geometries from clinical subdural grids (Ad-Tech Medical Inc) as controls, as shown in FIG. 21. FIG. 4A-4B summarizes the results obtained according to procedures outlined in the methods section. Double label immunohistochemistry for GFAP and Iba-1 reveal glial cell activation at 4 weeks post-implant (FIG. 4A-4B). In both control and bioresorbable devices, moderate subpial gliosis occurs at the implantation site, when compared to the control contralateral hemisphere. No significant astrogliosis is noted at distant sites within the ipsilateral hemisphere. Iba-1 immunohistochemistry demonstrates the presence of both resting ramified, as well as round activated microglia underneath the control electrode, which extends to the superficial layers I-III. In contrast, at the implantation site of the bioresorbable electrode, microglial cells show an almost exclusively ramified morphology. The contralateral side in both groups exhibits no microglial reaction. The sham-operated control demonstrates a similar moderate subpial gliosis, but with no change in microglial densities or morphology.

Figure 5C:
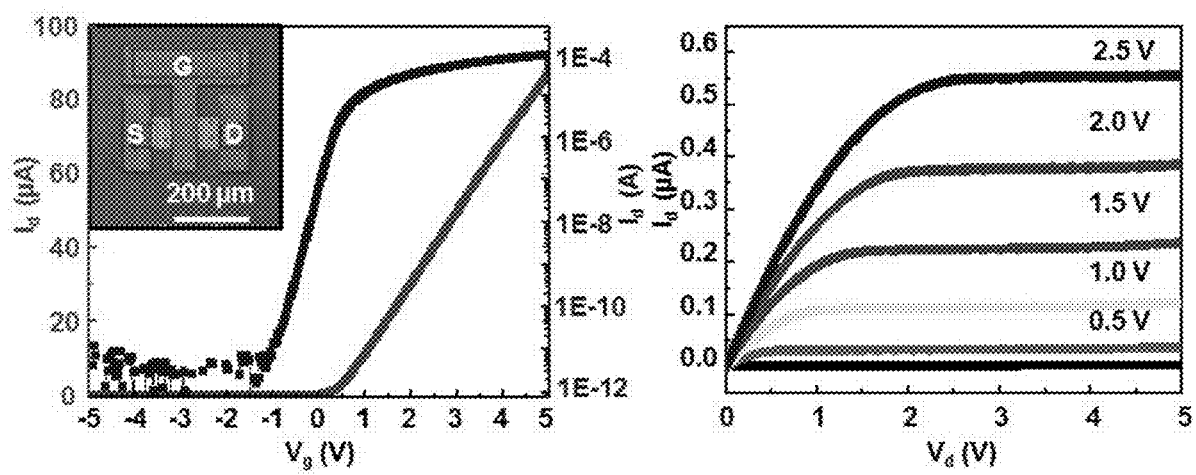
Figure 5D:
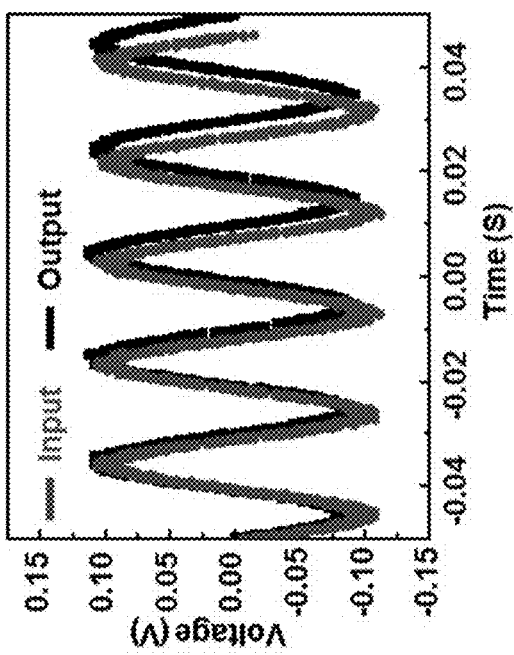

Actively multiplexed device designs enable high-resolution, high channel count neural interfaces by minimizing the number of wires needed for external data acquisition. In this context, Si NMs provide not only an excellent choice for the electrodes but also for the backplane electronics, including the necessary switching and buffer transistors as a scalable pathway toward systems with increased numbers of channels and area coverage. A fully bioresorbable design appears in FIG. 5A; a sequence of images at various stages of the fabrication appear on the right. This embodiment uses 128 n-channel metal-oxide-semiconductor field-effect transistors (MOSFETs), with Molybdenum (Mo) for the source, drain and gate electrodes, and $SiO_2$ (~100 nm) for the gate dielectrics. Additional layers of Mo and a trilayer of $SiO_2$ (~300 nm)/$Si_3N_4$ (~400 nm)/$SiO_2$ (~300 nm) form interconnects and interlayer dielectrics (ILD), respectively. A second layer of Mo (~300 nm) serves as column selects and additional sensing electrode pads. Another trilayer provides a blanket encapsulating layer that has openings only at the locations of the Mo interface electrodes. The amount of materials in a single device with active multiplexed addressing are 100 mcg of Mo, 1.43 mcg of Si, 306 mcg of $SiO_2$, 264 mcg of $S_3iN_4$, and 27 pg of P. For comparison, the daily intake limits, average daily intake values, and daily production of such materials appear in TABLE 1. The chemistry, dissolution kinetics and biocompatibility of each of the constituent materials can be found elsewhere[39-46]. The lot and functional electrode yields are ~10-20% and ~80%, respectively. Failures arise from leakage currents associated with pinholes in the encapsulating layer, introduced by particulate contamination in our academic cleanroom facilities. FIG. 5B presents photographs of a device, wrapped around a cylindrical tube, with an inset that shows arrays of active electrodes. FIG. 5C summarizes the electrical properties of a representative n-type MOSFET, where the mobility and on/off ratio are ~400 $cm^2$ $V^{-1}$ and ~$10^8$, respectively, as calculated using standard field-effect transistor models. FIG. 5D shows in vitro measurements on a representative unit cell. The output response was consistent with the input signal, thereby indicating proper operation. Details of in vitro experiments are provided below and in FIGS. 21-26.

Operation of the Multiplexing on a Representative Unit Cell.

Figure 23:
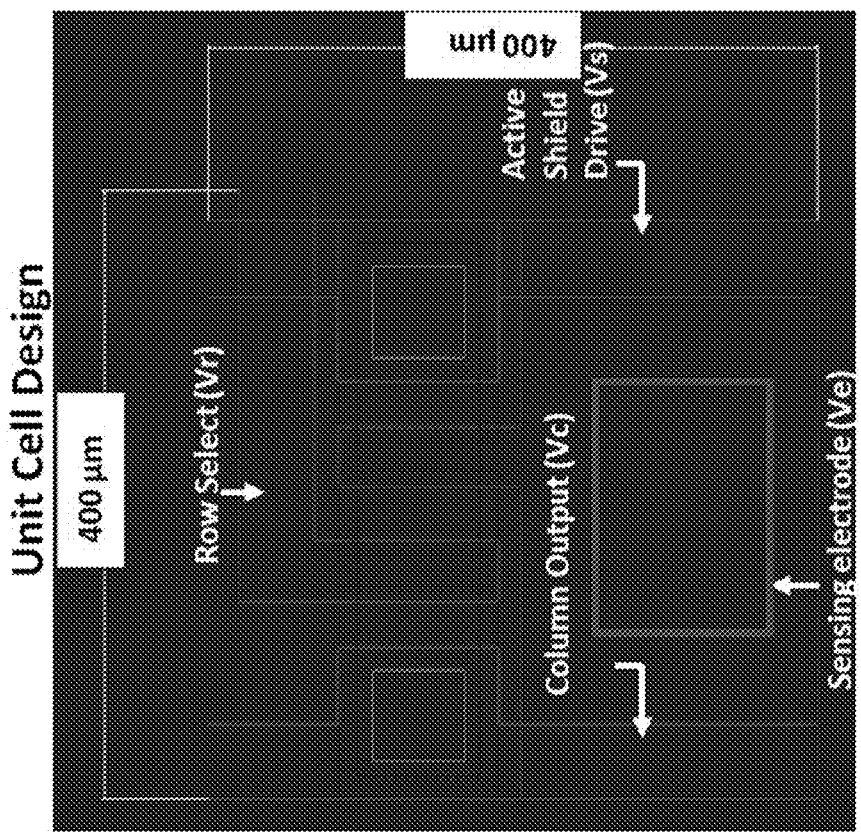
FIG. 23. Schematic illustration of a 8×8 array of actively multiplexed channels, showing the entire device (left), and the unit cell design (right).
Figure 23:
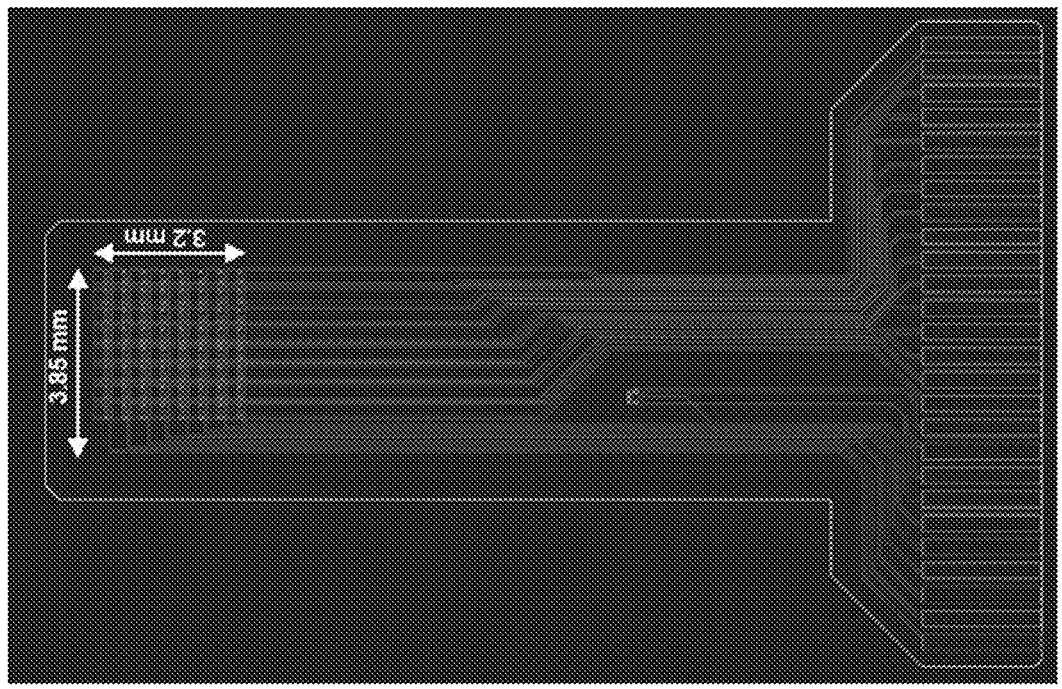
Figure 24:
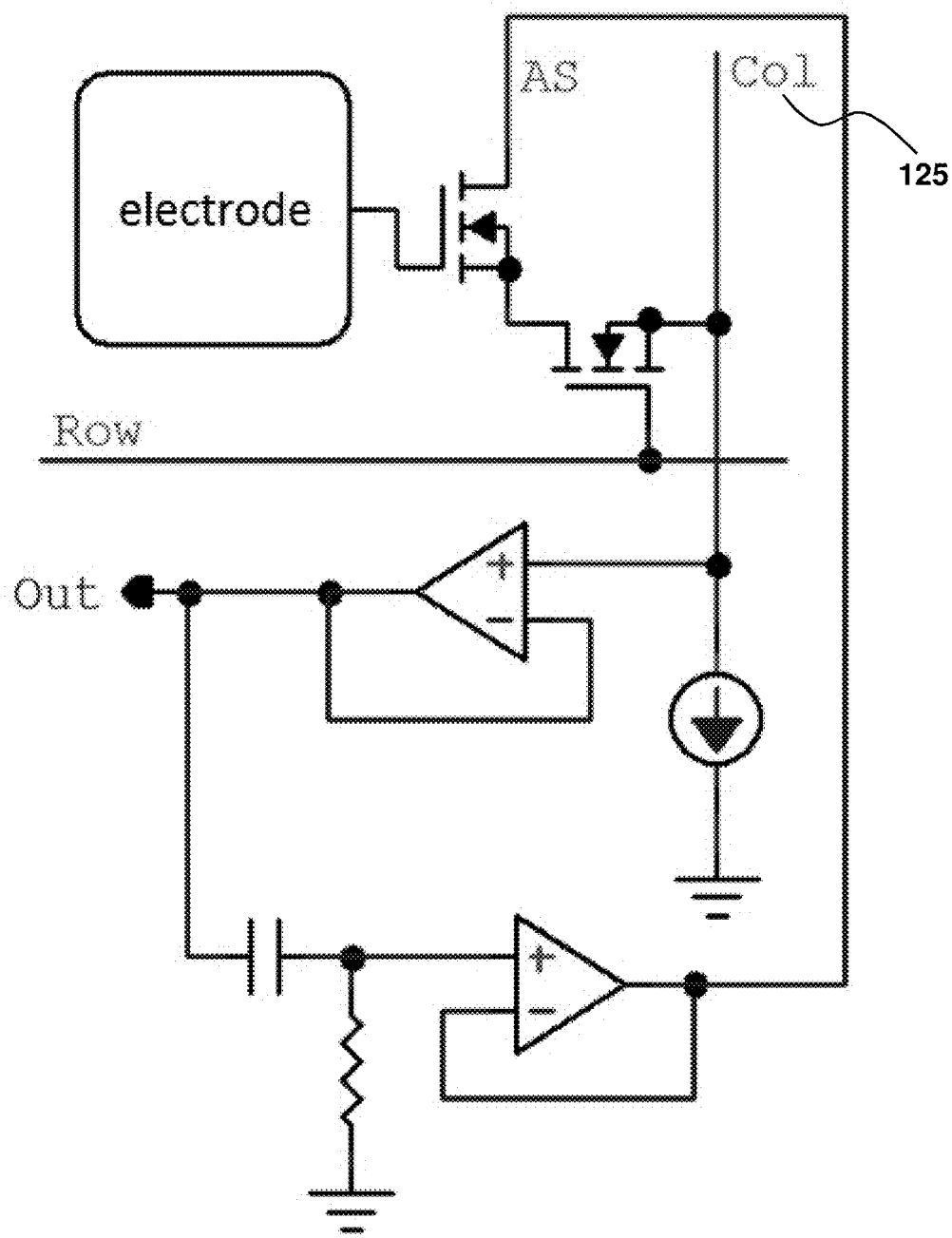
FIG. 24. Schematic circuit diagram for an active shielding circuit for the actively multiplexed array.
Figure 25:
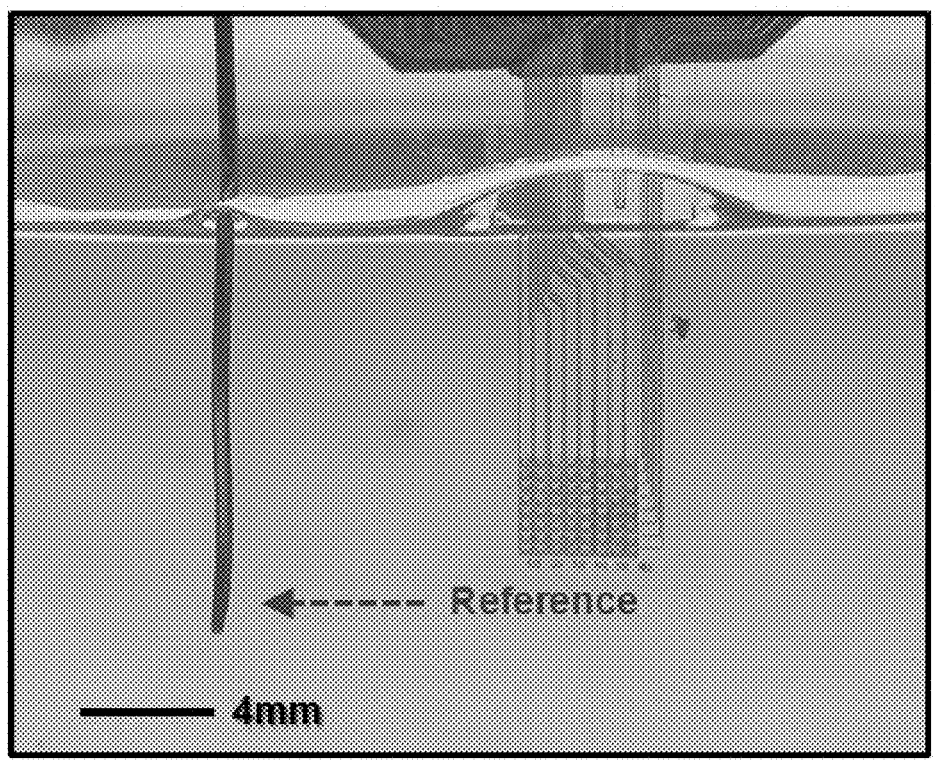
FIG. 25. In vitro test setup for actively multiplexed array.

FIGS. 22-24 summarize the key aspects of the designs of circuits that incorporate these transistors for multiplexed addressing. The approach involves two transistors per unit cell[12,14], in which a buffer transistor connects to the interface electrode to provide buffering of measured biopotentials, and a multiplexing transistor allows electrodes in a given column to share a single output wire. The surface electrodes appear in the top layer, where they come into physical contact with the brain; they connect to the underlying backplane circuit through vertical interconnect access holes (vias). An active shielding scheme described in FIG. 24 improves the signal to noise ratio of the system by reducing the parasitic capacitance and increases the gain of each site of the electrodes. The operation involved successive application of 3V ($V_r$) to the gate of the multiplexing transistor when a particular row was activated and −3V ($V_r$) when the row was not selected (FIGS. 22 and 23). A constant current of 4 µA was used to bias the column output and complete the source follower amplifier. The output voltage ($V_c$) was high-pass filtered to have an average DC bias of 2V and connected to the column power source line ($V_{as}$). By using analog feedback, the negative effects of parasitic capacitance in the drain of the buffer transistor are reduced and the AC signal gain of the electrode array is improved. A 50 Hz, 200 mV (peak to peak) sinusoidal waveform was applied to a metal reference electrode immersed in PBS at pH 7.4 and recorded from the active electrode array (FIG. 25). During multiplexed sampling, driving the row select signal selects a single row of electrodes at a time. This scheme allows the unit cells in the corresponding row to drive the column output lines which connect to a high-speed analog to digital converter. Row select signals are rapidly cycled to sample all electrodes on the array. The entire device connects to an external data acquisition (DAQ) system through a zero insertion force (ZIF) connector with 26 contact.

Figure 5E:
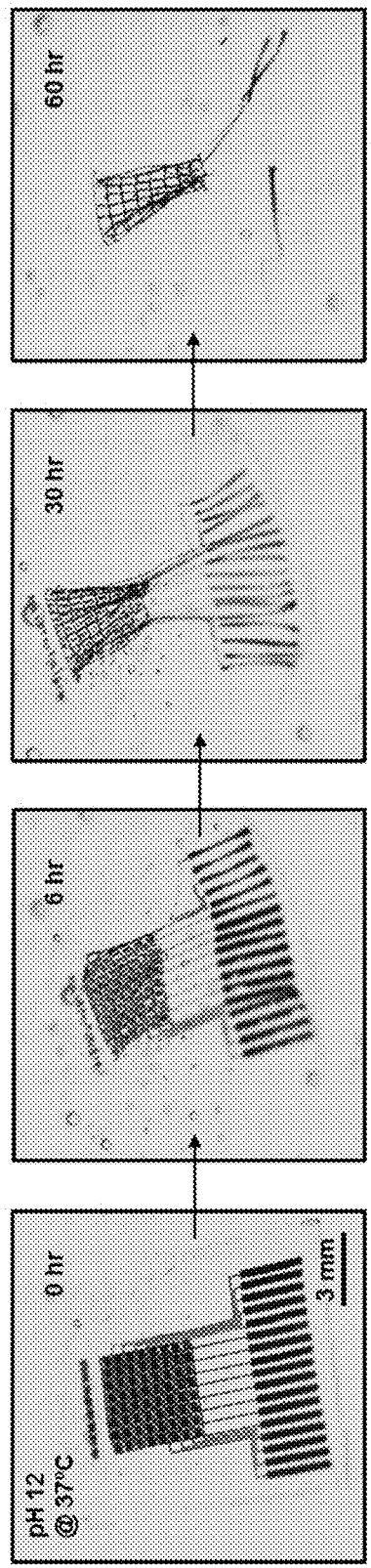
Figure 26:
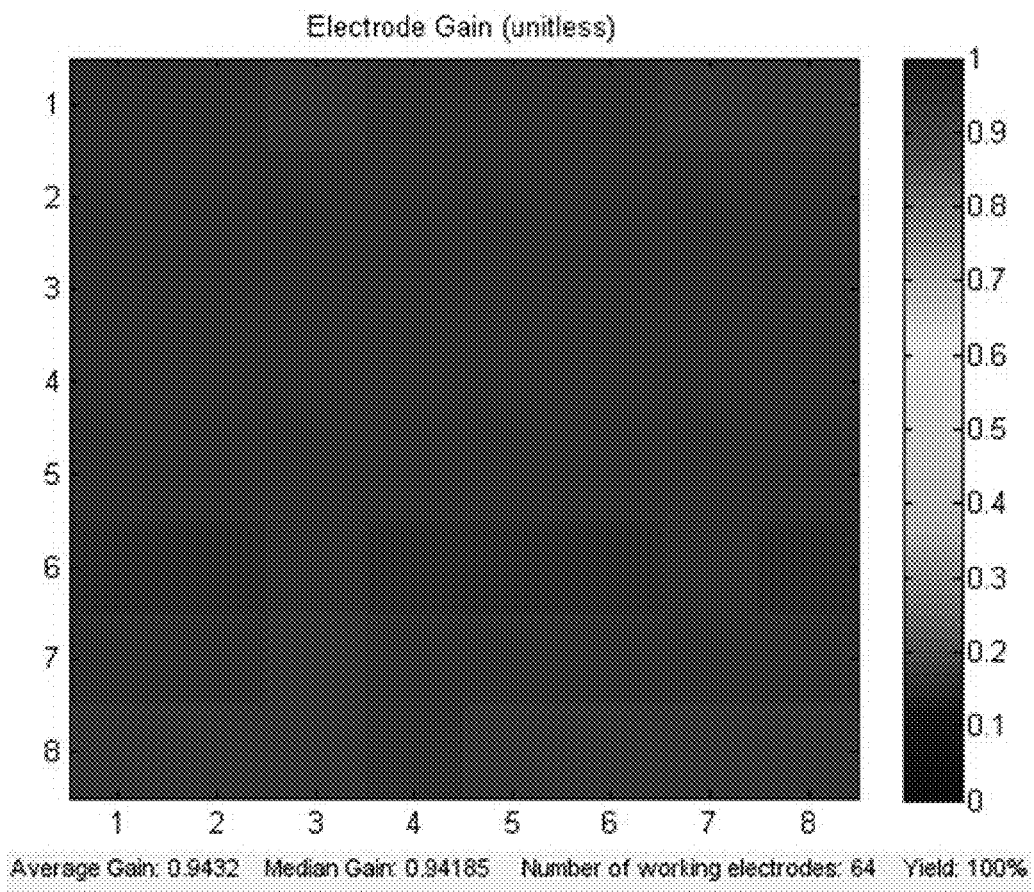
FIG. 26. Color map illustrating the spatial distribution of the electrode response, demonstrating the spatial uniformity of the gain of an actively multiplexed, bioresorbable electrode array and leakage current over time.
Figure 26:
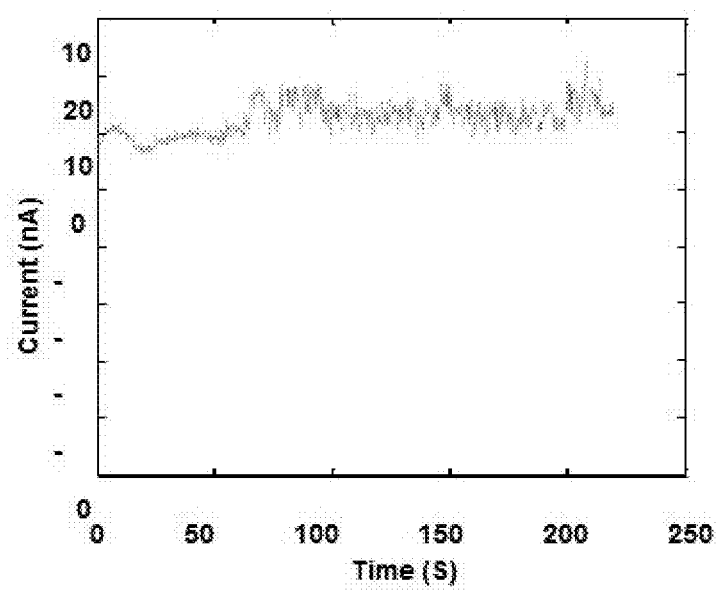

FIG. 5E shows a sequence of images during accelerated dissolution in PBS pH 12 at 37° C. PECVD $Si_3N_4$ and $Mo^{40,41}$ dissolves in biofluids at pH 7.4 at 37° C. at a rate of ~5.1 nm/day (FIG. 14) and ~16-25 nm/day, respectively. This system involves ~1.3 µm, ~800 nm, ~300 nm, ~600 nm and ~30 µm thick layers of PECVD $SiO_2$, $Si_3N_4$, Si, Mo and PLGA, respectively. PLGA, Si, and Mo in biofluids at 37° C. dissolve completely within in ~4-6 weeks. Both $SiO_2$ and $Si_3N_4$, dissolve in 6 months under the same conditions. FIG. 26 shows results of measurements of gain across the array and cumulative leakage current for a representative device immersed in PBS at pH 7.4. The average gain and yield were 94% and 100%, respectively.

Figure 6A:
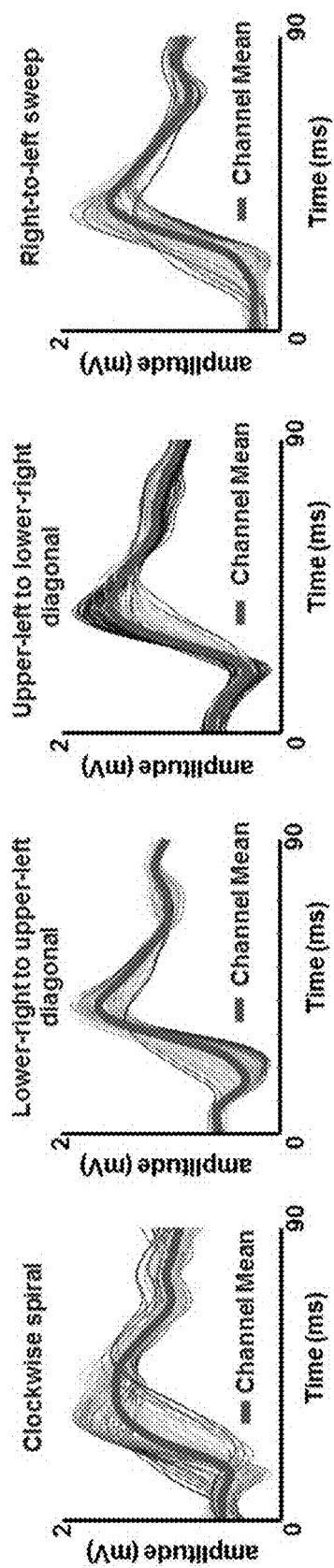
Figure 6D:
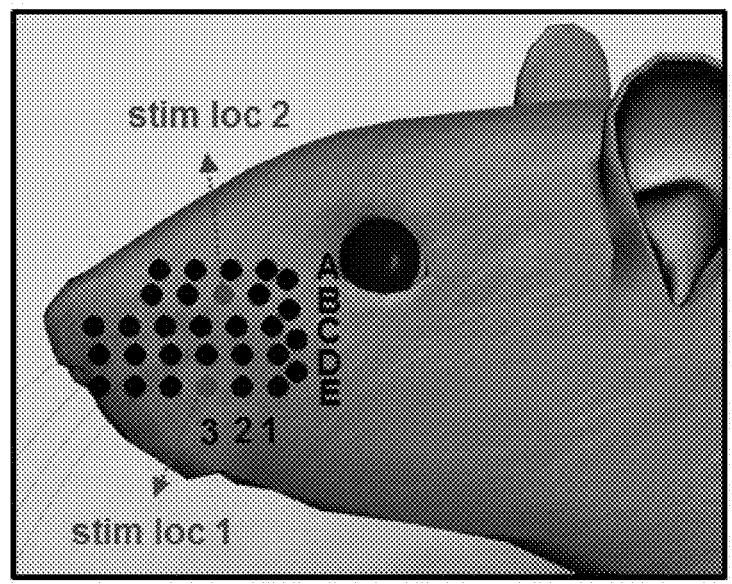
Figure 27:
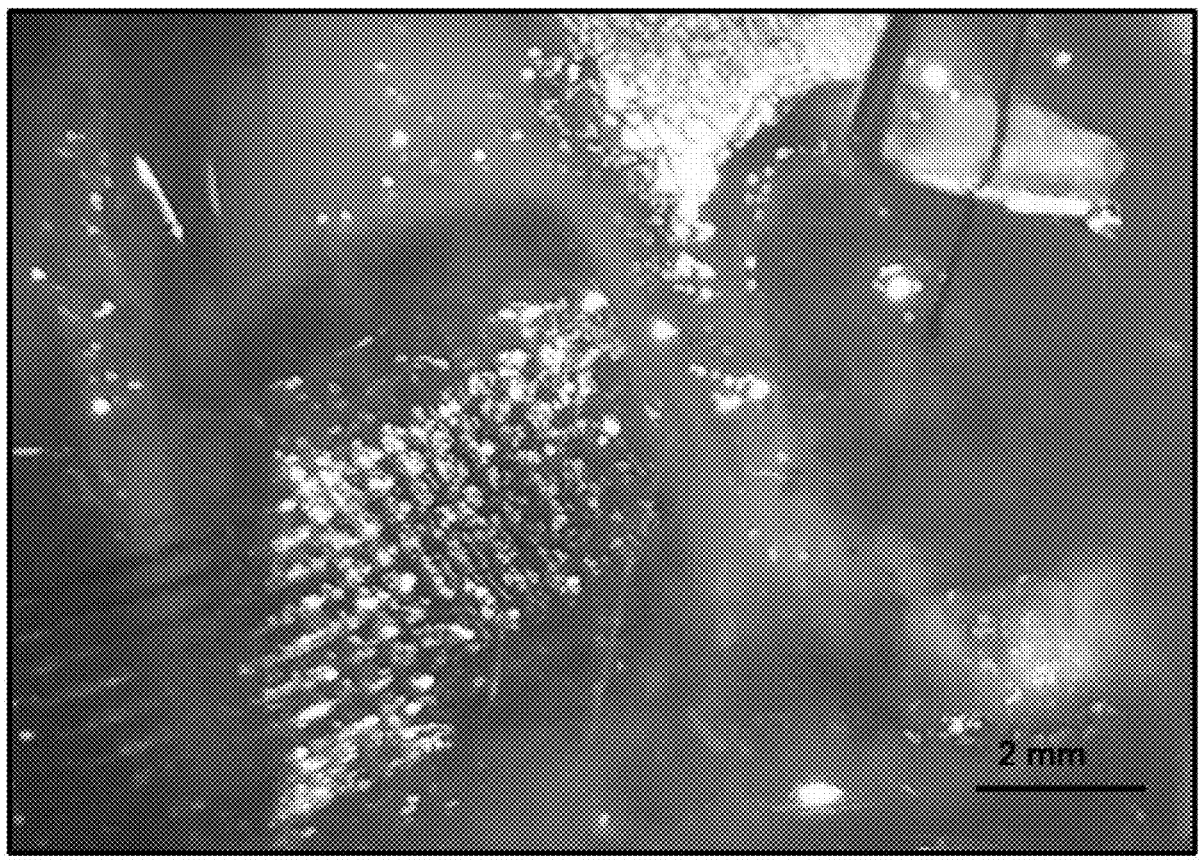
FIG. 27. Photograph of an implanted 8×8 actively multiplexed array (left hemisphere of rat brain) and a control electrode (right hemisphere of rat brain).
Figure 28:
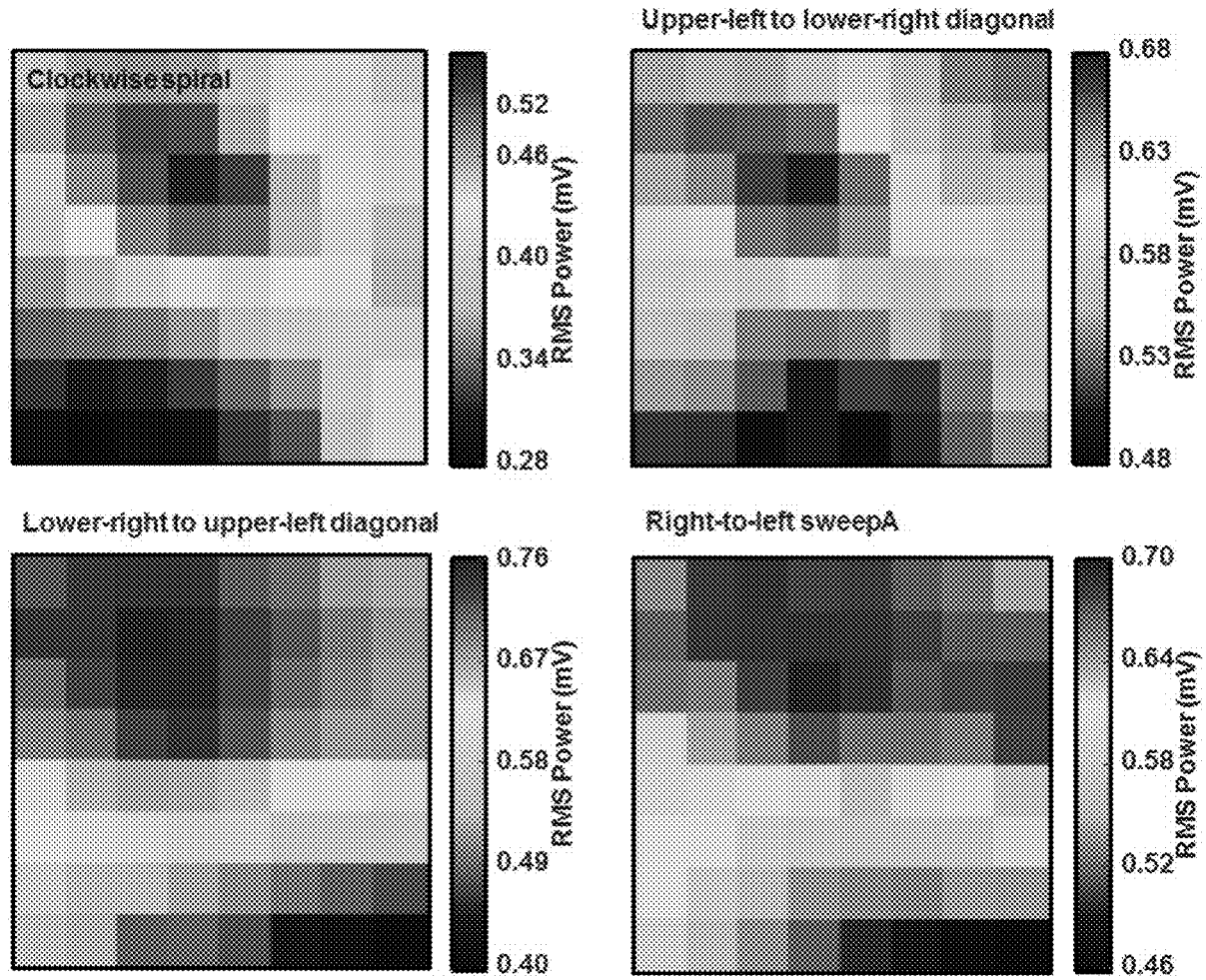
FIG. 28. Representative RMS power image maps from four different spike clusters (clockwise spiral, lower-right to upper-left diagonal, upper-left to lower-right diagonal, right-to-left sweep) illustrate the high sensitivity of the electrode array and the spatially localized nature of spikes.

FIG. 6A-6G provides details on in vivo recordings with a bioresorbable, multiplexed recording array. The leakage current is ~10 nA. The 64-electrode array was placed on the cortical surface of the left hemisphere of an anesthetized rat in a stereotaxic apparatus (FIG. 27). Picrotoxin was applied topically to induce epileptiform activity, just prior to the placement of the array. The data reveal epileptic spikes and discharges that last ~1-3 s and repeat every ~10-15 s. A set of different epileptic spikes (clockwise spiral, lower right to upper left diagonal, upper left to lower right diagonal, and right to left sweep) is shown in FIG. 6A as representative recordings. The sequence of eight movie frames corresponding to each spike (FIG. 6B) clearly reveals the propagation of neural waves and associated spatial-temporally resolved patterns. The delay maps represent the latency of the spike's peak at each site (FIG. 6C). Each spiking activity shows a distinctive spatial flow indicated by the yellow arrow in each delay map. RMS power maps, corresponding to each representative spike (FIGS. 6c and 28) show the spatially resolved patterns.

Figure 6E:
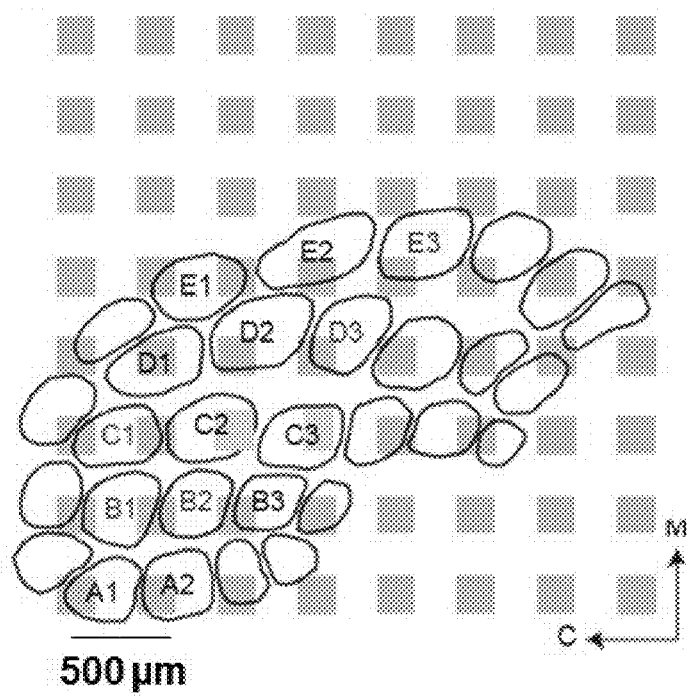
Figure 6F:
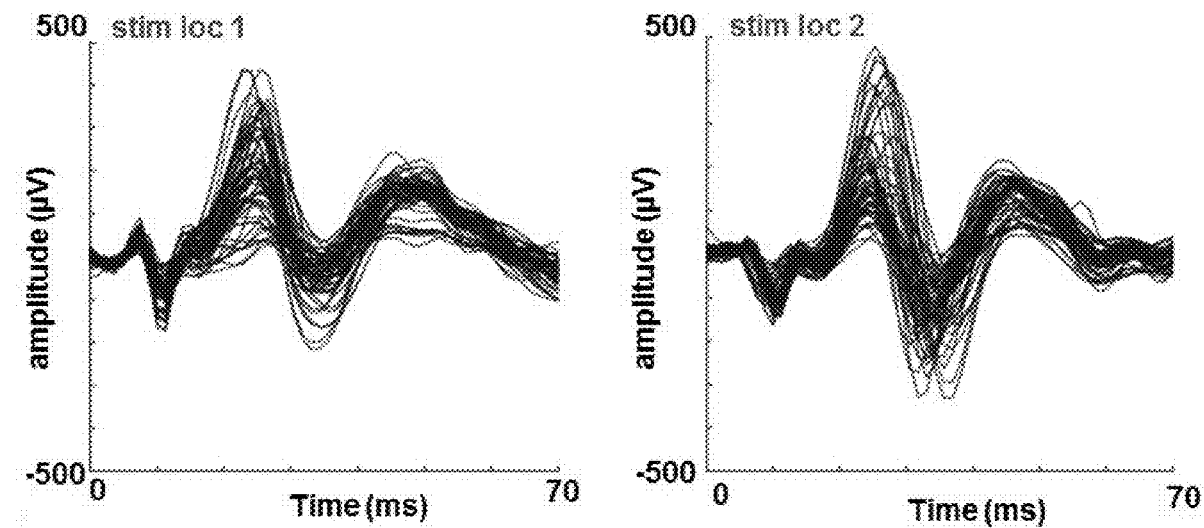
Figure 6G:
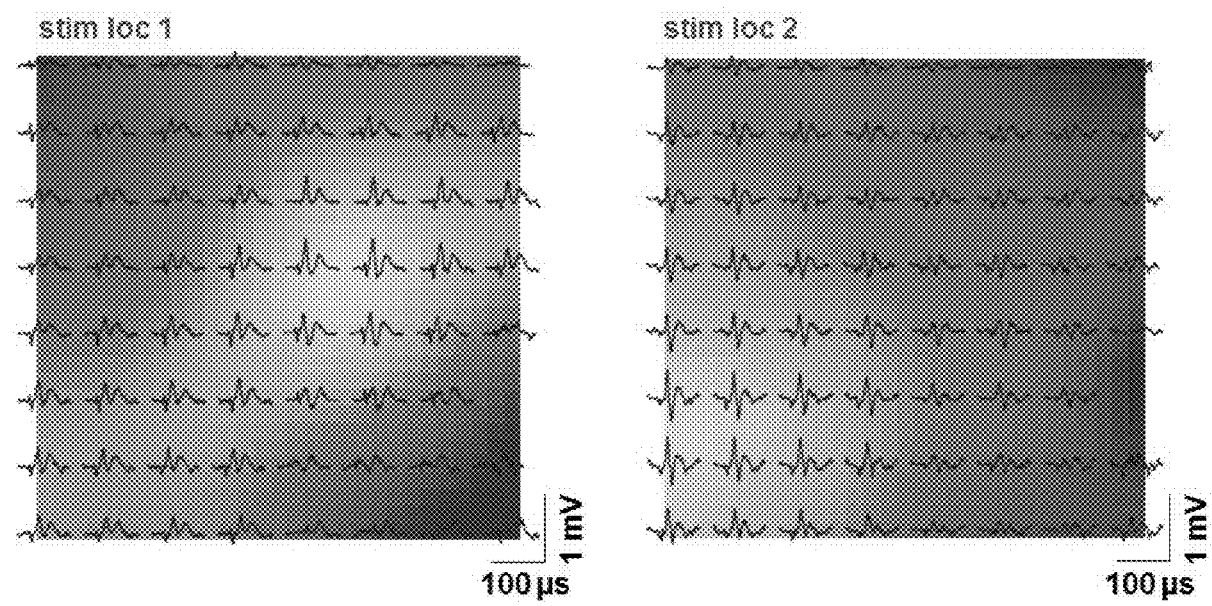

In addition to epileptiform activity, spatial distributions of low amplitude evoked cortical activity can be captured using the same device. Somatosensory evoked potential (SSEP) experiments were conducted in anesthetized rats using the bioresorbable multiplexed array on the surface of the exposed barrel cortex. Evoked potentials were produced by stimulating two different whiskers (B1 and E3, FIG. 6D), corresponding to the barrel cortex and estimated relative location (FIG. 6E). The temporally resolved patterns of the evoked potentials are shown in FIG. 6F. The spatial distribution of the amplitude of the evoked potentials measured at the cortical surface by the array is consistent with the relative location of the activated whiskers on the barrel cortex as described with the color map (FIG. 6G). These results collectively demonstrate an ability to record stimulus evoked and drug-induced neural activity with high SNR. The same materials and device architectures can be easily adapted to larger areas and increased channel counts with potential for use in large animal models and, in the future, for clinical monitoring applications.

The concepts introduced here form a robust foundation of capabilities in bioresorbable implantable electrode technology for various clinical problems, ranging from post-operation monitoring of brain activity to electrical monitoring of skeletal muscles or organ function. In all cases, the thin, flexible form factors minimize mechanical injury associated with implantation and chronic use. The use of Si as the active semiconductor material aligns the technology consumer electronics industry with the natural capacity to scale to higher densities of electrodes and larger areas.

REFERENCES

1. Niedermeyer, E. & da Silva, F. L. Electroencephalography: basic principles, clinical applications, and related fields. (Lippincott Williams & Wilkins, 2005).
2. Stacey, W. C. & Litt, B. Technology insight: neuroengineering and epilepsy-designing devices for seizure control. *Nat. Clin. Pract. Neurol.* 4, 190-201 (2008).
3. McKhann, G. M., Schoenfeld-McNeill, J., Born, D. E., Haglund, M. M. & Ojemann, G. A. Intraoperative hippocampal electrocorticography to predict the extent of hippocampal resection in temporal lobe epilepsy surgery. *Journal of neurosurgery* 93, 44-52 (2000).
4. Whitmer, D. et al. High frequency deep brain stimulation attenuates subthalamic and cortical rhythms in Parkinson's disease. *Frontiers in human neuroscience* 6 (2012).
5. Litt, B. et al. Epileptic seizures may begin hours in advance of clinical onset: a report of five patients. *Neuron* 30, 51-64 (2001).
6. Shapiro, M., Becske, T., Sahlein, D., Babb, J. & Nelson, P. K. Stent-supported aneurysm coiling: a literature survey of treatment and follow-up. *American Journal of Neuroradiology* 33, 159-163 (2012).
7. Wholey, M. H. et al. Global experience in cervical carotid artery stent placement. *Catheterization and Cardiovascular Interventions* 50, 160-167 (2000).
8. Frizzel, R. T. & Fisher III, W. S. Cure, Morbidity, and Mortality Associated with Embolization of Brain Arteriovenous Malformations: A Review of 1246 Patients in 32 Series over a 35-Year Period. *Neurosurgery* 37, 1031-1040 (1995).
9. McNett, M. M. & Horowitz, D. A. International multidisciplinary consensus conference on multimodality monitoring: ICU processes of care. *Neurocrit Care* 21, 215-228 (2014).
10. Mayevsky, A., Manor, T., Meilin, S., Doron, A. & Ouaknine, G. E. Real-time multiparametric monitoring of the injured human cerebral cortex—a new approach. *Acta Neurochir. Suppl.* 71, 78-81 (1998).
11. Khodagholy, D. et al. In vivo recordings of brain activity using organic transistors. Nature Commun. 4, 1575 (2013).
12. Viventi, J. et al. Flexible, foldable, actively multiplexed, high-density electrode array for mapping brain activity in vivo. Nature Neurosci. 14, 1599-1605 (2011).
13. Khodagholy, D. et al. NeuroGrid: recording action potentials from the surface of the brain. Nature Neurosci. 18, 310-315 (2015).

14. Escabí, M. A. et al. A high-density, high-channel count, multiplexed pECoG array for auditory-cortex recordings. *Journal of neurophysiology* 112, 1566-1583 (2014).
15. Qing, Q. et al. Nanowire transistor arrays for mapping neural circuits in acute brain slices. Proc. Natl Acad. Sci. USA 107, 1882-1887 (2010).
16. Xiang, Z. et al. Ultra-thin flexible polyimide neural probe embedded in a dissolvable maltose-coated microneedle. J. Micromech. Microeng. 24, 065015 (2014)).
17. Tian, B. et al. Three-dimensional, flexible nanoscale field-effect transistors as localized bioprobes. Science 329, 830-834 (2010)).
18. Kozai, T. D. Y et al. Ultrasmall implantable composite microelectrodes with bioactive surfaces for chronic neural interfaces. Nat. Mater. 11, 1065-1073 (2012)).
19. Kuzum, D. et al. Transparent and flexible low noise graphene electrodes for simultaneous electrophysiology and neuroimaging. Nat. Commun. 5, 5259 (2014)).
20. Vitale, F., Summerson, S. R., Aazhang, B., Kemere, C., & Pasquali, M. Neural stimulation and recording with bidirectional, soft carbon nanotube fiber microelectrodes. *ACS Nano* 9, 4465-4474 (2015).
21. Daube, J. & Rubin, D. *Clinical Neurophysiology*. (Oxford University Press, New York, N.Y., 2009).
22. King-Stephens, D. et al. Lateralization of mesial temporal lobe epilepsy with chronic ambulatory electrocorticography. *Epilepsia,* 56, 959-967 (2015).
23. Kang, S.-K. et al. Bioresorbable silicon electronic sensors for the brain. *Nature* 530, 71-76 (2016).
24. Saha, R. et al. Highly doped polycrystalline silicon microelectrodes reduce noise in neuronal recordings in vivo. *IEEE Trans Neural Sys Rehab Eng.* 18, 489-97 (2010).
25. Fontes, M. B. A. Electrodes for bio-application: recording and stimulation. *J. Phys. Conf. Ser.* 421 012019 (2013).
26. Oskam, G., Long, J. G., Natarajan, A. & Searson. P. C. Electrochemical deposition of metals onto silicon. *J. Phys. D: Appl. Phys.* 31, 1927-1949 (1998).
27. Zhang, X. G. *Electrochemistry of Silicon and its Oxide*. (Kluwer Academic, New York, N.Y., 2001).
28. Schmickler, W. & Santos, E. *Interfacial Electrochemistry*. Ch. 11 (Springer, Berlin Heidelberg, 2010).
29. Morita, M., Ohmi, T., Hasegawa, E., Kawakami, M. & Ohwada, M. Growth of native oxide on a silicon surface. *J. Appl. Phys.* 68, 1272 (1990).
30. Seidel, H., Csepregi, L., Heuberger, A. & Baumgartel, H. Anisotropic etching of crystalline silicon in alkaline solutions: I. orientation dependence and behavior of passivation layers. *J. Electrochem. Soc.* 137, 3612 (1990).
31. Gentile, P., Chiono, V., Carmagnola, I. & Hatton, P. V. An overview of poly(lactic-coglycolic) acid (PLGA)-based biomaterials for bone tissue engineering. *Int. J. Mol. Sci.* 15, 3640-3659 (2014).
32. Shaw, F.-Z. Is spontaneous high-voltage rhythmic spike discharge in Long Evans rats an absence-like seizure activity? *Journal of neurophysiology* 91, 63-77 (2004).
33. Pearce, P. S. et al. Spike-wave discharges in adult Sprague-Dawley rats and their implications for animal models of temporal lobe epilepsy. *Epilepsy & Behavior* 32, 121-131 (2014).
34. Rodgers, K. M., Dudek, F. E. & Barth, D. S. Progressive, seizure-like, spike-wave discharges are common in both injured and uninjured sprague-dawley rats: implications for the fluid percussion injury model of post-traumatic epilepsy. *The Journal of Neuroscience* 35, 9194-9204 (2015).
35. Polikov, V. S., Tresco, P. A. & Reichert, W. M. Response of brain tissue to chronically implanted neural electrodes. *Journal of neuroscience methods* 148, 1-18 (2005).
36. Ryu, S. I. & Shenoy, K. V. Human cortical prostheses: lost in translation? *Neurosurgical focus* 27, E5 (2009).
37. Biran, R., Martin, D. C. & Tresco, P. A. Neuronal cell loss accompanies the brain tissue response to chronically implanted silicon microelectrode arrays. *Experimental neurology* 195, 115-126 (2005).
38. Biran, R., Martin, D. C. & Tresco, P. A. The brain tissue response to implanted silicon microelectrode arrays is increased when the device is tethered to the skull. *Journal Biomedical Materials Research Part A* 82, 169-178 (2007).
39. Hwang, S.-W. et al. A physically transient form of silicon electronics. *Science* 337, 1640-1644 (2012).
40. Yin, L. et al. Dissolvable metals for transient electronics. *Adv. Func. Mater.* 24, 645-658 (2014).
41. Badawy, W. A. & Al-Kharafi, F. M. Corrosion and passivation behaviors of molybdenum in aqueous solutions of different pH. *Electrochimica Acta* 44, 693-702 (1998).
42. Kang, S.-K. et al. Biodegradable thin metal foils and spin-on glass materials for transient electronics. *Adv. Fund. Mater.* 7, 9297-9305 (2015).
43. Kang, S.-K. et al. Dissolution behaviors and applications of silicon oxides and nitrides in transient electronics. *Adv. Func. Mater.* 24, 4427-4434 (2014).
44. Hwang, S.-W. et al. Dissolution chemistry and biocompatibility of single-crystalline silicon nanomembranes and associated materials for transient electronics. *ACS Nano* 8, 5843-5851 (2014).
45. Kue, R. et al. Enhanced proliferation and osteocalcin production by human osteoblast-like MG63 cells on silicon nitride ceramic discs. *Biomaterials* 20, 1195-1201 (1999).
46. Bal B. S. & Rahaman M. N. Orthopedic applications of silicon nitride ceramics. *Acta Biomater.* 8, 2889-2898 (2012).

Fabrication of Passive Electrode Arrays.

Fabrication of the passive electrode arrays began with solid state phosphorus doping (PH-1000N Source, Saint Gobain, USA, 1000° C. for 10 minutes) of p-type device Si on a Si on insulator (SOI, top Si ~300 nm, SOITEC, France) wafer. Removing the buried oxide layer of the SOI by wet etching with concentrated HF released the device Si as a Si NM, retrieved with a slab of the elastomer poly(dimethylsiloxane) (PDMS) and transfer-printed to a spin-cast bilayer of poly(methylmethacrylate) (PMMA, ~800 nm thick) and polyimide (PI, ~300 nm thick) on a Si wafer. Photolithography and reactive ion etching (RIE) defined a pattern of electrodes and interconnects in the Si NMs. Plasma enhanced chemical vapor deposition (PECVD) formed a layer of $SiO_2$ (thickness 100 nm) as encapsulation. Patterned etching with buffered oxide etchant removed the $SiO_2$ from the electrode regions. Spin casting and patterning a top coating of PI (~300 nm thick) placed the Si NM electrodes and interconnects near the neutral mechanical plane. Patterning a mesh structure across the multilayer (i.e. PI, $SIO_2$, PI and PMMA) by RIE followed by immersion in buffered oxide etchant exposed the base layer of PMMA to allow its dissolution in acetone. Retrieval onto a slab of PDMS enabled removal of the bottom exposed layer of PI by RIE. Transfer onto a film of PLGA (~30 μm thick), facilitated by heating to temperatures close to the glass transition of the PLGA (55~60° C., lactide/glycolide ratio of 75:25 composition), followed by elimination of the top layer of PI by RIE completed the fabrication. Bonding an ACF cable to the terminal regions of the Si NM interconnects yielded connection points for interfaces to external data acquisition (DAQ) systems.

Fabrication of Actively Multiplexed Electrode Arrays.

The fabrication began with growth of 200 nm of thermal oxide on a p-type SOI wafer (top Si ~320 nm, SOITEC), photolithography and immersion in buffered oxide etchant to create a mask for solid state phosphorus diffusion (1000° C. for 6 minutes) to define the source and drain contacts. Releasing, retrieving and transferring the doped Si NMs onto a temporary substrate, consisting of Si wafer with a bilayer coating of PI/PMMA, followed procedures similar to those described for passive electrode arrays. Photolithography and RIE etching patterned the Si NMs into geometries for an 8×8 array of unit cells, each consisting of two transistors connected in series for purpose of actively multiplexed readout. A thin layer of $SiO_2$ (PECVD at 220° C., thickness ~100 nm) served as the gate dielectric. Buffered oxide etching through a photolithographically patterned mask formed openings through the $SiO_2$ to expose the source and drain contact regions. Photolithography and lift off in acetone defined a patterned layer of Mo (sputter deposited, thickness ~300 nm) for the gate electrodes and metal interconnects. Deposition of a trilayer of $SiO_2$ (~300 nm)/$Si_3N_4$ (~400 nm)/$SiO_2$ (~300 nm) by PECVD formed the interlayer dielectric. Photolithography and buffered oxide etching created vertical interconnect access (via) holes for electrical connections between layers. An additional layer of Mo (thickness ~300 nm) patterned by photolithography and liftoff defined column select lines. Another trilayer of $SiO_2$ (~300 nm)/$Si_3N_4$ (~400 nm)/$SiO_2$ (~300 nm) served as encapsulation, with openings at the locations of the sensing electrodes and peripheral contact pads for interfacing to an external DAQ system. A spin-cast layer of PI served as device passivation. Selective RIE and buffered oxide etching through these multilayer stacks (diluted PI/trilayers of inorganic materials/trilayers of inorganic materials/ Diluted PI) formed mesh structures that enabled release of active layers from the temporary substrate by dissolving the PMMA layer in acetone. Transfer printing steps followed, according to procedures similar to those for the passive electrode fabrication.

In Vivo Acute Recordings of Epileptiform Activity.

The in vivo data FIG. 2A-2G is representative of four different acute experiments, each of which lasted 5-6 hours. The procedures, which were approved by the Institutional Care and Use Committee of the University of Pennsylvania, involved an anaesthetized rat with its head fixed in a stereotaxic apparatus. Wild-type, adult Long Evans male and female rats were used. The animal was anesthetized with initially ketamine/xylazine and then isoflurane throughout the craniotomy and neural recordings. A craniotomy exposed a 4×8 mm region of cortex in either left or tight or in both hemispheres. All recordings were taken in reference to a distant stainless steel bone screw inserted through the skull during the surgery. A commercial stainless steel microwire electrode (~100 um stainless steel wire from California Fine Wire) placed at 0.5 mm depth from the cortical surface in close proximity to the bioresorbable electrodes served as a control during acute recordings. Neural data was acquired by a FHC multi-channel neural amplifier (FHC Inc, Bowdoin, Me., USA) and an acquisition system (16 bit Axon Instruments Digidata 1322A, Axon Instruments, Foster City, Calif.). Recordings were high pass filtered at 0.1 Hz. Neural recording data were analyzed offline using Clampfit software (Axon Instruments) and custom Matlab software for neural signal analysis.

In Vivo Acute Recordings of Evoked Responses by Whisker Stimulation.

The following procedures were approved by the Institutional Care and Use Committee of the University of Pennsylvania. One 150-g, Sprague-Dawley rat was anesthetized with a ketamine (60 mg/kg), dexdomitor (0.25 mg/kg) solution and placed in a stereotaxic frame. A craniotomy was performed to expose the right barrel cortex. A skull screw was placed in the left frontal bone to serve as the reference electrode for the recordings. The recording array was placed over the exposed cortical surface. A pair of needle stimulating electrode were inserted into the left mystacial pad at various locations. Brief electrical currents (~250-600 µA, 1 ms/phase, biphasic pulse) were passed between the electrodes to activate the intrinsic muscles of the vibrissae, causing a visible protraction of the whiskers. Current amplitude and electrode spacing was adjusted for focal activation, usually 1-4 whiskers. Cortical potentials evoked by the whisker stimulation were recorded at 781.25 samples/s.

In Vivo Chronic Recordings.

An adult Long Evans rat was anesthetized with isoflurane and placed in a stereotactic frame (David Kopf Instruments Tujunga, Calif.). Body temperature was maintained with a heating blanket and the eyes were covered with ointment to prevent drying. The skull was exposed and a large craniotomy (4×8 mm$^2$) was made between bregma and lambda and laterally to the midline. The electrode was placed on the exposed dura and a slurry of gel foam and saline was layered on top of the electrode. A screw electrode was placed contralaterally to the experimental array, with another such electrode placed posterior to lambda as a ground and reference. Additional screws were secured in the skull for anchoring. The skull and electrodes were then covered with dental cement and the connecting plug was secured on top. The rat was given meloxicam for postoperative pain and allowed to recover on a heating pad. The rat was given meloxicam daily for 3 days after surgery to minimize pain. After 1 week the animal was placed in a cage for video/EEG recording. EEG signals were collected continuously from 3 channels on the array and from the screw. The signals were amplified and low pass filtered at 600 Hz (Multichannel Systems, Reutlingen, Germany) and sampled at 2000 Hz with a 16 bit digitizer (National Instruments, Austin, Tex.). Data was acquired using a custom written MATLAB routine.

Chronic Evaluation of Immunohistochemistry.

Rats (n=14) were anesthetized and transcardiac perfusion was performed using phosphate buffered saline (PBS 10×, cat. #BM-220, Boston BioProducts, Ashland, Mass.), followed by 4% paraformaldehyde (PFA, cat. #BM-155, Boston BioProducts). Whole brains were then removed and post-fixed overnight at 4° C. in the same 4% PFA solution. Subsequently, fixed brains were cryoprotected in 30% sucrose (cat. #57-50-1, Sigma-Aldrich, Saint Louis, Mo.) at 4° C. and coronal sections were cut at 20 µm using a Leica CM3050 S cryostat (Leica Biosystems Inc.). Serial sections, spanning the entire craniotomy site, were mounted on charged slides and stored at −20° C. until use. For immunostaining, slides were first immersed in an antigen retrieval solution (0.1 M citrate buffer, pH 6.0, cat #ab64214, Abcam, Cambridge, Mass.) and placed in a water bath at 95° C. for 10 minute. After cooling, sections were rinsed in distilled water, incubated in a blocking solution containing 0.1% Triton X-100 (cat. #9002-93-1, Sigma-Aldrich) and 5% normal goat serum (cat. #GS-0500, Equitech-Bio Inc., Kerrville, Tex.) for one hour at room temperature (RT) and then incubated overnight at 4° C. with the following primary antibodies: anti-Glial Fibrillary Acidic Protein (GFAP, 1:1000, cat. #SMI-22R, Covance, Princeton, N.J.), and anti-ionized calcium binding adapter molecule 1 (Iba-1, 1:1000, cat. #019-19741, Wako Chemicals USA, Inc., Richmond, Va.). After 3×20-minute washes in PBS, sections were incubated with the corresponding fluorescent secondary antibodies (Alexa Fluor 488 goat anti-mouse IgG2b, 1:1000, cat. #A-21141, and Alexa Fluor 568 goat anti-rabbit IgG, 1:1000, cat. #A-11011, Invitrogen by Life Technologies, Grand Island, N.Y.). After the final washes (3×20 min in PBS), the slides were cover-slipped with an anti-fade medium containing the nuclear stain DAPI (Fluoromount-G+DAPI, cat. #0100-20, Southern Biotechnology, Birmingham, Ala.). Control sections were incubated with omission of one or both primary antibodies, adding only the secondary antibodies to exclude false-positive labeling. Slides were examined on an epifluorescence microscope (Zeiss Axioscope, Germany) and images were acquired with a 20× objective and a Spot RT3 digital camera, using the Spot Software 5.1 (Diagnostic Instruments, Sterling Heights, Mich.). Digital images were processed using Adobe Photoshop 12.0 (Adobe Systems, San Jose, Calif.).

SUPPLEMENTARY REFERENCES 1. http://iom.nationalacademies.org/Activities/Nutrition/SummaryDRIs/DRI-Tables.aspx
2. Pennington, J. A. T. Silicon in foods and diets Food. *Addit. Contam.* 8, 97-118 (1991).
3. Jugdaohsingh, R. et al. Dietary silicon intake and absorption. *Am. J. Clin. Nutr.* 75, 887-893 (2002).
4. Syracus research coporations. Toxicological profile for ammonia. (2004).
5. Kawahara, M, & Kato-Negishi, M. Link between aluminum and the pathogenesis of Alzheimer's Disease: the integration of the aluminum and amyloid cascade hypotheses. *Int. J. Alzheimer's Dis.* 2011, 276393 (2011).
6. Jurkic, L. M., Cepanec, I., Pavelic, S. K., & Pavelic, K. Biological and therapeutic effects of ortho-silicic acid and some ortho-silicic acid-releasing compounds: new perspectives for therapy. *Nutr. Metab.* 10, 2-12 (2013).
7. Davenward, S. et al. Silicon-rich mineral water as a non-invasive test of the 'aluminum hypothesis' in Alzheimer's disease. *J Alzheimers Dis.* 33, 423-430 (2013).

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a size range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The following references relate generally to fabrication methods, structures and systems for making electronic devices, and are hereby incorporated by reference to the extent not inconsistent with the disclosure in this application.

| Attorney Docket No. | Application No. | Filing Date | Publication No. | Publication Date | Pat. No. | Issue Date |
|---|---|---|---|---|---|---|
| 145-03 US | 11/001,689 | Dec. 1, 2004 | 2006/0286488 | Dec. 21, 2006 | 7,704,684 | Apr. 27, 2010 |
| 18-04 US | 11/115,954 | Apr. 27, 2005 | 2005/0238967 | Oct. 27, 2005 | 7,195,733 | Mar. 27, 2007 |
| 38-04A US | 11/145,574 | Jun. 2, 2005 | 2009/0294803 | Dec. 3, 2009 | 7,622,367 | Nov. 24, 2009 |
| 38-04B US | 11/145,542 | Jun. 2, 2005 | 2006/0038182 | Feb. 23, 2006 | 7,557,367 | Jul. 7, 2009 |
| 43-06 US | 11/421,654 | Jun. 1, 2006 | 2007/0032089 | Feb. 8, 2007 | 7,799,699 | Sep. 21, 2010 |
| 38-04C US | 11/423,287 | Jun. 9, 2006 | 2006/0286785 | Dec. 21, 2006 | 7,521,292 | Apr. 21, 2009 |
| 41-06 US | 11/423,192 | Jun. 9, 2006 | 2009/0199960 | Aug. 13, 2009 | 7,943,491 | May 17, 2011 |
| 25-06 US | 11/465,317 | Aug. 17, 2006 | — | — | — | — |
| 137-05 US | 11/675,659 | Feb. 16, 2007 | 2008/0055581 | Mar. 6, 2008 | — | — |
| 90-06 US | 11/782,799 | Jul. 25, 2007 | 2008/0212102 | Sep. 4, 2008 | 7,705,280 | Apr. 27, 2010 |
| 134-06 US | 11/851,182 | Sep. 6, 2007 | 2008/0157235 | Jul. 3, 2008 | 8,217,381 | Jul. 10, 2012 |
| 151-06 US | 11/585,788 | Sep. 20, 2007 | 2008/0108171 | May 8, 2008 | 7,932,123 | Apr. 26, 2011 |
| 216-06 US | 11/981,380 | Oct. 31, 2007 | 2010/0283069 | Nov. 11, 2010 | 7,972,875 | Jul. 5, 2011 |
| 116-07 US | 12/372,605 | Feb. 17, 2009 | — | — | — | — |
| 213-07 US | 12/398,811 | Mar. 5, 2009 | 2010/0002402 | Jan. 7, 2010 | 8,552,299 | Oct. 8, 2013 |
| 38-04D US | 12/405,475 | Mar. 17, 2009 | 2010/0059863 | Mar. 11, 2010 | 8,198,621 | Jun. 12, 2012 |
| 170-07 US | 12/418,071 | Apr. 3, 2009 | 2010/0052112 | Mar. 4, 2010 | 8,470,701 | Jun. 25, 2013 |
| 216-06A US | 12/522,582 | Jul. 9, 2009 | — | — | — | — |
| 38-04A1 US | 12/564,566 | Sep. 22, 2009 | 2010/0072577 | Mar. 25, 2010 | 7,982,296 | Jul. 19, 2011 |
| 71-07 US | 12/669,287 | Jan. 15, 2010 | 2011/0187798 | Aug. 4, 2011 | — | — |
| 60-09 US | 12/778,588 | May 12, 2010 | 2010/0317132 | Dec. 16, 2010 | — | — |
| 43-06A US | 12/844,492 | Jul. 27, 2010 | 2010/0289124 | Nov. 18, 2010 | 8,039,847 | Oct. 18, 2011 |
| 15-10 US | 12/892,001 | Sep. 28, 2010 | 2011/0230747 | Sep. 22, 2011 | 8,666,471 | Mar. 4, 2014 |
| 19-10 US | 12/916,934 | Nov. 1, 2010 | 2012/0105528 | May 3, 2012 | 8,562,095 | Oct. 22, 2013 |
| 3-10 US | 12/947,120 | Nov. 16, 2010 | 2011/0170225 | Jul. 14, 2011 | — | — |
| 118-08 US | 12/996,924 | Dec. 8, 2010 | 2011/0147715 | Jun. 23, 2011 | 8,946,683 | Feb. 3, 2015 |
| 126-09 US | 12/968,637 | Dec. 15, 2010 | 2012/0157804 | Jun. 21, 2012 | — | — |
| 50-10 US | 13/046,191 | Mar. 11, 2011 | 2012/0165759 | Jun. 28, 2012 | — | — |
| 151-06A US | 13/071,027 | Mar. 24, 2011 | 2011/0171813 | Jul. 14, 2011 | — | — |
| 137-05A US | 13/095,502 | Apr. 27, 2011 | — | — | — | — |
| 216-06B US | 13/100,774 | May 4, 2011 | 2011/0266561 | Nov. 3, 2011 | 8,722,458 | May 13, 2014 |
| 38-04A2 US | 13/113,504 | May 23, 2011 | 2011/0220890 | Sep. 15, 2011 | 8,440,546 | May 14, 2013 |
| 136-08 US | 13/120,486 | Aug. 4, 2011 | 2011/0277813 | Nov. 17, 2011 | 8,679,888 | Mar. 25, 2014 |
| 151-06B US | 13/228,041 | Sep. 8, 2011 | 2011/0316120 | Dec. 29, 2011 | — | — |
| 43-06B US | 13/270,954 | Oct. 11, 2011 | 2012/0083099 | Apr. 5, 2012 | 8,394,706 | Mar. 12, 2013 |
| 3-11 US | 13/349,336 | Jan. 12, 2012 | 2012/0261551 | Oct. 18, 2012 | — | — |
| 38-04E US | 13/441,618 | Apr. 6, 2012 | 2013/0100618 | Apr. 25, 2013 | 8,754,396 | Jun. 17, 2014 |
| 134-06B US | 13/441,598 | Apr. 6, 2012 | 2012/0327608 | Dec. 27, 2012 | 8,729,524 | May 20, 2014 |
| 28-11 US | 13/472,165 | May 15, 2012 | 2012/0320581 | Dec. 20, 2012 | — | — |
| 7-11 US | 13/486,726 | Jun. 1, 2012 | 2013/0072775 | Mar. 21, 2013 | 8,934,965 | Jan. 13, 2015 |
| 29-11 US | 13/492,636 | Jun. 8, 2012 | 2013/0041235 | Feb. 14, 2013 | — | — |
| 84-11 US | 13/549,291 | Jul. 13, 2012 | 2013/0036928 | Feb. 14, 2013 | — | — |
| 25-06A US | 13/596,343 | Aug. 28, 2012 | 2012/0321785 | Dec. 20, 2012 | 8,367,035 | Feb. 5, 2013 |
| 150-11 US | 13/624,096 | Sep. 21, 2012 | 2013/0140649 | Jun. 6, 2013 | — | — |
| 38-04A3 US | 13/801,868 | Mar. 13, 2013 | 2013/0320503 | Dec. 5, 2013 | 8,664,699 | Mar. 4, 2014 |
| 125-12 US | 13/835,284 | Mar. 15, 2013 | 2014/0220422 | Aug. 7, 2014 | — | — |
| 30-13 US | 13/853,770 | Mar. 29, 2013 | 2013/0333094 | Dec. 19, 2013 | — | — |
| 213-07A US | 13/974,963 | Aug. 23, 2013 | 2014/0140020 | May 22, 2014 | 8,905,772 | Dec. 9, 2014 |
| 19-10A US | 14/033,765 | Sep. 23, 2013 | 2014/0092158 | Apr. 3, 2014 | — | — |
| 15-10A US | 14/140,299 | Dec. 24, 2013 | 2014/0163390 | Jun. 12, 2014 | — | — |
| 38-04A4 US | 14/155,010 | Jan. 14, 2014 | 2014/0191236 | Jul. 10, 2014 | — | — |
| 136-08A US | 14/173,525 | Feb. 5, 2014 | 2014/0216524 | Aug. 7, 2014 | 9,105,782 | Aug. 11, 2015 |
| 216-06C US | 14/209,481 | Mar. 13, 2014 | 2014/0373898 | Dec. 25, 2014 | 9,117,940 | Aug. 25, 2015 |
| 134-06C US | 14/220,910 | Mar. 20, 2014 | 2014/0374872 | Dec. 25, 2014 | — | — |
| 38-04F US | 14/220,923 | Mar. 20, 2014 | 2015/0001462 | Jan. 1, 2015 | 9,105,555 | Aug. 11, 2015 |
| 151-06C US | 14/246,962 | Apr. 7, 2014 | 2014/0361409 | Dec. 11, 2014 | — | — |
| 62-13 US | 14/250,671 | Apr. 11, 2014 | 2014/0305900 | Oct. 16, 2014 | — | — |
| 56-13 US | 14/251,259 | Apr. 11, 2014 | 2014/0323968 | Oct. 30, 2014 | — | — |
| 60-09A US | 12/778,588 | Sep. 5, 2014 | 2015/0132873 | May 14, 2015 | — | — |
| 84-13 US | 14/504,736 | Oct. 2, 2014 | 2015/0141767 | May 21, 2015 | — | — |
| 213-07B US | 14/521,319 | Oct. 22, 2014 | 2015/0181700 | Jun. 25, 2015 | — | — |
| 7-11A US | 14/532,687 | Nov. 4, 2014 | 2015/0080695 | Mar. 19, 2015 | — | — |
| 2-14 US | 14/599,290 | Jan. 16, 2015 | 2015/0207012 | Jul. 23, 2015 | — | — |

-continued

| Attorney Docket No. | Application No. | Filing Date | Publication No. | Publication Date | Pat. No. | Issue Date |
| --- | --- | --- | --- | --- | --- | --- |
| 71-07A US | 12/669,287 | Apr. 14, 2015 | 2015/0290938 | Oct. 15, 2015 | — | — |
| 213-07C US | 12/398,811 | May 7, 2015 | 2015/0237711 | Aug. 20, 2015 | — | — |
| 38-04G US | 14/789,645 | Jul. 1, 2015 | — | — | — | — |
| 216-06D US | 14/800,363 | Jul. 15, 2015 | — | — | — | — |
| 97-14 US | 14/251,259 | Aug. 4, 2015 | — | — | — | — |
| 128-13 US | 14/766,333 | Aug. 6, 2015 | — | — | — | — |
| 8-14 US | 14/766,301 | Aug. 6, 2015 | — | — | — | — |
| 15-13 US | 14/766,926 | Aug. 10, 2015 | — | — | — | — |
| 54-13 US | 14/772,312 | Sep. 2, 2015 | — | — | — | — |
| 35-13 US | 14/772,354 | Sep. 2, 2015 | — | — | — | — |

TABLE 1

Recommended daily intake and upper limits[1] for ingestion of Mo, P and $SiO_2$, average daily intake of Si from food[2,3], and amounts in the blood and daily production of ammonia for adults[4].

| Nutrients | Mo | P | $SiO_2$ |
| --- | --- | --- | --- |
| Recommended Daily Intakes | 45 mcg | 700 mg | 5-10 mg |
| Upper Limits | 2000 mcg | 4 g | N/A |
| Element | | | Si (Source: food) |
| Average Daily Intakes | | | 20-50 mg |
| Compound | | | Ammonia (byproduct of $Si_3N_4$) |
| Amount of Daily Production | | | 17 g |
| In the blood | | | 0.7-2 mg/L |

*The amount of $Si_3N_4$ in a device is 264 mcg. The amount of ammonia generated by dissolution of the $Si_3N_4$ is 128.2 mcg.

*Literature studies report a geographical correlation between the prevalence of Alzheimer's disease (AD) or various adverse effects on the central nervous system (CNS) in human brain and the concentration of aluminium ions (Al) in the brain from drinking water supplies[5,6]. The level of Al ions in the body can be significantly reduced by $SiOH_4$ (byproduct of dissolution of Si and $SiO_2$) by forming hydroxy-aluminosilicates (HAS)[6]. Studies also suggest that silicon-rich mineral waters can reduce the burden of aluminium in both Alzheimer's patients and control group[7].

We claim:

1. An implantable and bioresorbable medical device comprising:
   a bioresorbable substrate;
   an electronic circuit supported by said bioresorbable substrate, wherein said electronic circuit comprises a membrane of silicon (Si) having a thickness less than or equal to 5 μm;
   an array of dissolvable electrodes, wherein said dissolvable electrodes are formed from said membrane of silicon; and
   wherein said electronic circuit is configured to conformally contact a biological tissue and electrically interface with the biological tissue during use.

2. The implantable and bioresorbable device of claim 1, wherein said dissolvable electrodes are configured to undergo hydrolysis upon contact with a biofluid.

3. The implantable and bioresorbable device of claim 1, wherein said array of dissolvable electrodes are a multiplexed array of dissolvable electrodes.

4. The implantable and bioresorbable device of claim 3, further comprising an array of backplane transistors formed from said membrane of silicon in electrical contact with said array of dissolvable electrodes for high speed multiplexed addressing of said array of dissolvable electrodes.

5. The implantable and bioresorbable device of claim 4, wherein said array of backplane transistors are MOSFETs.

6. The implantable and bioresorbable device of claim 5, wherein said MOSFETs comprise a thin film of a metal, a gate dielectric and an interlayer dielectric.

7. The implantable and bioresorbable device of claim 6, wherein:
   said metal comprises Molybdenum (Mo) having a thickness less than 500 nm;
   said gate dielectric comprises $SiO_2$ having a thickness less than 200 nm;
   said interlayer dielectric comprises a multilayer stack of $SiO_2$ with a thickness less than 400 nm, $Si_3N_4$ with a thickness less than 500 nm, and $SiO_2$ with a thickness less than 400 nm.

8. The implantable and bioresorbable device of claim 4, further comprising for each electrode of the array of dissolvable electrodes:
   a buffer transistor electrically connected to said electrode of the array of dissolvable electrodes for buffering of a measured tissue potential; and
   a multiplexing transistor electrically connected to said electrode of the array of dissolvable electrodes for multiplexing of said array of dissolvable electrodes.

9. The implantable and bioresorbable device of claim 8, further comprising a thin layer of metal electrically connected to said array of dissolvable electrodes to define column select lines.

10. The implantable and bioresorbable device of claim 4, further comprising vertical interconnects to electrically connect said array of dissolvable electrodes to said array of backplane transistors, and said array of dissolvable electrodes are configured for physical contact with underlying tissue.

11. The implantable and bioresorbable device of claim 10, wherein said vertical interconnects comprise vias.

12. The implantable and bioresorbable device of claim 4, further comprising an encapsulation layer that covers said array of backplane transistors and said membrane of silicon.

13. The implantable and bioresorbable device of claim 12, wherein said encapsulation layer comprises a bottom $SiO_2$ layer, a middle $Si_3N_4$ layer and a top $SiO_2$ layer.

14. The implantable and bioresorbable device of claim 13, wherein said encapsulation layer has a thickness less than or equal to 2 μm.

15. The implantable and bioresorbable device of claim 12, further comprising a plurality of passages through said encapsulation layer and in spatial alignment with an active region of each of said electrodes of said array of dissolvable electrodes.

16. The implantable and bioresorbable device of claim 1, wherein said membrane of silicon is patterned to form a plurality of parallel silicon ribbons, the device further comprising:
an encapsulation layer that covers a portion of said plurality of parallel silicon ribbons; and
a plurality of passages formed through said encapsulation layer, wherein the passages are aligned with said plurality of parallel silicon ribbons to form an array of exposed silicon electrically interconnected to regions of encapsulated silicon ribbons.

17. The implantable and bioresorbable device of claim 16, further comprising a plurality MOSFETs formed from said membrane of silicon, wherein said membrane of silicon serves as both an active semiconductor material and a tissue interface electrode.

18. The implantable and bioresorbable device of claim 16, further comprising an active region at a distal end of said plurality of parallel silicon ribbons connected to external electrical connectors separated from said distal end by a longitudinal distance that is greater than or equal to 3 mm.

19. The implantable and bioresorbable device of claim 1, wherein the membrane of silicon thickness, a dopant concentration in the membrane of silicon, or both the membrane of silicon thickness and the dopant concentration in the membrane of silicon are selected to provide for accurate measurement of a biological parameter over a device lifetime.

20. The implantable and bioresorbable device of claim 19, wherein the membrane of silicon thickness and/or the dopant concentration in the membrane of silicon is selected to provide a device lifetime that is greater than or equal to 10 days.

21. The implantable and bioresorbable device of claim 19, wherein the membrane of silicon thickness and/or the dopant concentration in the membrane of silicon is selected to provide a device lifetime that is less than or equal to 2 days.

22. The implantable and bioresorbable device of claim 19, wherein said membrane of silicon has a thickness that decreases as a function of implant duration, wherein said device maintains functionality for a decrease in thickness of up to 70%.

23. The implantable and bioresorbable device of claim 19, wherein device lifetime is increased with increasing dopant concentration in the membrane of silicon and/or increasing said membrane of silicon thickness.

24. The implantable and bioresorbable device of claim 1, wherein said membrane of silicon is doped with a high concentration of dopant.

25. The implantable and bioresorbable device of claim 24, wherein said high concentration of dopant is greater than or equal to $10^{18}$ cm$^{-3}$ and less than or equal to $2\times10^{20}$ cm$^{-3}$.

26. The implantable and bioresorbable device of claim 24, wherein said dopant is selected from the group consisting of phosphorus and boron.

27. The implantable and bioresorbable device of claim 1, further comprising an insulation layer and electrical interconnects that electrically connect said electrodes of said array of dissolvable electrodes, wherein said insulation layer electrically isolates the electrical interconnects from biofluids and biological tissue during use.

28. The implantable and bioresorbable device of claim 27, wherein the insulation layer comprises a layer of $SiO_2$ having a thickness less than or equal to 200 nm.

29. The implantable and bioresorbable device of claim 1, wherein said membrane of silicon further comprises terminal pads configured to electrically interface with a biological tissue.

30. The implantable and bioresorbable device of claim 29, wherein said terminal pads are exposed Si of said membrane of Si.

31. The implantable and bioresorbable device of claim 1, wherein:
said membrane of silicon is doped with a concentration of dopant that is greater than or equal to $10^{18}$ cm$^{-3}$ and less than or equal to $2\times10^{20}$ cm$^{-3}$;
and said membrane of silicon thickness and concentration of dopant are selected to provide a well-controlled dissolution rate of said membrane of silicon without cracking, fragmentation, flaking, or decrease in surface smoothness of the array of dissolvable electrodes over a time course of functional device lifetime.

32. The implantable and bioresorbable device of claim 31, wherein said controlled dissolution of said array of dissolvable electrodes is characterized by one or more of no observable: cracks, flakes, particulates, or decrease in surface smoothness of said array of dissolvable electrodes.

33. The implantable and bioresorbable device of claim 1, wherein said membrane of silicon has an average dissolution rate characterized by a decrease in Si membrane thickness that is greater than or equal to 5 nm/day and less than or equal to 15 nm/day.

34. The implantable and bioresorbable device of claim 31, having a dissolution rate for components of the device that are not the membrane of silicon, including an insulating layer or said bioresorbable substrate, that is between 3 nm/day and 12 nm/day.

35. The implantable and bioresorbable device of claim 1, having one or more material parameters selected to obtain a desired dissolution time of said device, the material parameters including one or more of silicon membrane thickness, silicon membrane doping level, or composition of polymer substrate.

36. The implantable and bioresorbable device of claim 1, wherein during use the bioresorbable substrate, electronic circuit and array of dissolvable electrodes are configured for removal from the implant site by breakdown with exposure to a biological environment and biofluid such that there is no detectable long-term adverse immune response.

37. The implantable and bioresorbable device of claim 1, wherein the bioresorbable substrate is configured to bend from a planar configuration to a curved configuration with a radius of curvature up to 3 mm without adverse degradation of device functionality.

38. The implantable and bioresorbable device of claim 1, configured for spatio-temporal mapping of electrical activity for a biological tissue.

39. The implantable and bioresorbable device of claim 38, configured for conformal contact with said biological tissue that is a cerebral cortex of brain.

40. The implantable and bioresorbable device of claim 1, wherein the membrane of silicon comprises polycrystalline silicon.

41. The implantable and bioresorbable device of claim 1, wherein the membrane of silicon comprises single-crystalline silicon.

42. The implantable and bioresorbable device of claim 1, configured to detect electrical activity, application of an electric potential, or both of said biological tissue.

43. A method of electrically interfacing with biological tissue, the method comprising the steps of:

implanting at an implant site the implantable and bioresorbable medical device of claim 1 adjacent to a biological tissue;

electrically interfacing the device with the biological tissue, wherein the interfacing is one or more of: electrically stimulating or electrically monitoring;

maintaining device functionality over a device lifetime; and dissolving said device so that after said device lifetime no detectable device remains at said implant site.

\* \* \* \* \*